(12) United States Patent
Wilson et al.

(10) Patent No.: US 11,473,106 B2
(45) Date of Patent: Oct. 18, 2022

(54) GENE THERAPY FOR TREATING WILSON'S DISEASE

(71) Applicant: The Trustees of the University of Pennsylvania, Philadelphia, PA (US)

(72) Inventors: James M. Wilson, Philadelphia, PA (US); Jenny Agnes Sidrane, Phoenixville, PA (US); Lakshmanan Govindasamy, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 572 days.

(21) Appl. No.: 16/474,958

(22) PCT Filed: Dec. 29, 2017

(86) PCT No.: PCT/US2017/068919
§ 371 (c)(1),
(2) Date: Jun. 28, 2019

(87) PCT Pub. No.: WO2018/126116
PCT Pub. Date: Jul. 5, 2018

(65) Prior Publication Data
US 2019/0338310 A1    Nov. 7, 2019

Related U.S. Application Data

(60) Provisional application No. 62/440,659, filed on Dec. 30, 2016, provisional application No. 62/473,656, filed on Mar. 20, 2017.

(51) Int. Cl.
*C12N 15/86* (2006.01)
*A61K 48/00* (2006.01)
*C07K 14/755* (2006.01)

(52) U.S. Cl.
CPC ............. *C12N 15/86* (2013.01); *A61K 48/00* (2013.01); *C07K 14/755* (2013.01)

(58) Field of Classification Search
None
See application file for complete search history.

(56) References Cited

U.S. PATENT DOCUMENTS

| | | | |
|---|---|---|---|
| 8,999,380 B2 | 4/2015 | Bancel et al. | |
| 11,147,887 B2 * | 10/2021 | Murillo Sauca | C12Y 306/03 |
| 2003/0228282 A1 | 12/2003 | Gao et al. | |
| 2006/0136184 A1 | 6/2006 | Gustafsson et al. | |
| 2014/0032186 A1 | 1/2014 | Gustafsson et al. | |
| 2015/0315612 A1 | 11/2015 | Wilson et al. | |
| 2017/0348435 A1 | 12/2017 | Murillo Sauca et al. | |

FOREIGN PATENT DOCUMENTS

| | | |
|---|---|---|
| WO | WO 2011/126808 | 10/2011 |
| WO | WO 2013/049493 | 4/2013 |
| WO | WO 2015/012924 | 1/2015 |
| WO | WO 2016/097218 | 6/2016 |
| WO | WO 2017/100676 | 6/2017 |
| WO | WO 2020/142653 | 7/2020 |

OTHER PUBLICATIONS

Yan, et al. (2012) "Human thyroxine binding (TBG) promoter directs efficient and sustaining transgene expression in liver-specific pattern", Gene 506 289-94. (Year: 2012).*
Chuah, et al. (2014) "Liver-Specific Transcriptional Modules Identified Genome-Wide In Silico Analysis Enable Efficient Gene Therapy in Mice and Non-Human Primates", Molecular Therapy, 22(9): 1605-132. (Year: 2014).*
McFarland, et al. (2006) "Evaluation of a novel short polyadenylation signal as an alternative to the SV40 polyadenylation signal", Plasmid, 56: 62-67. (Year: 2006).*
Loeb, et al. (1999) "Enhanced Expression of Transgenes from Adeno-Associated Virus Vectors with the Woodchuck Hepatitis Virus Posttranscriptional Regulatory Element: Implications for Gene Therapy", Human Gene Therapy, 10: 2295-305. (Year: 1999).*
Valencia, et al. (2008) "Splicing promotes rapid and efficient mRNA export in mammalian cells", Proceedings of the National Academy of Sciences, USA, 105(9): 3386-91. (Year: 2008).*
Dong, et al. (1996) "Quantitative Analysis of the Packaging Capacity of Recombinant Adeno-Associated Virus", Human Gene Therapy, 7: 2101-12. (Year: 1996).*
Samadani, et al. (1996) "Identification of a Transthyretin Enhancer Site That Selectively Binds the Hepatocyte Nuclear Factor-3β Isoform" Gene Expression, 6: 23-33. (Year: 1996).*
Bartee et al., The loop connecting metal-binding domains 3 and 4 of ATP7B is a target of a kinase-mediated phosphorylation, Biochemistry. Jun. 23, 2009;48(24):5573-81.
Braiterman et al. Communication between the N and C termini is required for copper-stimulated Ser/Thr phosphorylation of Cu(I)-ATPase (ATP7B). J Biol Chem. Apr. 3, 2015;290(14):8803-19.
Greig et al., A Gene Therapy Approach to Improve Copper Metabolism and Prevent Liver Damage in a Mouse Model of Wilson Disease, Hum Gene Ther Clin Dev. Mar. 2019;30(1):29-39.
Hasan et al., Molecular events initiating exit of a copper-transporting ATPase ATP7B from the trans-Golgi network, J Biol Chem. Oct. 19, 2012;287(43):36041-50.
Shanmugavel et al., Probing functional roles of Wilson disease protein (ATP7B) copper-binding domains in yeast, Metallomics. Jul. 19, 2017;9(7):981-988.
Supplementary Search Report in European Patent Application No. EP 17888104, dated Jul. 6, 2020.
International Search Report and Written Opinion in International Patent Application No. PCT/US2020/012131, dated Mar. 30, 2020.
Cardone et al., Correction of Hunter syndrome in the MPSII mouse model by AAV2/8-mediated gene delivery. Hum Mol Genet. Apr. 1, 2006;15(7):1225-36.

(Continued)

*Primary Examiner* — Robert M Kelly
(74) *Attorney, Agent, or Firm* — Howson & Howson LLP

(57) ABSTRACT

Compositions and regimens useful in treating Wilson's Disease are provided. The compositions include recombinant adeno-associated virus (rAAV) with a transthyretin enhancer and promoter driving expression of a human ATP7B.

16 Claims, 27 Drawing Sheets

Figure 1:
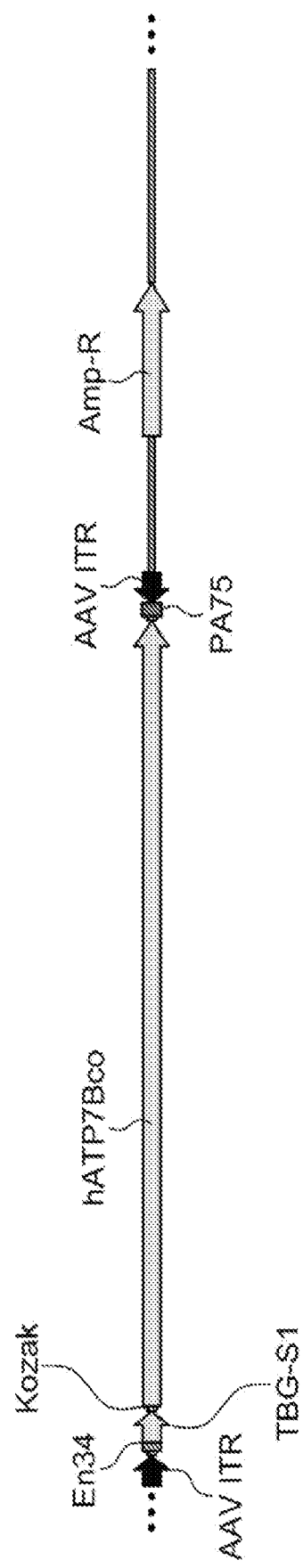

Specification includes a Sequence Listing.

(56) References Cited

OTHER PUBLICATIONS

Office Action issued in Japanese Patent Application No. 2019-535891 dated Oct. 27, 2021, with translation provided by local agent.
Bernard JM et al., Hepatic lesions in 90 captive nondomestic felids presented for autopsy, Vet Pathol. Mar. 2015;52(2):369-76. Epub May 1, 2014.
Bronson RT et al., Acute cerebral neuronal necrosis in copper deficient offspring of female mice with the toxic milk mutation, Mouse Genome 1995;93:152-154.
Buiakova OI et al., Null mutation of the murine ATP7B (Wilson disease) gene results in intracellular copper accumulation and late-onset hepatic nodular transformation, Hum Mol Genet. Sep. 1999;8(9):1665-71.
Bull PC et al., The Wilson disease gene is a putative copper transporting P-type ATPase similar to the Menkes gene, Blood. Jul. 15, 2003;102(2):480-8. Epub Mar. 13, 2003.
Calcedo et al., Worldwide Epidemiology of Neutralizing Antibodies to Adeno-Associated Viruses. J Infect Dis. Feb. 1, 2009;199(3):381-90.
Coronado V et al., the Jackson toxic milk mouse as a model for copper loading, Mamm Genome. Oct. 2001;12(10):793-5.
Davidoff AM et al., Sex significantly influences transduction of murine liver by recombinant adeno-associated viral vectors through an androgen-dependent pathway, Blood 2003;102:480-488.
European Association for Study of Liver, Easl Clinical Practice Guidelines: Wilson's disease, J Hepatol. Mar. 2012;56(3):671-85. doi: 10.1016/j.jhep.2011.11.007.
Gao et al., Adeno-associated viruses undergo substantial evolution in primates during natural infections. Proc Natl Acad Sci U S A. May 13, 2003;100(10):6081-6. Epub Apr. 25, 2003.
Gao G et al., Biology of AAV serotype vectors in liver-directed gene transfer to nonhuman primates, Mol Ther. Jan. 2006;13(1):77-87. Epub Oct. 10, 2005.
Gourdon et al., Structural models of the human copper P-type ATPases ATP7A and ATP7B, Biol Chem. Apr. 2012;393(4):205-16. doi: 10.1515/hsz-2011-0249.
Gray LW et al., Urinary copper elevation in a mouse model of Wilson's disease is a regulated process to specifically decrease the hepatic copper load, PLoS One. 2012;7(6):e38327. doi: 10.1371/journal.pone.0038327. Epub Jun. 22, 2012.
Greig JA et al., Characterization of Adeno-Associated Viral Vector-Mediated Human Factor VIII Gene Therapy in Hemophilia A Mice, May 2017;28(5):392-402. doi: 10.1089/hum.2016.128. Epub Jan. 5, 2017.
Grimm et al., Titration of AAV-2 particles via a novel capsid ELISA: packaging of genomes can limit production of recombinant AAV-2, Gene Ther. Jul. 1999;6(7):1322-30.
Huster D and Lutsenko S, The distinct roles of the N-terminal copper-binding sites in regulation of catalytic activity of the Wilson's disease protein, J Biol Chem. Aug. 22, 2003;278(34):32212-8, Epub Jun. 6, 2003.
Huster D et al., Consequences of copper accumulation in the livers of the Atp7b-/-(Wilson disease gene) knockout mice, Am J Pathol, Feb. 2006;168(2):423-34.
Irani AN et al., Correction of liver disease following transplantation of normal rat hepatocytes into Long-Evans Cinnamon rats modeling Wilson's disease. Mol Ther. Mar. 2001;3(3):302-9.
Lock et al., Absolute determination of single-stranded and self-complementary adeno-associated viral vector genome titers by droplet digital PCR. Hum Gene Ther Methods. Apr. 2014;25(2):115-25. Epub Feb. 14, 2014.
Lock M et al., Rapid, simple, and versatile manufacturing of recombinant adeno-associated viral vectors at scale, Hum Gene Ther. Oct. 2010;21(10):1259-71. doi: 10.1089/hum.2010.055.
Lutsenko S et al., Function and regulation of human copper-transporting ATPases, Physiol Rev. Jul. 2007;87(3):1011-46.
Mcintosh et al., Therapeutic levels of FVIII following a single peripheral vein administration of rAAV vector encoding a novel human factor VIII variant, Blood. Apr. 25, 2013;121(17):3335-44. doi: 10.1182/blood-2012-10-462200. Epub Feb. 20, 2013.
Mcmillin et al., Direct measurement of free copper in serum or plasma ultrafiltrate, Am J Clin Pathol. Feb. 2009;131(2):160-5.
Michalczyk A et al., ATP7B expression in human breast epithelial cells is mediated by lactational hormones, J Histochem Cytochem. Apr. 2008;56(4):389-99. doi: 10.1369/jhc.7A7300.2008. Epub Jan. 7, 2008.
Miyatake et al., Transcriptional targeting of herpes simplex virus for cell-specific replication, J Virol. Jul. 1997;71(7):5124-32.
Mizukami et al., A Protocol for AAV vector production and purification. Diss. Division of Genetic Therapeutics, Center for Molecular Medicine, 1998.
Murillo et al., Long-term metabolic correction of Wilson's disease in a murine model by gene therapy, J Hepatol. Feb. 2016;64(2):419-426. doi: 10.1016/j.jhep.2015.09.014. Epub Sep. 25, 2015.
NCBI Reference Sequence: NP_000044.2, copper-transporting ATPase 2 isoform a [*Homo sapiens*], Aug. 27, 2016.
NCBI Reference Sequence: NP_001005918.1, copper-transporting ATPase 2 isoform b [*Homo sapiens*], Aug. 27, 2016.
NCBI Reference Sequence: NP_001230111.1, copper-transporting ATPase 2 isoform c [*Homo sapiens*], Aug. 28, 2016.
NCBI Reference Sequence: NP_001317507.1, copper-transporting ATPase 2 isoform d [*Homo sapiens*], Sep. 11, 2016.
NCBI Reference Sequence: NP_001317508.1, copper-transporting ATPase 2 isoform e [*Homo sapiens*], Aug. 27, 2016.
NCBI Reference Sequence: XM_005266430.4, PREDICTED: *Homo sapiens* ATPase copper transporting beta (ATP7B), transcript variant XI, mRNA, Jun. 6, 2016.
Petrukhin K et al., Mapping, cloning and genetic characterization of the region containing the Wilson disease gene, Nat Genet. Dec. 1993;5(4):338-43.
Roberts EA and Schilsky ML, American Association for Study of Liver D. Diagnosis and treatment of Wilson disease: an update, Hepatology. Jun. 2008;47(6):2089-111. doi: 10.1002/hep.22261.
Roybal et al., Early gestational gene transfer with targeted ATP7B expression in the liver improves phenotype in a murine model of Wilson's disease, Gene Ther. Nov. 19, 2012(11):1085-94, doi: 10.1038/gt.2011.186. Epub Dec. 8, 2011.
Safaei R et al., The role of metal binding and phosphorylation domains in the regulation of cisplatin-induced trafficking of ATP7B, Metallomics. Aug. 2013;5(8):964-72, doi: 10.1039/c3mt00131h.
Sandig et al., HBV-derived promoters direct liver-specific expression of an adenovirally transduced LDL receptor gene, Gene Ther. Nov. 1996;3(11):1002-9.
Sasaki N et al., The gene responsible for LEC hepatitis, located on rat chromosome 16, is the homolog to the human Wilson disease gene, Biochem Biophys Res Commun. Jul. 15, 1994;202(1):512-8.
Schosinsky et al., Measurement of ceruloplasmin from its oxidase activity in serum by use of o-dianisidine dihydrochloride, Clin Chem. Dec. 1974;20(12):1556-63.
Smedley R et al., Copper-associated hepatitis in Labrador Retrievers, Vet Pathol. May 2009;46(3):484-90, doi: 10.1354/vp.08-VP-0197-S-FL. Epub Jan. 27, 2009.
Sommer JM et al., Quantification of adeno-associated virus particles and empty capsids by optical density measurement. Mol Ther. Jan. 2003;7(1):122-8.
Stromeyer FW and Ishak KG, Histology of the liver in Wilson's disease: a study of 34 cases, Am J Clin Pathol, Jan. 1980;73(1):12-24.
Tanzi RE et al., The Wilson disease gene is a copper transporting ATPase with homology to the Menkes disease gene. Nat Genet. Dec. 1993;5(4):344-50.
Terada K and Sugiyama T, The Long-Evans Cinnamon rat: an animal model for Wilson's disease, Pediatr Int. Aug. 1999;41(4):414-8.
Theophilos MB et al., The toxic milk mouse is a murine model of Wilson disease, Hum Mol Genet 1996;5:1619-1624.
Thompson et al., A comprehensive comparison of multiple sequence alignments, Nucleic Acids Res. Jul. 1, 1999;27(13):2682-90.
Thornburg LP et al., Hereditary copper toxicosis in West Highland white terriers, Vet Pathol. Mar. 1986;23(2):148-54.

(56) References Cited

OTHER PUBLICATIONS

Toole JJ et al., A large region (approximately equal to 95 kDa) of human factor VIII is dispensable for in vitro procoagulant activity, Proc Natl Acad Sci USA. Aug. 1986;83(16):5939-42.
Ward NJ et al., Codon optimization of human factor VTTT cDNAs leads to high-level expression, Blood. Jan. 20, 2011;117(3):798-807. doi: 10.1182/blood-2010-05-282707, Epub Nov. 1, 2010.
Wobus et al., Monoclonal antibodies against the adeno-associated virus type 2 (AAV-2) capsid: epitope mapping and identification of capsid domains involved in AAV-2-cell interaction and neutralization of AAV-2 infection, J Virol. Oct. 2000;74(19):9281-93.
Wu et al., Effect of genome size on AAV vector packaging, Mol Ther. Jan. 2010;18(1):80-6. Epub Nov. 10, 2009.
Wu et al., Optimization of self-complementary AAV vectors for liver-directed expression results in sustained correction of hemophilia B at low vector dose, Mol Ther, Feb. 2008;16(2):280-9, Epub Dec. 4, 2007.
Wu J et al., The LEC rat has a deletion in the copper transporting ATPase gene homologous to the Wilson disease gene, Nat Genet. Aug. 1994;7(4):541-5.
International Search Report and Written Opinion in International Patent Application No. PCT/US2017/068919, dated May 11, 2018.

* cited by examiner

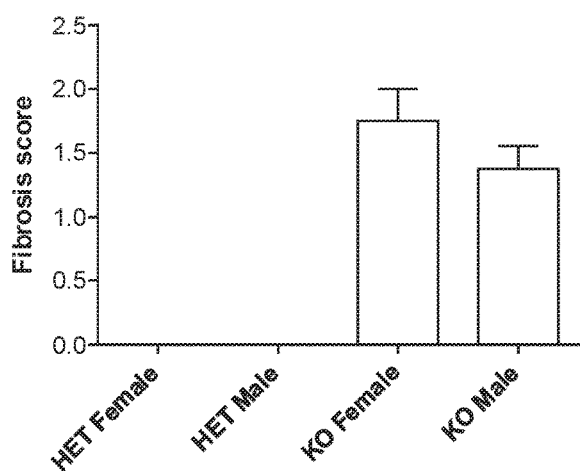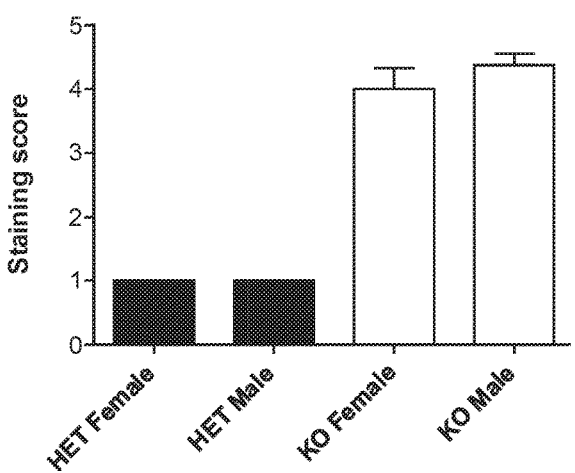

SEQUENCE LISTING

```
<160> NUMBER OF SEQ ID NOS: 35

<210> SEQ ID NO 1
<211> LENGTH: 4395
<212> TYPE: DNA
<213> ORGANISM: Artificial Sequence
<220> FEATURE:
<223> OTHER INFORMATION: constructed sequence

<400> SEQUENCE: 1
atgcccgagc aggaaagaca gatcaccgcc agagagggcg ccagccggaa gatcctgagc        60
aagctgagcc tgcccaccag agcctgggag cccgccatga agaagtcctt cgccttcgac       120
aacgtgggct acgagggcgg cctggacgga ctgggaccat cttctcaggt ggccacaagc       180
accgtgcgca tcctgggcat gacctgccag agctgcgtga agtccatcga ggaccggatc       240
agcaacctga agggcatcat cagcatgaag gtgtccctgg aacagggcag cgccaccgtg       300
aaatacgtgc cctctgtcgt gtgcctgcag caggtgtgcc accagatcgg cgacatgggc       360
ttcgaggcct ctatcgccga gggaaaggcc gcctcttggc cctctagaag cctgcctgct       420
caggaagccg tcgtgaagct gcgggtggaa gggatgacct gtcagtcctg cgtgtccagc       480 atcgaggca aagtgcggaa gctgcagggc gtggtgcgcg tgaaagtgtc tctgagcaac       540
caggaagctg tgatcaccta ccagcctac ctgatccagc ccgaggacct gagggaccac       600
```

```
gtgaacgata tgggatttga ggccgccatc aagagcaagg tggcccctct gtctctgggc    660
cccatcgaca tcgagagact gcagagcacc aaccccaagc ggcctctgag cagcgccaac    720
cagaacttca acaacagcga gacactgggc caccagggca gccacgtcgt gacactgcag    780
ctgcggatcg acggaatgca ctgcaagagc tgtgtgctga acatcgagga aaacatcggc    840
cagctgctgg gagtgcagag catccaggtg tcactggaaa acaagaccgc ccaggtgaag    900
tacgacccca gctgcacaag ccccgtggcc ctgcagagac ccattgaagc tctgcccccct   960 ggcaacttca aagtgtccct gcctgacgga gccgagggct ccggaacaga tcacagaagc   1020
agcagcagcc acagccctgg cagccccct agaaatcagg tgcagggcac ctgtagcacc    1080
accctgatcg ccattgccgg catgacatgc gccagctgcg tgcactctat tgagggcatg   1140
atctcccagc tggaaggcgt gcagcagatc agtgtgtctc tggccgaggg caccgccaca   1200
gtgctgtaca accctagcgt gatcagcccc gaagaactga gagccgccat tgaggacatg   1260
ggattcgaag ccagcgtggt gtccgagagc tgctccacca accctctggg caatcacagc   1320
gccggcaaca gcatggtgca gaccaccgac ggcacccccca ccagcgtgca ggaagtggcc   1380
ccacatacag gcagactgcc cgccaatcac gcccccgata tcctggccaa gagcccccag   1440
agtacaagag ccgtggcccc ccagaagtgc ttcctgcaga tcaagggcat gacttgtgcc   1500
tcttgtgtgt ccaatatcga gcggaacctg cagaaagagg ccggcgtgct gtctgtgctg   1560
gtggctctga tggccggcaa ggccgagatc aaatacgacc ccgaagtgat tcagcccctg   1620
gaaatcgccc agtttatcca ggacctgggc tttgaagccg ccgtgatgga agattacgcc   1680
ggctccgacg gcaacatcga gctgaccatc accggaatga cctgcgcctc ctgtgtgcac   1740
aacattgagt ccaagctgac ccggaccaac ggcatcacct acgcctctgt ggctctggcc   1800
acctccaagg ccctcgtgaa gttcgatccc gagatcatcg gcccagggga catcatcaag   1860
atcatcgaag atcggcttt ccacgccagc ctggcccaga ggaaccctaa cgcccaccac   1920
ctggaccaca agatggaaat caagcagtgg aagaaaagct tcctgtgcag cctggtgttc   1980
ggcatccccg tgatggccct gatgatctac atgctgatcc ccagcaacga gcccaccag   2040 tccatggtgc tggatcacaa catcatcccc ggcctgtcta tcctgaaacct gatcttcttc   2100 atcctgtgca ccttcgtgca gctgctgggc ggctggtact tctacgtgca ggcctacaag   2160
tccctgcggc acagatccgc caacatggac gtgctgatcg tgctggccac atctatcgcc   2220
tacgtgtact ccctcgtgat cctggtggtg gccgtggccg agaaagccga gagaagccct   2280 gtgacccttct tcgacacccc ccctatgctg ttcgtgttta tcgccctggg ccggtggctg   2340
gaacacctgg ccaaaagcaa gaccagcgag gccctggcta agctgatgag tctgcaggcc   2400
accgaggcca cagtcgtgac cctgggcgag acaacctga tcatccgcga ggaacaggtg   2460
ccaatggaac tggtgcagcg gggcgacatc gtgaaggtgg tgcctggcgg caagttcccc   2520
gtggacggaa aagtgctgga agggaatacc atggccgacg agagcctgat cacaggcgag   2580
gccatgcccg tgaccaagaa acctggcagc acagtgatcg ccggcagcat caatgcccac   2640
ggcagcgtgc tgattaaggc cacacacgtg ggcaacgata ccaccctggc tcagattgtg   2700
aagctggtgg aagaggccca gatgagcaag gcccccattc agcagctggc tgaccggttc   2760
agcggctact tcgtgccctt tatcatcatc atgagcaccc tgacactggt cgtgtggatc   2820
gtgatcggct ttatcgactt cggagtggtg cagagatact tccccaaccc taacaagcac   2880
atcagccaga cagaagtgat catcagattc gccttttcaga ccagcatcac cgtgctgtgt   2940
```

-continued

| | |
|---|---|
| atcgcctgcc cctgtagcct gggactggcc acacctaccg ctgtgatggt gggaacaggc | 3000 |
| gtggccgctc agaacggcat cctgatcaag gggggcaagc ctctggaaat ggctcacaag | 3060 |
| atcaagaccg tgatgttcga caagaccggc accatcaccc acggcgtgcc cagagtgatg | 3120 |
| agagtgctgc tgctgggggga tgtggccacc ctgcctctga aaaggtgct ggctgtcgtg | 3180 |
| ggcacagccg aggctagctc tgaacaccca ctgggagtgg ccgtgacaaa gtactgcaaa | 3240 |
| gaggaactgg gcaccgaaac cctgggctac tgcaccgact tcaggccgt gcctggctgt | 3300 |
| ggcatcggct gcaaggtgtc caacgtggaa ggcatcctgg cccacagcga gaggccactg | 3360 |
| tctgcccctg ccagccacct gaacgaggcc ggatctctgc ccgccgaaaa ggacgctgtg | 3420 |
| ccccagacct tctctgtgct gattggcaac agagagtggc tgcggcggaa cggcctgacc | 3480 |
| atctcctccg atgtgtccga cgccatgacc gaccacgaga tgaagggcca gaccgccatt | 3540 |
| ctggtggcca ttgacggggt gctgtgcggc atgatcgcaa tcgccgatgc cgtgaaacag | 3600 |
| gaagcagcac tggccgtgca caccctgcag tctatgggag tggatgtggt gctgatcacc | 3660 |
| ggcgacaaca gaaagaccgc cagggccatt gccacccagg tgggcatcaa caaggtgttc | 3720 |
| gccgaggtgc tgcccagcca caaagtggcc aaggtgcagg aactgcagaa caaaggcaaa | 3780 |
| aaggtggcca tggtgggaga tggcgtgaac gactctcctg ctctggccca ggcagatatg | 3840 |
| ggcgtggcca tcggcacagg caccgacgtg gcaattgagg ctgctgacgt ggtgctgatt | 3900 |
| cggaacgacc tgctggacgt ggtggcctcc atccacctgt ccaagagaac cgtgcggcgg | 3960 |
| atcagaatca acctggtgct ggcactgatc tataacctcg tgggcatccc tatcgccgct | 4020 |
| ggcgtgttca tgcctatcgg aatcgtgctg cagcccctgga tgggctctgc cgccatggct | 4080 |
| gcaagctccg tgtctgtggt gctgtccagc ctgcagctga agtgctacaa gaagcccgac | 4140 |
| ctggaaagat acgaggccca ggcccacgga cacatgaagc tctgacagc ctcccaggtg | 4200 |
| tccgtgcaca tcggcatgga cgacagatgg cgggacagcc ctagagccac cccttgggat | 4260 |
| caggtgtcat acgtgtcaca ggtgtccctg agcagcctga ccagcgacaa gcccagcaga | 4320 |
| catagcgccg ctgccgacga cgatggggac aagtggtccc tgctgctgaa cggccgggat | 4380 |
| gaggaacagt acatc | 4395 |

<210> SEQ ID NO 2
<211> LENGTH: 1465
<212> TYPE: PRT
<213> ORGANISM: Homo sapiens

<400> SEQUENCE: 2

Met Pro Glu Gln Glu Arg Gln Ile Thr Ala Arg Glu Gly Ala Ser Arg
1               5                   10                  15

Lys Ile Leu Ser Lys Leu Ser Leu Pro Thr Arg Ala Trp Glu Pro Ala
            20                  25                  30

Met Lys Lys Ser Phe Ala Phe Asp Asn Val Gly Tyr Glu Gly Gly Leu
        35                  40                  45

Asp Gly Leu Gly Pro Ser Ser Gln Val Ala Thr Ser Thr Val Arg Ile
    50                  55                  60

Leu Gly Met Thr Cys Gln Ser Cys Val Lys Ser Ile Glu Asp Arg Ile
65                  70                  75                  80

Ser Asn Leu Lys Gly Ile Ile Ser Met Lys Val Ser Leu Glu Gln Gly
                85                  90                  95

Ser Ala Thr Val Lys Tyr Val Pro Ser Val Val Cys Leu Gln Gln Val
            100                 105                 110

```
Cys His Gln Ile Gly Asp Met Gly Phe Glu Ala Ser Ile Ala Glu Gly
            115                 120                 125

Lys Ala Ala Ser Trp Pro Ser Arg Ser Leu Pro Ala Gln Glu Ala Val
130                 135                 140

Val Lys Leu Arg Val Glu Gly Met Thr Cys Gln Ser Cys Val Ser Ser
145                 150                 155                 160

Ile Glu Gly Lys Val Arg Lys Leu Gln Gly Val Val Arg Val Lys Val
                165                 170                 175

Ser Leu Ser Asn Gln Glu Ala Val Ile Thr Tyr Gln Pro Tyr Leu Ile
            180                 185                 190

Gln Pro Glu Asp Leu Arg Asp His Val Asn Asp Met Gly Phe Glu Ala
        195                 200                 205

Ala Ile Lys Ser Lys Val Ala Pro Leu Ser Leu Gly Pro Ile Asp Ile
    210                 215                 220

Glu Arg Leu Gln Ser Thr Asn Pro Lys Arg Pro Leu Ser Ser Ala Asn
225                 230                 235                 240

Gln Asn Phe Asn Asn Ser Glu Thr Leu Gly His Gln Gly Ser His Val
                245                 250                 255

Val Thr Leu Gln Leu Arg Ile Asp Gly Met His Cys Lys Ser Cys Val
            260                 265                 270

Leu Asn Ile Glu Glu Asn Ile Gly Gln Leu Leu Gly Val Gln Ser Ile
        275                 280                 285

Gln Val Ser Leu Glu Asn Lys Thr Ala Gln Val Lys Tyr Asp Pro Ser
    290                 295                 300

Cys Thr Ser Pro Val Ala Leu Gln Arg Ala Ile Glu Ala Leu Pro Pro
305                 310                 315                 320

Gly Asn Phe Lys Val Ser Leu Pro Asp Gly Ala Glu Gly Ser Gly Thr
                325                 330                 335

Asp His Arg Ser Ser Ser Ser His Ser Pro Gly Ser Pro Pro Arg Asn
            340                 345                 350

Gln Val Gln Gly Thr Cys Ser Thr Thr Leu Ile Ala Ile Ala Gly Met
        355                 360                 365

Thr Cys Ala Ser Cys Val His Ser Ile Glu Gly Met Ile Ser Gln Leu
370                 375                 380

Glu Gly Val Gln Gln Ile Ser Val Ser Leu Ala Glu Gly Thr Ala Thr
385                 390                 395                 400

Val Leu Tyr Asn Pro Ser Val Ile Ser Pro Glu Glu Leu Arg Ala Ala
                405                 410                 415

Ile Glu Asp Met Gly Phe Glu Ala Ser Val Val Ser Glu Ser Cys Ser
            420                 425                 430

Thr Asn Pro Leu Gly Asn His Ser Ala Gly Asn Ser Met Val Gln Thr
        435                 440                 445

Thr Asp Gly Thr Pro Thr Ser Val Gln Glu Val Ala Pro His Thr Gly
    450                 455                 460

Arg Leu Pro Ala Asn His Ala Pro Asp Ile Leu Ala Lys Ser Pro Gln
465                 470                 475                 480

Ser Thr Arg Ala Val Ala Pro Gln Lys Cys Phe Leu Gln Ile Lys Gly
                485                 490                 495

Met Thr Cys Ala Ser Cys Val Ser Asn Ile Glu Arg Asn Leu Gln Lys
            500                 505                 510

Glu Ala Gly Val Leu Ser Val Leu Val Ala Leu Met Ala Gly Lys Ala
        515                 520                 525

Glu Ile Lys Tyr Asp Pro Glu Val Ile Gln Pro Leu Glu Ile Ala Gln
```

-continued

```
                530             535             540
Phe Ile Gln Asp Leu Gly Phe Glu Ala Ala Val Met Glu Asp Tyr Ala
545                 550                 555                 560

Gly Ser Asp Gly Asn Ile Glu Leu Thr Ile Thr Gly Met Thr Cys Ala
                    565                 570                 575

Ser Cys Val His Asn Ile Glu Ser Lys Leu Thr Arg Thr Asn Gly Ile
                580                 585                 590

Thr Tyr Ala Ser Val Ala Leu Ala Thr Ser Lys Ala Leu Val Lys Phe
                595                 600                 605

Asp Pro Glu Ile Ile Gly Pro Arg Asp Ile Ile Lys Ile Ile Glu Glu
            610                 615                 620

Ile Gly Phe His Ala Ser Leu Ala Gln Arg Asn Pro Asn Ala His His
625                 630                 635                 640

Leu Asp His Lys Met Glu Ile Lys Gln Trp Lys Lys Ser Phe Leu Cys
                    645                 650                 655

Ser Leu Val Phe Gly Ile Pro Val Met Ala Leu Met Ile Tyr Met Leu
                    660                 665                 670

Ile Pro Ser Asn Glu Pro His Gln Ser Met Val Leu Asp His Asn Ile
                675                 680                 685

Ile Pro Gly Leu Ser Ile Leu Asn Leu Ile Phe Phe Ile Leu Cys Thr
            690                 695                 700

Phe Val Gln Leu Leu Gly Gly Trp Tyr Phe Tyr Val Gln Ala Tyr Lys
705                 710                 715                 720

Ser Leu Arg His Arg Ser Ala Asn Met Asp Val Leu Ile Val Leu Ala
                    725                 730                 735

Thr Ser Ile Ala Tyr Val Tyr Ser Leu Val Ile Leu Val Val Ala Val
                    740                 745                 750

Ala Glu Lys Ala Glu Arg Ser Pro Val Thr Phe Phe Asp Thr Pro Pro
                755                 760                 765

Met Leu Phe Val Phe Ile Ala Leu Gly Arg Trp Leu Glu His Leu Ala
            770                 775                 780

Lys Ser Lys Thr Ser Glu Ala Leu Ala Lys Leu Met Ser Leu Gln Ala
785                 790                 795                 800

Thr Glu Ala Thr Val Val Thr Leu Gly Glu Asp Asn Leu Ile Ile Arg
                    805                 810                 815

Glu Glu Gln Val Pro Met Glu Leu Val Gln Arg Gly Asp Ile Val Lys
                820                 825                 830

Val Val Pro Gly Gly Lys Phe Pro Val Asp Gly Lys Val Leu Glu Gly
                835                 840                 845

Asn Thr Met Ala Asp Glu Ser Leu Ile Thr Gly Glu Ala Met Pro Val
850                 855                 860

Thr Lys Lys Pro Gly Ser Thr Val Ile Ala Gly Ser Ile Asn Ala His
865                 870                 875                 880

Gly Ser Val Leu Ile Lys Ala Thr His Val Gly Asn Asp Thr Leu
                    885                 890                 895

Ala Gln Ile Val Lys Leu Val Glu Glu Ala Gln Met Ser Lys Ala Pro
                900                 905                 910

Ile Gln Gln Leu Ala Asp Arg Phe Ser Gly Tyr Phe Val Pro Phe Ile
            915                 920                 925

Ile Ile Met Ser Thr Leu Thr Leu Val Val Trp Ile Val Ile Gly Phe
            930                 935                 940

Ile Asp Phe Gly Val Val Gln Arg Tyr Phe Pro Asn Pro Asn Lys His
945                 950                 955                 960
```

-continued

```
Ile Ser Gln Thr Glu Val Ile Ile Arg Phe Ala Phe Gln Thr Ser Ile
            965                 970                 975
Thr Val Leu Cys Ile Ala Cys Pro Cys Ser Leu Gly Leu Ala Thr Pro
            980                 985                 990
Thr Ala Val Met Val Gly Thr Gly  Val Ala Ala Gln Asn  Gly Ile Leu
            995             1000                 1005
Ile Lys Gly Gly Lys Pro Leu  Glu Met Ala His Lys  Ile Lys Thr
           1010             1015                 1020
Val Met Phe Asp Lys Thr Gly  Thr Ile Thr His Gly  Val Pro Arg
           1025             1030                 1035
Val Met Arg Val Leu Leu  Gly Asp Val Ala Thr  Leu Pro Leu
           1040             1045                 1050
Arg Lys Val Leu Ala Val Val  Gly Thr Ala Glu Ala  Ser Ser Glu
           1055             1060                 1065
His Pro Leu Gly Val Ala Val  Thr Lys Tyr Cys Lys  Glu Glu Leu
           1070             1075                 1080
Gly Thr Glu Thr Leu Gly Tyr  Cys Thr Asp Phe Gln  Ala Val Pro
           1085             1090                 1095
Gly Cys Gly Ile Gly Cys Lys  Val Ser Asn Val Glu  Gly Ile Leu
           1100             1105                 1110
Ala His Ser Glu Arg Pro Leu  Ser Ala Pro Ala Ser  His Leu Asn
           1115             1120                 1125
Glu Ala Gly Ser Leu Pro Ala  Glu Lys Asp Ala Val  Pro Gln Thr
           1130             1135                 1140
Phe Ser Val Leu Ile Gly Asn  Arg Glu Trp Leu Arg  Arg Asn Gly
           1145             1150                 1155
Leu Thr Ile Ser Ser Asp Val  Ser Asp Ala Met Thr  Asp His Glu
           1160             1165                 1170
Met Lys Gly Gln Thr Ala Ile  Leu Val Ala Ile Asp  Gly Val Leu
           1175             1180                 1185
Cys Gly Met Ile Ala Ile Ala  Asp Ala Val Lys Gln  Glu Ala Ala
           1190             1195                 1200
Leu Ala Val His Thr Leu Gln  Ser Met Gly Val Asp  Val Val Leu
           1205             1210                 1215
Ile Thr Gly Asp Asn Arg Lys  Thr Ala Arg Ala Ile  Ala Thr Gln
           1220             1225                 1230
Val Gly Ile Asn Lys Val Phe  Ala Glu Val Leu Pro  Ser His Lys
           1235             1240                 1245
Val Ala Lys Val Gln Glu Leu  Gln Asn Lys Gly Lys  Lys Val Ala
           1250             1255                 1260
Met Val Gly Asp Gly Val Asn  Asp Ser Pro Ala Leu  Ala Gln Ala
           1265             1270                 1275
Asp Met Gly Val Ala Ile Gly  Thr Gly Thr Asp Val  Ala Ile Glu
           1280             1285                 1290
Ala Ala Asp Val Val Leu Ile  Arg Asn Asp Leu Leu  Asp Val Val
           1295             1300                 1305
Ala Ser Ile His Leu Ser Lys  Arg Thr Val Arg Arg  Ile Arg Ile
           1310             1315                 1320
Asn Leu Val Leu Ala Leu Ile  Tyr Asn Leu Val Gly  Ile Pro Ile
           1325             1330                 1335
Ala Ala Gly Val Phe Met Pro  Ile Gly Ile Val Leu  Gln Pro Trp
           1340             1345                 1350
```

```
Met Gly Ser Ala Ala Met Ala Ala Ser Ser Val Ser Val Val Leu
    1355                1360                1365
Ser Ser Leu Gln Leu Lys Cys Tyr Lys Lys Pro Asp Leu Glu Arg
    1370                1375                1380
Tyr Glu Ala Gln Ala His Gly His Met Lys Pro Leu Thr Ala Ser
    1385                1390                1395
Gln Val Ser Val His Ile Gly Met Asp Asp Arg Trp Arg Asp Ser
    1400                1405                1410
Pro Arg Ala Thr Pro Trp Asp Gln Val Ser Tyr Val Ser Gln Val
    1415                1420                1425
Ser Leu Ser Ser Leu Thr Ser Asp Lys Pro Ser Arg His Ser Ala
    1430                1435                1440
Ala Ala Asp Asp Asp Gly Asp Lys Trp Ser Leu Leu Leu Asn Gly
    1445                1450                1455
Arg Asp Glu Glu Gln Tyr Ile
    1460                1465

<210> SEQ ID NO 3
<211> LENGTH: 4395
<212> TYPE: DNA
<213> ORGANISM: Homo sapiens

<400> SEQUENCE: 3
atgcctgagc aggagagaca gatcacagcc agagaagggg ccagtcggaa aatcttatct    60
aagctttctt tgcctacccg tgcctgggaa ccagcaatga agaagagttt tgcttttgac   120
aatgttggct atgaaggtgg tctggatggc ctgggccctt cttctcaggt ggccaccagc   180
acagtcagga tcttgggcat gacttgccag tcatgtgtga agtccattga ggacaggatt   240
tccaatttga aaggcatcat cagcatgaag gtttccctgg aacaaggcag tgccactgtg   300
aaatatgtgc catcggttgt gtgcctgcaa caggtttgcc atcaaattgg ggacatgggc   360
ttcgaggcca gcattgcaga aggaaaggca gcctcctggc cctcaaggtc cttgcctgcc   420
caggaggctg tggtcaagct ccgggtggag ggcatgacct gccagtcctg tgtcagctcc   480
attgaaggca aggtccggaa actgcaagga gtagtgagag tcaaagtctc actcagcaac   540
caagaggccg tcatcactta tcagccttat ctcattcagc ccgaagacct cagggaccat   600
gtaaatgaca tgggatttga agctgccatc aagagcaaag tggctccctt aagcctggga   660
ccaattgata ttgagcggtt acaaagcact aacccaaaga gaccttttatc ttctgctaac   720
cagaattttta ataattctga gaccttgggg caccaaggaa gccatgtggt caccctccaa   780
ctgagaatag atggaatgca ttgtaagtct tgcgtcttga tattgaaga aaatattggc   840
cagctcctag gggttcaaag tattcaagtg tccttggaga caaaactgc ccaagtaaag   900
tatgaccctt cttgtaccag cccagtggct ctgcagaggg ctatcgaggc acttccacct   960
gggaatttta agtttctct tcctgatgga gccgaaggga gtgggacaga tcacaggtct  1020
tccagttctc attcccctgg ctccccaccg agaaaccagg tccagggcac atgcagtacc  1080
actctgattg ccattgccgg catgacctgt gcatcctgtg tccattccat gaaggcatg   1140
atctcccaac tggaagggggt gcagcaaata tcggtgtctt tggccgaagg gactgcaaca  1200
gttctttata atccctctgt aattagccca gaagaactca gagctgctat agaagacatg  1260
ggatttgagg cttcagtcgt ttctgaaagc tgttctacta accctcttgg aaaccacagt  1320
gctgggaatt ccatggtgca aactacgat ggtacaccta catctgtgca ggaagtggct  1380
ccccacactg ggaggctccc tgcaaaccat gccccggaca tcttggcaaa gtccccacaa  1440
```

```
tcaaccagag cagtggcacc gcagaagtgc ttcttacaga tcaaaggcat gacctgtgca    1500
tcctgtgtgt ctaacataga aaggaatctg cagaaagaag ctggtgttct ctccgtgttg    1560
gttgccttga tggcaggaaa ggcagagatc aagtatgacc cagaggtcat ccagcccctc    1620
gagatagctc agttcatcca ggacctgggt tttgaggcag cagtcatgga ggactacgca    1680
ggctccgatg gcaacattga gctgacaatc acagggatga cctgcgcgtc ctgtgtccac    1740
aacatagagt ccaaactcac gaggacaaat ggcatcactt atgcctccgt tgcccttgcc    1800
accagcaaag cccttgttaa gtttgacccg gaaattatcg gtccacggga tattatcaaa    1860
attattgagg aaattggctt tcatgcttcc ctggcccaga gaaacccaa cgctcatcac    1920 ttggaccaca agatggaaat aaagcagtgg aagaagtctt tcctgtgcag cctggtgttt    1980
ggcatccctg tcatggcctt aatgatctat atgctgatac ccagcaacga gccccaccag    2040
tccatggtcc tggaccacaa catcattcca ggactgtcca ttctaaatct catcttcttt    2100
atcttgtgta cctttgtcca gctcctcggt gggtggtact tctacgttca ggcctacaaa    2160
tctctgagac acaggtcagc caacatggac gtgctcatcg tcctggccac aagcattgct    2220
tatgtttatt ctctggtcat cctggtggtt gctgtggctg agaaggcgga gaggagccct    2280
gtgacattct tcgacacgcc ccccatgctc tttgtgttca ttgccctggg ccggtggctg    2340
gaacacttgg caaagagcaa aacctcagaa gccctggcta aactcatgtc tctccaagcc    2400
acagaagcca ccgttgtgac ccttggtgag gacaatttaa tcatcaggga ggagcaagtc    2460
cccatggagc tggtgcagcg gggcgatatc gtcaaggtgg tccctggggg aaagtttcca    2520
gtggatggga aagtcctgga aggcaatacc atggctgatg agtccctcat cacaggagaa    2580
gccatgccag tcactaagaa acccggaagc actgtaattg cggggtctat aaatgcacat    2640
ggctctgtgc tcattaaagc tacccacgtg ggcaatgaca ccactttggc tcagattgtg    2700
aaactggtgg aagaggctca gatgtcaaag gcacccattc agcagctggc tgaccggttt    2760
agtggatatt ttgtcccatt tatcatcatc atgtcaactt tgacgttggt ggtatggatt    2820
gtaatcggtt ttatcgattt tggtgttgtt cagagatact tcctaaccc caacaagcac    2880 atctcccaga cagaggtgat catccggttt gctttccaga cgtccatcac ggtgctgtgc    2940
attgcctgcc cctgctccct ggggctggcc acgcccacgg ctgtcatggt gggcaccggg    3000
gtggccgcgc agaacggcat cctcatcaag ggaggcaagc ccctggagat ggcgcacaag    3060
ataaagactg tgatgtttga caagactggc accattaccc atggcgtccc cagggtcatg    3120
cgggtgctcc tgctggggga tgtggccaca ctgcccctca ggaaggttct ggctgtggtg    3180
gggactgcgg aggccagcag tgaacacccc ttgggcgtgg cagtcaccaa atactgtaaa    3240
gaggaacttg gaacagagac cttgggatac tgcacggact ccaggcagt gccaggctgt    3300 ggaattgggt gcaaagtcag caacgtggaa ggcatcctgg cccacagtga gcgcccttg    3360 agtgcaccgg ccagtcacct gaatgaggct ggcagccttc ccgcagaaaa agatgcagtc    3420
ccccagacct tctctgtgct gattggaaac cgtgagtggc tgaggcgcaa cggtttaacc    3480
atttctagcg atgtcagtga cgctatgaca gaccacgaga tgaaaggaca gacagccatc    3540
ctggtggcta ttgacggtgt gctctgtggg atgatcgcaa tcgcagacgc tgtcaagcag    3600
gaggctgccc tggctgtgca cacgctgcag agcatgggtg tggacgtggt tctgatcacg    3660
ggggacaacc ggaagacagc cagagctatt gccacccagg ttggcatcaa caaagtcttt    3720
gcagaggtgc tgccttcgca caaggtggcc aaggtccagg agctccagaa taaagggaag    3780
```

| | |
|---|---|
| aaagtcgcca tggtggggga tggggtcaat gactccccgg ccttggccca ggcagacatg | 3840 |
| ggtgtggcca ttggcaccgg cacggatgtg gccatcgagg cagccgacgt cgtccttatc | 3900 |
| agaaatgatt tgctggatgt ggtggctagc attcaccttt ccaagaggac tgtccgaagg | 3960 |
| atacgcatca acctggtcct ggcactgatt tataacctgg ttgggatacc cattgcagca | 4020 |
| ggtgtcttca tgcccatcgg cattgtgctg cagccctgga tgggctcagc ggccatggca | 4080 |
| gcctcctctg tgtctgtggt gctctcatcc ctgcagctca agtgctataa gaagcctgac | 4140 |
| ctggagaggt atgaggcaca ggcgcatggc cacatgaagc ccctgacggc atcccaggtc | 4200 |
| agtgtgcaca taggcatgga tgacaggtgg cgggactccc ccaggccac accatgggac | 4260 |
| caggtcagct atgtcagcca ggtgtcgctg tcctccctga cgtccgacaa gccatctcgg | 4320 |
| cacagcgctg cagcagacga tgatggggac aagtggtctc tgctcctgaa tggcagggat | 4380 |
| gaggagcagt acatc | 4395 |

```
<210> SEQ ID NO 4
<211> LENGTH: 34
<212> TYPE: DNA
<213> ORGANISM: Artificial Sequence
<220> FEATURE:
<223> OTHER INFORMATION: constructed sequence

<400> SEQUENCE: 4
```

| | |
|---|---|
| tgtttgctgc ttgcaatgtt tgcccatttt aggg | 34 |

```
<210> SEQ ID NO 5
<211> LENGTH: 100
<212> TYPE: DNA
<213> ORGANISM: Artificial Sequence
<220> FEATURE:
<223> OTHER INFORMATION: constructed sequence

<400> SEQUENCE: 5
```

| | |
|---|---|
| ctacctcgtg atcgcccggc ccctgttcaa acatgtccta atactctgtc tctgcaaggg | 60 |
| tcatcagtag ttttccatct tactcaacat cctcccagtg | 100 |

```
<210> SEQ ID NO 6
<211> LENGTH: 42
<212> TYPE: DNA
<213> ORGANISM: Artificial Sequence
<220> FEATURE:
<223> OTHER INFORMATION: constructed sequence

<400> SEQUENCE: 6
```

| | |
|---|---|
| aggttaattt ttaaactgtt tgctctggtt aataatctca gg | 42 |

```
<210> SEQ ID NO 7
<211> LENGTH: 322
<212> TYPE: DNA
<213> ORGANISM: Artificial Sequence
<220> FEATURE:
<223> OTHER INFORMATION: constructed sequence

<400> SEQUENCE: 7
```

| | |
|---|---|
| aaggctcaga ggcacacagg agtttctggg ctcaccctgc cccttccaa cccctcagtt | 60 |
| cccatcctcc agcagctgtt tgtgtgctgc ctctgaagtc cacactgaac aaacttcagc | 120 |
| ctactcatgt ccctaaaatg ggcaaacatt gcaagcagca aacagcaaac acacagccct | 180 |
| ccctgcctgc tgaccttgga gctggggcag aggtcagaga cctctctggg cccatgccac | 240 |
| ctccaacatc cactcgaccc cttggaattt cggtggagag gagcagaggt tgtcctggcg | 300 |

```
tggtttaggt agtgtgagag gg                                             322

<210> SEQ ID NO 8
<211> LENGTH: 178
<212> TYPE: DNA
<213> ORGANISM: Artificial Sequence
<220> FEATURE:
<223> OTHER INFORMATION: constructed sequence

<400> SEQUENCE: 8
actcaaagtt caaaccttat cattttttgc tttgttcctc ttggccttgg ttttgtacat    60
cagctttgaa ataccatcc cagggttaat gctggggtta atttataact aagagtgctc    120
tagttttgca atacaggaca tgctataaaa atggaaagat gttgctttct gagagaca     178

<210> SEQ ID NO 9
<211> LENGTH: 477
<212> TYPE: DNA
<213> ORGANISM: Artificial Sequence
<220> FEATURE:
<223> OTHER INFORMATION: constructed sequence

<400> SEQUENCE: 9
agggctggaa gctacctttg acatcatttc ctctgcgaat gcatgtataa tttctacaga    60
acctattaga aaggatcacc cagcctctgc ttttgtacaa ctttccctta aaaaactgcc   120
aattccactg ctgtttggcc caatagtgag aactttttcc tgctgcctct tggtgctttt   180
gcctatggcc cctattctgc ctgctgaaga cactcttgcc agcatggact aaacccctc    240 cagctctgac aatcctcttt ctcttttgtt ttacatgaag ggtctggcag ccaaagcaat   300
cactcaaagt tcaaaccttg tcattttttg ctttgttcct cttggccttg gttttgtaca   360
tcagctttga aaataccatc ccagggttaa tgctggggtt aatttataac taagagtgct   420
ctagttttgc aatacaggac atgctataaa aatggaaaga tgttgctttc tgagaga      477

<210> SEQ ID NO 10
<211> LENGTH: 218
<212> TYPE: DNA
<213> ORGANISM: Artificial Sequence
<220> FEATURE:
<223> OTHER INFORMATION: constructed sequence

<400> SEQUENCE: 10
tggacacagg acgctgtggt ttctgagcca gggggcgact cagatcccag ccagtggact    60
tagcccctgt ttgctcctcc gataactggg gtgaccttgg ttaatattca ccagcagcct   120
cccccgttgc ccctctggat ccactgctta aatacggacg aggacagggc cctgtctcct   180
cagcttcagg caccaccact gacctgggac agtgaata                           218

<210> SEQ ID NO 11
<211> LENGTH: 190
<212> TYPE: DNA
<213> ORGANISM: Artificial Sequence
<220> FEATURE:
<223> OTHER INFORMATION: constructed sequence

<400> SEQUENCE: 11
atttcataga acgaatgttc cgatgctcta atctctctag acaaggttca tatttgtatg    60
ggttacttat tctctctttg ttgactaagt caataatcag aatcagcagg tttgcagtca   120
gattggcagg gataagcagc ctagctcagg agaagtgagt ataaaagccc caggctggga   180
```

<210> SEQ ID NO 12
<211> LENGTH: 215
<212> TYPE: DNA
<213> ORGANISM: Artificial Sequence
<220> FEATURE:
<223> OTHER INFORMATION: constructed sequence

<400> SEQUENCE: 12

```
gcctcgactg tgccttctag ttgccagcca tctgttgttt gcccctcccc cgtgccttcc      60
ttgaccctgg aaggtgccac tcccactgtc ctttcctaat aaaatgagga aattgcatcg     120
cattgtctga gtaggtgtca ttctattctg ggggtgggg tggggcagga cagcaagggg      180
gaggattggg aagacaatag caggcatgct gggga                                215
```

<210> SEQ ID NO 13
<211> LENGTH: 75
<212> TYPE: DNA
<213> ORGANISM: Artificial Sequence
<220> FEATURE:
<223> OTHER INFORMATION: constructed sequence

<400> SEQUENCE: 13

```
aataaagtct gagtgggcgg cagcctgtgt gtgcctgggt tctctctgtc ccggaatgtg      60
caaacaatgg aggtg                                                       75
```

<210> SEQ ID NO 14
<211> LENGTH: 168
<212> TYPE: DNA
<213> ORGANISM: Artificial Sequence
<220> FEATURE:
<223> OTHER INFORMATION: constructed sequence

<400> SEQUENCE: 14

```
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact     120
aggggttcct tgtagttaat gattaacccg ccatgctact tatctacg                  168
```

<210> SEQ ID NO 15
<211> LENGTH: 168
<212> TYPE: DNA
<213> ORGANISM: Artificial Sequence
<220> FEATURE:
<223> OTHER INFORMATION: constructed sequence

<400> SEQUENCE: 15

```
cgtagataag tagcatggcg ggttaatcat taactacaag gaaccccta gtgatggagtt      60
ggccactccc tctctgcgcg ctcgctcgct cactgaggcc gggcgaccaa aggtcgcccg     120
acgcccgggc tttgcccggg cggcctcagt gagcgagcga gcgcgcag                  168
```

<210> SEQ ID NO 16
<211> LENGTH: 738
<212> TYPE: PRT
<213> ORGANISM: adeno-associated virus 8

<400> SEQUENCE: 16

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

```
Lys Ala Asn Gln Gln Lys Gln Asp Asp Gly Arg Gly Leu Val Leu Pro
         35                  40                  45

Gly Tyr Lys Tyr Leu Gly Pro Phe Asn Gly Leu Asp Lys Gly Glu Pro
 50                  55                  60

Val Asn Ala Ala Asp Ala Ala Leu Glu His Asp Lys Ala Tyr Asp
 65              70                  75                  80

Gln Gln Leu Gln Ala Gly Asp Asn Pro Tyr Leu Arg Tyr Asn His Ala
             85                  90                  95

Asp Ala Glu Phe Gln Glu Arg Leu Gln Glu Asp Thr Ser Phe Gly Gly
             100                 105                 110

Asn Leu Gly Arg Ala Val Phe Gln Ala Lys Lys Arg Val Leu Glu Pro
             115                 120                 125

Leu Gly Leu Val Glu Glu Gly Ala Lys Thr Ala Pro Gly Lys Lys Arg
 130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
             165                 170                 175

Thr Gly Asp Ser Glu Ser Val Pro Asp Pro Gln Pro Leu Gly Glu Pro
             180                 185                 190

Pro Ala Ala Pro Ser Gly Val Gly Pro Asn Thr Met Ala Ala Gly Gly
             195                 200                 205

Gly Ala Pro Met Ala Asp Asn Asn Glu Gly Ala Asp Gly Val Gly Ser
 210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
             245                 250                 255

Leu Tyr Lys Gln Ile Ser Asn Gly Thr Ser Gly Gly Ala Thr Asn Asp
             260                 265                 270

Asn Thr Tyr Phe Gly Tyr Ser Thr Pro Trp Gly Tyr Phe Asp Phe Asn
             275                 280                 285

Arg Phe His Cys His Phe Ser Pro Arg Asp Trp Gln Arg Leu Ile Asn
             290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
             325                 330                 335

Asn Asn Leu Thr Ser Thr Ile Gln Val Phe Thr Asp Ser Glu Tyr Gln
             340                 345                 350

Leu Pro Tyr Val Leu Gly Ser Ala His Gln Gly Cys Leu Pro Pro Phe
             355                 360                 365

Pro Ala Asp Val Phe Met Ile Pro Gln Tyr Gly Tyr Leu Thr Leu Asn
370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
             405                 410                 415

Thr Phe Glu Asp Val Pro Phe His Ser Ser Tyr Ala His Ser Gln Ser
             420                 425                 430

Leu Asp Arg Leu Met Asn Pro Leu Ile Asp Gln Tyr Leu Tyr Tyr Leu
             435                 440                 445
```

Ser Arg Thr Gln Thr Thr Gly Gly Thr Ala Asn Thr Gln Thr Leu Gly
450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
            485                 490                 495

Gln Asn Asn Asn Ser Asn Phe Ala Trp Thr Ala Gly Thr Lys Tyr His
            500                 505                 510

Leu Asn Gly Arg Asn Ser Leu Ala Asn Pro Gly Ile Ala Met Ala Thr
            515                 520                 525

His Lys Asp Asp Glu Glu Arg Phe Phe Pro Ser Asn Gly Ile Leu Ile
530                 535                 540

Phe Gly Lys Gln Asn Ala Ala Arg Asp Asn Ala Asp Tyr Ser Asp Val
545                 550                 555                 560

Met Leu Thr Ser Glu Glu Ile Lys Thr Thr Asn Pro Val Ala Thr
                565                 570                 575

Glu Glu Tyr Gly Ile Val Ala Asp Asn Leu Gln Gln Asn Thr Ala
            580                 585                 590

Pro Gln Ile Gly Thr Val Asn Ser Gln Gly Ala Leu Pro Gly Met Val
        595                 600                 605

Trp Gln Asn Arg Asp Val Tyr Leu Gln Gly Pro Ile Trp Ala Lys Ile
610                 615                 620

Pro His Thr Asp Gly Asn Phe His Pro Ser Pro Leu Met Gly Gly Phe
625                 630                 635                 640

Gly Leu Lys His Pro Pro Gln Ile Leu Ile Lys Asn Thr Pro Val
                645                 650                 655

Pro Ala Asp Pro Pro Thr Thr Phe Asn Gln Ser Lys Leu Asn Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
        690                 695                 700

Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Tyr Leu Thr Arg
                725                 730                 735

Asn Leu

<210> SEQ ID NO 17
<211> LENGTH: 3966
<212> TYPE: DNA
<213> ORGANISM: Artificial Sequence
<220> FEATURE:
<223> OTHER INFORMATION: constructed sequence

<400> SEQUENCE: 17

```
atgcccgagc aggaaagaca gatcaccgcc agagagggcg ccagccggaa gatcctgagc      60
aagctgagcc tgcccaccag agcctgggag cccgccatga agaagtcctt cgccttcgac     120
aacgtgggct acgagggcgg cctggacgga ctgggaccat cttctcaggt ggccacaagc     180
accgtgcgcg aggccgccat caagagcaag gtggcccctc tgtctctggg ccccatcgac     240
atcgagagac tgcagagcac caaccccaag cggcctctga gcagcgccaa ccagaacttc     300
aacaacagcg agacactggg ccaccagggc agccacgtcg tgacactgca gctgcggatc     360
gacggaatgc actgcaagag ctgtgtgctg aacatcgagg aaaacatcgg ccagctgctg     420
```

```
ggagtgcaga gcatccaggt gtcactggaa acaagaccg cccaggtgaa gtacgacccc    480
agctgcacaa gccccgtggc cctgcagaga gccattgaag ctctgccccc tggcaacttc    540
aaagtgtccc tgcctgacgg agccgagggc tccggaacag atcacagaag cagcagcagc    600
cacagccctg gcagcccccc tagaaatcag gtgcagggca cctgtagcac caccctgatc    660
gccattgccg gcatgacatg cgccagctgc gtgcactcta ttgagggcat gatctcccag    720
ctggaaggcg tgcagcagat cagtgtgtct ctggccgagg gcaccgccac agtgctgtac    780
aaccctagcg tgatcagccc cgaagaactg agagccgcca ttgaggacat gggattcgaa    840
gccagcgtgg tgtccgagag ctgctccacc aaccctctgg gcaatcacag cgccggcaac    900
agcatggtgc agaccaccga cggcaccccc accagcgtgc aggaagtggc cccacataca    960
ggcagactgc cgccaatca cgcccccgat atcctggcca agagccccca gagtacaaga   1020
gccgtggccc cccagaagtg cttcctgcag atcaagggca tgacttgtgc ctcttgtgtg   1080
tccaatatcg agcggaacct gcagaaagag gccggcgtgc tgtctgtgct ggtggctctg   1140
atggccggca aggccgagat caaatacgac cccgaagtga ttcagcccct ggaaatcgcc   1200
cagtttatcc aggacctggg cttttgaagcc gccgtgatgg aagattacgc cggctccgac   1260
ggcaacatcg agctgaccat caccggaatg acctgcgcct cctgtgtgca acacattgag   1320
tccaagctga cccggaccaa cggcatcacc tacgcctctg tggctctggc cacctccaag   1380
gccctcgtga gttcgatcc cgagatcatc ggccccaggg acatcatcaa gatcatcgaa   1440
gagatcggct ccacgccag cctggcccag aggaaccta acgccacca cctggaccac   1500 aagatggaaa tcaagcagtg gaagaaaagc ttcctgtgca gcctggtgtt cggcatcccc   1560
gtgatggccc tgatgatcta catgctgatc cccagcaacg agcccacca gtccatggtg   1620 ctggatcaca acatcatccc cggcctgtct atcctgaacc tgatcttctt catcctgtgc   1680
accttcgtgc agctgctggg cggctggtac ttctacgtgc aggcctacaa gtccctgcgg   1740
cacagatccg ccaacatgga cgtgctgatc gtgctggcca catctatcgc ctacgtgtac   1800
tccctcgtga tcctggtggt ggccgtggcc gagaaagccg agagaagccc tgtgaccttc   1860
ttcgacaccc cccctatgct gttcgtgttt atcgccctgg gccggtggct ggaacacctg   1920
gccaaaagca agaccagcga ggccctggct aagctgatga gtctgcaggc caccgaggcc   1980
acagtcgtga ccctgggcga ggacaacctg atcatccgcg aggaacaggt gccaatggaa   2040
ctggtgcagc ggggcgacat cgtgaaggtg gtgcctggcg gcaagttccc cgtggacgga   2100
aaagtgctga agggaataca catggccgac gagagcctga tcacaggcga ggccatgccc   2160
gtgaccaaga aacctggcag cacagtgatc gccggcagca tcaatgccca cggcagcgtg   2220
ctgattaagg ccacacacgt gggcaacgat accaccctgg ctcagattgt gaagctggtg   2280
gaagaggccc agatgagcaa ggcccccatt cagcagctgg ctgaccggtt cagcggctac   2340
ttcgtgccct ttatcatcat catgagcacc ctgactggt cgtgtggat cgtgatcggc   2400 tttatcgact cggagtggt gcagagatac ttccccaacc ctaacaagca catcagccag   2460
acagaagtga tcatcagatt cgcctttcag accagcatca ccgtgctgtg tatcgcctgc   2520
ccctgtagcc tgggactggc cacacctacc gctgtgatgg tgggaacagg cgtggccgct   2580
cagaacggca tcctgatcaa ggggggcaag cctctggaaa tggctcacaa gatcaagacc   2640
gtgatgttcg acaagaccgg caccatcacc acggcgtgc ccagagtgat gagagtgctg   2700 ctgctgggg atgtggccac cctgcctctg agaaaggtgc tggctgtcgt gggcacagcc   2760
```

```
gaggctagct ctgaacaccc actgggagtg gccgtgacaa agtactgcaa agaggaactg    2820
ggcaccgaaa ccctgggcta ctgcaccgac tttcaggccg tgcctggctg tggcatcggc    2880
tgcaaggtgt ccaacgtgga aggcatcctg gcccacagcg agaggccact gtctgcccct    2940
gccagccacc tgaacgaggc cggatctctg cccgccgaaa aggacgctgt gccccagacc    3000
ttctctgtgc tgattggcaa cagagagtgg ctgcggcgga acggcctgac catctcctcc    3060
gatgtgtccg acgccatgac cgaccacgag atgaagggcc agaccgccat tctggtggcc    3120
attgacgggg tgctgtgcgg catgatcgca atcgccgatg ccgtgaaaca ggaagcagca    3180
ctggccgtgc acaccctgca gtctatggga gtggatgtgg tgctgatcac cggcgacaac    3240
agaaagaccg ccagggccat tgccacccag gtgggcatca acaaggtgtt cgccgaggtg    3300
ctgcccagcc acaaagtggc caaggtgcag gaactgcaga acaaaggcaa aaaggtggcc    3360
atggtgggag atggcgtgaa cgactctcct gctctggccc aggcagatat gggcgtggcc    3420
atcggcacag gcaccgacgt ggcaattgag gctgctgacg tggtgctgat tcggaacgac    3480
ctgctggacg tggtggcctc catccacctg tccaagagaa ccgtgcggcg gatcagaatc    3540
aacctggtgc tggcactgat ctataacctc gtgggcatcc ctatcgccgc tggcgtgttc    3600
atgcctatcg gaatcgtgct gcagccctgg atgggtctg ccgccatggc tgcaagctcc    3660
gtgtctgtgg tgctgtccag cctgcagctg aagtgctaca agaagcccga cctggaaaga    3720
tacgaggccc aggcccacgg acacatgaag cctctgacag cctcccaggt gtccgtgcac    3780
atcggcatgg acgacagatg gcgggacagc cctagagcca ccccttggga tcaggtgtca    3840
tacgtgtcac aggtgtccct gagcagcctg accagcgaca agcccagcag acatagcgcc    3900
gctgccgacg acgatgggga caagtggtcc ctgctgctga acggccggga tgaggaacag    3960
tacatc                                                              3966

<210> SEQ ID NO 18
<211> LENGTH: 3360
<212> TYPE: DNA
<213> ORGANISM: Artificial Sequence
<220> FEATURE:
<223> OTHER INFORMATION: constructed sequence

<400> SEQUENCE: 18
atgcccgagc aggaaagaca gatcaccgcc agagagggcg ccagccggaa gatcctgagc      60
aagctgagcc tgcccaccag agcctgggag cccgccatga agaagtcctt cgccttcgac     120
aacgtgggct acgagggcgg cctggacgga ctgggaccat cttctcaggt ggccacaagc     180
accgtgcgca gccccgaaga actgagagcc gccattgagg acatgggatt cgaagccagc     240
gtggtgtccg agagctgctc caccaaccct ctgggcaatc acagcgccgg caacagcatg     300
gtgcagacca ccgacggcac ccccaccagc gtgcaggaag tggccccaca tacaggcaga     360
ctgcccgcca tcacgcccc cgatatcctg gccaagagcc cccagagtac aagagccgtg     420 gcccccaga agtgcttcct gcagatcaag ggcatgactt gtgcctcttg tgtgtccaat     480
atcgagcgga acctgcagaa agaggccggc gtgctgtctg tgctggtggc tctgatggcc     540
ggcaaggcca agatcaaata cgaccccgaa gtgattcagc ccctggaaat cgcccagttt     600
atccaggacc tgggctttga agccgccgtg atggaagatt acgccggctc cgacggcaac     660
atcgagctga ccatcaccgg aatgacctgc gcctcctgtg tgcacaacat tgagtccaag     720
ctgacccgga ccaacggcat cacctacgcc tctgtggctc tggccacctc aaggccctc     780 gtgaagttcg atcccgagat catcggcccc aggacatca tcaagatcat cgaagagatc     840
```

```
ggcttccacg ccagcctggc ccagaggaac cctaacgccc accacctgga ccacaagatg      900
gaaatcaagc agtggaagaa aagcttcctg tgcagcctgg tgttcggcat ccccgtgatg      960
gccctgatga tctacatgct gatccccagc aacgagcccc accagtccat ggtgctggat     1020
cacaacatca tccccggcct gtctatcctg aacctgatct tcttcatcct gtgcaccttc     1080
gtgcagctgc tgggcggctg gtacttctac gtgcaggcct acaagtccct gcggcacaga     1140
tccgccaaca tggacgtgct gatcgtgctg gccacatcta tcgcctacgt gtactccctc     1200
gtgatcctgg tggtggccgt ggccgagaaa gccgagagaa gccctgtgac cttcttcgac     1260 accccccta tgctgttcgt gtttatcgcc ctgggccggt ggctggaaca cctggccaaa     1320
agcaagacca gcgaggccct ggctaagctg atgagtctgc aggccaccga ggccacagtc     1380
gtgaccctgg gcgaggacaa cctgatcatc cgcgaggaac aggtgccaat ggaactggtg     1440
cagcggggcg acatcgtgaa ggtggtgcct ggcggcaagt tccccgtgga cggaaaagtg     1500
ctggaaggga ataccatggc cgacgagagc ctgatcacag cgaggccat gcccgtgacc      1560 aagaaacctg gcagcacagt gatcgccggc agcatcaatg cccacggcag cgtgctgatt     1620
aaggccacac acgtgggcaa cgataccacc ctggctcaga ttgtgaagct ggtggaagag     1680
gcccagatga gcaaggcccc cattcagcag ctggctgacc ggttcagcgg ctacttcgtg     1740 cccttatca tcatcatgag caccctgaca ctggtcgtgt ggatcgtgat cggctttatc      1800
gacttcggag tggtgcagag atacttcccc aaccctaaca agcacatcag ccagacagaa     1860
gtgatcatca gattcgcctt tcagaccagc atcaccgtgc tgtgtatcgc ctgcccctgt     1920
agcctgggac tggccacacc taccgctgtg atggtgggaa caggcgtggc cgctcagaac     1980
ggcatcctga tcaaggggg caagcctctg gaaatggctc acaagatcaa gaccgtgatg     2040
ttcgacaaga ccggcaccat cacccacggc gtgcccagag tgatgagagt gctgctgctg     2100
ggggatgtgg ccaccctgcc tctgagaaag gtgctggctg tcgtgggcac agccgaggct     2160
agctctgaac acccactggg agtggccgtg acaaagtact gcaaagagga actgggcacc     2220
gaaaccctgg gctactgcac cgactttcag gccgtgcctg gctgtggcat cggctgcaag     2280
gtgtccaacg tggaaggcat cctggcccac agcgagaggc cactgtctgc ccctgccagc     2340
cacctgaacg aggccggatc tctgcccgcc gaaaaggacg ctgtgcccca gaccttctct     2400
gtgctgattg caacagaga gtggctgcgg cggaacggcc tgaccatctc ctccgatgtg     2460
tccgacgcca tgaccgacca cgagatgaag ggccagaccg ccattctggt ggccattgac     2520
ggggtgctgt gcggcatgat cgcaatcgcc gatgccgtga acaggaagc agcactggcc     2580 gtgcacaccc tgcagtctat gggagtggat gtggtgctga tcaccggcga caacagaaag     2640
accgccaggc ccattgccac ccaggtgggc atcaacaagg tgttcgccga ggtgctgccc     2700
agccacaaag tggccaaggt gcaggaactg cagaacaaag gcaaaaaggt ggccatggtg     2760
ggagatggcg tgaacgactc tcctgctctg gccaggcag atatgggcgt ggccatcggc     2820
acaggcaccg acgtggcaat tgaggctgct gacgtggtgc tgattcggaa cgacctgctg     2880
gacgtggtgg cctccatcca cctgtccaag agaaccgtgc ggcggatcag aatcaacctg     2940
gtgctggcac tgatctataa cctcgtgggc atccctatcg ccgctggcgt gttcatgcct     3000
atcggaatcg tgctgcagcc ctggatgggc tctgccgcca tggctgcaag ctccgtgtct     3060
gtggtgctgt ccagcctgca gctgaagtgc tacaagaagc ccgacctgga aagatacgag     3120
gcccaggccc acggacacat gaagcctctg acagcctccc aggtgtccgt gcacatcggc     3180
```

```
atggacgaca gatggcggga cagccctaga gccacccctt gggatcaggt gtcatacgtg      3240
tcacaggtgt ccctgagcag cctgaccagc gacaagccca gcagacatag cgccgctgcc      3300
gacgacgatg gggacaagtg gtccctgctg ctgaacggcc gggatgagga acagtacatc      3360

<210> SEQ ID NO 19
<211> LENGTH: 2967
<212> TYPE: DNA
<213> ORGANISM: Artificial Sequence
<220> FEATURE:
<223> OTHER INFORMATION: constructed sequence

<400> SEQUENCE: 19
atgcccgagc aggaaagaca gatcaccgcc agagagggcg ccagccggaa gatcctgagc       60
aagctgagcc tgcccaccag agcctgggag cccgccatga gaagtccctt cgccttcgac      120
aacgtgggct acgagggcgg cctggacgga ctgggaccat cttctcaggt ggccacaagc      180
accgtgcgcc tggaaatcgc ccagtttatc caggacctgg gctttgaagc cgccgtgatg      240
gaagattacg ccggctccga cggcaacatc gagctgacca tcaccggaat gacctgcgcc      300
tcctgtgtgc acaacattga gtccaagctg acccggacca acggcatcac ctacgcctct      360
gtggctctgg ccacctccaa ggccctcgtg aagttcgatc ccgagatcat cggccccagg      420
gacatcatca agatcatcga agagatcggc ttccacgcca gcctggccca gaggaaccct      480
aacgcccacc acctggacca agatgaggaa atcaagcagt ggaagaaaag cttcctgtgc      540
agcctggtgt cggcatcccc gtgatggcc ctgatgatct acatgctgat ccccagcaac      600
gagccccacc agtccatggt gctggatcac aacatcatcc ccggcctgtc tatcctgaac      660
ctgatcttct tcatcctgtg caccttcgtg cagctgctgg gcggctggta cttctacgtg      720
caggcctaca gtccctgcg gcacagatcc gccaacatgg acgtgctgat cgtgctggcc      780
acatctatcg cctacgtgta ctccctcgtg atcctggtgg tggccgtggc cgagaaagcc      840
gagagaagcc ctgtgacctt cttcgacacc ccctatgc tgttcgtgtt tatcgccctg      900
ggccggtggc tggaacacct ggccaaaagc aagaccagcg aggccctggc taagctgatg      960
agtctgcagg ccaccgaggc cacagtcgtg acctgggcg aggacaacct gatcatccgc      1020
gaggaacagg tgccaatgga actggtgcag cggggcgaca tcgtgaaggt ggtgcctggc      1080
ggcaagttcc ccgtggacgg aaaagtgctg gaagggaata ccatggccga cgagagcctg      1140
atcacaggcg aggccatgcc cgtgaccaag aaacctggca gcacagtgat cgccggcagc      1200
atcaatgccc acggcagcgt gctgattaag gccacacacg tgggcaacga taccaccctg      1260
gctcagattg tgaagctggt ggaagaggcc cagatgagca aggcccccat tcagcagctg      1320
gctgaccggt tcagcggcta cttcgtgccc tttatcatca tcatgagcac cctgacactg      1380
gtcgtgtgga tcgtgatcgg ctttatcgac ttcggagtgg tgcagagata cttccccaac      1440
cctaacaagc acatcagcca gacagaagtg atcatcagat cgcctttca gaccagcatc      1500 accgtgctgt gtatcgcctg ccctgtagc ctggactgg ccacacctac cgctgtgatg      1560
gtgggaacag gcgtggccgc tcagaacggc atcctgatca agggggcaa gcctctggaa      1620 atggctcaca gatcaagac cgtgatgttc gacaagaccg gcaccatcac ccacggcgtg      1680
cccagagtga tgagagtgct gctgctgggg gatgtggcca ccctgcctct gagaaaggtg      1740
ctggctgtcg tgggcacagc cgaggctagc tctgaacacc cactgggagt ggccgtgaca      1800
aagtactgca aagaggaact gggcaccgaa acctgggct actgcaccga ctttcaggcc      1860
gtgcctggct gtggcatcgg ctgcaaggtg tccaacgtgg aaggcatcct ggcccacagc      1920
```

```
gagaggccac tgtctgcccc tgccagccac ctgaacgagg ccggatctct gcccgccgaa   1980
aaggacgctg tgccccagac cttctctgtg ctgattggca acagagagtg gctgcggcgg   2040
aacggcctga ccatctcctc cgatgtgtcc gacgccatga ccgaccacga gatgaagggc   2100
cagaccgcca ttctggtggc cattgacggg gtgctgtgcg gcatgatcgc aatcgccgat   2160
gccgtgaaac aggaagcagc actggccgtg cacaccctgc agtctatggg agtggatgtg   2220
gtgctgatca ccggcgacaa cagaaagacc gccagggcca ttgccaccca ggtgggcatc   2280
aacaaggtgt tcgccgaggt gctgcccagc cacaaagtgg ccaaggtgca ggaactgcag   2340
aacaaaggca aaaaggtggc catggtggga gatggcgtga acgactctcc tgctctggcc   2400
caggcagata tgggcgtggc catcggcaca ggcaccgacg tgcaattgga ggctgctgac   2460
gtggtgctga ttcggaacga cctgctggac gtggtggcct ccatccacct gtccaagaga   2520
accgtgcggc ggatcagaat caacctggtg ctggcactga tctataacct cgtgggcatc   2580
cctatcgccg ctggcgtgtt catgcctatc ggaatcgtgc tgcagccctg gatgggctct   2640
gccgccatgg ctgcaagctc cgtgtctgtg gtgctgtcca gcctgcagct gaagtgctac   2700
aagaagcccg acctggaaag atacgaggcc caggcccacg acacatgaa gcctctgaca    2760 gcctcccagg tgtccgtgca catcggcatg gacgacagat ggcgggacag ccctagagcc   2820 acccctttggg atcaggtgtc atacgtgtca caggtgtccc tgagcagcct gaccagcgac   2880
aagcccagca gacatagcgc cgctgccgac gacgatgggg acaagtggtc cctgctgctg   2940
aacggccggg atgaggaaca gtacatc                                      2967

<210> SEQ ID NO 20
<211> LENGTH: 4284
<212> TYPE: DNA
<213> ORGANISM: Artificial Sequence
<220> FEATURE:
<223> OTHER INFORMATION: constructed sequence

<400> SEQUENCE: 20
atgcccgagc aggaaagaca gatcaccgcc agagagggcg ccagccggaa gatcctgagc     60
aagctgagcc tgcccaccag agcctgggag cccgccatga agaagtcctt cgccttcgac    120
aacgtgggct acgagggcgg cctggacgga ctgggaccat cttctcaggt ggccacaagc    180
accgtgcgca aatacgtgcc ctctgtcgtg tgcctgcagc aggtgtgcca ccagatcggc    240
gacatgggct tcgaggcctc tatcgccgag ggaaaggccg cctcttggcc ctctagaagc    300
ctgcctgctc aggaagccgt cgtgaagctg cgggtggaag gatgacctg tcagtcctgc    360 gtgtccagca tcgagggcaa agtgcggaag ctgcagggcg tggtgcgcgt gaaagtgtct    420
ctgagcaacc aggaagctgt gatcacctac cagccctacc tgatccagcc cgaggacctg    480
agggaccacg tgaacgatat gggatttgag gccgccatca agagcaaggt ggcccctctg    540
tctctgggcc ccatcgacat cgagagactg cagagcacca accccaagcg gcctctgagc    600
agcgccaacc agaacttcaa caacagcgag acactgggcc accagggcag ccacgtcgtg    660
acactgcagc tgcggatcga cggaatgcac tgcaagagct gtgtgctgaa catcgaggaa    720
aacatcggcc agctgctggg agtgcagagc atccaggtgt cactggaaaa caagaccgcc    780
caggtgaagt acgaccccag ctgcacaagc cccgtggccc tgcagagagc cattgaagct    840
ctgccccctg gcaacttcaa agtgtccctg cctgacggag ccgagggctc cggaacagat    900
cacagaagca gcagcagcca cagccctggc agccccccta gaaatcaggt gcagggcacc    960
```

```
tgtagcacca ccctgatcgc cattgccggc atgacatgcg ccagctgcgt gcactctatt    1020
gagggcatga tctcccagct ggaaggcgtg cagcagatca gtgtgtctct ggccgagggc    1080
accgccacag tgctgtacaa ccctagcgtg atcagccccg aagaactgag agccgccatt    1140
gaggacatgg gattcgaagc cagcgtggtg tccgagagct gctccaccaa ccctctgggc    1200
aatcacagcg ccggcaacag catggtgcag accaccgacg gcaccccac cagcgtgcag     1260 gaagtggccc cacatacagg cagactgccc gccaatcacg cccccgatat cctggccaag    1320
agcccccaga gtacaagagc cgtggccccc cagaagtgct tcctgcagat caagggcatg    1380
acttgtgcct cttgtgtgtc caatatcgag cggaacctgc agaaagaggc cggcgtgctg    1440
tctgtgctgg tggctctgat ggccggcaag gccgagatca aatacgaccc cgaagtgatt    1500
cagcccctgg aaatcgccca gtttatccag gacctgggct tgaagccgcg cgtgatggaa    1560
gattacgccg gctccgacgg caacatcgag ctgaccatca ccggaatgac ctgcgcctcc    1620
tgtgtgcaca acattgagtc caagctgacc cggaccaacg gcatcaccta cgcctctgtg    1680
gctctggcca cctccaaggc cctcgtgaag ttcgatcccg agatcatcgg ccccagggac    1740
atcatcaaga tcatcgaaga gatcggcttc cacgccagcc tggcccagag gaaccctaac    1800
gcccaccacc tggaccacaa gatggaaatc aagcagtgga agaaaagctt cctgtgcagc    1860
ctggtgttcg gcatccccgt gatggccctg atgatctaca tgctgatccc cagcaacgag    1920
ccccaccagt ccatggtgct ggatcacaac atcatccccg gcctgtctat cctgaacctg    1980
atcttcttca tcctgtgcac cttcgtgcag ctgctgggcg gctggtactt ctacgtgcag    2040
gcctacaagt ccctgcggca cagatccgcc aacatggacg tgctgatcgt gctggccaca    2100
tctatcgcct acgtgtactc cctcgtgatc ctggtggtgg ccgtggccga aaagccgag    2160 agaagccctg tgaccttctt cgacaccccc cctatgctgt tcgtgtttat cgccctgggc    2220
cggtggctgg aacacctggc caaaagcaag accagcgagg ccctggctaa gctgatgagt    2280
ctgcaggcca ccgaggccac agtcgtgacc ctgggcgagg acaacctgat catccgcgag    2340
gaacaggtgc caatggaact ggtgcagcgg ggcgacatcg tgaaggtggt gcctggcggc    2400
aagttccccg tggacggaaa agtgctggaa gggaatacca tggccgacga gagcctgatc    2460
acaggcgagg ccatgcccgt gaccaagaaa cctggcagca cagtgatcgc cggcagcatc    2520
aatgccacgg cagcgtgct gattaaggcc acacacgtgg gcaacgatac cacccctggct    2580 cagattgtga agctggtgga agaggcccag atgagcaagg cccccattca gcagctggct    2640
gaccggttca gcggctactt cgtgcccttt atcatcatca tgagcaccct gacactggtc    2700
gtgtggatcg tgatcggctt tatcgacttc ggagtggtgc agagatactt ccccaaccct    2760
aacaagcaca tcagccagac agaagtgatc atcagattcg cctttcagac cagcatcacc    2820
gtgctgtgta tcgcctgccc ctgtagcctg ggactggcca cctaccgc tgtgatggtg      2880 ggaacaggcg tggccgctca gaacggcatc ctgatcaagg ggcaagcc tctggaaatg      2940 gctcacaaga tcaagaccgt gatgttcgac aagaccggca ccatcaccca cggcgtgccc    3000
agagtgatga gagtgctgct gctgggggat gtggccaccc tgcctctgag aaaggtgctg    3060
gctgtcgtgg gcagccgga ggctagctct gaacacccac tgggagtggc cgtgacaaag    3120
tactgcaaag aggaactggg caccgaaacc ctgggctact gcaccgactt tcaggccgtg    3180
cctggctgtg gcatcggctg caaggtgtcc aacgtggaag gcatcctggc ccacagcgag    3240
aggccactgt ctgcccctgc cagccaccctg aacgaggccg atctctgcc cgccgaaaag    3300 gacgctgtgc cccagacctt ctctgtgctg attggcaaca gagagtggct gcggcggaac    3360
```

-continued

| | |
|---|---|
| ggcctgacca tctcctccga tgtgtccgac gccatgaccg accacgagat gaagggccag | 3420 |
| accgccattc tggtggccat tgacggggtg ctgtgcggca tgatcgcaat cgccgatgcc | 3480 |
| gtgaaacagg aagcagcact ggccgtgcac accctgcagt ctatgggagt ggatgtggtg | 3540 |
| ctgatcaccg gcgacaacag aaagaccgcc agggccattg ccacccaggt gggcatcaac | 3600 |
| aaggtgttcg ccgaggtgct gcccagccac aaagtggcca aggtgcagga actgcagaac | 3660 |
| aaaggcaaaa aggtggccat ggtgggagat ggcgtgaacg actctcctgc tctggcccag | 3720 |
| gcagatatgg gcgtggccat cggcacaggc accgacgtgg caattgaggc tgctgacgtg | 3780 |
| gtgctgattc ggaacgacct gctggacgtg gtggcctcca tccacctgtc caagagaacc | 3840 |
| gtgcggcgga tcagaatcaa cctggtgctg cactgatct ataacctcgt gggcatccct | 3900 |
| atcgccgctg gcgtgttcat gcctatcgga atcgtgctgc agccctggat gggctctgcc | 3960 |
| gccatggctg caagctccgt gtctgtggtg ctgtccagcc tgcagctgaa gtgctacaag | 4020 |
| aagcccgacc tggaaagata cgaggcccag gcccacggac acatgaagcc tctgacagcc | 4080 |
| tcccaggtgt ccgtgcacat cggcatggac gacagatggc gggacagccc tagagccacc | 4140 |
| ccttgggatc aggtgtcata cgtgtcacag gtgtccctga gcagcctgac cagcgacaag | 4200 |
| cccagcagac atagcgccgc tgccgacgac gatggggaca agtggtccct gctgctgaac | 4260 |
| ggccgggatg aggaacagta catc | 4284 |

<210> SEQ ID NO 21
<211> LENGTH: 4215
<212> TYPE: DNA
<213> ORGANISM: Artificial Sequence
<220> FEATURE:
<223> OTHER INFORMATION: constructed sequence

<400> SEQUENCE: 21

| | |
|---|---|
| atgcccgagc aggaaagaca gatcaccgcc agagagggcg ccagccggaa gatcctgagc | 60 |
| aagctgagcc tgcccaccag agcctgggag cccgccatga agaagtcctt cgccttcgac | 120 |
| aacgtgggct acgagggcgg cctggacgga ctgggaccat cttctcaggt ggccacaagc | 180 |
| accgtgcgca tcctgggcat gacctgccag agctgcgtga agtccatcga ggaccggatc | 240 |
| agcaacctga agggcatcat cagcatgaag gtgtccctgg aacagggcag cgccaccgtg | 300 |
| aaatacgtgc cctctgtcgt gtgcctgcag caggtgtgcc accagatcgg cgacatgggc | 360 |
| ttcgaggcct ctatcgccga gggaaaggcc gcctcttggc cctctagaag cctgcctgct | 420 |
| caggaagccg tcgtgaagga ggccgccatc aagagcaagg tggcccctct gtctctgggc | 480 |
| cccatcgaca tcgagagact gcagagcacc aaccccaagc ggcctctgag cagcgccaac | 540 |
| cagaacttca caacagcga gacactgggc caccagggca gccacgtcgt gacactgcag | 600 |
| ctgcggatcg acggaatgca ctgcaagagc tgtgtgctga acatcgagga aaacatcggc | 660 |
| cagctgctgg gagtgcagag catccaggtg tcactggaaa acaagaccgc ccaggtgaag | 720 |
| tacgaccca gctgcacaag ccccgtggcc ctgcagagag ccattgaagc tctgccccct | 780 |
| ggcaacttca agtgtccct gcctgacgga gccgagggct ccggaacaga tcacagaagc | 840 |
| agcagcagcc acagccctgg cagccccct agaaatcagg tgcagggcac ctgtagcacc | 900 |
| accctgatcg ccattgccgg catgacatgc gccagctgcg tgcactctat tgagggcatg | 960 |
| atctcccagc tggaaggcgt gcagcagatc agtgtgtctc tggccgaggg caccgccaca | 1020 |
| gtgctgtaca accctagcgt gatcagcccc gaagaactga gagccgccat tgaggacatg | 1080 |

```
ggattcgaag ccagcgtggt gtccgagagc tgctccacca accctctggg caatcacagc    1140
gccggcaaca gcatggtgca gaccaccgac ggcacccca ccagcgtgca ggaagtggcc     1200
ccacatacag gcagactgcc cgccaatcac gcccccgata tcctggccaa gagcccccag    1260
agtacaagag ccgtggcccc ccagaagtgc ttcctgcaga tcaagggcat gacttgtgcc    1320
tcttgtgtgt ccaatatcga gcggaacctg cagaaagagg ccggcgtgct gtctgtgctg    1380
gtggctctga tggccggcaa ggccgagatc aaatacgacc ccgaagtgat tcagccctg     1440 gaaatcgccc agtttatcca ggacctgggc tttgaagccg ccgtgatgga agattacgcc    1500
ggctccgacg gcaacatcga gctgaccatc accggaatga cctgcgcctc ctgtgtgcac    1560
aacattgagt ccaagctgac ccggaccaac ggcatcacct acgcctctgt ggctctggcc    1620
acctccaagg ccctcgtgaa gttcgatccc gagatcatcg cccccaggga catcatcaag    1680
atcatcgaag agatcggctt ccacgccagc ctggcccaga ggaaccctaa cgcccaccac    1740
ctggaccaca agatggaaat caagcagtgg aagaaaagct tcctgtgcag cctggtgttc    1800
ggcatccccg tgatggccct gatgatctac atgctgatcc ccagcaacga gccccaccag    1860
tccatggtgc tggatcacaa catcatcccc ggcctgtcta tcctgaacct gatcttcttc    1920
atcctgtgca ccttcgtgca gctgctgggc ggctggtact tctacgtgca ggcctacaag    1980
tccctgcggc acagatccgc caacatggac gtgctgatcg tgctggccac atctatcgcc    2040
tacgtgtact ccctcgtgat cctggtggtg gccgtgccg agaaagccga gagaagccct     2100
gtgaccttct tcgacacccc ccctatgctg ttcgtgttta tcgccctggg ccggtggctg    2160
gaacacctgg ccaaaagcaa gaccagcgag gccctggcta agctgatgag tctgcaggcc    2220
accgaggcca cagtcgtgac cctgggcgag gacaacctga tcatccgcga ggaacaggtg    2280
ccaatggaac tggtgcagcg gggcgacatc gtgaaggtgg tgcctggcgg caagttcccc    2340
gtggacggaa aagtgctgga agggaatacc atggccgacg agagcctgat cacaggcgag    2400
gccatgcccg tgaccaagaa acctggcagc acagtgatcg ccggcagcat caatgcccac    2460
ggcagcgtgc tgattaaggc cacacacgtg ggcaacgata ccaccctggc tcagattgtg    2520
aagctggtgg aagaggccca gatgagcaag gcccccattc agcagctggc tgaccggttc    2580
agcggctact tcgtgccctt tatcatcatc atgagcaccc tgacactggt cgtgtggatc    2640
gtgatcggct ttatcgactt cggagtggtg cagagatact tccccaaccc taacaagcac    2700
atcagccaga cagaagtgat catcagattc gcctttcaga ccagcatcac cgtgctgtgt    2760
atcgcctgcc cctgtagcct gggactggcc acacctaccg ctgtgatggt gggaacaggc    2820
gtggccgctc agaacggcat cctgatcaag gggggcaagc ctctggaaat ggctcacaag    2880
atcaagaccg tgatgttcga caagaccggc accatcaccc acggcgtgcc cagagtgatg    2940
agagtgctgc tgctggggga tgtggccacc ctgcctctga aaaggtgct ggctgtcgtg     3000 ggcacagccg aggctagctc tgaacaccca ctgggagtgg ccgtgacaaa gtactgcaaa    3060
gaggaactgg gcaccgaaac cctgggctac tgcaccgact tcaggccgt gcctggctgt     3120 ggcatcggct gcaaggtgtc caacgtggaa ggcatcctgg cccacagcga gaggccactg    3180
tctgcccctg ccagccacct gaacgaggcc ggatctctgc ccgccgaaaa ggacgctgtg    3240
ccccagacct tctctgtgct gattggcaac agagagtggc tgcggcggaa cggcctgacc    3300
atctcctccg atgtgtccga cgccatgacc gaccacgaga tgaagggcca gaccgccatt    3360
ctggtggcca ttgacggggt gctgtgcggc atgatcgcaa tcgccgatgc cgtgaaacag    3420
gaagcagcac tggccgtgca caccctgcag tctatgggag tggatgtggt gctgatcacc    3480
```

```
ggcgacaaca gaaagaccgc cagggccatt gccacccagg tgggcatcaa caaggtgttc    3540
gccgaggtgc tgcccagcca caaagtggcc aaggtgcagg aactgcagaa caaaggcaaa    3600
aaggtggcca tggtgggaga tggcgtgaac gactctcctg ctctggccca ggcagatatg    3660
ggcgtggcca tcggcacagg caccgacgtg gcaattgagg ctgctgacgt ggtgctgatt    3720
cggaacgacc tgctggacgt ggtggcctcc atccacctgt ccaagagaac cgtgcggcgg    3780
atcagaatca acctggtgct ggcactgatc tataacctcg tgggcatccc tatcgccgct    3840
ggcgtgttca tgcctatcgg aatcgtgctg cagccctgga tgggctctgc cgccatggct    3900
gcaagctccg tgtctgtggt gctgtccagc ctgcagctga agtgctacaa gaagcccgac    3960
ctggaaagat acgaggccca ggcccacgga cacatgaagc tctgacagc  ctcccaggtg    4020 tccgtgcaca tcggcatgga cgacagatgg cgggacagcc ctagagccac cccttgggat    4080
caggtgtcat acgtgtcaca ggtgtccctg agcagcctga ccagcgacaa gcccagcaga    4140
catagcgccg ctgccgacga cgatggggac aagtggtccc tgctgctgaa cggccgggat    4200
gaggaacagt acatc                                                     4215
```

<210> SEQ ID NO 22
<211> LENGTH: 4317
<212> TYPE: DNA
<213> ORGANISM: Artificial Sequence
<220> FEATURE:
<223> OTHER INFORMATION: constructed sequence

<400> SEQUENCE: 22

```
atgcccgagc aggaaagaca gatcaccgcc agagagggcg ccagccggaa gatcctgagc      60
aagctgagcc tgcccaccag agcctgggag cccgccatga agaagtcctt cgccttcgac     120
aacgtgggct acgagggcgg cctggacgga ctgggaccat cttctcaggt ggccacaagc     180
accgtgcgca tcctgggcat gacctgccag agctgcgtga agtccatcga ggaccggatc     240
agcaacctga agggcatcat cagcatgaag gtgtccctgg aacagggcag cgccaccgtg     300
aaatacgtgc cctctgtcgt gtgcctgcag caggtgtgcc accagatcgg cgacatgggc     360
ttcgaggcct ctatcgccga gggaaaggcc gcctcttggc cctctagaag cctgcctgct     420
caggaagccg tcgtgaagct gcgggtggaa gggatgacct gtcagtcctg cgtgtccagc     480
atcgagggca aagtgcggaa gctgcagggc gtggtgcgcg tgaaagtgtc tctgagcaac     540
caggaagctg tgatcaccta ccagccctac ctgatccagc ccgaggacct gagggaccac     600
gtgaacgata tgggatttga ggccgccatc aagagcaagg tggcccctct gtctctgggc     660
cccatcgaca tcgagagact gcagagcacc aaccccaagc ggcctctgag cagcgccaac     720
cagaacttca caacagcga gacactgggc caccagggca gccacgtcgt gacactgcag     780
agcatccagg tgtcactgga aaacaagacc gcccaggtga agtacgaccc cagctgcaca     840
agccccgtgg ccctgcagag agccattgaa gctctgcccc ctggcaactt caaagtgtcc     900
ctgcctgacg gagccgaggg ctccggaaca gatcacagaa gcagcagcag ccacagccct     960
ggcagccccc ctagaaatca ggtgcagggc acctgtagca ccaccctgat cgccattgcc    1020
ggcatgacat gcgccagctg cgtgcactct attgagggca tgatctccca gctggaaggc    1080
gtgcagcaga tcagtgtgtc tctggccgag ggcaccgcca cagtgctgta acccctagc    1140 gtgatcagcc ccgaagaact gagagccgcc attgaggaca tgggattcga agccagcgtg    1200
gtgtccgaga gctgctccac caaccctctg ggcaatcaca gcgccggcaa cagcatggtg    1260
```

```
cagaccaccg acggcacccc caccagcgtg caggaagtgg ccccacatac aggcagactg    1320
cccgccaatc acgcccccga tatcctggcc aagagccccc agagtacaag agccgtggcc    1380
ccccagaagt gcttcctgca gatcaagggc atgacttgtg cctcttgtgt gtccaatatc    1440
gagcggaacc tgcagaaaga ggccggcgtg ctgtctgtgc tggtggctct gatggccggc    1500
aaggccgaga tcaaatacga ccccgaagtg attcagcccc tggaaatcgc ccagtttatc    1560
caggacctgg gctttgaagc cgccgtgatg aagattacg ccggctccga cggcaacatc     1620
gagctgacca tcaccggaat gacctgcgcc tcctgtgtgc acaacattga gtccaagctg    1680
acccggacca acggcatcac ctacgcctct gtggctctgg ccacctccaa ggccctcgtg    1740
aagttcgatc ccgagatcat cggccccagg gacatcatca agatcatcga agagatcggc    1800
ttccacgcca gcctggccca gaggaaccct aacgcccacc acctggacca caagatggaa    1860
atcaagcagt ggaagaaaag cttcctgtgc agcctggtgt tcggcatccc cgtgatggcc    1920
ctgatgatct acatgctgat ccccagcaac gagccccacc agtccatggt gctggatcac    1980
aacatcatcc ccggcctgtc tatcctgaac ctgatcttct tcatcctgtg caccttcgtg    2040
cagctgctgg gcggctggta cttctacgtg caggcctaca agtccctgcg gcacagatcc    2100
gccaacatgg acgtgctgat cgtgctggcc acatctatcg cctacgtgta ctccctcgtg    2160
atcctggtgg tggccgtggc cgagaaagcc gagagaagcc ctgtgacctt cttcgacacc    2220
cccccctatg ctgttcgtgtt tatcgccctg ggccggtggc tggaacacct ggccaaaagc    2280
aagaccagcg aggccctggc taagctgatg agtctgcagg ccaccgaggc cacagtcgtg    2340
accctgggcg aggacaacct gatcatccgc gaggaacagg tgccaatgga actggtgcag    2400
cggggcgaca tcgtgaaggt ggtgcctggc ggcaagttcc ccgtggacgg aaaagtgctg    2460
gaagggaata ccatggccga cgagagcctg atcacaggcg aggccatgcc cgtgaccaag    2520
aaacctggca gcacagtgat cgccggcagc atcaatgccc acggcagcgt gctgattaag    2580
gccacacacg tgggcaacga taccaccctg gctcagattg tgaagctggt ggaagaggcc    2640
cagatgagca aggcccccat tcagcagctg gctgaccggt tcagcggcta cttcgtgccc    2700
tttatcatca tcatgagcac cctgacactg gtcgtgtgga tcgtgatcgg ctttatcgac    2760
ttcggagtgg tgcagagata cttccccaac cctaacaagc acatcagcca gacagaagtg    2820
atcatcgat tcgcctttca gaccagcatc accgtgctgt gtatcgcctg cccctgtagc    2880
ctgggactgg ccacacctac cgctgtgatg gtgggaacag gcgtggccgc tcagaacggc    2940
atcctgatca ggggggcaa gcctctggaa atggctcaca agatcaagac cgtgatgttc    3000
gacaagaccg gcaccatcac ccacggcgtg cccagagtga tgagagtgct gctgctgggg    3060
gatgtggcca ccctgcctct gagaaaggtg ctggctgtcg tgggcacagc cgaggctagc    3120
tctgaacacc cactgggagt ggccgtgaca aagtactgca agaggaact gggcaccgaa     3180
accctgggct actgcaccga ctttcaggcc gtgcctggct gtggcatcgg ctgcaaggtg    3240
tccaacgtgg aaggcatcct ggcccacagc gagaggccac tgtctgcccc tgccagccac    3300
ctgaacgagg ccggatctct gcccgccgaa aaggacgctg tgccccagac cttctctgtg    3360
ctgattggca cagagagtg gctgcggcg aacggcctga ccatctcctc cgatgtgtcc      3420
gacgccatga ccgaccacga gatgaagggc cagaccgcca ttctggtggc cattgacggg    3480
gtgctgtgcg gcatgatcgc aatcgccgat gccgtgaaaa aggaagcagc actggccgtg    3540
cacaccctgc agtctatggg agtggatgtg gtgctgatca ccggcgacaa cagaaagacc    3600
gccagggcca ttgccaccca ggtgggcatc aacaaggtgt cgccgaggt gctgcccagc     3660
```

```
cacaaagtgg ccaaggtgca ggaactgcag aacaaaggca aaaggtggc  catggtggga    3720 gatggcgtga acgactctcc tgctctggcc caggcagata tgggcgtggc catcggcaca    3780
ggcaccgacg tggcaattga ggctgctgac gtggtgctga ttcggaacga cctgctggac    3840
gtggtggcct ccatccacct gtccaagaga accgtgcggc ggatcagaat caacctggtg    3900
ctggcactga tctataacct cgtgggcatc cctatcgccg ctggcgtgtt catgcctatc    3960
ggaatcgtgc tgcagccctg gatgggctct gccgccatgg ctgcaagctc cgtgtctgtg    4020
gtgctgtcca gcctgcagct gaagtgctac aagaagcccg acctggaaag atacgaggcc    4080
caggcccacg gacacatgaa gcctctgaca gcctcccagg tgtccgtgca catcggcatg    4140
gacgacagat ggcgggacag ccctagagcc accccttggg atcaggtgtc atacgtgtca    4200
caggtgtccc tgagcagcct gaccagcgac aagcccagca gacatagcgc cgctgccgac    4260
gacgatgggg acaagtggtc cctgctgctg aacggccggg atgaggaaca gtacatc      4317
```

<210> SEQ ID NO 23
<211> LENGTH: 7944
<212> TYPE: DNA
<213> ORGANISM: Artificial Sequence
<220> FEATURE:
<223> OTHER INFORMATION: constructed sequence

<400> SEQUENCE: 23

```
ctgcgcgctc gctcgctcac tgaggccgcc cgggcaaagc ccgggcgtcg ggcgaccttt     60
ggtcgcccgg cctcagtgag cgagcgagcg cgcagagagg gagtggccaa ctccatcact    120
aggggttcct tgtagttaat gattaacccg ccatgctact tatctactta agctacctcg    180
tgatcgcccg gcccctgttc aaacatgtcc taatactctg tctctgcaag gtcatcagt    240 agttttccat cttactcaac atcctcccag tggaattcat ttcatagaac gaatgttccg    300
atgctctaat ctctctagac aaggttcata tttgtatggg ttacttattc tctctttgtt    360
gactaagtca ataatcagaa tcagcaggtt tgcagtcaga ttggcaggga taagcagcct    420
agctcaggag aagtgagtat aaaagcccca ggctgggagc agccatcagc ggccgccacc    480
atgcccgagc aggaaagaca gatcaccgcc agagagggcg ccagccggaa gatcctgagc    540
aagctgagcc tgcccaccag agcctgggag cccgccatga agaagtcctt cgccttcgac    600
aacgtgggct acgagggcgg cctggatgga ctgggaccat cttctcaggt ggccacaagc    660
accgtgcgca tcctgggcat gacctgccag agctgcgtga agtccatcga ggaccggatc    720
agcaacctga aggcatcat cagcatgaag gtgtccctgg aacagggcag cgccaccgtg    780
aaatacgtgc cctctgtcgt gtgcctgcag caagtgtgcc accagatcgg cgacatgggc    840
ttcgaggcct ctatcgccga gggaaaggcc gcctcttggc cctctagaag cctgcctgct    900
caggaagccg tcgtgaagct gcgggtggaa gggatgacct gtcagtcctg cgtgtccagc    960
atcgagggca agtgcggaa gctgcagggc gtggtgcgcg tgaaagtgtc tctgagcaac    1020
caggaagctg tgatcaccta ccagccctac ctgatccagc ccgaggacct gagggaccac    1080
gtgaacgata tgggatttga ggccgccatc aagagcaagg tggccccctct gtctctgggc    1140 cccatcgaca tcgagagact gcagagcacc aaccccaagc ggcctctgag cagcgccaac    1200
cagaacttca caacagcga gacactgggc caccagggca gccacgtcgt gacactgcag    1260
ctgcggatcg acgaatgca ctgcaagagc tgtgtgctga acatcgagga aaacatcggc    1320
cagctgctgg gagtgcagag catccaggtg tcactggaaa acaagaccgc ccaagtgaag    1380
```

```
tacgacccca gctgcacaag ccccgtggcc ctgcagagag ccattgaagc tctgcccct    1440 ggcaacttca aagtgtccct gcctgatggc gccgagggct ccggaacaga tcacagaagc   1500
agcagcagcc acagccctgg cagccccct agaaatcagg tgcagggcac ctgtagcacc    1560
accctgatcg ccattgccgg catgacatgc gccagctgcg tgcactctat tgagggcatg   1620
atctcccagc tggaaggcgt gcagcagatc agtgtgtctc tggccgaggg caccgccaca  1680
gtgctgtaca accctagcgt gatcagcccc gaagaactga gagccgccat tgaggacatg  1740
ggattcgaag ccagcgtggt gtccgagagc tgctccacca accctctggg caatcacagc  1800
gccggcaaca gcatggtgca gaccaccgat ggcaccccca ccagcgtgca ggaagtggcc   1860
ccacatacag gcagactgcc cgccaatcac gcccccgata tcctggccaa gagcccccag  1920
agtacaagag ccgtggcccc ccagaagtgc ttcctgcaga tcaagggcat gacttgtgcc  1980
tcttgtgtgt ccaatatcga gcggaacctg cagaaagagg ccggcgtgct gtctgtgctg  2040
gtggctctga tggccggcaa ggccgagatc aaatacgacc ccgaagtgat tcagcccctg  2100
gaaatcgccc agtttatcca ggacctgggc tttgaagccg ccgtgatgga agattacgcc  2160
ggctccgacg gcaacatcga gctgaccatc accggaatga cctgcgcctc ctgtgtgcac  2220
aacattgagt ccaagctgac ccggaccaac ggcatcacct acgcctctgt ggctctggcc  2280
acctccaagg ccctcgtgaa gttcgatccc gagatcatcg cccagggga catcatcaag   2340 atcatcgaag agatcggctt ccacgccagc ctggcccaga ggaaccctaa tgcccaccac   2400
ctggaccaca agatggaaat caagcagtgg aagaaaagct tcctgtgcag cctggtgttc   2460
ggcatccccg tgatggccct gatgatctac atgctgatcc ccagcaacga gccccaccag   2520
tccatggtgc tggatcacaa catcatcccc ggcctgtcta tcctgaacct gatcttcttc   2580
atcctgtgca cctccgtgca gctgctgggc ggctggtact tctatgtgca agcctacaag   2640
tccctgcggc acagatccgc caacatggac gtgctgatcg tgctggccac atctatcgcc   2700
tacgtgtact ccctcgtgat cctggtggtg gccgtggccg agaaagccga gagaagccct   2760
gtgaccttct tcgacacccc ccctatgctg ttcgtgttta tcgccctggg ccggtggctg   2820
gaacacctgg ccaaaagcaa gaccagcgag gccctggcta agctgatgag tctgcaggcc  2880
accgaggcca cagtcgtgac cctgggcgag acaacctga tcatccgcga ggaacaggtg    2940
ccaatggaac tggtgcagcg gggcgacatc gtgaaggtgg tgcctggcgg caagttcccc   3000
gtggacggaa aagtgctgga agggaatacc atggccgacg agagcctgat cacaggcgag   3060
gccatgcccg tgaccaagaa acctggcagc acagtgatcg ccggcagcat caatgcccac   3120
ggcagcgtgc tgattaaggc cacacacgtg ggcaacgata ccaccctggc tcagattgtg   3180
aagctggtgg aagaggccca gatgagcaag gcccccattc agcagctggc tgaccggttc   3240
agcggctact tcgtgcccti tatcatcatc atgagcaccc tgacactggt cgtgtggatc   3300
gtgatcggct ttatcgactt cggagtggtg cagagatact tccccaaccc taacaagcac   3360
atcagccaga cagaagtgat catcagattc gcctttcaga ccagcatcac cgtgctgtgt   3420
atcgcctgcc cctgtagcct gggactggcc acacctaccg ctgtgatggt gggaacaggc   3480
gtggccgctc agaacggcat cctgatcaag gggggcaagc tctggaaat ggctcacaag    3540 atcaagaccg tgatgttcga caagaccggc accatcaccc acggcgtgcc cagagtgatg   3600
agagtgctgc tgctggggga tgtggccacc ctgcctctga aaaggtgct ggctgtcgtg     3660 ggcacagccg aggctagctc tgaacacca ctggagtgg ccgtgacaaa gtactgcaaa     3720
gaggaactgg gcaccgaaac cctgggctac tgcaccgact ttcaggccgt gcctggctgt    3780
```

```
ggcatcggct gcaaggtgtc caacgtggaa ggcatcctgg cccacagcga gaggccactg   3840
tctgcccctg ccagccacct gaatgaggcc ggatctctgc ccgccgaaaa ggacgctgtg   3900
ccccagacct tctctgtgct gattggcaac agagagtggc tgcggcggaa cggcctgacc   3960
atctcctccg atgtgtccga cgccatgacc gaccacgaga tgaagggcca gaccgccatt   4020
ctggtggcca ttgacggggt gctgtgcggc atgatcgcaa tcgccgatgc cgtgaaacag   4080
gaagcagcac tggccgtgca caccctgcag tctatgggag tggatgtggt gctgatcacc   4140
ggcgacaaca gaaagaccgc cagggccatt gccacccaag tgggcatcaa caaggtgttc   4200
gccgaggtgc tgcccagcca caaagtggcc aaggtgcagg aactgcagaa caaaggcaaa   4260
aaggtggcca tggtgggaga tggcgtgaac gactctcctg ctctggccca ggcagatatg   4320
ggcgtggcca tcggcacagg caccgacgtg gcaattgagg ctgctgacgt ggtgctgatt   4380
cggaacgacc tgctggacgt ggtggcctcc atccacctgt ccaagagaac cgtgcggcgg   4440
atcagaatca acctggtgct ggcactgatc tataacctcg tgggcatccc tatcgccgct   4500
ggcgtgttca tgcctatcgg aatcgtgctg cagccctgga tgggctctgc cgccatggct   4560
gcaagctccg tgtctgtggt gctgtccagc ctgcagctga agtgctacaa gaagcccgac   4620
ctggaaagat acgaggccca gcccacggga cacatgaagc tctgacagc ctcccaggtg   4680 tccgtgcaca tcggcatgga cgacagatgg cgggacagcc ctagagccac cccttgggat   4740
caggtgtcat acgtgtcaca ggtgtccctg agcagcctga ccagcgacaa gcccagcaga   4800
catagcgccg ctgccgacga cgatggggac aaatggtccc tgctgctgaa cggccgggat   4860
gaggaacagt acatctgata agcatgcaat aaagtctgag tgggcggcag cctgtgtgtg   4920
cctgggttct ctctgtcccg gaatgtgcaa acaatggagg tgctcgagta gataagtagc   4980
atggcgggtt aatcattaac tacaaggaac ccctagtgat ggagttggcc actccctctc   5040
tgcgcgctcg ctcgctcact gaggccgggc gaccaaaggt cgcccgacgc ccgggctttg   5100
cccgggcggc ctcagtgagc gagcgagcgc gcagccttaa ttaacctaat tcactggccg   5160
tcgttttaca acgtcgtgac tgggaaaacc ctggcgttac ccaacttaat cgccttgcag   5220
cacatccccc tttcgccagc tggcgtaata gcgaagaggc ccgcaccgat cgcccttccc   5280
aacagttgcg cagcctgaat ggcgaatggg acgcgccctg tagcggcgca ttaagcgcgg   5340
cgggtgtggt ggttacgcgc agcgtgaccg ctacacttgc cagcgcccta gcgcccgctc   5400 cttttcgcttt cttcccttcc tttctcgcca cgttcgccgg ctttccccgt caagctctaa   5460
atcgggggct ccctttaggg ttccgattta gtgctttacg gcacctcgac cccaaaaaac   5520
ttgattaggg tgatggttca cgtagtgggc catcgccctg atagacggtt tttcgccctt   5580
tgacgttgga gtccacgttc tttaatagtg gactcttgtt ccaaactgga acaacactca   5640
accctatctc ggtctattct tttgatttat aagggatttt gccgatttcg gcctattggt   5700
taaaaaatga gctgatttaa caaaaattta acgcgaattt taacaaaata ttaacgctta   5760
caatttaggt ggcacttttc ggggaaatgt gcgcggaacc cctatttgtt tatttttcta   5820
aatacattca aatatgtatc cgctcatgag acaataaccc tgataaatgc ttcaataata   5880
ttgaaaaagg aagagtatga gtattcaaca tttccgtgtc gcccttattc ccttttttgc   5940
ggcattttgc cttcctgttt ttgctcaccc agaaacgctg gtgaaagtaa aagatgctga   6000
agatcagttg ggtgcacgag tgggttacat cgaactggat ctcaacagcg gtaagatcct   6060
tgagagtttt cgccccgaag aacgttttcc aatgatgagc acttttaaag ttctgctatg   6120
```

```
tggcgcggta ttatcccgta ttgacgccgg gcaagagcaa ctcggtcgcc gcatacacta      6180
ttctcagaat gacttggttg agtactcacc agtcacagaa aagcatctta cggatggcat      6240
gacagtaaga gaattatgca gtgctgccat aaccatgagt gataacactg cggccaactt      6300
acttctgaca acgatcggag gaccgaagga gctaaccgct tttttgcaca acatgggggga      6360 tcatgtaact cgccttgatc gttgggaacc ggagctgaat gaagccatac caaacgacga      6420
gcgtgacacc acgatgcctg tagcaatggc aacaacgttg cgcaaactat taactggcga      6480
actacttact ctagcttccc ggcaacaatt aatagactgg atggaggcgg ataaagttgc      6540
aggaccactt ctgcgctcgg cccttccggc tggctggttt attgctgata atctggagc       6600 cggtgagcgt gggtctcgcg gtatcattgc agcactgggg ccagatggta agccctcccg      6660
tatcgtagtt atctacacga cggggagtca ggcaactatg gatgaacgaa atagacagat      6720
cgctgagata ggtgcctcac tgattaagca ttggtaactg tcagaccaag tttactcata      6780
tatactttag attgatttaa aacttcattt ttaatttaaa aggatctagg tgaagatcct      6840 tttttgataat ctcatgacca aaatccctta acgtgagttt cgttccact gagcgtcaga      6900 ccccgtagaa aagatcaaag gatcttcttg agatcctttt tttctgcgcg taatctgctg      6960
cttgcaaaca aaaaaaccac cgctaccagc ggtggtttgt ttgccggatc aagagctacc      7020
aactcttttt ccgaaggtaa ctggcttcag cagagcgcag ataccaaata ctgttcttct      7080
agtgtagccg tagttaggcc accacttcaa gaactctgta gcaccgccta catacctcgc      7140
tctgctaatc ctgttaccag tggctgctgc cagtggcgat aagtcgtgtc ttaccgggtt      7200
ggactcaaga cgatagttac cggataaggc gcagcggtcg ggctgaacgg ggggttcgtg      7260
cacacagccc agcttggagc gaacgaccta caccgaactg agatacctac agcgtgagct      7320
atgagaaagc gccacgcttc ccgaagggag aaaggcggac aggtatccgg taagcggcag      7380
ggtcggaaca ggagagcgca cgagggagct tccaggggga aacgcctggt atctttatag      7440
tcctgtcggg tttcgccacc tctgacttga gcgtcgattt ttgtgatgct cgtcaggggg      7500
gcggagccta tggaaaaacg ccagcaacgc ggccttttta cggttcctgg ccttttgctg      7560
gccttttgct cacatgttct ttcctgcgtt atccctgat tctgtggata accgtattac      7620
cgcctttgag tgagctgata ccgctcgccg cagccgaacg accgagcgca gcgagtcagt      7680
gagcgaggaa gcggaagagc gcccaatacg caaaccgcct ctccccgcgc gttggccgat      7740
tcattaatgc agctggcacg acaggtttcc cgactggaaa gcgggcagtg agcgcaacgc      7800
aattaatgtg agttagctca ctcattaggc accccaggct ttacacttta tgcttccggc      7860
tcgtatgttg tgtggaattg tgagcggata acaatttcac acaggaaaca gctatgacca      7920
tgattacgcc agatttaatt aagg                                             7944
```

<210> SEQ ID NO 24
<211> LENGTH: 7866
<212> TYPE: DNA
<213> ORGANISM: Artificial Sequence
<220> FEATURE:
<223> OTHER INFORMATION: constructed sequence

<400> SEQUENCE: 24

```
ctgcgcgctc gctcgctcac tgaggccgcc cgggcaaagc ccgggcgtcg ggcgaccttt       60
ggtcgcccgg cctcagtgag cgagcgagcg cgcagagagg gagtggccaa ctccatcact      120 agggggttcct tgtagttaat gattaacccg ccatgctact tatctactta agtgtttgct     180
gcttgcaatg tttgcccatt ttaggggaat tcactcaaag ttcaaacctt atcattttt       240
```

-continued

```
gctttgttcc tcttggcctt ggttttgtac atcagctttg aaaataccat cccagggtta      300
atgctgggt  taatttataa ctaagagtgc tctagttttg caatacagga catgctataa      360
aaatggaaag atgttgcttt ctgagagaca gcggccgcca ccatgcccga gcaggaaaga      420
cagatcaccg ccagagaggg cgccagccgg aagatcctga gcaagctgag cctgcccacc      480
agagcctggg agcccgccat gaagaagtcc ttcgccttcg acaacgtggg ctacagggc       540
ggcctggacg gactgggacc atcttctcag gtggccacaa gcaccgtgcg catcctgggc      600
atgacctgcc agagctgcgt gaagtccatc gaggaccgga tcagcaacct gaagggcatc      660
atcagcatga aggtgtccct ggaacagggc agcgccaccg tgaaatacgt gccctctgtc      720
gtgtgcctgc agcaggtgtg ccaccagatc ggcgacatgg gcttcgaggc ctctatcgcc      780
gagggaaagg ccgcctcttg gccctctaga agcctgcctg ctcaggaagc cgtcgtgaag      840
ctgcgggtgg aagggatgac ctgtcagtcc tgcgtgtcca gcatcgaggg caaagtgcgg      900
aagctgcagg gcgtggtgcg cgtgaaagtg tctctgagca accaggaagc tgtgatcacc      960
taccagccct acctgatcca gcccgaggac ctgagggacc acgtgaacga tatgggattt     1020
gaggccgcca tcaagagcaa ggtggcccct ctgtctctgg gccccatcga catcgagaga     1080
ctgcagagca ccaaccccaa gcggcctctg agcagcgcca accagaactt caacaacagc     1140
gagacactgg ccaccagggg cagccacgtc gtgacactgc agctgcggat cgacggaatg     1200
cactgcaaga gctgtgtgct gaacatcgag gaaaacatcg ccagctgct  gggagtgcag     1260
agcatccagg tgtcactgga aaacaagacc gcccaggtga agtacgaccc cagctgcaca     1320
agccccgtgg ccctgcagag agccattgaa gctctgcccc tggcaacttc aaagtgtcc      1380
ctgcctgacg gagccgaggg ctccggaaca gatcacagaa gcagcagcag ccacagccct     1440
ggcagccccc ctagaaatca ggtgcagggc acctgtagca ccaccctgat cgccattgcc     1500
ggcatgacat cgccagctg cgtgcactct attgagggca tgatctccca gctggaaggc     1560
gtgcagcaga tcagtgtgtc tctggccgag ggcaccgcca cagtgctgta caaccctagc     1620
gtgatcagcc ccgaagaact gagagccgcc attgaggaca tgggattcga agccagcgtg     1680
gtgtccgaga gctgctccac caaccctctg ggcaatcaca gcgccggcaa cagcatggtg     1740
cagaccaccg acggcacccc caccagcgtg caggaagtgg ccccacatac aggcagactg     1800
cccgccaatc acgccccga  tatcctggcc aagagccccc agagtacaag agccgtggcc     1860
ccccagaagt gcttcctgca gatcaagggc atgacttgtg cctcttgtgt gtccaatatc     1920
gagcggaacc tgcagaaaga ggccggcgtg ctgtctgtgc tggtggctct gatgccggc      1980
aaggccgaga tcaaatacga ccccgaagtg attcagcccc tgaaatcgc  ccagtttatc     2040
caggacctgg gctttgaagc cgccgtgatg aagattacg  ccggctccga cggcaacatc     2100
gagctgacca tcaccggaat gacctgcgcc tcctgtgtgc acaacattga gtccaagctg     2160
acccggacca acggcatcac ctacgcctct gtggctctgg ccacctccaa ggccctcgtg     2220
aagttcgatc ccgagatcat cggccccagg gacatcatca agatcatcga agagatcggc     2280
ttccacgcca gctggcccca gagaaccct  aacgcccacc acctggacca aagatggaa      2340
atcaagcagt ggaagaaaag cttcctgtgc agcctggtgt cgcatccc  cgtgatggcc      2400
ctgatgatct acatgctgat ccccagcaac gagcccacc  agtccatggt gctggatcac     2460
aacatcatcc ccgcctgtc  tatcctgaac ctgatcttct tcatcctgtg caccttcgtg     2520
cagctgctgg gcggctggta cttctacgtg caggcctaca agtccctgcg gcacagatcc     2580
```

```
gccaacatgg acgtgctgat cgtgctggcc acatctatcg cctacgtgta ctccctcgtg    2640
atcctggtgg tggccgtggc cgagaaagcc gagagaagcc ctgtgacctt cttcgacacc    2700 cccctatgc tgttcgtgtt tatcgccctg ggccggtggc tggaacacct ggccaaaagc    2760
aagaccagcg aggccctggc taagctgatg agtctgcagg ccaccgaggc cacagtcgtg    2820
accctgggcg aggacaacct gatcatccgc gaggaacagg tgccaatgga actggtgcag    2880
cggggcgaca tcgtgaaggt ggtgcctggc ggcaagttcc ccgtggacgg aaaagtgctg    2940
gaagggaata ccatggccga cgagagcctg atcacaggcg aggccatgcc cgtgaccaag    3000
aaacctggca gcacagtgat cgccggcagc atcaatgccc acggcagcgt gctgattaag    3060
gccacacacg tgggcaacga taccaccctg gctcagattg tgaagctggt ggaagaggcc    3120
cagatgagca aggcccccat tcagcagctg gctgaccggt tcagcggcta cttcgtgccc    3180
tttatcatca tcatgagcac cctgacactg gtcgtgtgga tcgtgatcgg ctttatcgac    3240
ttcggagtgg tgcagagata cttccccaac cctaacaagc acatcagcca gacagaagtg    3300
atcatcagat tcgcctttca gaccagcatc accgtgctgt gtatcgcctg ccctgtagc    3360 ctgggactgg ccacacctac cgctgtgatg gtgggaacag cgtggccgc tcagaacggc    3420 atcctgatca aggggggcaa gcctctggaa atggctcaca agatcaagac cgtgatgttc    3480
gacaagaccg gcaccatcac ccacggcgtg cccagagtga tgagagtgct gctgctgggg    3540
gatgtggcca ccctgcctct gagaaaggtg ctggctgtcg tgggcacagc cgaggctagc    3600
tctgaacacc cactgggagt ggccgtgaca aagtactgca agaggaact gggcaccgaa    3660 accctgggct actgcaccga ctttcaggcc gtgcctggct gtggcatcgg ctgcaaggtg    3720
tccaacgtgg aaggcatcct ggcccacagc gagaggccac tgtctgcccc tgccagccac    3780
ctgaacgagg ccggatctct gcccgccgaa aaggacgctg tgcccagac cttctctgtg    3840 ctgattggca acagagagtg gctgcggcgg aacggcctga ccatctcctc cgatgtgtcc    3900
gacgccatga ccgaccacga gatgaagggc cagaccgcca ttctggtggc cattgacggg    3960
gtgctgtgcg gcatgatcgc aatcgccgat gccgtgaaac aggaagcagc actggccgtg    4020 cacacccctgc agtctatggg agtggatgtg gtgctgatca ccggcgacaa cagaaagacc    4080
gccagggcca ttgccaccca ggtgggcatc aacaaggtgt cgccgaggt gctgcccagc    4140 cacaaagtgg ccaaggtgca ggaactgcag aacaaaggca aaaagtggc catggtggga    4200 gatggcgtga acgactctcc tgctctggcc caggcagata tgggcgtggc catcggcaca    4260
ggcaccgacg tggcaattga ggctgctgac gtggtgctga ttcggaacga cctgctggac    4320
gtggtggcct ccatccacct gtccaagaga accgtgcggc ggatcagaat caacctggtg    4380
ctggcactga tctataacct cgtgggcatc cctatcgccg ctggcgtgtt catgcctatc    4440
ggaatcgtgc tgcagccctg gatgggctct gccgccatgg ctgcaagctc cgtgtctgtg    4500
gtgctgtcca gcctgcagct gaagtgctac aagaagcccg acctggaaag atacgaggcc    4560
caggcccacg gacacatgaa gcctctgaca gcctcccagg tgtccgtgca catccggcatg    4620 gacgacagat ggcgggacag ccctagagcc acccccttggg atcaggtgtc atacgtgtca    4680
caggtgtccc tgagcagcct gaccagcgac aagcccagca gacatagcgc cgctgccgac    4740
gacgatgggg acaagtggtc cctgctgctg aacggccggg atgaggaaca gtacatctga    4800
taagcatgca ataaagtctg agtgggcggc agcctgtgtg tgcctgggtt ctctctgtcc    4860
cggaatgtgc aaacaatgga ggtgctcgag tagataagta gcatggcggg ttaatcatta    4920
actacaagga accccctagtg atggagttgg ccactccctc tctgcgcgct cgctcgctca    4980
```

```
ctgaggccgg gcgaccaaag gtcgcccgac gcccgggctt tgcccgggcg gcctcagtga    5040
gcgagcgagc gcgcagcctt aattaaccta attcactggc cgtcgtttta caacgtcgtg    5100
actgggaaaa ccctggcgtt acccaactta atcgccttgc agcacatccc cctttcgcca    5160
gctggcgtaa tagcgaagag gcccgcaccg atcgcccttc ccaacagttg cgcagcctga    5220
atggcgaatg gacgcgccc tgtagcggcg cattaagcgc ggcgggtgtg gtggttacgc     5280
gcagcgtgac cgctacactt gccagcgccc tagcgcccgc tcctttcgct ttcttccctt    5340
cctttctcgc cacgttcgcc ggctttcccc gtcaagctct aaatcggggg ctccctttag    5400
ggttccgatt tagtgcttta cggcacctcg accccaaaaa acttgattag ggtgatggtt    5460
cacgtagtgg gccatcgccc tgatagacgg ttttcgccc tttgacgttg gagtccacgt     5520
tctttaatag tggactcttg ttccaaactg gaacaacact caaccctatc tcggtctatt    5580
cttttgattt ataagggatt ttgccgattt cggcctattg gttaaaaaat gagctgattt    5640
aacaaaaatt taacgcgaat tttaacaaaa tattaacgct tacaatttag gtggcacttt    5700
tcggggaaat gtgcgcggaa cccctatttg tttattttc taaatacatt caaatatgta     5760
tccgctcatg agacaataac cctgataaat gcttcaataa tattgaaaaa ggaagagtat    5820
gagtattcaa catttccgtg tcgcccttat ccctttttt gcggcatttt gccttcctgt     5880
ttttgctcac ccagaaacgc tggtgaaagt aaaagatgct gaagatcagt tgggtgcacg    5940
agtgggttac atcgaactgg atctcaacag cggtaagatc cttgagagtt ttcgccccga    6000
agaacgtttt ccaatgatga gcacttttaa agttctgcta tgtggcgcgg tattatcccg    6060
tattgacgcc gggcaagagc aactcggtcg ccgcatacac tattctcaga atgacttggt    6120
tgagtactca ccagtcacag aaaagcatct tacggatggc atgacagtaa gagaattatg    6180
cagtgctgcc ataaccatga gtgataacac tgcggccaac ttacttctga acgatcgg     6240 aggaccgaag gagctaaccg cttttttgca acatgggg gatcatgtaa ctcgccttga      6300
tcgttgggaa ccggagctga atgaagccat accaaacgac gagcgtgaca ccacgatgcc    6360
tgtagcaatg gcaacaacgt tgcgcaaact attaactggc gaactactta ctctagcttc    6420
ccggcaacaa ttaatagact ggatggaggc ggataaagtt gcaggaccac ttctgcgctc    6480
ggcccttccg gctggctggt ttattgctga taaatctgga gccggtgagc gtgggtctcg    6540
cggtatcatt gcagcactgg ggccagatgg taagccctcc cgtatcgtag ttatctacac    6600 gacgggagt caggcaacta tggatgaacg aaatagacag atcgctgaga taggtgcctc    6660
actgattaag cattggtaac tgtcagacca agtttactca tatatacttt agattgattt    6720
aaaacttcat ttttaattta aaaggatcta ggtgaagatc ctttttgata atctcatgac    6780
caaaatccct taacgtgagt tttcgttcca ctgagcgtca ccccgtag aaaagatcaa      6840 aggatcttct tgagatcctt tttttctgcg cgtaatctgc tgcttgcaaa caaaaaaacc    6900
accgctacca gcggtggttt gtttgccgga tcaagagcta ccaactcttt ttccgaaggt    6960
aactggcttc agcagagcgc agataccaaa tactgttctt ctagtgtagc cgtagttagg    7020
ccaccacttc aagaactctg tagcaccgcc tacatacctc gctctgctaa tcctgttacc    7080
agtggctgct gccagtggcg ataagtcgtg tcttaccggg ttggactcaa gacgatagtt    7140
accggataag gcgcagcggt cgggctgaac ggggggttcg tgcacacagc ccagcttgga    7200
gcgaacgacc tacaccgaac tgagatacct acagcgtgag ctatgagaaa gcgccacgct    7260
tcccgaaggg agaaaggcgg acaggtatcc ggtaagcggc agggtcggaa caggagagcg    7320
```

| | |
|---|---|
| cacgagggag cttccagggg gaaacgcctg gtatctttat agtcctgtcg ggtttcgcca | 7380 |
| cctctgactt gagcgtcgat ttttgtgatg ctcgtcaggg gggcggagcc tatggaaaaa | 7440 |
| cgccagcaac gcggccttt tacggttcct ggccttttgc tggccttttg ctcacatgtt | 7500 |
| ctttcctgcg ttatcccctg attctgtgga taaccgtatt accgcctttg agtgagctga | 7560 |
| taccgctcgc cgcagccgaa cgaccgagcg cagcgagtca gtgagcgagg aagcggaaga | 7620 |
| gcgcccaata cgcaaaccgc ctctccccgc gcgttggccg attcattaat gcagctggca | 7680 |
| cgacaggttt cccgactgga aagcgggcag tgagcgcaac gcaattaatg tgagttagct | 7740 |
| cactcattag gcaccccagg ctttacactt tatgcttccg gctcgtatgt tgtgtggaat | 7800 |
| tgtgagcgga taacaatttc acacaggaaa cagctatgac catgattacg ccagatttaa | 7860 |
| ttaagg | 7866 |

<210> SEQ ID NO 25
<211> LENGTH: 7874
<212> TYPE: DNA
<213> ORGANISM: Artificial Sequence
<220> FEATURE:
<223> OTHER INFORMATION: constructed sequence

<400> SEQUENCE: 25

| | |
|---|---|
| ctgcgcgctc gctcgctcac tgaggccgcc cgggcaaagc ccgggcgtcg ggcgaccttt | 60 |
| ggtcgcccgg cctcagtgag cgagcgagcg cgcagagagg gagtggccaa ctccatcact | 120 |
| aggggttcct tgtagttaat gattaacccg ccatgctact tatctactta agaggttaat | 180 |
| ttttaaactg tttgctctgg ttaataatct cagggaattc actcaaagtt caaaccttat | 240 |
| cattttttgc tttgttcctc ttggccttgg ttttgtacat cagctttgaa aataccatcc | 300 |
| cagggttaat gctggggtta atttataact aagagtgctc tagttttgca atacaggaca | 360 |
| tgctataaaa atggaaagat gttgctttct gagagacagc ggccgccacc atgcccgagc | 420 |
| aggaaagaca gatcaccgcc agagagggcg ccagccggaa gatcctgagc aagctgagcc | 480 |
| tgcccaccag agcctggagc ccgccatga agaagtcctt cgccttcgac aacgtgggct | 540 |
| acgagggcgg cctggacgga ctgggaccat cttctcaggt ggccacaagc accgtgcgca | 600 |
| tcctgggcat gacctgccag agctgcgtga agtccatcga ggaccggatc agcaacctga | 660 |
| agggcatcat cagcatgaag gtgtccctgg aacagggcag cgccaccgtg aaatacgtgc | 720 |
| cctctgtcgt gtgcctgcag caggtgtgcc accagatcgg cgacatgggc ttcgaggcct | 780 |
| ctatcgccga gggaaaggcc gcctcttggc cctctagaag cctgcctgct caggaagccg | 840 |
| tcgtgaagct gcgggtggaa gggatgacct gtcagtcctg cgtgtccagc atcgagggca | 900 |
| aagtgcggaa gctgcagggc gtggtgcgcg tgaaagtgtc tctgagcaac caggaagctg | 960 |
| tgatcaccta ccagccctac ctgatccagc ccgaggacct gagggaccac gtgaacgata | 1020 |
| tgggatttga ggccgccatc aagagcaagg tggcccctct gtctctgggc cccatcgaca | 1080 |
| tcgagagact gcagagcacc aaccccaagc ggcctctgag cagcgccaac cagaacttca | 1140 |
| acaacagcga gacactgggc caccagggca gccacgtcgt gacactgcag ctgcggatcg | 1200 |
| acggaatgca ctgcaagagc tgtgtgctga acatcgagga aaacatcggc cagctgctgg | 1260 |
| gagtgcagag catccaggtg tcactggaaa acaagaccgc ccaggtgaag tacgaccca | 1320 |
| gctgcacaag cccgtggcc ctgcagagag ccattgaagc tctgcccct ggcaacttca | 1380 |
| aagtgtccct gcctgacgga gccgagggct ccggaacaga tcacagaagc agcagcagcc | 1440 |
| acagccctgg cagccccct agaaatcagg tgcagggcac ctgtagcacc accctgatcg | 1500 |

```
ccattgccgg catgacatgc gccagctgcg tgcactctat tgagggcatg atctcccagc      1560
tggaaggcgt gcagcagatc agtgtgtctc tggccgaggg caccgccaca gtgctgtaca      1620
accctagcgt gatcagcccc gaagaactga gagccgccat tgaggacatg ggattcgaag      1680
ccagcgtggt gtccgagagc tgctccacca accctctggg caatcacagc gccggcaaca      1740
gcatggtgca gaccaccgac ggcaccccca ccagcgtgca ggaagtggcc ccacatacag      1800
gcagactgcc cgccaatcac gcccccgata tcctggccaa gagcccccag agtacaagag      1860
ccgtggcccc ccagaagtgc ttcctgcaga tcaagggcat gacttgtgcc tcttgtgtgt      1920
ccaatatcga gcggaacctg cagaaagagg ccggcgtgct gtctgtgctg gtggctctga      1980
tggccggcaa ggccgagatc aaatacgacc ccgaagtgat tcagcccctg gaaatcgccc      2040
agtttatcca ggacctgggc tttgaagccg ccgtgatgga agattacgcc ggctccgacg      2100
gcaacatcga gctgaccatc accggaatga cctgcgcctc ctgtgtgcac aacattgagt      2160
ccaagctgac ccggaccaac ggcatcacct acgcctctgt ggctctggcc acctccaagg      2220
ccctcgtgaa gttcgatccc gagatcatcg gccccaggga catcatcaag atcatcgaag      2280
agatcggctt ccacgccagc ctggcccaga ggaaccctaa cgcccaccac ctggaccaca      2340
agatggaaat caagcagtgg aagaaaagct tcctgtgcag cctggtgttc ggcatccccg      2400
tgatggccct gatgatctac atgctgatcc ccagcaacga gccccaccag tccatggtgc      2460
tggatcacaa catcatcccc ggcctgtcta tcctgaacct gatcttcttc atcctgtgca      2520
ccttcgtgca gctgctgggc ggctggtact tctacgtgca ggcctacaag tccctgcggc      2580
acagatccgc caacatggac gtgctgatcg tgctggccac atctatcgcc tacgtgtact      2640
ccctcgtgat cctggtggtg gccgtggccg agaaagccga gagaagccct gtgaccttct      2700
tcgacacccc ccctatgctg ttcgtgttta tcgccctggg ccggtggctg aacacctgg      2760 ccaaaagcaa gaccagcgag gccctggcta agctgatgag tctgcaggcc accgaggcca      2820
cagtcgtgac cctgggcgag gacaacctga tcatccgcga ggaacaggtg ccaatggaac      2880
tggtgcagcg gggcgacatc gtgaaggtgg tgcctggcgg caagttcccc gtggacggaa      2940
aagtgctgga agggaatacc atggccgacg agagcctgat cacaggcgag gccatgcccg      3000
tgaccaagaa acctggcagc acagtgatcg ccggcagcat caatgcccac ggcagcgtgc      3060
tgattaaggc cacacacgtg ggcaacgata ccaccctggc tcagattgtg aagctggtgg      3120
aagaggccca gatgagcaag gcccccattc agcagctggc tgaccggttc agcggctact      3180
tcgtgccctt tatcatcatc atgagcaccc tgacactggt cgtgtggatc gtgatcggct      3240
ttatcgactt cggagtggtg cagagatact cccccaaccc taacaagcac atcagccaga      3300
cagaagtgat catcagattc gcctttcaga ccagcatcac cgtgctgtgt atcgcctgcc      3360
cctgtagcct gggactggcc acacctaccg ctgtgatggt gggaacaggc gtggccgctc      3420
agaacggcat cctgatcaag gggggcaagc tctggaaaat ggctcacaag atcaagaccg      3480
tgatgttcga caagaccggc accatcaccc acggcgtgcc cagagtgatg agagtgctgc      3540
tgctggggga tgtggccacc ctgcctctga gaaaggtgct ggctgtcgtg ggcacagccg      3600
aggctagctc tgaacaccca ctgggagtgg ccgtgacaaa gtactgcaaa gaggaactgg      3660
gcaccgaaac cctgggctac tgcaccgact tcaggccgt gcctggctgt ggcatcggct      3720
gcaaggtgtc caacgtggaa ggcatcctgg cccacagcga gaggccactg tctgcccctg      3780
ccagccacct gaacgaggcc ggatctctgc ccgccgaaaa ggacgctgtg ccccagacct      3840
```

```
tctctgtgct gattggcaac agagagtggc tgcggcggaa cggcctgacc atctcctccg    3900
atgtgtccga cgccatgacc gaccacgaga tgaagggcca gaccgccatt ctggtggcca    3960
ttgacggggt gctgtgcggc atgatcgcaa tcgccgatgc cgtgaaacag gaagcagcac    4020
tggccgtgca caccctgcag tctatgggag tggatgtggt gctgatcacc ggcgacaaca    4080
gaaagaccgc cagggccatt gccacccagg tgggcatcaa caaggtgttc gccgaggtgc    4140
tgcccagcca caaagtggcc aaggtgcagg aactgcagaa caaaggcaaa aaggtggcca    4200
tggtgggaga tggcgtgaac gactctcctg ctctggccca ggcagatatg ggcgtggcca    4260
tcggcacagg caccgacgtg gcaattgagg ctgctgacgt ggtgctgatt cggaacgacc    4320
tgctggacgt ggtggcctcc atccacctgt ccaagagaac cgtgcggcgg atcagaatca    4380
acctggtgct ggcactgatc tataacctcg tgggcatccc tatcgccgct ggcgtgttca    4440
tgcctatcgg aatcgtgctg cagccctgga tgggctctgc cgccatggct gcaagctccg    4500
tgtctgtggt gctgtccagc ctgcagctga agtgctacaa gaagcccgac ctggaaagat    4560
acgaggccca ggcccacgga cacatgaagc ctctgacagc ctcccaggtg tccgtgcaca    4620
tcggcatgga cgacagatgg cgggacagcc ctagagccac cccttgggat caggtgtcat    4680
acgtgtcaca ggtgtccctg agcagcctga ccagcgacaa gccagcagaa catagcgccg    4740
ctgccgacga cgatggggac aagtggtccc tgctgctgaa cggccgggat gaggaacagt    4800
acatctgata agcatgcaat aaagtctgag tgggcggcag cctgtgtgtg cctgggttct    4860
ctctgtcccg aatgtgcaa acaatggagg tgctcgagta gataagtagc atggcgggtt    4920
aatcattaac tacaaggaac ccctagtgat ggagttggcc actccctctc tgcgcgctcg    4980
ctcgctcact gaggccgggc gaccaaaggt cgcccgacgc ccgggctttg cccgggcggc    5040
ctcagtgagc gagcgagcgc gcagccttaa ttaacctaat tcactggccg tcgttttaca    5100
acgtcgtgac tgggaaaacc ctggcgttac ccaacttaat cgccttgcag cacatccccc    5160
tttcgccagc tggcgtaata gcgaagaggc ccgcaccgat cgcccttccc aacagttgcg    5220
cagcctgaat ggcgaatggg acgcgccctg tagcggcgca ttaagcgcgg cgggtgtggt    5280
ggttacgcgc agcgtgaccg ctacacttgc cagcgcccta gcgcccgctc ctttcgcttt    5340
cttcccttcc tttctcgcca cgttcgccgg ctttccccgt caagctctaa atcgggggct    5400
ccctttaggg ttccgattta gtgctttacg gcacctcgac cccaaaaaac ttgattaggg    5460
tgatggttca cgtagtgggc catcgccctg atagacggtt tttcgccctt tgacgttgga    5520
gtccacgttc tttaatagtg gactcttgtt ccaaactgga acaacactca acctatctc    5580 ggtctattct tttgatttat aagggatttt gccgatttcg gcctattggt taaaaaatga    5640
gctgatttaa caaaaattta acgcgaattt taacaaaata ttaacgctta caatttaggt    5700 ggcactttc ggggaaatgt gcgcggaacc cctatttgtt tatttttcta aatacattca    5760
aatatgtatc cgctcatgag acaataaccc tgataaatgc ttcaataata ttgaaaaagg    5820
aagagtatga gtattcaaca tttccgtgtc gcccttattc cctttttgc ggcatttttgc    5880 cttcctgttt ttgctcaccc agaaacgctg gtgaaagtaa agatgctga agatcagttg    5940 ggtgcacgag tgggttacat cgaactggat ctcaacagcg gtaagatcct tgagagtttt    6000
cgccccgaag aacgttttcc aatgatgagc acttttaaag ttctgctatg tggcgcggta    6060
ttatcccgta ttgacgccgg gcaagagcaa ctcggtcgcc gcatacacta ttctcagaat    6120
gacttggttg agtactcacc agtcacagaa aagcatctta cggatggcat gacagtaaga    6180
gaattatgca gtgctgccat aaccatgagt gataacactg cggccaactt acttctgaca    6240
```

```
acgatcggag gaccgaagga gctaaccgct tttttgcaca acatggggga tcatgtaact      6300
cgccttgatc gttgggaacc ggagctgaat gaagccatac caaacgacga gcgtgacacc      6360
acgatgcctg tagcaatggc aacaacgttg cgcaaactat taactggcga actacttact      6420
ctagcttccc ggcaacaatt aatagactgg atggaggcgg ataaagttgc aggaccactt      6480
ctgcgctcgg cccttccggc tggctggttt attgctgata atctggagc cggtgagcgt      6540 gggtctcgcg gtatcattgc agcactgggg ccagatggta agccctcccg tatcgtagtt      6600
atctacacga cggggagtca ggcaactatg gatgaacgaa atagacagat cgctgagata      6660
ggtgcctcac tgattaagca ttggtaactg tcagaccaag tttactcata tatactttag      6720
attgatttaa aacttcattt ttaatttaaa aggatctagg tgaagatcct ttttgataat      6780
ctcatgacca aaatccctta acgtgagttt tcgttccact gagcgtcaga ccccgtagaa      6840
aagatcaaag gatcttcttg agatcctttt tttctgcgcg taatctgctg cttgcaaaca      6900
aaaaaaccac cgctaccagc ggtggtttgt ttgccggatc aagagctacc aactctttt      6960 ccgaaggtaa ctggcttcag cagagcgcag ataccaaata ctgttcttct agtgtagccg      7020
tagttaggcc accacttcaa gaactctgta gcaccgccta catacctcgc tctgctaatc      7080
ctgttaccag tggctgctgc cagtggcgat aagtcgtgtc ttaccgggtt ggactcaaga      7140
cgatagttac cggataaggc gcagcggtcg ggctgaacgg ggggttcgtg cacacagccc      7200
agcttggagc gaacgaccta caccgaactg agatacctac agcgtgagct atgagaaagc      7260
gccacgcttc ccgaagggag aaaggcggac aggtatccgg taagcggcag gtcggaaca       7320 ggagagcgca cgagggagct tccaggggga aacgcctggt atctttatag tcctgtcggg      7380
tttcgccacc tctgacttga gcgtcgattt ttgtgatgct cgtcagggg gcggagccta       7440 tggaaaaacg ccagcaacgc ggccttttta cggttcctgg ccttttgctg ccttttgct      7500 cacatgttct ttcctgcgtt atcccctgat tctgtggata accgtattac cgcctttgag      7560
tgagctgata ccgctcgccg cagccgaacg accgagcgca gcgagtcagt gagcgaggaa      7620
gcggaagagc gcccaatacg caaaccgcct ctccccgcgc gttggccgat tcattaatgc      7680
agctggcacg acaggtttcc cgactggaaa gcgggcagtg agcgcaacgc aattaatgtg      7740
agttagctca ctcattaggc accccaggct ttacacttta tgcttccggc tcgtatgttg      7800
tgtggaattg tgagcggata acaatttcac acaggaaaca gctatgacca tgattacgcc      7860
agatttaatt aagg                                                        7874
```

<210> SEQ ID NO 26
<211> LENGTH: 7878
<212> TYPE: DNA
<213> ORGANISM: Artificial Sequence
<220> FEATURE:
<223> OTHER INFORMATION: constructed sequence

<400> SEQUENCE: 26

```
ctgcgcgctc gctcgctcac tgaggccgcc cgggcaaagc ccgggcgtcg ggcgaccttt       60
ggtcgcccgg cctcagtgag cgagcgagcg cgcagagagg gagtggccaa ctccatcact      120
aggggttcct tgtagttaat gattaacccg ccatgctact tatctactta agtgtttgct      180
gcttgcaatg tttgcccatt ttaggggaat tcatttcata gaacgaatgt tccgatgctc      240
taatctctct agacaaggtt catatttgta tgggttactt attctctctt tgttgactaa      300
gtcaataatc agaatcagca ggtttgcagt cagattggca gggataagca gcctagctca      360
```

```
ggagaagtga gtataaaagc cccaggctgg gagcagccat cagcggccgc caccatgccc    420
gagcaggaaa gacagatcac cgccagagag ggcgccagcc ggaagatcct gagcaagctg    480
agcctgccca ccagagcctg ggagcccgcc atgaagaagt ccttcgcctt cgacaacgtg    540
ggctacgagg cgcgcctgga cggactggga ccatcttctc aggtggccac aagcaccgtg    600
cgcatcctgg gcatgaccct ccagagctgc gtgaagtcca tcgaggaccg gatcagcaac    660
ctgaagggca tcatcagcat gaaggtgtcc tggaacaggg cagcgccac cgtgaaatac    720 gtgccctctg tcgtgtgcct gcagcaggtg tgccaccaga tcggcgacat gggcttcgag    780
gcctctatcg ccgagggaaa ggccgcctct tggccctcta gaagcctgcc tgctcaggaa    840
gccgtcgtga agctgcgggt ggaagggatg acctgtcagt cctgcgtgtc cagcatcgag    900
ggcaaagtgc ggaagctgca gggcgtggtg cgcgtgaaag tgtctctgag caaccaggaa    960
gctgtgatca cctaccagcc ctacctgatc cagcccgagg acctgaggga ccacgtgaac   1020
gatatgggat ttgaggccgc catcaagagc aaggtggccc ctctgtctct gggccccatc   1080
gacatcgaga actgcagag caccaacccc aagcggcctc tgagcagcgc caaccagaac   1140
ttcaacaaca gcgagacact gggccaccag ggcagccacg tcgtgacact gcagctgcgg   1200
atcgacggaa tgcactgcaa gagctgtgtg ctgaacatcg aggaaaacat cggccagctg   1260
ctgggagtgc agagcatcca ggtgtcactg gaaaacaaga ccgcccaggt gaagtacgac   1320
cccagctgca aagccccgt ggccctgcag agagccattg aagctctgcc cctggcaac    1380 ttcaaagtgt ccctgcctga cggagccgag ggctccggaa cagatcacag aagcagcagc   1440
agccacagcc ctggcagccc ccctagaaat caggtgcagg gcacctgtag caccacccctg  1500 atcgccattg ccggcatgac atgcgccagc tgcgtgcact ctattgaggg catgatctcc   1560
cagctggaag gcgtgcagca gatcagtgtg tctctggccg agggcaccgc cacagtgctg   1620
tacaacccta gcgtgatcag ccccgaagaa ctgagagccg ccattgagga catgggattc   1680
gaagccagcg tggtgtccga gagctgctcc accaaccctc tgggcaatca cagcgccggc   1740
aacagcatgg tgcagaccac cgacggcacc cccaccagcg tgcaggaagt ggccccacat   1800
acaggcagac tgcccgccaa tcacgccccc gatatcctgg ccaagagccc ccagagtaca   1860
agagccgtgg cccccagaa gtgcttcctg cagatcaagg gcatgacttg tgcctcttgt    1920
gtgtccaata tcgagcggaa cctgcagaaa gaggccggcg tgctgtctgt gctggtggct   1980
ctgatggccg gcaaggccga gatcaaatac gaccccgaag tgattcagcc cctggaaatc   2040
gcccagttta tccaggacct gggctttgaa gccgccgtga tggaagatta cgccggctcc   2100
gacggcaaca tcgagctgac catcaccgga atgacctgcg cctcctgtgt gcacaacatt   2160
gagtccaagc tgacccggac caacggcatc acctacgcct ctgtggctct ggccacctcc   2220
aaggccctcg tgaagttcga tcccgagatc atcgccccca gggacatcat caagatcatc   2280
gaagagatcg gcttccacgc cagcctggcc cagaggaacc taacgccca ccacctggac   2340 cacaagatgg aaatcaagca gtggaagaaa agcttcctgt gcagcctggt gttcggcatc   2400
cccgtgatgg ccctgatgat ctacatgctg atccccagca cgagccccca ccagtccatg   2460
gtgctggatc acaacatcat ccccggcctg tctatcctga acctgatctt cttcatcctg   2520
tgcaccttcg tgcagctgct gggcggctgg tacttctacg tgcaggccta caagtccctg   2580
cggcacagat ccgccaacat ggacgtgctg atcgtgctgg ccacatctat cgcctacgtg   2640
tactccctcg tgatcctggt ggtggccgtg gccgagaaag ccgagagaag ccctgtgacc   2700
ttcttcgaca ccccccctat gctgttcgtg tttatcgccc tgggccggtg gctggaacac   2760
```

```
ctggccaaaa gcaagaccag cgaggccctg gctaagctga tgagtctgca ggccaccgag    2820
gccacagtcg tgaccctggg cgaggacaac ctgatcatcc gcgaggaaca ggtgccaatg    2880
gaactggtgc agcggggcga catcgtgaag gtggtgcctg gcggcaagtt ccccgtggac    2940
ggaaaagtgc tggaagggaa taccatggcc gacgagagcc tgatcacagg cgaggccatg    3000
cccgtgacca agaaacctgg cagcacagtg atcgccggca gcatcaatgc ccacggcagc    3060
gtgctgatta aggccacaca cgtgggcaac gataccaccc tggctcagat tgtgaagctg    3120
gtggaagagg cccagatgag caaggccccc attcagcagc tggctgaccg gttcagcggc    3180
tacttcgtgc cctttatcat catcatgagc accctgacac tggtcgtgtg gatcgtgatc    3240
ggctttatcg acttcggagt ggtgcagaga tacttcccca accctaacaa gcacatcagc    3300
cagacagaag tgatcatcag attcgccttt cagaccagca tcaccgtgct gtgtatcgcc    3360
tgcccctgta gcctgggact ggccacacct accgctgtga tggtgggaac aggcgtggcc    3420
gctcagaacg catcctgat caaggggggc aagcctctgg aaatggctca caagatcaag    3480
accgtgatgt tcgacaagac cggcaccatc acccacggcg tgcccagagt gatgagagtg    3540
ctgctgctgg gggatgtggc cacccctgcct ctgagaaagg tgctggctgt cgtgggcaca    3600
gccgaggcta gctctgaaca cccactggga gtggccgtga caaagtactg caaagaggaa    3660
ctgggcaccg aaaccctggg ctactgcacc gactttcagg ccgtgcctgg ctgtggcatc    3720
ggctgcaagg tgtccaacgt ggaaggcatc ctggcccaca gcgagaggcc actgtctgcc    3780
cctgccagcc acctgaacga ggccggatct ctgcccgccg aaaaggacgc tgtgccccag    3840
accttctctg tgctgattgg caacagagag tggctgcggc ggaacggcct gaccatctcc    3900
tccgatgtgt ccgacgccat gaccgaccac gagatgaagg ccagaccgc cattctggtg    3960
gccattgacg gggtgctgtg cggcatgatc gcaatcgccg atgccgtgaa acaggaagca    4020
gcactggccg tgcacaccct gcagtctatg ggagtggatg tggtgctgat caccggcgac    4080
aacagaaaga ccgccagggc cattgccacc caggtgggca tcaacaaggt gttcgccgag    4140
gtgctgccca gccacaaagt ggccaaggtg caggaactgc agaacaaagg caaaaaggtg    4200
gccatggtgg gagatggcgt gaacgactct cctgctctgg cccaggcaga tatgggcgtg    4260
gccatcggca caggcaccga cgtggcaatt gaggctgctg acgtggtgct gattcggaac    4320
gacctgctgg acgtggtggc ctccatccac ctgtccaaga gaaccgtgcg gcggatcaga    4380
atcaacctgg tgctggcact gatctataac ctcgtgggca tccctatcgc cgctggcgtg    4440
ttcatgccta tcggaatcgt gctgcagccc tggatgggct ctgccgccat ggctgcaagc    4500
tccgtgtctg tggtgctgtc cagcctgcag ctgaagtgct acaagaagcc cgacctggaa    4560
agatacgagg cccaggccca cggacacatg aagcctctga cagcctccca ggtgtccgtg    4620
cacatcggca tggacgacag atggcgggac agccctagag ccacccccttg ggatcaggtg    4680
tcatacgtgt cacaggtgtc cctgagcagc ctgaccagcg acaagcccag cagacatagc    4740
gccgctgccg acgacgatgg ggacaagtgg tccctgctgc tgaacggccg ggatgaggaa    4800
cagtacatct gataagcatg caataaagtc tgagtgggcg gcagcctgtg tgtgcctggg    4860
ttctctctgt cccggaatgt gcaaacaatg gaggtgctcg agtagataag tagcatggcg    4920
ggttaatcat taactacaag gaacccctag tgatggagtt ggccactccc tctctgcgcg    4980
ctcgctcgct cactgaggcc gggcgaccaa aggtcgcccg acgcccgggc tttgcccggg    5040
cggcctcagt gagcgagcga gcgcgcagcc ttaattaacc taattcactg gccgtcgttt    5100
```

```
tacaacgtcg tgactgggaa accctggcg ttacccaact taatcgcctt gcagcacatc    5160
cccctttcgc cagctggcgt aatagcgaag aggcccgcac cgatcgccct tcccaacagt    5220
tgcgcagcct gaatggcgaa tgggacgcgc cctgtagcgg cgcattaagc gcggcgggtg    5280
tggtggttac gcgcagcgtg accgctacac ttgccagcgc cctagcgccc gctcctttcg    5340
ctttcttccc ttcctttctc gccacgttcg ccggctttcc ccgtcaagct ctaaatcggg    5400
ggctcccttt agggttccga tttagtgctt tacggcacct cgaccccaaa aaacttgatt    5460
agggtgatgg ttcacgtagt gggccatcgc cctgatagac ggtttttcgc cctttgacgt    5520
tggagtccac gttctttaat agtggactct tgttccaaac tggaacaaca ctcaacccta    5580
tctcggtcta ttcttttgat ttataaggga ttttgccgat ttcggcctat tggttaaaaa    5640
atgagctgat ttaacaaaaa tttaacgcga attttaacaa atattaacg cttacaattt    5700 aggtggcact tttcggggaa atgtgcgcgg aacccctatt tgtttatttt tctaaataca    5760
ttcaaatatg tatccgctca tgagacaata accctgataa atgcttcaat aatattgaaa    5820
aaggaagagt atgagtattc aacatttccg tgtcgccctt attcccttt ttgcggcatt    5880 ttgccttcct gttttgctc acccagaaac gctggtgaaa gtaaaagatg ctgaagatca    5940
gttgggtgca cgagtgggtt acatcgaact ggatctcaac agcggtaaga tccttgagag    6000
ttttcgcccc gaagaacgtt ttccaatgat gagcactttt aaagttctgc tatgtggcgc    6060
ggtattatcc cgtattgacg ccgggcaaga gcaactcggt cgccgcatac actattctca    6120
gaatgacttg gttgagtact caccagtcac agaaaagcat cttacggatg catgacagt    6180 aagagaatta tgcagtgctg ccataaccat gagtgataac actgcggcca acttacttct    6240
gacaacgatc ggaggaccga aggagctaac cgcttttttg cacaacatgg gggatcatgt    6300
aactcgcctt gatcgttggg aaccggagct gaatgaagcc ataccaaacg acgagcgtga    6360
caccacgatg cctgtagcaa tggcaacaac gttgcgcaaa ctattaactg gcgaactact    6420
tactctagct tcccggcaac aattaataga ctggatggag gcggataaag ttgcaggacc    6480
acttctgcgc tcggcccttc cggctggctg gtttattgct gataaatctg gagccggtga    6540
gcgtgggtct cgcggtatca ttgcagcact ggggccagat ggtaagccct cccgtatcgt    6600
agttatctac acgacgggga gtcaggcaac tatggatgaa cgaaatagac agatcgctga    6660
gataggtgcc tcactgatta agcattggta actgtcagac caagtttact catatatact    6720
ttagattgat ttaaaacttc atttttaatt taaaaggatc taggtgaaga tcctttttga    6780
taatctcatg accaaaatcc cttaacgtga gttttcgttc cactgagcgt cagaccccgt    6840
agaaaagatc aaaggatctt cttgagatcc ttttttttctg cgcgtaatct gctgcttgca    6900
aacaaaaaaa ccaccgctac cagcggtggt ttgtttgccg gatcaagagc taccaactct    6960
ttttccgaag gtaactggct tcagcagagc gcagatacca atactgttc ttctagtgta    7020 gccgtagtta ggccaccact tcaagaactc tgtagcaccg cctacatacc tcgctctgct    7080
aatcctgtta ccagtggctg ctgccagtgg cgataagtcg tgtcttaccg ggttggactc    7140
aagacgatag ttaccggata aggcgcagcg gtcgggctga cgggggggtt cgtgcacaca    7200
gcccagcttg gagcgaacga cctacaccga actgagatac ctacagcgtg agctatgaga    7260
aagcgccacg cttcccgaag ggagaaaggc ggacaggtat ccggtaagcg cagggtcgg    7320 aacaggagag cgcacgaggg agcttccagg gggaaacgcc tggtatcttt atagtcctgt    7380
cgggtttcgc cacctctgac ttgagcgtcg attttttgtga tgctcgtcag ggggcggag    7440 cctatggaaa aacgccagca acgcggcctt tttacggttc ctggccttt gctggccttt    7500
```

```
tgctcacatg ttctttcctg cgttatcccc tgattctgtg gataaccgta ttaccgcctt    7560
tgagtgagct gataccgctc gccgcagccg aacgaccgag cgcagcgagt cagtgagcga    7620
ggaagcggaa gagcgcccaa tacgcaaacc gcctctcccc gcgcgttggc cgattcatta    7680
atgcagctgg cacgacaggt ttcccgactg gaaagcgggc agtgagcgca acgcaattaa    7740
tgtgagttag ctcactcatt aggcacccca ggctttacac tttatgcttc cggctcgtat    7800
gttgtgtgga attgtgagcg gataacaatt tcacacagga aacagctatg accatgatta    7860
cgccagattt aattaagg                                                 7878

<210> SEQ ID NO 27
<211> LENGTH: 7858
<212> TYPE: DNA
<213> ORGANISM: Artificial Sequence
<220> FEATURE:
<223> OTHER INFORMATION: constructed sequence

<400> SEQUENCE: 27
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact     120
aggggttcct tgtagttaat gattaacccg ccatgctact tatctactta agtgtttgct     180
gcttgcaatg tttgcccatt ttaggggaat tccgatgctc taatctctct agacaaggtt     240
catatttgta tgggttactt attctctctt tgttgactaa gtcaataatc agaatcagca     300
ggtttgcagt cagattggca gggataagca gcctagctca ggagaagtga gtataaaagc     360
cccaggctgg gagcagccat cagcggccgc caccatgccc gagcaggaaa gacagatcac     420
cgccagagag ggcgccagcc ggaagatcct gagcaagctg agcctgccca ccagagcctg     480
ggagcccgcc atgaagaagt ccttcgcctt cgacaacgtg ggctacgagg gcggcctgga     540
cggactggga ccatcttctc aggtggccac aagcaccgtg cgcatcctgg gcatgacctg     600
ccagagctgc gtgaagtcca tcgaggaccg gatcagcaac ctgaagggca tcatcagcat     660
gaaggtgtcc ctggaacagg gcagcgccac cgtgaaatac gtgccctctg tcgtgtgcct     720
gcagcaggtg tgccaccaga tcggcgacat gggcttcgag gcctctatcg ccgagggaaa     780
ggccgcctct tggcccctcta gaagcctgcc tgctcaggaa gccgtcgtga agctgcgggt     840
ggaagggatg acctgtcagt cctgcgtgtc cagcatcgag ggcaaagtgc ggaagctgca     900
gggcgtggtg cgcgtgaaag tgtctctgag caaccaggaa gctgtgatca cctaccagcc     960
ctacctgatc cagcccgagg acctgaggga ccacgtgaac gatatgggat tgaggccgc     1020 catcaagagc aaggtggccc ctctgtctct gggccccatc gacatcgaga gactgcagag    1080
caccaacccc aagcggcctc tgagcagcgc caaccagaac ttcaacaaca gcgagacact    1140
gggccaccag ggcagccacg tcgtgacact gcagctgcgg atcgacggaa tgcactgcaa    1200
gagctgtgtg ctgaacatcg aggaaaacat cggccagctg ctgggagtgc agagcatcca    1260
ggtgtcactg gaaaacaaga ccgcccaggt gaagtacgac cccagctgca agcccgt      1320 ggccctgcag agagccattg aagctctgcc ccctggcaac ttcaaagtgt ccctgcctga    1380
cggagccgag ggctccggaa cagatcacag aagcagcagc agccacagcc ctggcagccc    1440
ccctagaaat caggtgcagg gcacctgtag caccacctg atcgccattg ccggcatgac    1500
atgcgccagc tgcgtgcact ctattgaggg catgatctcc cagctggaag gcgtgcagca    1560
gatcagtgtg tctctggccg agggcaccgc cacagtgctg tacaacccta gcgtgatcag    1620
```

```
ccccgaagaa ctgagagccg ccattgagga catgggattc gaagccagcg tggtgtccga    1680
gagctgctcc accaaccctc tgggcaatca cagcgccggc aacagcatgg tgcagaccac    1740
cgacggcacc cccaccagcg tgcaggaagt ggccccacat acaggcagac tgcccgccaa    1800
tcacgccccc gatatcctgg ccaagagccc cagagtaca agagccgtgg ccccccagaa     1860
gtgcttcctg cagatcaagg gcatgacttg tgcctcttgt gtgtccaata cgagcggaa     1920
cctgcagaaa gaggccggcg tgctgtctgt gctggtggct ctgatggccg gcaaggccga    1980
gatcaaatac gaccccgaag tgattcagcc cctggaaatc gcccagttta ccaggaccct    2040
gggctttgaa gccgccgtga tggaagatta cgccggctcc gacggcaaca tcgagctgac    2100
catcaccgga atgacctgcg cctcctgtgt gcacaacatt gagtccaagc tgacccggac    2160
caacggcatc acctacgcct ctgtggctct ggccacctcc aaggccctcg tgaagttcga    2220
tcccgagatc atcggcccca gggacatcat caagatcatc gaagagatcg gcttccacgc    2280
cagcctggcc cagaggaacc ctaacgccca ccacctggac cacaagatgg aaatcaagca    2340
gtggaagaaa agcttcctgt gcagcctggt gttcggcatc cccgtgatgg ccctgatgat    2400
ctacatgctg atccccagca acgagcccca ccagtccatg gtgctggatc acaacatcat    2460
ccccggcctg tctatcctga acctgatctt cttcatcctg tgcaccttcg tgcagctgct    2520
gggcggctgg tacttctacg tgcaggccta caagtccctg cggcacagat ccgccaacat    2580
ggacgtgctg atcgtgctgg ccacatctat cgcctacgtg tactccctcg tgatcctggt    2640
ggtggccgtg gccgagaaag ccgagagaag ccctgtgacc ttcttcgaca cccccccctat   2700
gctgttcgtg tttatcgccc tgggccggtg gctggaacac ctggccaaaa gcaagaccag    2760
cgaggccctg gctaagctga tgagtctgca ggccaccgag gccacagtcg tgaccctggg    2820
cgaggacaac ctgatcatcc gcgaggaaca ggtgccaatg gaactggtgc agcggggcga    2880
catcgtgaag gtggtgcctg cggcaagtt ccccgtggac ggaaaagtgc tggaagggaa     2940
taccatggcc gacgagagcc tgatcacagg cgaggccatg cccgtgacca agaaacctgg    3000
cagcacagtg atcgccggca gcatcaatgc ccacggcagc gtgctgatta aggccacaca    3060
cgtgggcaac gataccaccc tggctcagat tgtgaagctg gtggaagagg cccagatgag    3120
caaggccccc attcagcagc tggctgaccg gttcagcggc tacttcgtgc cctttatcat    3180
catcatgagc accctgacac tggtcgtgtg gatcgtgatc ggctttatcg acttcggagt    3240
ggtgcagaga tacttcccca ccctaacaa gcacatcagc cagacagaag tgatcatcag    3300
attcgccttt cagaccagca tcaccgtgct gtgtatcgcc tgccctgta gcctgggact    3360
ggccacacct accgctgtga tggtgggaac aggcgtggcc gctcagaacg gcatcctgat   3420
caagggggc aagcctctgg aaatggctca caagatcaag accgtgatgt tcgacaagac    3480
cggcaccatc acccacggcg tgcccagagt gatgagagtg ctgctgctgg gggatgtggc    3540
cacccctgcct ctgagaaagg tgctggctgt cgtgggcaca gccgaggcta gctctgaaca   3600
cccactggga gtggccgtga caaagtactg caaagaggaa ctgggcaccg aaaccctggg    3660
ctactgcacc gactttcagg ccgtgcctgg ctgtggcatc ggctgcaagg tgtccaacgt    3720
ggaaggcatc ctgccccaca gcgagaggcc actgtctgcc cctgccagcc acctgaacga    3780
ggccggatct ctgcccgccg aaaaggacgc tgtgcccag accttctctg tgctgattgg    3840
caacagagag tggctgcggc ggaacggcct gaccatctcc tccgatgtgt ccgacgccat    3900
gaccgaccac gagatgaagg ccagaccgc cattctggtg ccattgacg gggtgctgtg     3960
cggcatgatc gcaatcgccg atgccgtgaa acaggaagca gcactggccg tgcacaccct    4020
```

```
gcagtctatg ggagtggatg tggtgctgat caccggcgac aacagaaaga ccgccagggc   4080
cattgccacc caggtgggca tcaacaaggt gttcgccgag gtgctgccca gccacaaagt   4140
ggccaaggtg caggaactgc agaacaaagg caaaaaggtg ccatggtgg gagatggcgt    4200 gaacgactct cctgctctgg cccaggcaga tatgggcgtg ccatcggca caggcaccga    4260 cgtggcaatt gaggctgctg acgtggtgct gattcggaac gacctgctgg acgtggtggc   4320
ctccatccac ctgtccaaga gaaccgtgcg gcggatcaga atcaacctgg tgctggcact   4380
gatctataac ctcgtgggca tccctatcgc cgctggcgtg ttcatgccta tcggaatcgt   4440
gctgcagccc tggatgggct ctgccgccat ggctgcaagc tccgtgtctg tggtgctgtc   4500
cagcctgcag ctgaagtgct acaagaagcc cgacctggaa agatacgagg cccaggccca   4560
cggacacatg aagcctctga cagcctccca ggtgtccgtg cacatcggca tggacgacag   4620
atggcgggac agccctagag ccaccccttg ggatcaggtg tcatacgtgt cacaggtgtc   4680
cctgagcagc ctgaccagcg acaagcccag cagacatagc gccgctgccg acgacgatgg   4740
ggacaagtgg tccctgctgc tgaacggccg ggatgaggaa cagtacatct gataagcatg   4800
caataaagtc tgagtgggcg gcagcctgtg tgtgcctggg ttctctctgt cccggaatgt   4860
gcaaacaatg gaggtgctcg agtagataag tagcatggcg ggttaatcat taactacaag   4920 gaaccctag tgatggagtt ggccactccc tctctgcgcg ctcgctcgct cactgaggcc    4980
gggcgaccaa aggtcgcccg acgcccgggc tttgcccggg cggcctcagt gagcgagcga   5040
gcgcgcagcc ttaattaacc taattcactg gccgtcgttt tacaacgtcg tgactgggaa   5100
aaccctggcg ttacccaact taatcgcctt gcagcacatc cccctttcgc cagctggcgt   5160
aatagcgaag aggcccgcac cgatcgccct tcccaacagt tgcgcagcct gaatggcgaa   5220
tgggacgcgc cctgtagcgg cgcattaagc gcggcgggtg tggtggttac gcgcagcgtg   5280
accgctacac ttgccagcgc cctagcgccc gctcctttcg ctttcttccc ttcctttctc   5340
gccacgttcg ccggctttcc ccgtcaagct ctaaatcggg ggctcccttt agggttccga   5400
tttagtgctt tacggcacct cgaccccaaa aaacttgatt agggtgatgg ttcacgtagt   5460
gggccatcgc cctgatagac ggtttttcgc cctttgacgt tggagtccac gttctttaat   5520
agtggactct tgttccaaac tggaacaaca ctcaaccta tctcggtcta ttcttttgat    5580
ttataaggga ttttgccgat ttcggcctat tggttaaaaa atgagctgat ttaacaaaaa   5640
tttaacgcga attttaacaa aatattaacg cttacaattt aggtggcact tttcggggaa   5700
atgtgcgcgg aacccctatt tgtttatttt tctaaataca ttcaaatatg tatccgctca   5760
tgagacaata accctgataa atgcttcaat aatattgaaa aaggaagagt atgagtattc   5820
aacatttccg tgtcgccctt attcccttt ttgcggcatt ttgccttcct gttttgctc     5880 acccagaaac gctggtgaaa gtaaaagatg ctgaagatca gttgggtgca cgagtgggtt   5940
acatcgaact ggatctcaac agcggtaaga tccttgagag ttttcgcccc gaagaacgtt   6000
ttccaatgat gagcactttt aaagttctgc tatgtggcgc ggtattatcc cgtattgacg   6060
ccgggcaaga gcaactcggt cgccgcatac actattctca gaatgacttg gttgagtact   6120
caccagtcac agaaaagcat cttacggatg gcatgacagt aagagaatta tgcagtgctg   6180
ccataaccat gagtgataac actgcggcca acttacttct gacaacgatc ggaggaccga   6240
aggagctaac cgcttttttg cacaacatgg gggatcatgt aactcgcctt gatcgttggg   6300
aaccggagct gaatgaagcc ataccaaacg acgagcgtga ccaccacgatg cctgtagcaa   6360
```

```
tggcaacaac gttgcgcaaa ctattaactg gcgaactact tactctagct tcccggcaac    6420
aattaataga ctggatggag gcggataaag ttgcaggacc acttctgcgc tcggcccttc    6480
cggctggctg gtttattgct gataaatctg gagccggtga gcgtgggtct cgcggtatca    6540
ttgcagcact ggggccagat ggtaagccct cccgtatcgt agttatctac acgacgggga    6600
gtcaggcaac tatggatgaa cgaaatagac agatcgctga gataggtgcc tcactgatta    6660
agcattggta actgtcagac caagtttact catatatact ttagattgat ttaaaacttc    6720 attttttaatt taaaaggatc taggtgaaga tcctttttga taatctcatg accaaaatcc    6780
cttaacgtga gttttcgttc cactgagcgt cagaccccgt agaaaagatc aaaggatctt    6840
cttgagatcc tttttttctg cgcgtaatct gctgcttgca acaaaaaaa ccaccgctac    6900 cagcggtggt ttgtttgccg gatcaagagc taccaactct ttttccgaag gtaactggct    6960
tcagcagagc gcagatacca aatactgttc ttctagtgta gccgtagtta ggccaccact    7020
tcaagaactc tgtagcaccg cctacatacc tcgctctgct aatcctgtta ccagtggctg    7080
ctgccagtgg cgataagtcg tgtcttaccg ggttggactc aagacgatag ttaccggata    7140
aggcgcagcg gtcgggctga acggggggtt cgtgcacaca gcccagcttg gagcgaacga    7200
cctacaccga actgagatac ctacagcgtg agctatgaga aagcgccacg cttcccgaag    7260
ggagaaaggc ggacaggtat ccggtaagcg gcagggtcgg aacaggagag cgcacgaggg    7320
agcttccagg gggaaacgcc tggtatcttt atagtcctgt cgggtttcgc cacctctgac    7380
ttgagcgtcg attttttgtga tgctcgtcag ggggcggag cctatggaaa aacgccagca    7440
acgcggcctt tttacggttc ctggcctttt gctggccttt tgctcacatg ttctttcctg    7500
cgttatcccc tgattctgtg gataaccgta ttaccgcctt tgagtgagct gataccgctc    7560
gccgcagccg aacgaccgag cgcagcgagt cagtgagcga ggaagcggaa gagcgcccaa    7620
tacgcaaacc gcctctcccc gcgcgttggc cgattcatta atgcagctgg cacgacaggt    7680
ttcccgactg gaaagcgggc agtgagcgca acgcaattaa tgtgagttag ctcactcatt    7740
aggcacccca ggctttacac tttatgcttc cggctcgtat gttgtgtgga attgtgagcg    7800
gataacaatt tcacacagga aacagctatg accatgatta cgccagattt aattaagg    7858
```

<210> SEQ ID NO 28
<211> LENGTH: 7094
<212> TYPE: DNA
<213> ORGANISM: Artificial Sequence
<220> FEATURE:
<223> OTHER INFORMATION: constructed sequence
<400> SEQUENCE: 28

```
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact     120 agggggttcct tgtagttaat gattaacccg ccatgctact tatctactta agctagcagg    180
ttaattttta aaaagcagtc aaaagtccaa gtggcccttg gcagcattta ctctctctgt    240
ttgctctggt taataatctc aggagcacaa acattccaga tccaggttaa ttttaaaaa    300 gcagtcaaaa gtccaagtgg cccttggcag catttactct ctctgtttgc tctggttaat    360
aatctcagga gcacaaacat tccagatccg gcgcgccagg gctggaagct acctttgaca    420 tcattttcctc tgcgaatgca tgtataattt ctacagaacc tattagaaag gatcacccag    480
cctctgcttt tgtacaactt tccctttaaaa aactgccaat tccactgctg tttggccaa    540 tagtgagaac ttttttcctgc tgcctcttgg tgcttttgcc tatggcccct attctgcctg    600
```

```
ctgaagacac tcttgccagc atggacttaa accctccag ctctgacaat cctctttctc      660
ttttgtttta catgaagggt ctggcagcca aagcaatcac tcaaagttca aaccttatca      720 tttttgctt  tgttcctctt ggccttggtt ttgtacatca gctttgaaaa taccatccca     780
gggttaatgc tggggttaat ttataactaa gagtgctcta gttttgcaat acaggacatg      840
ctataaaaat ggaaagatgt tgctttctga gagactgcag aagttggtcg tgaggcactg      900
ggcaggtaag tatcaaggtt acaagacagg tttaaggaga ccaatagaaa ctgggcttgt      960
cgagacagag aagactcttg cgtttctgat aggcacctat tggtcttact gacatccact     1020
ttgcctttct ctccacaggt gtccaggcgg ccgccaccat gcccgagcag aaagacaga     1080 tcaccgccag agagggcgcc agccggaaga tcctgagcaa gctgagcctg cccaccagag     1140
cctgggagcc cgccatgaag aagtccttcg ccttcgacaa cgtgggctac gagggcggcc     1200
tggacggact gggaccatct tctcaggtgg ccacaagcac cgtgcgcctg gaaatcgccc     1260
agtttatcca ggacctgggc tttgaagcgc ccgtgatgga agattacgcc ggctccgacg     1320
gcaacatcga gctgaccatc accggaatga cctgcgcctc ctgtgtgcac aacattgagt     1380
ccaagctgac ccggaccaac ggcatcacct acgcctctgt ggctctggcc acctccaagg     1440
ccctcgtgaa gttcgatccc gagatcatcg gcccaggga catcatcaag atcatcgaag     1500
agatcggctt ccacgccagc ctggcccaga ggaaccctaa cgcccaccac ctggaccaca     1560
agatggaaat caagcagtgg aagaaaagct tcctgtgcag cctggtgttc ggcatccccg     1620
tgatggccct gatgatctac atgctgatcc ccagcaacga gcccaccag tccatggtgc      1680 tggatcacaa catcatcccc ggcctgtcta tcctgaacct gatcttcttc atcctgtgca     1740
ccttcgtgca gctgctgggc ggctggtact tctacgtgca ggcctacaag tccctgcggc     1800
acagatccgc caacatggac gtgctgatcg tgctggccac atctatcgcc tacgtgtact     1860
ccctcgtgat cctggtggtg gccgtggccg agaaagccga gaagagccct gtgaccttct     1920
tcgacacccc ccctatgctg ttcgtgttta tcgccctggg ccggtggctg aacacctgg     1980 ccaaaagcaa gaccagcgag gccctggcta agctgatgag tctgcaggcc accgaggcca     2040
cagtcgtgac cctgggcgag gacaacctga tcatccgcga ggaacaggtg ccaatggaac     2100
tggtgcagcg gggcgacatc gtgaaggtgg tgcctggcgg caagttcccc gtggacggaa     2160
aagtgctgga agggaatacc atggccgacg agagcctgat cacaggcgag gccatgcccg     2220
tgaccaagaa acctggcagc acagtgatcg ccggcagcat caatgcccac ggcagcgtgc     2280
tgattaaggc cacacacgtg ggcaacgata ccaccctggc tcagattgtg aagctggtgg     2340
aagaggccca gatgagcaag gcccccattc agcagctggc tgaccggttc agcggctact     2400
tcgtgccctt tatcatcatc atgagcaccc tgacactggt cgtgtggatc gtgatcggct     2460
ttatcgactt cggagtggtg cagagatact cccccaaccc taacaagcac atcagccaga     2520
cagaagtgat catcagattc gcctttcaga ccagcatcac cgtgctgtgt atcgcctgcc     2580
cctgtagcct gggactggcc acacctaccg ctgtgatggt gggaacaggc gtggccgctc     2640
agaacggcat cctgatcaag gggggcaagc ctctggaaat ggctcacaag atcaagaccg     2700
tgatgttcga caagaccggc accatcaccc acggcgtgcc cagagtgatg agagtgctgc     2760 tgctgggga tgtggccacc ctgcctctga aaaggtgct ggctgtcgtg ggcacagccg     2820
aggctagctc tgaacacca ctgggagtgg ccgtgacaaa gtactgcaaa gaggaactgg     2880
gcaccgaaac cctgggctac tgcaccgact ttcaggccgt gcctggctgt ggcatcggct     2940
```

```
gcaaggtgtc caacgtggaa ggcatcctgg cccacagcga gaggccactg tctgcccctg    3000
ccagccacct gaacgaggcc ggatctctgc ccgccgaaaa ggacgctgtg ccccagacct    3060
tctctgtgct gattggcaac agagagtggc tgcggcggaa cggcctgacc atctcctccg    3120
atgtgtccga cgccatgacc gaccacgaga tgaaggccca gaccgccatt ctggtggcca    3180
ttgacggggt gctgtgcggc atgatcgcaa tcgccgatgc cgtgaaacag gaagcagcac    3240
tggccgtgca caccctgcag tctatgggag tggatgtggt gctgatcacc ggcgacaaca    3300
gaaagaccgc cagggccatt gccacccagg tgggcatcaa caaggtgttc gccgaggtgc    3360
tgcccagcca caaagtggcc aaggtgcagg aactgcagaa caaggcaaa aaggtggcca    3420 tggtgggaga tggcgtgaac gactctcctg ctctggccca ggcagatatg ggcgtggcca    3480
tcggcacagg caccgacgtg gcaattgagg ctgctgacgt ggtgctgatt cggaacgacc    3540
tgctggacgt ggtggcctcc atccacctgt ccaagagaac cgtgcggcgg atcagaatca    3600
acctggtgct ggcactgatc tataacctcg tgggcatccc tatcgccgct ggcgtgttca    3660
tgcctatcgg aatcgtgctg cagccctgga tgggctctgc cgccatggct gcaagctccg    3720
tgtctgtggt gctgtccagc ctgcagctga agtgctacaa gaagcccgac ctggaaagat    3780
acgaggccca ggcccacgga cacatgaagc ctctgacagc ctcccaggtg tccgtgcaca    3840
tcggcatgga cgacagatgg cgggacagcc ctagagccac cccttgggat caggtgtcat    3900
acgtgtcaca ggtgtccctg agcagcctga ccagcgacaa gccagcaga catagcgccg    3960 ctgccgacga cgatggggac aagtggtccc tgctgctgaa cggccgggat gaggaacagt    4020
acatctgata agcatgcaat aaagtctgag tgggcggcag cctgtgtgtg cctgggttct    4080
ctctgtcccg gaatgtgcaa acaatggagg tgctcgagta gataagtagc atggcgggtt    4140
aatcattaac tacaaggaac ccctagtgat ggagttggcc actccctctc tgcgcgctcg    4200
ctcgctcact gaggccgggc gaccaaaggt cgcccgacgc ccgggctttg cccgggcggc    4260
ctcagtgagc gagcgagcgc gcagccttaa ttaacctaat tcactggccg tcgttttaca    4320
acgtcgtgac tgggaaaacc ctggcgttac ccaacttaat cgccttgcag cacatccccc    4380
tttcgccagc tggcgtaata gcgaagaggc ccgcaccgat cgcccttccc aacagttgcg    4440
cagcctgaat ggcgaatggg acgcgccctg tagcggcgca ttaagcgcgg cgggtgtggt    4500
ggttacgcgc agcgtgaccg ctacacttgc cagcgcccta gcgcccgctc ctttcgcttt    4560
cttcccttcc tttctcgcca cgttcgccgg ctttccccgt caagctctaa atcggggggct    4620 ccctttaggg ttccgattta gtgctttacg gcacctcgac cccaaaaaac ttgattaggg    4680
tgatggttca cgtagtgggc catcgccctg atagacggtt tttcgccctt tgacgttgga    4740
gtccacgttc tttaatagtg gactcttgtt ccaaactgga acaacactca acctatctc    4800 ggtctattct tttgatttat aagggatttt gccgatttcg gcctattggt taaaaatga    4860 gctgatttaa caaaaattta acgcgaattt taacaaaata ttaacgctta caatttaggt    4920
ggcacttttc ggggaaatgt gcgcggaacc cctatttgtt tatttttcta aatacattca    4980
aatatgtatc cgctcatgag acaataaccc tgataaatgc ttcaataata ttgaaaaagg    5040
aagagtatga gtattcaaca tttccgtgtc gcccttattc cctttttgc ggcatttgc    5100 cttcctgttt ttgctcaccc agaaacgctg gtgaaagtaa aagatgctga agatcagttg    5160
ggtgcacgag tgggttacat cgaactggat ctcaacagcg gtaagatcct tgagagtttt    5220
cgccccgaag aacgttttcc aatgatgagc acttttaaag ttctgctatg tggcgcggta    5280
ttatcccgta ttgacgccgg gcaagagcaa ctcggtcgcc gcatacacta ttctcagaat    5340
```

```
gacttggttg agtactcacc agtcacagaa aagcatctta cggatggcat gacagtaaga      5400
gaattatgca gtgctgccat aaccatgagt gataacactg cggccaactt acttctgaca      5460
acgatcggag gaccgaagga gctaaccgct tttttgcaca acatggggga tcatgtaact      5520
cgccttgatc gttgggaacc ggagctgaat gaagccatac aaacgacga gcgtgacacc       5580
acgatgcctg tagcaatggc aacaacgttg cgcaaactat taactggcga actacttact      5640
ctagcttccc ggcaacaatt aatagactgg atggaggcgg ataaagttgc aggaccactt      5700
ctgcgctcgg cccttccggc tggctggttt attgctgata atctggagc cggtgagcgt       5760
gggtctcgcg gtatcattgc agcactgggg ccagatggta agccctcccg tatcgtagtt      5820
atctacacga cggggagtca ggcaactatg gatgaacgaa atagacagat cgctgagata      5880
ggtgcctcac tgattaagca ttggtaactg tcagaccaag tttactcata tactttag       5940
attgatttaa aacttcattt ttaatttaaa aggatctagg tgaagatcct ttttgataat      6000
ctcatgacca aaatccctta acgtgagttt tcgttccact gagcgtcaga ccccgtagaa      6060
aagatcaaag gatcttcttg agatcctttt tttctgcgcg taatctgctg cttgcaaaca      6120
aaaaaaccac cgctaccagc ggtggtttgt ttgccggatc aagagctacc aactcttttt      6180
ccgaaggtaa ctggcttcag cagagcgcag ataccaaata ctgttcttct agtgtagccg      6240
tagttaggcc accacttcaa gaactctgta gcaccgccta catacctcgc tctgctaatc      6300
ctgttaccag tggctgctgc cagtggcgat aagtcgtgtc ttaccgggtt ggactcaaga      6360
cgatagttac cggataaggc gcagcggtcg ggctgaacgg ggggttcgtg cacacagccc      6420
agcttggagc gaacgaccta caccgaactg agatacctac agcgtgagct atgagaaagc      6480
gccacgcttc ccgaagggag aaaggcggac aggtatccgg taagcggcag gtcggaaca      6540
ggagagcgca cgagggagct ccaggggga aacgcctggt atctttatag tcctgtcggg      6600
tttcgccacc tctgacttga gcgtcgattt tgtgatgct cgtcaggggg gcggagccta      6660
tggaaaaacg ccagcaacgc ggccttttta cggttcctgg ccttttgctg ccttttgct      6720
cacatgttct ttcctgcgtt atcccctgat tctgtggata accgtattac cgcctttgag      6780
tgagctgata ccgctcgccg cagccgaacg accgagcgca gcgagtcagt gagcgaggaa      6840
gcggaagagc gcccaatacg caaaccgcct ctccccgcgc gttggccgat tcattaatgc      6900
agctggcacg acaggtttcc cgactggaaa gcgggcagtg agcgcaacgc aattaatgtg      6960
agttagctca ctcattaggc accccaggct ttacactttta tgcttccggc tcgtatgttg      7020
tgtggaattg tgagcggata acaatttcac acaggaaaca gctatgacca tgattacgcc      7080
agatttaatt aagg                                                        7094
```

<210> SEQ ID NO 29
<211> LENGTH: 7487
<212> TYPE: DNA
<213> ORGANISM: Artificial Sequence
<220> FEATURE:
<223> OTHER INFORMATION: constructed sequence

<400> SEQUENCE: 29

```
ctgcgcgctc gctcgctcac tgaggccgcc cgggcaaagc ccgggcgtcg ggcgaccttt       60
ggtcgcccgg cctcagtgag cgagcgagcg cgcagagagg gagtggccaa ctccatcact     120
aggggttcct tgtagttaat gattaacccg ccatgctact tatctactta agctagcagg     180
ttaattttta aaagcagtc aaaagtccaa gtggcccttg gcagcattta ctctctctgt      240
```

```
ttgctctggt taataatctc aggagcacaa acattccaga tccaggttaa tttttaaaaa        300
gcagtcaaaa gtccaagtgg cccttggcag catttactct ctctgtttgc tctggttaat        360
aatctcagga gcacaaacat tccagatccg gcgcgccagg gctggaagct acctttgaca        420
tcatttcctc tgcgaatgca tgtataattt ctacagaacc tattagaaag gatcacccag        480
cctctgcttt tgtacaactt tcccttaaaa aactgccaat tccactgctg tttggcccaa        540
tagtgagaac ttttcctgc tgcctcttgg tgcttttgcc tatggcccct attctgcctg         600
ctgaagacac tcttgccagc atggacttaa accctccag ctctgacaat cctctttctc         660
ttttgtttta catgaagggt ctggcagcca aagcaatcac tcaaagttca aaccttatca        720
ttttttgctt tgttcctctt ggccttggtt ttgtacatca gctttgaaaa taccatccca        780
gggttaatgc tggggttaat ttataactaa gagtgctcta gttttgcaat acaggacatg        840
ctataaaaat ggaaagatgt tgctttctga gagactgcag aagttggtcg tgaggcactg        900
ggcaggtaag tatcaaggtt acaagacagg tttaaggaga ccaatagaaa ctgggcttgt        960
cgagacagag aagactcttg cgtttctgat aggcaccrat tggtcttact gacatccact       1020
ttgcctttct ctccacaggt gtccaggcgg ccgccaccat gcccgagcag gaaagacaga       1080
tcaccgccag agagggcgcc agccggaaga tcctgagcaa gctgagcctg cccaccagag       1140
cctgggagcc cgccatgaag aagtccttcg ccttcgacaa cgtgggctac gagggcggcc       1200
tggacggact gggaccatct tctcaggtgg ccacaagcac cgtgcgcagc cccgaagaac       1260
tgagagccgc cattgaggac atgggattcg aagccagcgt ggtgtccgag agctgctcca       1320
ccaaccctct gggcaatcac agcgccggca acagcatggt gcagaccacc gacggcaccc       1380
ccaccagcgt gcaggaagtg gccccacata caggcagact gcccgccaat cacgcccccg       1440
atatcctggc caagagcccc cagagtacaa gagccgtggc cccccagaag tgcttcctgc       1500
agatcaaggg catgacttgt gcctcttgtg tgtccaatat cgagcggaac ctgcagaaag       1560
aggccggcgt gctgtctgtg ctggtggctc tgatggccgg caaggccgag atcaaatacg       1620
accccgaagt gattcagccc ctggaaatcg cccagtttat ccaggacctg ggctttgaag       1680
ccgccgtgat ggaagattac gccggctccg acggcaacat cgagctgacc atcaccggaa       1740
tgacctgcgc ctcctgtgtg cacaacattg agtccaagct gacccggacc aacggcatca       1800
cctacgcctc tgtggctctg gccacctcca aggccctcgt gaagttcgat cccgagatca       1860
tcggccccag ggacatcatc aagatcatcg aagagatcgg cttccacgcc agcctggccc       1920
agaggaaccc taacgcccac cacctggacc acaagatgga aatcaagcag tggaagaaaa       1980
gcttcctgtg cagcctggtg ttcggcatcc ccgtgatggc cctgatgatc tacatgctga       2040
tccccagcaa cgagcccccac cagtccatgg tgctggatca aacatcatc cccggcctgt        2100 ctatcctgaa cctgatcttc ttcatcctgt gcaccttcgt gcagctgctg ggcggctggt       2160
acttctacgt gcaggcctac aagtccctgc ggcacagatc cgccaacatg gacgtgctga       2220
tcgtgctggc cacatctatc gcctacgtgt actccctcgt gatcctggtg gtggccgtgg       2280
ccgagaaagc cgagagaagc cctgtgacct tcttcgacac ccccccatatg ctgttcgtgt       2340 ttatcgccct gggccggtgg ctggaacacc tggccaaaag caagaccagc gaggccctgg       2400
ctaagctgat gagtctgcag gccaccgagg ccacagtcgt gaccctgggc gaggacaacc       2460
tgatcatccg cgaggaacag gtgccaatgg aactggtgca gcggggcgac atcgtgaagg       2520
tggtgcctgg cggcaagttc cccgtggacg gaaaagtgct ggaagggaat accatggccg       2580
acgagagcct gatcacaggc gaggccatgc ccgtgaccaa gaaacctggc agcacagtga       2640
```

```
tcgccggcag catcaatgcc cacggcagcg tgctgattaa ggccacacac gtgggcaacg      2700
ataccaccct ggctcagatt gtgaagctgg tggaagaggc ccagatgagc aaggccccca      2760
ttcagcagct ggctgaccgg ttcagcggct acttcgtgcc ctttatcatc atcatgagca      2820
ccctgacact ggtcgtgtgg atcgtgatcg gctttatcga cttcggagtg gtgcagagat      2880
acttccccaa ccctaacaag cacatcagcc agacagaagt gatcatcaga ttcgcctttc      2940
agaccagcat caccgtgctg tgtatcgcct gccctgtag cctgggactg ccacaccta       3000 ccgctgtgat ggtgggaaca ggcgtggccg ctcagaacgg catcctgatc aagggggca      3060 agcctctgga aatggctcac aagatcaaga ccgtgatgtt cgacaagacc ggcaccatca      3120
cccacggcgt gcccagagtg atgagagtgc tgctgctggg ggatgtggcc accctgcctc      3180
tgagaaaggt gctggctgtc gtgggcacag ccgaggctag ctctgaacac ccactgggag      3240
tggccgtgac aaagtactgc aaagaggaac tgggcaccga aaccctgggc tactgcaccg      3300
actttcaggc cgtgcctggc tgtggcatcg gctgcaaggt gtccaacgtg gaaggcatcc      3360
tggcccacag cgagaggcca ctgtctgccc ctgccagcca cctgaacgag gccggatctc      3420
tgcccgccga aaaggacgct gtgccccaga ccttctctgt gctgattggc aacagagagt      3480
ggctgcggcg gaacggcctg accatctcct ccgatgtgtc cgacgccatg accgaccacg      3540
agatgaaggg ccagaccgcc attctggtgg ccattgacgg ggtgctgtgc ggcatgatcg      3600
caatcgccga tgccgtgaaa caggaagcag cactggccgt gcacaccctg cagtctatgg      3660
gagtggatgt ggtgctgatc accggcgaca acagaaagac cgccagggcc attgccaccc      3720
aggtgggcat caacaaggtg ttcgccgagg tgctgcccag ccacaaagtg gccaaggtgc      3780
aggaactgca gaacaaaggc aaaaaggtgg ccatggtggg agatgccgtg aacgactctc      3840
ctgctctggc ccaggcagat atgggcgtgg ccatcggcac aggcaccgac gtggcaattg      3900
aggctgctga cgtggtgctg attcggaacg acctgctgga cgtggtggcc tccatccacc      3960
tgtccaagag aaccgtgcgg cggatcagaa tcaacctggt gctggcactg atctataacc      4020
tcgtgggcat ccctatcgcc gctggcgtgt tcatgcctat cggaatcgtg ctgcagccct      4080
ggatgggctc tgccgccatg gctgcaagct ccgtgtctgt ggtgctgtcc agcctgcagc      4140
tgaagtgcta caagaagccc gacctggaaa gatacgaggc ccaggcccac ggacacatga      4200
agcctctgac agcctcccag gtgtccgtgc acatcggcat ggacgacaga tggcgggaca      4260
gccctagagc caccccttgg gatcaggtgt catacgtgtc acaggtgtcc ctgagcagcc      4320
tgaccagcga caagcccagc agacatagcg ccgctgccga cgacgatggg acaagtggt      4380 ccctgctgct gaacggccgg gatgaggaac agtacatctg ataagcatgc aataaagtct      4440
gagtgggcgg cagcctgtgt gtgcctgggt tctctctgtc ccggaatgtg caaacaatgg      4500
aggtgctcga gtagataagt agcatggcgg gttaatcatt aactacaagg aaccccctagt      4560 gatggagttg gccactccct ctctgcgcgc tcgctcgctc actgaggccg ggcgaccaaa      4620
ggtcgcccga cgcccgggct ttgcccgggc ggcctcagtg agcgagcgag cgcgcagcct      4680
taattaacct aattcactgg ccgtcgtttt acaacgtcgt gactgggaaa accctggcgt      4740
tacccaactt aatcgccttg cagcacatcc ccctttcgcc agctggcgta atagcgaaga      4800
ggcccgcacc gatcgccctt cccaacagtt gcgcagcctg aatggcgaat gggacgcgcc      4860
ctgtagcggc gcattaagcg cggcgggtgt ggtggttacg cgcagcgtga ccgctacact      4920
tgccagcgcc ctagcgcccg ctcctttcgc tttcttccct tcctttctcg ccacgttcgc      4980
```

```
cggctttccc cgtcaagctc taaatcgggg gctcccttta gggttccgat ttagtgcttt    5040
acggcacctc gaccccaaaa aacttgatta gggtgatggt tcacgtagtg ggccatcgcc    5100
ctgatagacg gttttccgcc ctttgacgtt ggagtccacg ttctttaata gtggactctt    5160
gttccaaact ggaacaacac tcaaccctat ctcggtctat tcttttgatt tataagggat    5220
tttgccgatt tcggcctatt ggttaaaaaa tgagctgatt taacaaaaat ttaacgcgaa    5280
ttttaacaaa atattaacgc ttacaattta gtggcactt tcggggaaa tgtgcgcgga    5340 accccctattt gtttattttt ctaaatacat tcaaatatgt atccgctcat gagacaataa    5400
ccctgataaa tgcttcaata atattgaaaa aggaagagta tgagtattca acatttccgt    5460
gtcgccctta ttcccttttt tgcggcattt tgccttcctg ttttgctca cccagaaacg    5520 ctggtgaaag taaaagatgc tgaagatcag ttgggtgcac gagtgggtta catcgaactg    5580
gatctcaaca gcggtaagat ccttgagagt tttcgccccg aagaacgttt tccaatgatg    5640 agcacttta aagttctgct atgtggcgcg gtattatccc gtattgacgc cgggcaagag    5700
caactcggtc gccgcataca ctattctcag aatgacttgg ttgagtactc accagtcaca    5760
gaaaagcatc ttacggatgg catgacagta agagaattat gcagtgctgc cataaccatg    5820
agtgataaca ctgcggccaa cttacttctg acaacgatcg gaggaccgaa ggagctaacc    5880
gcttttttgc acaacatggg ggatcatgta actcgccttg atcgttggga accggagctg    5940
aatgaagcca taccaaacga cgagcgtgac accacgatgc ctgtagcaat ggcaacaacg    6000
ttgcgcaaac tattaactgg cgaactactt actctagctt cccggcaaca attaatagac    6060
tggatggagg cggataaagt tgcaggacca cttctgcgct cggcccttcc ggctggctgg    6120
tttattgctg ataaatctgg agccggtgag cgtgggtctc gcggtatcat tgcagcactg    6180
gggccagatg gtaagccctc ccgtatcgta gttatctaca cgacggggag tcaggcaact    6240
atggatgaac gaaatagaca gatcgctgag ataggtgcct cactgattaa gcattggtaa    6300
ctgtcagacc aagtttactc atatatactt tagattgatt taaaacttca ttttttaattt    6360 aaaaggatct aggtgaagat cctttttgat aatctcatga ccaaaatccc ttaacgtgag    6420
ttttcgttcc actgagcgtc agaccccgta gaaaagatca aggatcttc ttgagatcct    6480 ttttttctgc gcgtaatctg ctgcttgcaa acaaaaaaac caccgctacc agcggtggtt    6540
tgtttgccgg atcaagagct accaactctt tttccgaagg taactggctt cagcagagcg    6600
cagataccaa atactgttct tctagtgtag ccgtagttag gccaccactt caagaactct    6660
gtagcaccgc ctacatacct cgctctgcta atcctgttac cagtggctgc tgccagtggc    6720
gataagtcgt gtcttaccgg gttggactca agacgatagt taccggataa ggcgcagcgg    6780
tcgggctgaa cggggggttc gtgcacacag cccagcttgg agcgaacgac ctacaccgaa    6840
ctgagatacc tacagcgtga gctatgagaa agcgccacgc ttcccgaagg gagaaaggcg    6900
gacaggtatc cggtaagcgg cagggtcgga acaggagagc gcacgaggga gcttccaggg    6960
ggaaacgcct ggtatcttta tagtcctgtc gggtttcgcc acctctgact tgagcgtcga    7020
tttttgtgat gctcgtcagg gggcggagc ctatggaaaa acgccagcaa cgcggccttt    7080
ttacggttcc tggccttttg ctggcctttt gctcacatgt tctttcctgc gttatcccct    7140
gattctgtgg ataaccgtat taccgccttt gagtgagctg ataccgctcg ccgcagccga    7200
acgaccgagc gcagcgagtc agtgagcgag gaagcggaag agcgcccaat acgcaaaccg    7260
cctctccccg cgcgttggcc gattcattaa tgcagctggc acgacaggtt cccgactgg     7320 aaagcgggca gtgagcgcaa cgcaattaat gtgagttagc tcactcatta ggcaccccag    7380
```

-continued

| | |
|---|---|
| gctttacact ttatgcttcc ggctcgtatg ttgtgtggaa ttgtgagcgg ataacaattt | 7440 |
| cacacaggaa acagctatga ccatgattac gccagattta attaagg | 7487 |

<210> SEQ ID NO 30
<211> LENGTH: 7788
<212> TYPE: DNA
<213> ORGANISM: Artificial Sequence
<220> FEATURE:
<223> OTHER INFORMATION: constructed sequence

<400> SEQUENCE: 30

| | |
|---|---|
| ctgcgcgctc gctcgctcac tgaggccgcc cgggcaaagc ccgggcgtcg ggcgaccttt | 60 |
| ggtcgcccgg cctcagtgag cgagcgagcg cgcagagagg gagtggccaa ctccatcact | 120 |
| aggggttcct tgtagttaat gattaacccg ccatgctact tatctactta agtgtttgct | 180 |
| gcttgcaatg tttgcccatt ttaggggaat tcactcaaag ttcaaacctt atcattttt | 240 |
| gctttgttcc tcttggcctt ggttttgtac atcagctttg aaaataccat cccagggtta | 300 |
| atgctggggt taatttataa ctaagagtgc tctagttttg caatacagga catgctataa | 360 |
| aaatggaaag atgttgcttt ctgagagaca gcggccgcca ccatgcccga gcaggaaaga | 420 |
| cagatcaccg ccagagaggg cgccagccgg aagatcctga gcaagctgag cctgcccacc | 480 |
| agagcctggg agcccgccat gaagaagtcc ttcgccttcg acaacgtggg ctacgagggc | 540 |
| ggcctggacg gactgggacc atcttctcag gtggccacaa gcaccgtgcg catcctgggc | 600 |
| atgacctgcc agagctgcgt gaagtccatc gaggaccgga tcagcaacct gaagggcatc | 660 |
| atcagcatga aggtgtccct ggaacagggc agcgccaccg tgaaatacgt gccctctgtc | 720 |
| gtgtgcctgc agcaggtgtg ccaccagatc ggcgacatgg gcttcgaggc ctctatcgcc | 780 |
| gagggaaagg ccgcctcttg gccctctaga agcctgcctg ctcaggaagc cgtcgtgaag | 840 |
| ctgcgggtgg aagggatgac ctgtcagtcc tgcgtgtcca gcatcgaggg caaagtgcgg | 900 |
| aagctgcagg gcgtggtgcg cgtgaaagtg tctctgagca accaggaagc tgtgatcacc | 960 |
| taccagccct acctgatcca gcccgaggac ctgagggacc acgtgaacga tatgggattt | 1020 |
| gaggccgcca tcaagagcaa ggtggcccct ctgtctctgg gccccatcga catcgagaga | 1080 |
| ctgcagagca ccaaccccaa gcggcctctg agcagcgcca accagaactt caacaacagc | 1140 |
| gagacactgg gccaccaggg cagccacgtc gtgacactgc agagcatcca ggtgtcactg | 1200 |
| gaaaacaaga ccgcccaggt gaagtacgac cccagctgca caagcccgt ggccctgcag | 1260 |
| agagccattg aagctctgcc ccctggcaac ttcaaagtgt ccctgcctga cggagccgag | 1320 |
| ggctccggaa cagatcacag aagcagcagc agccacagcc tggcagcccc cctagaaat | 1380 |
| caggtgcagg gcacctgtag caccaccctg atcgccattg ccggcatgac atgcgccagc | 1440 |
| tgcgtgcact ctattgaggg catgatctcc cagctggaag gcgtgcagca gatcagtgtg | 1500 |
| tctctggccg agggcaccgc cacagtgctg tacaaccta gcgtgatcag ccccgaagaa | 1560 |
| ctgagagccg ccattgagga catgggattc gaagccagcg tggtgtccga gagctgctcc | 1620 |
| accaaccctc tgggcaatca cagcgccggc aacagcatgg tgcagaccac cgacggcacc | 1680 |
| cccaccagcg tgcaggaagt ggccccacat acaggcagac tgcccgccaa tcacgccccc | 1740 |
| gatatcctgg ccaagagccc ccagagtaca agagccgtgg ccccccagaa gtgcttcctg | 1800 |
| cagatcaagg gcatgacctg tgcctcttgt gtgtccaata tcgagcggaa cctgcagaaa | 1860 |
| gaggccggcg tgctgtctgt gctggtggct ctgatggccg gcaaggccga gatcaaatac | 1920 |

```
gaccccgaag tgattcagcc cctggaaatc gcccagttta tccaggacct gggctttgaa   1980
gccgccgtga tggaagatta cgccggctcc gacggcaaca tcgagctgac catcaccgga   2040
atgacctgcg cctcctgtgt gcacaacatt gagtccaagc tgacccggac caacggcatc   2100
acctacgcct ctgtggctct ggccacctcc aaggccctcg tgaagttcga tcccgagatc   2160
atcggcccca gggacatcat caagatcatc gaagagatcg gcttccacgc cagcctggcc   2220
cagaggaacc ctaacgccca ccacctggac cacaagatgg aaatcaagca gtggaagaaa   2280
agcttcctgt gcagcctggt gttcggcatc ccgtgatgg ccctgatgat ctacatgctg   2340
atccccagca cgagcccca ccagtccatg gtgctggatc acaacatcat ccccggcctg   2400
tctatcctga acctgatctt cttcatcctg tgcaccttcg tgcagctgct gggcggctgg   2460
tacttctacg tgcaggccta caagtccctg cggcacagat ccgccaacat ggacgtgctg   2520
atcgtgctgg ccacatctat cgcctacgtg tactccctcg tgatcctggt ggtggccgtg   2580
gccgagaaag ccgagagaag ccctgtgacc ttcttcgaca ccccccctat gctgttcgtg   2640
tttatcgccc tgggccggtg gctggaacac ctggccaaaa gcaagaccag cgaggccctg   2700
gctaagctga tgagtctgca ggccaccgag gccacagtcg tgaccctggg cgaggacaac   2760
ctgatcatcc gcgaggaaca ggtgccaatg gaactggtgc agcggggcga catcgtgaag   2820
gtggtgcctg gcggcaagtt ccccgtggac ggaaaagtgc tggaagggaa taccatggcc   2880
gacgagagcc tgatcacagg cgaggccatg cccgtgacca agaaacctgg cagcacagtg   2940
atcgccggca gcatcaatgc ccacggcagc gtgctgatta aggccacaca cgtgggcaac   3000
gataccaccc tggctcagat tgtgaagctg gtggaagagg cccagatgag caaggccccc   3060
attcagcagc tggctgaccg gttcagcggc tacttcgtgc cctttatcat catcatgagc   3120
accctgacac tggtcgtgtg gatcgtgatc ggctttatcg acttcggagt ggtgcagaga   3180
tacttcccca accctaacaa gcacatcagc cagacagaag tgatcatcag attcgccttt   3240
cagaccagca tcaccgtgct gtgtatcgcc tgccctgta gcctgggact ggccacacct   3300
accgctgtga tggtgggaac aggcgtggcc gctcagaacg catcctgat caaggggggc   3360 aagcctctgg aaatggctca caagatcaag accgtgatgt tcgacaagac cggcaccatc   3420
acccacggcg tgcccagagt gatgagagtg ctgctgctgg gggatgtggc caccctgcct   3480
ctgagaaagg tgctggctgt cgtgggcaca gccgaggcta gctctgaaca cccactggga   3540
gtggccgtga caaagtactg caaagaggaa ctgggcaccg aaaccctggg ctactgcacc   3600
gactttcagg ccgtgcctgg ctgtggcatc ggctgcaagg tgtccaacgt ggaaggcatc   3660
ctggcccaca gcgagaggcc actgtctgcc cctgccagcc acctgaacga ggccggatct   3720
ctgcccgccg aaaaggacgc tgtgcccag accttctctg tgctgattgg caacagagag   3780
tggctgcggc ggaacggcct gaccatctcc tccgatgtgt ccgacgccat gaccgaccac   3840
gagatgaagg ccagaccgc cattctggtg gccattgacg gggtgctgtg cggcatgatc   3900
gcaatcgccg atgccgtgaa acaggaagca gcactggccg tgcacaccct gcagtctatg   3960
ggagtggatg tggtgctgat caccggcgac aacagaaaga ccgccagggc cattgccacc   4020
caggtgggca tcaacaaggt gttcgccgag gtgctgccca gcacaaagt ggccaaggtg   4080 caggaactgc agaacaaagg caaaaaggtg gccatggtgg agatggcgt gaacgactct   4140 cctgctctgg cccaggcaga tatgggcgtg ccatcggca caggcaccga cgtggcaatt   4200
gaggctgcta cgtgtgtgct gattcggaac gacctgctgg acgtggtggc ctccatccac   4260
ctgtccaaga gaaccgtgcg gcggatcaga atcaacctgg tgctggcact gatctataac   4320
```

```
ctcgtgggca tccctatcgc cgctggcgtg ttcatgccta tcggaatcgt gctgcagccc    4380
tggatgggct ctgccgccat ggctgcaagc tccgtgtctg tggtgctgtc cagcctgcag    4440
ctgaagtgct acaagaagcc cgacctggaa agatacgagg cccaggccca cggacacatg    4500
aagcctctga cagcctccca ggtgtccgtg cacatcggca tggacgacag atggcgggac    4560
agccctagag ccaccccttg ggatcaggtg tcatacgtgt cacaggtgtc cctgagcagc    4620
ctgaccagcg acaagcccag cagacatagc gccgctgccg acgacgatgg ggacaagtgg    4680
tccctgctgc tgaacggccg ggatgaggaa cagtacatct gataagcatg caataaagtc    4740
tgagtgggcg gcagcctgtg tgtgcctggg ttctctctgt cccggaatgt gcaaacaatg    4800
gaggtgctcg agtagataag tagcatggcg ggttaatcat taactacaag gaacccctag    4860
tgatggagtt ggccactccc tctctgcgcg ctcgctcgct cactgaggcc gggcgaccaa    4920
aggtcgcccg acgcccgggc tttgcccggg cggcctcagt gagcgagcga gcgcgcagcc    4980
ttaattaacc taattcactg gccgtcgttt tacaacgtcg tgactgggaa aaccctggcg    5040
ttacccaact taatcgcctt gcagcacatc cccctttcgc cagctggcgt aatagcgaag    5100
aggcccgcac cgatcgccct tcccaacagt tgcgcagcct gaatggcgaa tgggacgcgc    5160
cctgtagcgg cgcattaagc gcggcgggtg tggtggttac gcgcagcgtg accgctacac    5220
ttgccagcgc cctagcgccc gctcctttcg ctttcttccc ttcctttctc gccacgttcg    5280
ccggctttcc ccgtcaagct ctaaatcggg ggctcccttt agggttccga tttagtgctt    5340
tacggcacct cgaccccaaa aaacttgatt agggtgatgg ttcacgtagt gggccatcgc    5400
cctgatagac ggtttttcgc cctttgacgt tggagtccac gttctttaat agtggactct    5460
tgttccaaac tggaacaaca ctcaacccta tctcggtcta ttcttttgat ttataaggga    5520
ttttgccgat ttcggcctat tggttaaaaa atgagctgat ttaacaaaaa tttaacgcga    5580
attttaacaa aatattaacg cttacaattt aggtggcact tttcggggaa atgtgcgcgg    5640 aaccccctatt tgtttatttt tctaaataca ttcaaatatg tatccgctca tgagacaata    5700
accctgataa atgcttcaat aatattgaaa aaggaagagt atgagtattc aacatttccg    5760
tgtcgccctt attcccttt ttgcggcatt ttgccttcct gtttttgctc acccagaaac    5820
gctggtgaaa gtaaaagatg ctgaagatca gttgggtgca cgagtgggtt acatcgaact    5880
ggatctcaac agcggtaaga tccttgagag ttttcgcccc gaagaacgtt ttccaatgat    5940
gagcactttt aaagttctgc tatgtggcgc ggtattatcc cgtattgacg ccgggcaaga    6000
gcaactcggt cgccgcatac actattctca gaatgacttg gttgagtact caccagtcac    6060
agaaaagcat cttacggatg gcatgacagt aagagaatta tgcagtgctg ccataaccat    6120
gagtgataac actgcggcca acttacttct gacaacgatc ggaggaccga aggagctaac    6180
cgcttttttg cacaacatgg ggatcatgt aactcgcctt gatcgttggg aaccggagct    6240
gaatgaagcc ataccaaacg acgagcgtga ccacacgatg cctgtagcaa tggcaacaac    6300
gttgcgcaaa ctattaactg gcgaactact tactctagct tcccggcaac aattaataga    6360
ctggatggag gcggataaag ttgcaggacc acttctgcgc tcggcccttc cggctggctg    6420
gtttattgct gataaatctg gagccggtga gcgtgggtct cgcggtatca ttgcagcact    6480
ggggccagat ggtaagccct cccgtatcgt agttatctac acgacgggga gtcaggcaac    6540 tatgatgaa cgaaatagac agatcgctga gataggtgcc tcactgatta agcattggta    6600
actgtcagac caagtttact catatatact ttagattgat ttaaaacttc attttttaatt    6660
```

```
taaaaggatc taggtgaaga tccttttttga taatctcatg accaaaatcc cttaacgtga    6720
gttttcgttc cactgagcgt cagacccegt agaaaagatc aaaggatctt cttgagatcc    6780
ttttttttctg cgcgtaatct gctgcttgca acaaaaaaaa ccaccgctac cagcggtggt    6840
ttgtttgccg gatcaagagc taccaactct ttttccgaag gtaactggct tcagcagagc    6900
gcagatacca atactgttc ttctagtgta gccgtagtta ggccaccact tcaagaactc    6960
tgtagcaccg cctacatacc tcgctctgct aatcctgtta ccagtggctg ctgccagtgg    7020
cgataagtcg tgtcttaccg ggttggactc aagacgatag ttaccggata aggcgcagcg    7080
gtcgggctga acggggggtt cgtgcacaca gcccagcttg gagcgaacga cctacaccga    7140
actgagatac ctacagcgtg agctatgaga aagcgccacg cttcccgaag ggagaaaggc    7200
ggacaggtat ccggtaagcg gcagggtcgg aacaggagag cgcacgaggg agcttccagg    7260
gggaaacgcc tggtatcttt atagtcctgt cgggtttcgc cacctctgac ttgagcgtcg    7320
atttttgtga tgctcgtcag ggggcggag cctatggaaa aacgccagca acgcggcctt    7380
tttacggttc ctggccttt gctggccttt tgctcacatg ttctttcctg cgttatcccc    7440
tgattctgtg gataaccgta ttaccgcctt tgagtgagct gataccgctc gccgcagccg    7500
aacgaccgag cgcagcgagt cagtgagcga ggaagcggaa gagcgcccaa tacgcaaacc    7560
gcctctcccc gcgcgttggc cgattcatta atgcagctgg cacgacaggt ttcccgactg    7620
gaaagcgggc agtgagcgca acgcaattaa tgtgagttag ctcactcatt aggcacccca    7680
ggctttacac tttatgcttc cggctcgtat gttgtgtgga attgtgagcg gataacaatt    7740
tcacacagga aacagctatg accatgatta cgccagattt aattaagg                 7788
```

<210> SEQ ID NO 31
<211> LENGTH: 7686
<212> TYPE: DNA
<213> ORGANISM: Artificial Sequence
<220> FEATURE:
<223> OTHER INFORMATION: constructed sequence

<400> SEQUENCE: 31

```
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact    120
agggggttcct tgtagttaat gattaacccg ccatgctact tatctactta agtgtttgct    180
gcttgcaatg tttgcccatt ttaggggaat tcactcaaag ttcaaacctt atcattttt     240
gctttgttcc tcttggcctt ggttttgtac atcagctttg aaaataccat cccagggtta    300
atgctggggt taatttataa ctaagagtgc tctagttttg caatacagga catgctataa    360
aaatggaaag atgttgcttt ctgagagaca gcggccgcca ccatgcccga gcaggaaaga    420
cagatcaccg ccagagaggg cgccagccgg aagatcctga gcaagctgag cctgcccacc    480
agagcctggg agcccgccat gaagaagtcc ttcgccttcg acaacgtggg ctacgagggc    540
ggcctggacg gactgggacc atcttctcag gtggccacaa gcaccgtgcg catcctgggc    600
atgacctgcc agagctgcgt gaagtccatc gaggaccgga tcagcaacct gaagggcatc    660
atcagcatga aggtgtccct ggaacagggc agcgccaccg tgaaatacgt gccctctgtc    720
gtgtgcctgc agcaggtgtg ccaccagatc ggcgacatgg gcttcgaggc ctctatcgcc    780
gagggaaagg ccgcctcttg gccctctaga agcctgcctg tcaggaagc cgtcgtgaag    840
gaggccgcca tcaagagcaa ggtggcccct ctgtctctgg gccccatcga catcgagaga    900
ctgcagagca ccaaccccaa gcggcctctg agcagcgcca ccagaacctt caacaacagc    960
```

```
gagacactgg gccaccaggg cagccacgtc gtgacactgc agctgcggat cgacggaatg   1020
cactgcaaga gctgtgtgct gaacatcgag gaaaacatcg ccagctgct gggagtgcag    1080 agcatccagg tgtcactgga aaacaagacc gcccaggtga agtacgaccc cagctgcaca   1140
agccccgtgg ccctgcagag agccattgaa gctctgcccc ctggcaactt caaagtgtcc   1200
ctgcctgacg gagccgaggg ctccggaaca gatcacagaa gcagcagcag ccacagccct   1260
ggcagccccc ctagaaatca ggtgcagggc acctgtagca ccaccctgat cgccattgcc   1320
ggcatgacat gcgccagctg cgtgcactct attgagggca tgatctccca gctggaaggc   1380
gtgcagcaga tcagtgtgtc tctggccgag ggcaccgcca cagtgctgta caaccctagc   1440
gtgatcagcc ccgaagaact gagagccgcc attgaggaca tgggattcga agccagcgtg   1500
gtgtccgaga gctgctccac caaccctctg ggcaatcaca cgccggcaa cagcatggtg    1560 cagaccaccg acggcacccc caccagcgtg caggaagtgg ccccacatac aggcagactg   1620
cccgccaatc acgcccccga tatcctggcc aagagccccc agagtacaag agccgtggcc   1680
ccccagaagt gcttcctgca gatcaagggc atgacttgtg cctcttgtgt gtccaatatc   1740
gagcggaacc tgcagaaaga ggccggcgtg ctgtctgtgc tggtggctct gatggccggc   1800
aaggccgaga tcaaatacga ccccgaagtg attcagcccc tggaaatcgc ccagtttatc   1860
caggacctgg gctttgaagc cgccgtgatg gaagattacg ccggctccga cggcaacatc   1920
gagctgacca tcaccggaat gacctgcgcc tcctgtgtgc acaacattga gtccaagctg   1980
acccggacca acggcatcac ctacgcctct gtggctctgg ccacctccaa ggccctcgtg   2040
aagttcgatc ccgagatcat cggccccagg gacatcatca gatcatcga agagatcggc   2100 ttccacgcca gcctggccca gaggaaccct aacgcccacc acctggacca caagatggaa   2160
atcaagcagt ggaagaaaag cttcctgtgc agcctggtgt cggcatccc cgtgatggcc    2220 ctgatgatct acatgctgat ccccagcaac gagccccacc agtccatggt gctggatcac   2280
aacatcatcc ccggcctgtc tatcctgaac ctgatcttct tcatcctgtg caccttcgtg   2340
cagctgctgg gcggctggta cttctacgtg caggcctaca gtccctgcg gcacagatcc    2400 gccaacatgg acgtgctgat cgtgctggcc acatctatcg cctacgtgta ctccctcgtg   2460
atcctggtgg tggccgtggc cgagaaagcc gagagaagcc ctgtgacctt cttcgacacc   2520 cccccctatgc tgttcgtgtt tatcgccctg gccggtggc tggaacacct ggccaaaagc   2580
aagaccagcg aggccctggc taagctgatg agtctgcagg ccaccgaggc cacagtcgtg   2640
accctgggcg aggacaacct gatcatccgc gaggaacagg tgccaatgga actggtgcag   2700
cggggcgaca tcgtgaaggt ggtgcctggc ggcaagttcc ccgtggacgg aaaagtgctg   2760
gaagggaata ccatggccga cgagagcctg atcacaggcg aggccatgcc cgtgaccaag   2820
aaacctggca gcacagtgat cgccggcagc atcaatgccc acggcagcgt gctgattaag   2880
gccacacacg tgggcaacga taccacccct gctcagattg tgaagctggt ggaagaggcc   2940
cagatgagca aggcccccat tcagcagctg gctgaccggt tcagcggcta cttcgtgccc   3000
tttatcatca tcatgagcac cctgactctg gtcgtgtgga tcgtgatcgg ctttatcgac   3060
ttcggagtgg tgcagagata cttccccaac cctaacaagc acatcagcca gacagaagtg   3120
atcatcagat cgcctttca gaccagcatc accgtgctgt gtatcgccctg ccctgtagc    3180 ctgggactgg ccacacctac cgctgtgatg gtgggaacag cgctggccgc tcagaacggc   3240
atcctgatca agggggggcaa gcctctggaa atggctcaca agatcaagac cgtgatgttc   3300
```

```
gacaagaccg gcaccatcac ccacggcgtg cccagagtga tgagagtgct gctgctgggg   3360
gatgtggcca ccctgcctct gagaaaggtg ctggctgtcg tgggcacagc cgaggctagc   3420
tctgaacacc cactgggagt ggccgtgaca aagtactgca aagaggaact gggcaccgaa   3480
accctgggct actgcaccga ctttcaggcc gtgcctggct gtggcatcgg ctgcaaggtg   3540
tccaacgtgg aaggcatcct ggcccacagc gagaggccac tgtctgcccc tgccagccac   3600
ctgaacgagg ccggatctct gcccgccgaa aaggacgctg tgccccagac cttctctgtg   3660
ctgattggca acagagagtg gctgcggcgg aacggcctga ccatctcctc cgatgtgtcc   3720
gacgccatga ccgaccacga gatgaagggc cagaccgcca ttctggtggc cattgacggg   3780
gtgctgtgcg gcatgatcgc aatcgccgat gccgtgaaac aggaagcagc actggccgtg   3840
cacaccctgc agtctatggg agtggatgtg gtgctgatca ccggcgacaa cagaaagacc   3900
gccagggcca ttgccaccca ggtgggcatc aacaaggtgt cgccgaggt gctgcccagc   3960 cacaaagtgg ccaaggtgca ggaactgcag aacaaaggca aaaggtggc catggtggga   4020 gatggcgtga acgactctcc tgctctggcc caggcagata tgggcgtggc catcggcaca   4080
ggcaccgacg tggcaattga ggctgctgac gtggtgctga ttcggaacga cctgctggac   4140
gtggtggcct ccatccacct gtccaagaga accgtgcggc ggatcagaat caacctggtg   4200
ctggcactga tctataacct cgtgggcatc cctatcgccg ctggcgtgtt catgcctatc   4260
ggaatcgtgc tgcagccctg gatgggctct gccgccatgg ctgcaagctc cgtgtctgtg   4320
gtgctgtcca gcctgcagct gaagtgctac aagaagcccg acctggaaag atacgaggcc   4380
caggcccacg gacacatgaa gcctctgaca gcctcccagg tgtccgtgca catcggcatg   4440
gacgacagat ggcgggacag ccctagagcc accccttggg atcaggtgtc atacgtgtca   4500
caggtgtccc tgagcagcct gaccagcgac aagcccagca gacatagcgc cgctgccgac   4560
gacgatgggg acaagtggtc cctgctgctg aacggccggg atgaggaaca gtacatctga   4620
taagcatgca ataaagtctg agtgggcggc agcctgtgtg tgcctgggtt ctctctgtcc   4680
cggaatgtgc aaacaatgga ggtgctcgag tagataagta gcatggcggg ttaatcatta   4740
actacaagga ccccctagtg atggagttgg ccactccctc tctgcgcgct cgctcgctca   4800
ctgaggccgg gcgaccaaag gtcgcccgac gcccgggctt gcccgggcg gcctcagtga   4860 gcgagcgagc gcgcagcctt aattaaccta attcactggc cgtcgtttta caacgtcgtg   4920
actgggaaaa ccctggcgtt acccaactta atcgccttgc agcacatccc cctttcgcca   4980
gctggcgtaa tagcgaagag gcccgcaccg atcgcccttc ccaacagttg cgcagcctga   5040
atggcgaatg gacgcgcccc tgtagcggcg cattaagcgc ggcgggtgtg gtggttacgc   5100
gcagcgtgac cgctacactt gccagcgccc tagcgcccgc tcctttcgct ttcttccctt   5160
cctttctcgc cacgttcgcc ggctttcccc gtcaagctct aaatcggggg ctccctttag   5220
ggttccgatt tagtgcttta cggcacctcg accccaaaaa acttgattag ggtgatggtt   5280
cacgtagtgg gccatcgccc tgatagacgg ttttcgccc tttgacgttg gagtccacgt   5340
tctttaatag tggactcttg ttccaaactg gaacaacact caaccctatc tcggtctatt   5400
cttttgattt ataagggatt tgccgattt cggcctattg gttaaaaaat gagctgattt   5460
aacaaaaatt taacgcgaat tttaacaaaa tattaacgct tacaatttag gtggcacttt   5520
tcggggaaat gtgcgcggaa cccctatttg tttatttttc taaatacatt caaatatgta   5580
tccgctcatg agacaataac cctgataaat gcttcaataa tattgaaaaa ggaagagtat   5640
gagtattcaa catttccgtg tcgcccttat tccctttttt gcggcatttt gccttcctgt   5700
```

-continued

```
ttttgctcac ccagaaacgc tggtgaaagt aaaagatgct gaagatcagt tgggtgcacg    5760
agtgggttac atcgaactgg atctcaacag cggtaagatc cttgagagtt ttcgccccga    5820
agaacgtttt ccaatgatga gcacttttaa agttctgcta tgtggcgcgg tattatcccg    5880
tattgacgcc gggcaagagc aactcggtcg ccgcatacac tattctcaga atgacttggt    5940
tgagtactca ccagtcacag aaaagcatct tacggatggc atgacagtaa gagaattatg    6000
cagtgctgcc ataaccatga gtgataacac tgcggccaac ttacttctga caacgatcgg    6060
aggaccgaag gagctaaccg cttttttgca caacatgggg gatcatgtaa ctcgccttga    6120
tcgttgggaa ccgagctga atgaagccat accaaacgac gagcgtgaca ccacgatgcc    6180
tgtagcaatg gcaacaacgt tgcgcaaact attaactggc gaactactta ctctagcttc    6240
ccggcaacaa ttaatagact ggatggaggc ggataaagtt gcaggaccac ttctgcgctc    6300
ggcccttccg gctggctggt ttattgctga taaatctgga gccggtgagc gtgggtctcg    6360
cggtatcatt gcagcactgg ggccagatgg taagccctcc cgtatcgtag ttatctacac    6420
gacggggagt caggcaacta tggatgaacg aaatagacag atcgctgaga taggtgcctc    6480
actgattaag cattggtaac tgtcagacca agtttactca tatatacttt agattgattt    6540
aaaacttcat ttttaattta aaaggatcta ggtgaagatc ctttttgata atctcatgac    6600
caaaatccct taacgtgagt tttcgttcca ctgagcgtca gacccgtag aaaagatcaa    6660 aggatcttct tgagatcctt ttttctgcg cgtaatctgc tgcttgcaaa caaaaaaacc    6720
accgctacca gcggtggttt gtttgccgga tcaagagcta ccaactcttt ttccgaaggt    6780
aactggcttc agcagagcgc agataccaaa tactgttctt ctagtgtagc cgtagttagg    6840
ccaccacttc aagaactctg tagcaccgcc tacatacctc gctctgctaa tcctgttacc    6900
agtggctgct gccagtggcg ataagtcgtg tcttaccggg ttggactcaa gacgatagtt    6960
accggataag gcgcagcggt cgggctgaac ggggggttcg tgcacacagc ccagcttgga    7020
gcgaacgacc tacaccgaac tgagatacct acagcgtgag ctatgagaaa gcgccacgct    7080
tcccgaaggg agaaaggcgg acaggtatcc ggtaagcggc agggtcggaa caggagagcg    7140
cacgagggag cttccagggg gaaacgcctg gtatctttat agtcctgtcg ggtttcgcca    7200
cctctgactt gagcgtcgat ttttgtgatg ctcgtcaggg gggcggagcc tatgaaaaa    7260 cgccagcaac gcggcctttt tacggttcct ggccttttgc tggccttttg ctcacatgtt    7320
ctttcctgcg ttatcccctg attctgtgga taaccgtatt accgcctttg agtgagctga    7380
taccgctcgc cgcagccgaa cgaccgagcg cagcgagtca gtgagcgagg aagcggaaga    7440
gcgcccaata cgcaaaccgc ctctccccgc gcgttggccg attcattaat gcagctggca    7500
cgacaggttt cccgactgga aagcgggcag tgagcgcaac gcaattaatg tgagttagct    7560
cactcattag gcaccccagg ctttacactt tatgcttccg gctcgtatgt tgtgtggaat    7620
tgtgagcgga taacaatttc acacaggaaa cagctatgac catgattacg ccagatttaa    7680
ttaagg                                                              7686
```

<210> SEQ ID NO 32
<211> LENGTH: 7755
<212> TYPE: DNA
<213> ORGANISM: Artificial Sequence
<220> FEATURE:
<223> OTHER INFORMATION: constructed sequence

<400> SEQUENCE: 32

```
ctgcgcgctc gctcgctcac tgaggccgcc cgggcaaagc ccgggcgtcg ggcgaccttt    60
ggtcgcccgg cctcagtgag cgagcgagcg cgcagagagg gagtggccaa ctccatcact   120
aggggttcct tgtagttaat gattaacccg ccatgctact tatctactta agtgtttgct   180
gcttgcaatg tttgcccatt ttaggggaat tcactcaaag ttcaaacctt atcatttttt   240
gctttgttcc tcttggcctt ggttttgtac atcagctttg aaaataccat cccagggtta   300
atgctggggt taatttataa ctaagagtgc tctagttttg caatacagga catgctataa   360
aaatggaaag atgttgcttt ctgagagaca gcggccgcca ccatgcccga gcaggaaaga   420
cagatcaccg ccagagaggg cgccagccgg aagatcctga gcaagctgag cctgcccacc   480
agagcctggg agcccgccat gaagaagtcc ttcgccttcg acaacgtggg ctacgagggc   540
ggcctggacg gactgggacc atcttctcag gtggccacaa gcaccgtgcg caaatacgtg   600
ccctctgtcg tgtgcctgca gcaggtgtgc caccagatcg gcgacatggg cttcgaggcc   660
tctatcgccg agggaaaggc cgcctcttgg ccctctagaa gcctgcctgc tcaggaagcc   720
gtcgtgaagc tgcgggtgga agggatgacc tgtcagtcct gcgtgtccag catcgagggc   780
aaagtgcgga agctgcaggg cgtggtgcgc gtgaaagtgt ctctgagcaa ccaggaagct   840
gtgatcacct accagcccta cctgatccag cccgaggacc tgagggacca cgtgaacgat   900
atgggatttg aggccgccat caagagcaag gtggcccctc tgtctctggg ccccatcgac   960
atcgagagac tgcagagcac caaccccaag cggcctctga gcagcgccaa ccagaacttc  1020
aacaacagcg agacactggg ccaccagggc agccacgtcg tgacactgca gctgcggatc  1080
gacggaatgc actgcaagag ctgtgtgctg aacatcgagg aaaacatcgg ccagctgctg  1140
ggagtgcaga gcatccaggt gtcactggaa acaagaccg cccaggtgaa gtacgacccc  1200
agctgcacaa gccccgtggc cctgcagaga gccattgaag ctctgccccc tgcaacttc   1260
aaagtgtccc tgcctgacgg agccgagggc tccggaacag atcacagaag cagcagcagc  1320
cacagccctg gcagcccccc tagaaatcag gtgcagggca cctgtagcac caccctgatc  1380
gccattgccg gcatgacatg cgccagctgc gtgcactcta ttgagggcat gatctcccag  1440
ctggaaggcg tgcagcagat cagtgtgtct ctggccgagg gcaccgccac agtgctgtac  1500
aaccctagcg tgatcagccc cgaagaactg agagccgcca ttgaggacat gggattcgaa  1560
gccagcgtgg tgtccgagag ctgctccacc aaccctctgg gcaatcacag cgccggcaac  1620
agcatggtgc agaccaccga cggcacccc accagcgtgc aggaagtggc cccacataca  1680
ggcagactgc ccgccaatca cgcccccgat atcctggcca agagccccca gagtacaaga  1740
gccgtggccc cccagaagtg cttcctgcag atcaagggca tgacttgtgc ctcttgtgtg  1800
tccaatatcg agcggaacct gcagaaagag gccggcgtgc tgtctgtgct ggtggctctg  1860
atggccggca aggccgagat caaatacgac cccgaagtga ttcagcccct ggaaatcgcc  1920
cagtttatcc aggacctggg cttgaagcc gccgtgatgg aagattacgc cggctccgac  1980
ggcaacatcg agctgaccat caccggaatg acctgcgcct cctgtgtgca aacattgag   2040
tccaagctga cccggaccaa cggcatcacc tacgcctctg tggctctggc cacctccaag  2100
gccctcgtga agttcgatcc cgagatcatc ggccccaggg acatcatcaa gatcatcgaa  2160
gagatcggct ccacgccag cctggcccag aggaacccta acgcccacca cctggaccac  2220
aagatggaaa tcaagcagtg gaagaaaagc ttcctgtgca gcctggtgtt cggcatcccc  2280
gtgatggccc tgatgatcta catgctgatc cccagcaacg agcccaccaa gtccatggtg  2340
ctggatcaca acatcatccc cggcctgtct atcctgaacc tgatcttctt catcctgtgc  2400
```

```
accttcgtgc agctgctggg cggctggtac ttctacgtgc aggcctacaa gtccctgcgg    2460
cacagatccg ccaacatgga cgtgctgatc gtgctggcca catctatcgc ctacgtgtac    2520
tccctcgtga tcctggtggt ggccgtggcc gagaaagccg agagaagccc tgtgaccttc    2580
ttcgacaccc cccctatgct gttcgtgttt atcgccctgg ccggtggct ggaacacctg     2640 gccaaaagca agaccagcga ggccctggct aagctgatga gtctgcaggc caccgaggcc    2700
acagtcgtga ccctgggcga ggacaacctg atcatccgcg aggaacaggt gccaatggaa    2760
ctggtgcagc ggggcgacat cgtgaaggtg gtgcctggcg gcaagttccc cgtggacgga    2820
aaagtgctgg aagggaatac catggccgac gagagcctga tcacaggcga ggccatgccc    2880
gtgaccaaga aacctggcag cacagtgatc gccggcagca tcaatgccca cggcagcgtg    2940
ctgattaagg ccacacacgt gggcaacgat accaccctgg ctcagattgt gaagctggtg    3000
gaagaggccc agatgagcaa ggccccatt cagcagctgg ctgaccggtt cagcggctac      3060
ttcgtgccct ttatcatcat catgagcacc ctgacactgg tcgtgtggat cgtgatcggc    3120
tttatcgact tcggagtggt gcagagatac ttccccaacc ctaacaagca catcagccag    3180
acagaagtga tcatcagatt cgcctttcag accagcatca ccgtgctgtg tatcgcctgc    3240
ccctgtagcc tgggactggc cacacctacc gctgtgatgg tgggaacagg cgtggccgct    3300
cagaacggca tcctgatcaa gggggcaag cctctggaaa tggctcacaa gatcaagacc      3360
gtgatgttcg acaagaccgg caccatcacc cacggcgtgc ccagagtgat gagagtgctg    3420
ctgctggggg atgtggccac cctgcctctg agaaaggtgc tggctgtcgt gggcacagcc    3480
gaggctagct ctgaacaccc actgggagtg gccgtgacaa agtactgcaa agaggaactg    3540
ggcaccgaaa ccctgggcta ctgcaccgac tttcaggccg tgcctggctg tggcatcggc    3600
tgcaaggtgt ccaacgtgga aggcatcctg gcccacagcg agaggccact gtctgcccct    3660
gccagccacc tgaacgaggc cggatctctg cccgccgaaa aggacgctgt gccccagacc    3720
ttctctgtgc tgattggcaa cagagagtgg ctgcggcgga acggcctgac catctcctcc    3780
gatgtgtccg acgccatgac cgaccacgag atgaagggcc agaccgccat tctggtggcc    3840
attgacgggg tgctgtgcgg catgatcgca atcgccgatg ccgtgaaaca ggaagcagca    3900
ctggccgtgc acaccctgca gtctatggga gtggatgtgg tgctgatcac cggcgacaac    3960
agaaagaccg ccagggccat tgccacccag gtgggcatca acaaggtgtt cgccgaggtg    4020
ctgcccagcc acaaagtggc caaggtgcag gaactgcaga acaaaggcaa aaaggtggcc    4080
atggtgggag atggcgtgaa cgactctcct gctctggccc aggcagatat gggcgtggcc    4140
atcggcacag gcaccgacgt ggcaattgag gctgctgacg tggtgctgat tcggaacgac    4200
ctgctggacg tggtggcctc catccacctg tccaagagaa ccgtgcggcg gatcagaatc    4260
aacctggtgc tggcactgat ctataacctc gtgggcatcc ctatcgccgc tggcgtgttc    4320
atgcctatcg gaatcgtgct gcagcccctg atgggctctg ccgccatggc tgcaagctcc    4380
gtgtctgtgg tgctgtccag cctgcagctg aagtgctaca gaagcccga cctggaaaga    4440 tacgaggccc aggcccacgg acacatgaag cctctgacag cctcccaggt gtccgtgcac    4500
atcggcatgg acgacagatg gcgggacagc cctagagcca ccccttggga tcaggtgtca    4560
tacgtgtcac aggtgtccct gagcagcctg accagcgaca agcccagcag acatagcgcc    4620
gctgccgacg acgatgggga caagtggtcc ctgctgctga acggccggga tgaggaacag    4680
tacatctgat aagcatgcaa taaagtctga gtgggcggca gcctgtgtgt gcctgggttc    4740
```

```
tctctgtccc ggaatgtgca acaatggag gtgctcgagt agataagtag catggcggt    4800
taatcattaa ctacaaggaa ccctagtga tggagttggc cactccctct ctgcgcgctc   4860
gctcgctcac tgaggccggg cgaccaaagg tcgcccgacg cccgggcttt gcccgggcgg  4920
cctcagtgag cgagcgagcg cgcagcctta attaacctaa ttcactggcc gtcgttttac  4980
aacgtcgtga ctgggaaaac cctggcgtta cccaacttaa tcgccttgca gcacatcccc  5040
ctttcgccag ctggcgtaat agcgaagagg cccgcaccga tcgcccttcc caacagttgc  5100
gcagcctgaa tggcgaatgg gacgcgccct gtagcggcgc attaagcgcg cgggtgtgg   5160
tggttacgcg cagcgtgacc gctacacttg ccagcgccct agcgcccgct cctttcgctt  5220
tcttcccttc ctttctcgcc acgttcgccg gctttccccg tcaagctcta atcgggggc   5280
tcccttttagg gttccgattt agtgctttac ggcacctcga ccccaaaaaa cttgattagg  5340
gtgatggttc acgtagtggg ccatcgccct gatagacggt ttttcgccct ttgacgttgg  5400
agtccacgtt ctttaatagt ggactcttgt tccaaactgg aacaacactc aaccctatct  5460
cggtctattc ttttgattta taagggattt tgccgatttc ggcctattgg ttaaaaatg   5520
agctgattta acaaaaattt aacgcgaatt ttaacaaaat attaacgctt acaatttagg  5580
tggcactttt cggggaaatg tgcgcggaac ccctatttgt ttatttttct aaatacattc  5640
aaatatgtat ccgctcatga gacaataacc ctgataaatg cttcaataat attgaaaaag  5700
gaagagtatg agtattcaac atttccgtgt cgcccttatt cccttttttg cggcattttg  5760
ccttcctgtt tttgctcacc cagaaacgct ggtgaaagta aaagatgctg aagatcagtt  5820
gggtgcacga gtgggttaca tcgaactgga tctcaacagc ggtaagatcc ttgagagttt  5880
tcgccccgaa gaacgttttc caatgatgag cacttttaaa gttctgctat gtggcgcggt  5940
attatcccgt attgacgccg ggcaagagca actcggtcgc cgcatacact attctcagaa  6000
tgacttggtt gagtactcac cagtcacaga aaagcatctt acggatggca tgacagtaag  6060
agaattatgc agtgctgcca taaccatgag tgataacact gcggccaact tacttctgac  6120
aacgatcgga ggaccgaagg agctaaccgc ttttttgcac aacatggggg atcatgtaac  6180
tcgccttgat cgttgggaac cggagctgaa tgaagccata ccaaacgacg agcgtgacac  6240
cacgatgcct gtagcaatgg caacaacgtt gcgcaaacta ttaactggcg aactacttac  6300
tctagcttcc cggcaacaat taatagactg gatggaggcg gataaagttg caggaccact  6360
tctgcgctcg gcccttccgg ctggctggtt tattgctgat aaatctggag ccggtgagcg  6420
tgggtctcgc ggtatcattg cagcactggg gccagatggt aagccctccc gtatcgtagt  6480
tatctacacg acggggagtc aggcaactat ggatgaacga aatagacaga tcgctgagat  6540
aggtgcctca ctgattaagc attggtaact gtcagaccaa gtttactcat atatacttta  6600
gattgattta aaacttcatt tttaatttaa aaggatctag gtgaagatcc ttttttgataa  6660
tctcatgacc aaaatccctt aacgtgagtt ttcgttccac tgagcgtcag accccgtaga  6720
aaagatcaaa ggatcttctt gagatccttt ttttctgcgc gtaatctgct gcttgcaaac  6780
aaaaaaacca ccgctaccag cggtggtttg tttgccggat caagagctac caactctttt  6840
tccgaaggta actggcttca gcagagcgca gataccaaat actgttcttc tagtgtagcc  6900
gtagttaggc caccacttca agaactctgt agcaccgcct acatacctcg ctctgctaat  6960
cctgttacca gtggctgctg ccagtggcga taagtcgtgt cttaccgggt tggactcaag  7020
acgatagtta ccggataagg cgcagcggtc gggctgaacg ggggttcgt gcacacagcc   7080
cagcttggag cgaacgacct acaccgaact gagatacta cagcgtgagc tatgagaaag   7140
```

-continued

| | |
|---|---|
| cgccacgctt cccgaaggga gaaaggcgga caggtatccg gtaagcggca gggtcggaac | 7200 |
| aggagagcgc acgagggagc ttccaggggg aaacgcctgg tatctttata gtcctgtcgg | 7260 |
| gtttcgccac ctctgacttg agcgtcgatt tttgtgatgc tcgtcagggg ggcggagcct | 7320 |
| atggaaaaac gccagcaacg cggcctttt acgttcctg ccttttgct ggccttttgc | 7380 |
| tcacatgttc tttcctgcgt tatcccctga ttctgtggat aaccgtatta ccgcctttga | 7440 |
| gtgagctgat accgctcgcc gcagccgaac gaccgagcgc agcgagtcag tgagcgagga | 7500 |
| agcggaagag cgcccaatac gcaaaccgcc tctccccgcg cgttggccga ttcattaatg | 7560 |
| cagctgcac acaggtttc ccgactgaa agcgggcagt gagcgcaacg caattaatgt | 7620 |
| gagttagctc actcattagg cacccaggc tttacactt atgcttccgg ctcgtatgtt | 7680 |
| gtgtggaatt gtgagcggat aacaatttca cacaggaaac agctatgacc atgattacgc | 7740 |
| cagatttaat taagg | 7755 |

<210> SEQ ID NO 33
<211> LENGTH: 6438
<212> TYPE: DNA
<213> ORGANISM: Artificial Sequence
<220> FEATURE:
<223> OTHER INFORMATION: constructed sequence

<400> SEQUENCE: 33

| | |
|---|---|
| ctgcgcgctc gctcgctcac tgaggccgcc cgggcaaagc ccgggcgtcg ggcgaccttt | 60 |
| ggtcgcccgg cctcagtgag cgagcgagcg cgcagagagg gagtggccaa ctccatcact | 120 |
| aggggttcct tgtagttaat gattaacccg ccatgctact tatctactta agtgtttgct | 180 |
| gcttgcaatg tttgcccatt ttaggggaat tcactcaaag ttcaaacctt atcattttt | 240 |
| gctttgttcc tcttggcctt ggttttgtac atcagcttg aaaataccat cccagggtta | 300 |
| atgctggggt taatttataa ctaagagtgc tctagttttg caatacagga catgctataa | 360 |
| aaatggaaag atgttgcttt ctgagagaca gcggccgcca ccatgcccga gcaggaaaga | 420 |
| cagatcaccg ccagagaggg cgccagccgg aagatcctga gcaagctgag cctgcccacc | 480 |
| agagcctggg agcccgccat gaagaagtcc ttcgccttcg acaacgtggg ctacgagggc | 540 |
| ggcctggacg gactgggacc atcttctcag gtggccacaa gcaccgtgcg cctggaaatc | 600 |
| gcccagttta tccaggacct gggctttgaa gccgccgtga tggaagatta cgccggctcc | 660 |
| gacggcaaca tcgagctgac catcaccgga atgacctgcg cctcctgtgt gcacaacatt | 720 |
| gagtccaagc tgacccggac caacggcatc acctacgcct ctgtggctct ggccacctcc | 780 |
| aaggccctcg tgaagttcga tcccgagatc atcgccccca gggacatcat caagatcatc | 840 |
| gaagagatcg gcttccacgc cagcctggcc cagaggaacc taacgcccca ccacctggac | 900 |
| cacaagatgg aaatcaagca gtggaagaaa agcttcctgt gcagcctggt gttcggcatc | 960 |
| cccgtgatgg ccctgatgat ctacatgctg atccccagca acgagcccca ccagtccatg | 1020 |
| gtgctggatc acaacatcat ccccggcctg tctatcctga acctgatctt cttcatcctg | 1080 |
| tgcaccttcg tgcagctgct gggcggctgg tacttctacg tgcaggccta caagtccctg | 1140 |
| cggcacagat ccgccaacat ggacgtgctg atcgtgctgg ccacatctat cgcctacgtg | 1200 |
| tactccctcg tgatcctggt ggtggccgtg gccgagaaag ccgagagaag ccctgtgacc | 1260 |
| ttcttcgaca ccccccctat gctgttcgtg tttatcgccc tgggccggtg gctgaacac | 1320 |
| ctggccaaaa gcaagaccag cgaggccctg gctaagctga tgagtctgca ggccaccgag | 1380 |

```
gccacagtcg tgaccctggg cgaggacaac ctgatcatcc gcgaggaaca ggtgccaatg   1440
gaactggtgc agcggggcga catcgtgaag gtggtgcctg gcggcaagtt ccccgtggac   1500
ggaaaagtgc tggaagggaa taccatggcc gacgagagcc tgatcacagg cgaggccatg   1560
cccgtgacca agaaacctgg cagcacagtg atcgccggca gcatcaatgc ccacggcagc   1620
gtgctgatta aggccacaca cgtgggcaac gataccaccc tggctcagat tgtgaagctg   1680
gtggaagagg cccagatgag caaggccccc attcagcagc tggctgaccg gttcagcggc   1740
tacttcgtgc cctttatcat catcatgagc accctgacac tggtcgtgtg gatcgtgatc   1800
ggctttatcg acttcggagt ggtgcagaga tacttcccca accctaacaa gcacatcagc   1860
cagacagaag tgatcatcag attcgccttt cagaccagca tcaccgtgct gtgtatcgcc   1920
tgcccctgta gcctgggact ggccacacct accgctgtga tggtgggaac aggcgtggcc   1980
gctcagaacg gcatcctgat caagggggc aagcctctgg aaatggctca caagatcaag   2040
accgtgatgt tcgacaagac cggcaccatc acccacggcg tgcccagagt gatgagagtg   2100
ctgctgctgg gggatgtggc caccctgcct ctgagaaagg tgctggctgt cgtgggcaca   2160
gccgaggcta gctctgaaca cccactggga gtggccgtga caaagtactg caaagaggaa   2220
ctgggcaccg aaaccctggg ctactgcacc gactttcagg ccgtgcctgg ctgtggcatc   2280
ggctgcaagg tgtccaacgt ggaaggcatc ctggcccaca gcgagaggcc actgtctgcc   2340
cctgccagcc acctgaacga ggccggatct ctgcccgccg aaaaggacgc tgtgccccag   2400
accttctctg tgctgattgg caacagagag tggctgcggc ggaacggcct gaccatctcc   2460
tccgatgtgt ccgacgccat gaccgaccac gagatgaagg ccagaccgc cattctggtg   2520 gccattgacg gggtgctgtg cggcatgatc gcaatcgccg atgccgtgaa acaggaagca   2580
gcactggccg tgcacaccct gcagtctatg ggagtggatg tggtgctgat caccggcgac   2640
aacagaaaga ccgccagggc cattgccacc caggtgggca tcaacaaggt gttcgccgag   2700
gtgctgccca gccacaaagt ggccaaggtg caggaactgc agaacaaagg caaaaaggtg   2760
gccatggtgg agatggcgt gaacgactct cctgctctgg cccaggcaga tatgggcgtg   2820
gccatcggca caggcaccga cgtggcaatt gaggctgctg acgtggtgct gattcggaac   2880
gacctgctgg acgtggtggc ctccatccac ctgtccaaga gaaccgtgcg gcggatcaga   2940
atcaacctgg tgctggcact gatctataac ctcgtgggca tccctatcgc cgctggcgtg   3000
ttcatgccta tcggaatcgt gctgcagccc tggatgggct ctgccgccat ggctgcaagc   3060
tccgtgtctg tggtgctgtc cagcctgcag ctgaagtgct acaagaagcc cgacctggaa   3120
agatacgagg cccaggccca cggacacatg aagcctctga cagcctccca ggtgtccgtg   3180
cacatcggca tggacgacag atggcgggac agccctagag ccacccttg ggatcaggtg   3240 tcatacgtgt cacaggtgtc cctgagcagc ctgaccagcg acaagcccag cagacatagc   3300
gccgctgccg acgacgatgg ggacaagtgg tccctgctgc tgaacggccg ggatgaggaa   3360
cagtacatct gataagcatg caataaagtc tgagtgggcg gcagcctgtg tgtgcctggg   3420
ttctctctgt cccggaatgt gcaaacaatg gaggtgctcg agtagataag tagcatggcg   3480
ggttaatcat taactacaag gaaccctag tgatggagtt ggccactccc tctctgcgcg   3540
ctcgctcgct cactgaggcc gggcgaccaa aggtcgcccg acgcccgggc tttgcccggg   3600
cggcctcagt gagcgagcga gcgcgcagcc ttaattaacc taattcactg gccgtcgttt   3660
tacaacgtcg tgactgggaa aaccctggcg ttacccaact taatcgcctt gcagcacatc   3720 ccctttcgc cagctggcgt aatagcgaag aggcccgcac cgatcgccct tcccaacagt   3780
```

```
tgcgcagcct gaatggcgaa tgggacgcgc cctgtagcgg cgcattaagc gcggcgggtg    3840
tggtggttac gcgcagcgtg accgctacac ttgccagcgc cctagcgccc gctcctttcg    3900
ctttcttccc ttcctttctc gccacgttcg ccggctttcc ccgtcaagct ctaaatcggg    3960
ggctcccttt agggttccga tttagtgctt tacggcacct cgaccccaaa aaacttgatt    4020
agggtgatgg ttcacgtagt gggccatcgc cctgatagac ggttttttcgc cctttgacgt    4080 tggagtccac gttctttaat agtggactct tgttccaaac tggaacaaca ctcaaccta    4140 tctcggtcta ttcttttgat ttataaggga ttttgccgat ttcggcctat tggttaaaaa    4200
atgagctgat ttaacaaaaa tttaacgcga ttttaacaa atattaacg cttacaattt    4260 aggtggcact tttcggggaa atgtgcgcgg aacccctatt tgtttatttt tctaaataca    4320
ttcaaatatg tatccgctca tgagacaata accctgataa atgcttcaat aatattgaaa    4380
aaggaagagt atgagtattc aacatttccg tgtcgccctt attcccttt ttgcggcatt    4440 ttgccttcct gtttttgctc acccagaaac gctggtgaaa gtaaaagatg ctgaagatca    4500
gttgggtgca cgagtgggtt acatcgaact ggatctcaac agcggtaaga tccttgagag    4560
ttttcgcccc gaagaacgtt ttccaatgat gagcactttt aaagttctgc tatgtggcgc    4620
ggtattatcc cgtattgacg ccgggcaaga gcaactcggt cgccgcatac actattctca    4680
gaatgacttg gttgagtact caccagtcac agaaaagcat cttacggatg gcatgacagt    4740
aagagaatta tgcagtgctg ccataaccat gagtgataac actgcggcca acttacttct    4800
gacaacgatc ggaggaccga aggagctaac cgcttttttg cacaacatgg ggatcatgt    4860 aactcgcctt gatcgttggg aaccggagct gaatgaagcc ataccaaacg acgagcgtga    4920
caccacgatg cctgtagcaa tggcaacaac gttgcgcaaa ctattaactg gcgaactact    4980
tactctagct tcccggcaac aattaataga ctggatggag gcggataaag ttgcaggacc    5040
acttctgcgc tcggcccttc cggctggctg gtttattgct gataaatctg gagccggtga    5100
gcgtgggtct cgcggtatca ttgcagcact ggggccagat ggtaagccct cccgtatcgt    5160
agttatctac acgacgggga gtcaggcaac tatggatgaa cgaaatagac agatcgctga    5220
gataggtgcc tcactgatta agcattggta actgtcagac caagtttact catatatact    5280
ttagattgat ttaaaacttc atttttaatt taaaaggatc taggtgaaga tcctttttga    5340
taatctcatg accaaaatcc cttaacgtga gttttcgttc cactgagcgt cagacccgt    5400 agaaaagatc aaaggatctt cttgagatcc ttttttctg cgcgtaatct gctgcttgca    5460
aacaaaaaaa ccaccgctac cagcggtggt ttgtttgccg gatcaagagc taccaactct    5520
ttttccgaag gtaactggct tcagcagagc gcagatacca atactgttc ttctagtgta    5580 gccgtagtta ggccaccact tcaagaactc tgtagcaccg cctacatacc tcgctctgct    5640
aatcctgtta ccagtggctg ctgccagtgg cgataagtcg tgtcttaccg ggttggactc    5700
aagacgatag ttaccggata aggcgcagcg gtcgggctga acggggggtt cgtgcacaca    5760
gcccagcttg gagcgaacga cctacaccga actgagatac ctacagcgtg agctatgaga    5820
aagcgccacg cttcccgaag ggagaaaggc ggacaggtat ccggtaagcg gcagggtcgg    5880
aacaggagag cgcacgaggg agcttccagg gggaaacgcc tggtatcttt atagtcctgt    5940
cgggtttcgc cacctctgac ttgagcgtcg atttttgtga tgctcgtcag ggggcggag    6000 cctatggaaa aacgccagca acgcggcctt ttacggttc ctggcctttt gctggccttt    6060
tgctcacatg ttctttcctg cgttatcccc tgattctgtg gataaccgta ttaccgcctt    6120
```

```
tgagtgagct gataccgctc gccgcagccg aacgaccgag cgcagcgagt cagtgagcga    6180
ggaagcggaa gagcgcccaa tacgcaaacc gcctctcccc gcgcgttggc cgattcatta    6240
atgcagctgg cacgacaggt ttcccgactg gaaagcgggc agtgagcgca acgcaattaa    6300
tgtgagttag ctcactcatt aggcacccca ggctttacac tttatgcttc cggctcgtat    6360
gttgtgtgga attgtgagcg gataacaatt tcacacagga aacagctatg accatgatta    6420
cgccagattt aattaagg                                                  6438

<210> SEQ ID NO 34
<211> LENGTH: 6831
<212> TYPE: DNA
<213> ORGANISM: Artificial Sequence
<220> FEATURE:
<223> OTHER INFORMATION: constructed sequence

<400> SEQUENCE: 34
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact     120
aggggttcct tgtagttaat gattaacccg ccatgctact tatctactta agtgtttgct     180
gcttgcaatg tttgcccatt ttaggggaat tcactcaaag ttcaaacctt atcatttttt     240
gctttgttcc tcttggcctt ggttttgtac atcagctttg aaaataccat cccagggtta     300
atgctggggt taatttataa ctaagagtgc tctagttttg caatacagga catgctataa     360
aaatggaaag atgttgcttt ctgagagaca gcggccgcca ccatgcccga gcaggaaaga     420
cagatcaccg ccagagaggg cgccagccgg aagatcctga gcaagctgag cctgcccacc     480
agagcctggg agcccgccat gaagaagtcc ttcgccttcg acaacgtggg ctacagggc      540 ggcctggacg gactgggacc atcttctcag gtggccacaa gcaccgtgcg cagcccgaa      600 gaactgagag ccgccattga ggacatggga ttcgaagcca gcgtggtgtc cgagagctgc     660
tccaccaacc ctctgggcaa tcacagcgcc ggcaacagca tggtgcagac caccgacggc     720 accccccacca gcgtgcagga agtggcccca catacaggca gactgccgc caatcacgcc     780 cccgatatcc tggccaagag ccccccagagt acaagagccg tggccccca gaagtgcttc     840 ctgcagatca agggcatgac ttgtgcctct tgtgtgtcca atatcgagcg gaacctgcag     900
aaagaggccg gcgtgctgtc tgtgctggtg gctctgatgg ccggcaaggc cgagatcaaa     960 tacgacccccg aagtgattca gcccctggaa atcgcccagt ttatccagga cctgggcttt    1020
gaagccgcct gatgaagaa ttacgccggc tccgacggca acatcgagct gaccatcacc     1080
ggaatgacct gcgcctcctg tgtgcacaac attgagtcca agctgacccg gaccaacggc     1140
atcacctacg cctctgtggc tctgccacc tccaaggccc tcgtgaagtt cgatcccgag     1200
atcatcggcc caggacat catcaagatc atcgaagaga tcggcttcca cgccagcctg     1260
gcccagagga accctaacgc ccaccacctg gaccacaaga tggaaatcaa gcagtggaag     1320
aaaagcttcc tgtgcagcct ggtgttcggc atcccgtga tggccctgat gatctacatg     1380
ctgatcccca gcaacgagcc ccaccagtcc atggtgctgg atcaaacat catccccggc     1440 ctgtctatcc tgaacctgat cttcttcatc ctgtgcacct tcgtgcagct gctgggcggc     1500
tggtacttct acgtgcaggc ctacaagtcc ctgcggcaca gatccgccaa catggacgtg     1560
ctgatcgtgc tggccacatc tatcgcctac gtgtactccc tcgtgatcct ggtggtggcc     1620
gtggccgaga agccgagag aagccctgtg accttcttcg acacccccc tatgctgttc     1680 gtgttatcg ccctgggccg gtggctggaa cacctggcca aaagcaagac cagcgaggcc     1740
```

```
ctggctaagc tgatgagtct gcaggccacc gaggccacag tcgtgaccct gggcgaggac   1800
aacctgatca tccgcgagga acaggtgcca atggaactgg tgcagcgggg cgacatcgtg   1860
aaggtggtgc ctggcggcaa gttccccgtg gacggaaaag tgctggaagg aataccatg    1920
gccgacgaga gcctgatcac aggcgaggcc atgcccgtga ccaagaaacc tggcagcaca   1980
gtgatcgccg gcagcatcaa tgcccacggc agcgtgctga ttaaggccac acacgtgggc   2040
aacgatacca ccctggctca gattgtgaag ctggtggaag aggcccagat gagcaaggcc   2100
cccattcagc agctggctga ccggttcagc ggctacttcg tgcccttat catcatcatg    2160
agcaccctga cactggtcgt gtggatcgtg atcggcttta tcgacttcgg agtggtgcag   2220
agatacttcc ccaaccctaa caagcacatc agccagacag aagtgatcat cagattcgcc   2280
tttcagacca gcatcaccgt gctgtgtatc gcctgcccct gtagcctggg actgccaca    2340
cctaccgctg tgatggtggg aacaggcgtg gccgctcaga acggcatcct gatcaagggg   2400
ggcaagcctc tggaaatggc tcacaagatc aagaccgtga tgttcgacaa gaccggcacc   2460
atcacccacg gcgtgcccag agtgatgaga gtgctgctgc tggggatgt ggccaccctg    2520
cctctgagaa aggtgctggc tgtcgtgggc acagccgagg ctagctctga cacccactg    2580
ggagtggccg tgacaaagta ctgcaaagag gaactgggca ccgaaaccct gggctactgc   2640
accgactttc aggccgtgcc tggctgtggc atcggctgca aggtgtccaa cgtggaaggc   2700
atcctggccc acagcgagag gccactgtct gcccctgcca gccacctgaa cgaggccgga   2760
tctctgcccg ccgaaaagga cgctgtgccc cagaccttct ctgtgctgat tggcaacaga   2820
gagtggctgc ggcggaacgg cctgaccatc tcctccgatg tgtccgacgc catgaccgac   2880
cacgagatga agggccagac cgccattctg tgggccattg acgggtgct gtgcggcatg   2940
atcgcaatcg ccgatgccgt gaaacaggaa gcagcactgg ccgtgcacac cctgcagtct   3000
atgggagtgg atgtggtgct gatcaccggc gacaacagaa agaccgccag gccattgcc    3060
acccaggtgg gcatcaacaa ggtgttcgcc gaggtgctgc ccagccacaa gtggccaag    3120
gtgcaggaac tgcagaacaa aggcaaaaag gtggccatgg tgggagatgg cgtgaacgac   3180
tctcctgctc tggcccaggc agatatgggc gtggccatcg gcacaggcac cgacgtggca   3240
attgaggctg ctgacgtggg gctgattcgg aacgacctgc tggacgtggt ggcctccatc   3300
cacctgtcca agagaaccgt gcggcggatc agaatcaacc tggtgctggc actgatctat   3360
aacctcgtgg gcatccctat cgccgctggc gtgttcatgc ctatcggaat cgtgctgcag   3420
ccctggatgg gctctgccgc catggctgca agctccgtgt ctgtggtgct gtccagcctg   3480
cagctgaagt gctacaagaa gcccgacctg gaaagatacg aggcccaggc ccacggacac   3540
atgaagcctc tgacagcctc ccaggtgtcc gtgcacatcg gcatgacga cagatggcgg   3600
gacagcccta gagccacccc ttgggatcag gtgtcatacg tgtcacaggt gtccctgagc   3660
agcctgacca gcgacaagcc cagcagacat agcgccgctg ccgacgacga tgggacaag   3720
tggtccctgc tgctgaacgg ccgggatgag gaacagtaca tctgataagc atgcaataaa   3780
gtctgagtgg gcggcagcct gtgtgtgcct gggttctctc tgtcccggaa tgtgcaaaca   3840
atggaggtgc tcgagtagat aagtagcatg gcgggttaat cattaactac aaggaacccc   3900
tagtgatgga gttggccact ccctctctgc gcgctcgctc gctcactgag gccgggcgac   3960
caaaggtcgc ccgacgcccg ggctttgccc gggcggcctc agtgagcgag cgagcgcgca   4020
gccttaatta acctaattca ctggccgtcg ttttacaacg tcgtgactgg gaaaaccctg   4080
```

```
gcgttaccca acttaatcgc cttgcagcac atcccccttt cgccagctgg cgtaatagcg    4140
aagaggcccg caccgatcgc ccttcccaac agttgcgcag cctgaatggc gaatgggacg    4200
cgccctgtag cggcgcatta agcgcggcgg gtgtggtggt tacgcgcagc gtgaccgcta    4260
cacttgccag cgccctagcg cccgctcctt tcgctttctt cccttccttt ctcgccacgt    4320
tcgccggctt tccccgtcaa gctctaaatc gggggctccc tttagggttc cgatttagtg    4380
ctttacggca cctcgacccc aaaaaacttg attagggtga tggttcacgt agtgggccat    4440
cgccctgata gacggttttt cgccctttga cgttggagtc cacgttcttt aatagtggac    4500
tcttgttcca aactgaaaca cactcaacc ctatctcggt ctattctttt gatttataag    4560
ggattttgcc gatttcggcc tattggttaa aaaatgagct gatttaacaa aaatttaacg    4620
cgaattttaa caaaatatta acgcttacaa tttaggtggc acttttcggg gaaatgtgcg    4680
cggaacccct atttgtttat ttttctaaat acattcaaat atgtatccgc tcatgagaca    4740
ataaccctga taaatgcttc aataatattg aaaaaggaag agtatgagta ttcaacattt    4800
ccgtgtcgcc cttattccct tttttgcggc attttgcctt cctgttttg ctcacccaga    4860 aacgctggtg aaagtaaaag atgctgaaga tcagttgggt gcacgagtgg gttacatcga    4920
actggatctc aacagcggta agatccttga gagttttcgc cccgaagaac gttttccaat    4980
gatgagcact tttaaagttc tgctatgtgg cgcggtatta tcccgtattg acgccgggca    5040
agagcaactc ggtcgccgca tacactattc tcagaatgac ttggttgagt actcaccagt    5100
cacagaaaag catcttacgg atggcatgac agtaagagaa ttatgcagtg ctgccataac    5160
catgagtgat aacactgcgg ccaacttact tctgacaacg atcggaggac cgaaggagct    5220
aaccgctttt ttgcacaaca tgggggatca tgtaactcgc cttgatcgtt gggaaccgga    5280
gctgaatgaa gccataccaa acgacgagcg tgacaccacg atgcctgtag caatggcaac    5340
aacgttgcgc aaactattaa ctggcgaact acttactcta gcttcccggc aacaattaat    5400
agactggatg gaggcggata aagttgcagg accacttctg cgctcggccc ttccggctgg    5460
ctggtttatt gctgataaat ctggagccgg tgagcgtggg tctcgcggta tcattgcagc    5520
actggggcca gatggtaagc cctcccgtat cgtagttatc tacacgacgg ggagtcaggc    5580
aactatggat gaacgaaata gacagatcgc tgagataggt gcctcactga ttaagcattg    5640
gtaactgtca gaccaagttt actcatatat actttagatt gatttaaaac ttcatttta    5700 atttaaaagg atctaggtga agatcctttt tgataatctc atgaccaaaa tcccttaacg    5760
tgagttttcg ttccactgag cgtcagaccc cgtagaaaag atcaaaggat cttcttgaga    5820
tccttttttt ctgcgcgtaa tctgctgctt gcaaacaaaa aaaccaccgc taccagcggt    5880
ggtttgtttg ccggatcaag agctaccaac tctttttccg aaggtaactg gcttcagcag    5940
agcgcagata ccaaatactg ttcttctagt gtagccgtag ttaggccacc acttcaagaa    6000
ctctgtagca ccgcctacat acctcgctct gctaatcctg ttaccagtgg ctgctgccag    6060
tggcgataag tcgtgtctta ccgggttgga ctcaagacga tagttaccgg ataaggcgca    6120
gcggtcgggc tgaacggggg gttcgtgcac acagcccagc ttggagcgaa cgacctacac    6180
cgaactgaga tacctacagc gtgagctatg agaaagcgcc acgcttcccg aagggagaaa    6240
ggcggacagg tatccggtaa gcggcagggt cggaacagga gagcgcacga gggagcttcc    6300
agggggaaac gcctggtatc tttatagtcc tgtcgggttt cgccacctct gacttgagcg    6360
tcgatttttg tgatgctcgt caggggggcg gagcctatgg aaaaacgcca gcaacgcggc    6420
ctttttacgg ttcctggcct tttgctggcc ttttgctcac atgttctttc ctgcgttatc    6480
```

```
ccctgattct gtggataacc gtattaccgc ctttgagtga gctgataccg ctcgccgcag    6540
ccgaacgacc gagcgcagcg agtcagtgag cgaggaagcg gaaagagcgcc caatacgcaa    6600 accgcctctc cccgcgcgtt ggccgattca ttaatgcagc tggcacgaca ggtttcccga    6660
ctggaaagcg ggcagtgagc gcaacgcaat taatgtgagt tagctcactc attaggcacc    6720
ccaggcttta cactttatgc ttccggctcg tatgttgtgt ggaattgtga gcggataaca    6780
atttcacaca ggaaacagct atgaccatga ttacgccaga tttaattaag g             6831

<210> SEQ ID NO 35
<211> LENGTH: 7437
<212> TYPE: DNA
<213> ORGANISM: Artificial Sequence
<220> FEATURE:
<223> OTHER INFORMATION: constructed sequence

<400> SEQUENCE: 35
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact    120
aggggttcct tgtagttaat gattaacccg ccatgctact tatctactta agtgtttgct    180
gcttgcaatg tttgcccatt ttaggggaat tcactcaaag ttcaaacctt atcattttt     240 gctttgttcc tcttggcctt ggttttgtac atcagctttg aaaataccat cccagggtta    300
atgctggggt taatttataa ctaagagtgc tctagttttg caatacagga catgctataa    360
aaatggaaag atgttgcttt ctgagagaca gcggccgcca ccatgcccga gcaggaaaga    420
cagatcaccg ccagagaggg cgccagccgg aagatcctga gcaagctgag cctgcccacc    480
agagcctggg agcccgccat gaagaagtcc ttcgccttcg acaacgtggg ctacgagggc    540
ggcctggacg gactgggacc atcttctcag gtggccacaa gcaccgtgcg cgaggccgcc    600
atcaagagca aggtggcccc tctgtctctg gccccatcg acatcgagag actgcagagc    660
accaacccca gcggcctct gagcagcgcc aaccagaact tcaacaacag cgagacactg    720
ggccaccagg gcagccacgt cgtgacactg cagctgcgga tcgacggaat gcactgcaag    780
agctgtgtgc tgaacatcga ggaaaacatc ggccagctgc tgggagtgca gagcatccag    840
gtgtcactgg aaaacaagac cgcccaggtg aagtacgacc ccagctgcac aagccccgtg    900
gccctgcaga gagccattga agctctgccc cctggcaact tcaaagtgtc cctgcctgac    960
ggagccgagg gctccggaac agatcacaga agcagcagca gccacagccc tggcagcccc   1020
cctagaaatc aggtgcaggg cacctgtagc accaccctga tcgccattgc cggcatgaca   1080
tgcgccagct gcgtgcactc tattgagggc atgatctccc agctggaagg cgtgcagcag   1140
atcagtgtgt ctctggccga gggcaccgcc acagtgctgt acaaccctag cgtgatcagc   1200
cccgaagaac tgagagccgc cattgaggac atgggattcg aagccagcgt ggtgtccgag   1260
agctgctcca ccaaccctct gggcaatcac agcgccggca acagcatggt gcagaccacc   1320
gacggcaccc ccaccagcgt gcaggaagtg gccccacata caggcagact gcccgccaat   1380
cacgcccccg atatcctggc caagagcccc cagagtacaa gagccgtggc ccccagaaag   1440
tgcttcctgc agatcaaggg catgacttgt gcctcttgtg tgtccaatat cgagcggaac   1500
ctgcagaaag aggccggcgt gctgtctgtg ctggtggctc tgatggccgg caaggccgag   1560
atcaaatacg accccgaagt gattcagccc ctggaaatcg cccagttat ccaggacctg   1620 ggctttgaag ccgccgtgat ggaagattac gccggctccg acggcaacat cgagctgacc   1680
```

```
atcaccggaa tgacctgcgc ctcctgtgtg cacaacattg agtccaagct gacccggacc    1740
aacggcatca cctacgcctc tgtggctctg gccacctcca aggccctcgt gaagttcgat    1800
cccgagatca tcggccccag ggacatcatc aagatcatcg aagagatcgg cttccacgcc    1860
agcctggccc agaggaaccc taacgcccac cacctggacc acaagatgga aatcaagcag    1920
tggaagaaaa gcttcctgtg cagcctggtg ttcggcatcc ccgtgatggc cctgatgatc    1980
tacatgctga tccccagcaa cgagcccac cagtccatgg tgctggatca acatcatc    2040
cccggcctgt ctatcctgaa cctgatcttc ttcatcctgt gcaccttcgt gcagctgctg    2100
ggcggctggt acttctacgt gcaggcctac aagtccctgc ggcacagatc cgccaacatg    2160
gacgtgctga tcgtgctggc cacatctatc gcctacgtgt actccctcgt gatcctggtg    2220
gtggccgtgg ccgagaaagc cgagagaagc cctgtgacct tcttcgacac ccccctatg    2280
ctgttcgtgt ttatcgccct gggccggtgg ctggaacacc tggccaaaag caagaccagc    2340
gaggccctgg ctaagctgat gagtctgcag gccaccgagg ccacagtcgt gaccctgggc    2400
gaggacaacc tgatcatccg cgaggaacag gtgccaatgg aactggtgca gcgggcgac    2460
atcgtgaagg tggtgcctgg cggcaagttc cccgtggacg aaaagtgct ggaagggaat    2520
accatggccg acgagagcct gatcacaggc gaggccatgc ccgtgaccaa gaaacctggc    2580
agcacagtga tcgccggcag catcaatgcc cacggcagcg tgctgattaa ggccacacac    2640
gtgggcaacg ataccaccct ggctcagatt gtgaagctgg tggaagaggc ccagatgagc    2700
aaggccccca ttcagcagct ggctgaccgg ttcagcggct acttcgtgcc ctttatcatc    2760
atcatgagca ccctgacact ggtcgtgtgg atcgtgatcg gctttatcga cttcggagtg    2820
gtgcagagat acttccccaa ccctaacaag cacatcagcc agacagaagt gatcatcaga    2880
ttcgcctttc agaccagcat caccgtgctg tgtatcgcct gccctgtag cctgggactg    2940
gccacaccta ccgctgtgat ggtgggaaca ggcgtggccg ctcagaacgg catcctgatc    3000
aagggggca agcctctgga aatggctcac aagatcaaga ccgtgatgtt cgacaagacc    3060
ggcaccatca cccacggcgt gcccagagtg atgagagtgc tgctgctggg ggatgtggcc    3120
accctgcctc tgagaaaggt gctggctgtc gtgggcacag ccgaggctag ctctgaacac    3180
ccactgggag tggccgtgac aaagtactgc aaagaggaac tgggcaccga aaccctgggc    3240
tactgcaccg actttcaggc cgtgcctggc tgtggcatcg gctgcaaggt gtccaacgtg    3300
gaaggcatcc tggcccacag cgagaggcca ctgtctgccc ctgccagcca cctgaacgag    3360
gccggatctc tgcccgccga aaaggacgct gtgcccagaa ccttctctgt gctgattggc    3420
aacagagagt ggctgcggcg gaacggcctg accatctcct ccgatgtgtc cgacgccatg    3480
accgaccacg agatgaaggg ccagaccgcc attctggtgg ccattgacgg ggtgctgtgc    3540
ggcatgatcg caatcgccga tgccgtgaaa caggaagcag cactggccgt gcacaccctg    3600
cagtctatgg gagtggatgt ggtgctgatc accggcgaca acagaaagac cgccagggcc    3660
attgccaccc aggtgggcat caacaaggtg ttcgccgagg tgctgcccag ccacaaagtg    3720
gccaaggtgc aggaactgca gaacaaaggc aaaaaggtgg ccatggtggg agatggcgtg    3780
aacgactctc ctgctctggc ccaggcagat atgggcgtgg ccatcggcac aggcaccgac    3840
gtggcaattg aggctgctga cgtggtgctg attcggaacg acctgctgga cgtggtggcc    3900
tccatccacc tgtccaagag aaccgtgcgc cggatcagaa tcaacctggt gctggcactg    3960
atctataacc tcgtgggcat ccctatcgcc gctggcgtgt tcatgcctat cggaatcgtg    4020
ctgcagccct ggatgggctc tgccgccatg gctgcaagct ccgtgtctgt ggtgctgtcc    4080
```

```
agcctgcagc tgaagtgcta caagaagccc gacctggaaa gatacagagc ccaggcccac   4140
ggacacatga agcctctgac agcctcccag gtgtccgtgc acatcggcat ggacgacaga   4200
tggcgggaca gccctagagc cacccttgg gatcaggtgt catacgtgtc acaggtgtcc    4260
ctgagcagcc tgaccagcga caagcccagc agacatagcg ccgctgccga cgacgatggg   4320
gacaagtggt ccctgctgct gaacggccgg gatgaggaac agtacatctg ataagcatgc   4380
aataaagtct gagtgggcgg cagcctgtgt gtgcctgggt tctctctgtc ccggaatgtg   4440
caaacaatgg aggtgctcga gtagataagt agcatggcgg gttaatcatt aactacaagg   4500 aaccccttagt gatggagttg gccactccct ctctgcgcgc tcgctcgctc actgaggccg   4560
ggcgaccaaa ggtcgcccga cgcccgggct tgcccgggc ggcctcagtg agcgagcgag    4620
cgcgcagcct taattaacct aattcactgg ccgtcgtttt acaacgtcgt gactgggaaa   4680
accctggcgt tacccaactt aatcgccttg cagcacatcc ccctttcgcc agctggcgta   4740
atagcgaaga ggcccgcacc gatcgccctt cccaacagtt gcgcagcctg aatggcgaat   4800
gggacgcgcc ctgtagcggc gcattaagcg cggcgggtgt ggtggttacg cgcagcgtga   4860
ccgctacact tgccagcgcc ctagcgcccg ctcctttcgc tttcttccct tcctttctcg   4920
ccacgttcgc cggctttccc cgtcaagctc taaatcgggg gctcccttta gggttccgat   4980
ttagtgcttt acggcacctc gaccccaaaa aacttgatta gggtgatggt tcacgtagtg   5040
ggccatcgcc ctgatagacg gtttttcgcc ctttgacgtt ggagtccacg ttctttaata   5100
gtggactctt gttccaaact ggaacaacac tcaaccctat ctcggtctat tcttttgatt   5160
tataagggat tttgccgatt tcggcctatt ggttaaaaaa tgagctgatt taacaaaaat   5220
ttaacgcgaa ttttaacaaa atattaacgc ttacaattta ggtggcactt ttcggggaaa   5280
tgtgcgcgga acccctattt gtttatttt ctaaatacat tcaaatatgt atccgctcat   5340
gagacaataa ccctgataaa tgcttcaata atattgaaaa aggaagagta tgagtattca   5400
acatttccgt gtcgccctta ttccctttt tgcggcattt tgccttcctg ttttttgctca   5460 cccagaaacg ctggtgaaag taaaagatgc tgaagatcag ttgggtgcac gagtgggtta   5520
catcgaactg gatctcaaca gcggtaagat ccttgagagt tttcgccccg aagaacgttt   5580
tccaatgatg agcactttta aagttctgct atgtggcgcg gtattatccc gtattgacgc   5640
cgggcaagag caactcggtc gccgcataca ctattctcag aatgacttgg ttgagtactc   5700
accagtcaca gaaaagcatc ttacggatgg catgacagta agagaattat gcagtgctgc   5760
cataaccatg agtgataaca ctgcggccaa cttacttctg acaacgatcg gaggaccgaa   5820
ggagctaacc gcttttttgc acaacatggg ggatcatgta actcgccttg atcgttggga   5880
accggagctg aatgaagcca taccaaacga cgagcgtgac accacgatgc ctgtagcaat   5940
ggcaacaacg ttgcgcaaac tattaactgg cgaactactt actctagctt cccggcaaca   6000
attaatagac tggatggagg cggataaagt tgcaggacca cttctgcgct cggcccttcc   6060
ggctggctgg tttattgctg ataaatctgg agccggtgag cgtgggtctc gcggtatcat   6120
tgcagcactg gggccagatg gtaagccctc ccgtatcgta gttatctaca cgacggggag   6180
tcaggcaact atggatgaac gaaatagaca gatcgctgag ataggtgcct cactgattaa   6240
gcattggtaa ctgtcagacc aagtttactc atatatactt tagattgatt taaaacttca   6300
tttttaattt aaaaggatct aggtgaagat cctttttgat aatctcatga ccaaaatccc   6360
ttaacgtgag ttttcgttcc actgagcgtc agaccccgta gaaaagatca aaggatcttc   6420
```

```
ttgagatcct tttttctgc gcgtaatctg ctgcttgcaa acaaaaaaac caccgctacc  6480
agcggtggtt tgtttgccgg atcaagagct accaactctt tttccgaagg taactggctt  6540
cagcagagcg cagataccaa atactgttct tctagtgtag ccgtagttag gccaccactt  6600
caagaactct gtagcaccgc ctacatacct cgctctgcta atcctgttac cagtggctgc  6660
tgccagtggc gataagtcgt gtcttaccgg gttggactca agacgatagt taccggataa  6720
ggcgcagcgg tcgggctgaa cggggggttc gtgcacacag cccagcttgg agcgaacgac  6780
ctacaccgaa ctgagatacc tacagcgtga gctatgagaa agcgccacgc ttcccgaagg  6840
gagaaaggcg gacaggtatc cggtaagcgg cagggtcgga acaggagagc gcacgaggga  6900
gcttccaggg ggaaacgcct ggtatcttta tagtcctgtc gggtttcgcc acctctgact  6960
tgagcgtcga tttttgtgat gctcgtcagg gggcggagc ctatggaaaa acgccagcaa  7020
cgcggccttt ttacggttcc tggccttttg ctggccttt gctcacatgt tctttcctgc  7080
gttatcccct gattctgtgg ataaccgtat taccgccttt gagtgagctg ataccgctcg  7140
ccgcagccga acgaccgagc gcagcgagtc agtgagcgag gaagcggaag agcgcccaat  7200
acgcaaaccg cctctccccg cgcgttggcc gattcattaa tgcagctggc acgacaggtt  7260
tcccgactgg aaagcgggca gtgagcgcaa cgcaattaat gtgagttagc tcactcatta  7320
ggcaccccag gctttacact ttatgcttcc ggctcgtatg ttgtgtggaa ttgtgagcgg  7380
ataacaattt cacacaggaa acagctatga ccatgattac gccagattta attaagg     7437
```

GENE THERAPY FOR TREATING WILSON'S DISEASE

CROSS-REFERENCE TO RELATED APPLICATIONS

This is a National Stage Entry under 35 U.S.C. 371 of International Patent Application No. PCT/US2017/068919, filed Dec. 29, 2017, which claims the benefit of priority of U.S. Provisional Patent Application No. 62/440,659, filed Dec. 30, 2016 and U.S. Provisional Patent Application No. 62/473,656 filed Mar. 20, 2017. These applications are incorporated by reference herein.

INCORPORATION-BY-REFERENCE OF MATERIAL SUBMITTED IN ELECTRONIC FORM

Applicant hereby incorporates by reference the Sequence Listing material filed in electronic form herewith. This file is labeled "UPN-16-7940PCT_ST25.txt".

1. INTRODUCTION

The application relates to embodiments useful for a gene therapy for treating Wilson's Disease.

2. BACKGROUND

The application relates to embodiments useful for a gene therapy for treating Wilson's disease. Wilson's disease is an autosomal recessive genetic disorder copper storage disorder due to mutations in the copper-transporting ATPase 2 (ATP7B) gene on chromosome 13. Copper accumulates in tissues manifesting as neurological or psychiatric symptoms and liver disease typically observed between the ages of 12 and 23. Over time without proper treatments, high copper levels can cause life-threatening organ damage.

Current treatment approaches for Wilson's disease are daily oral therapy with chelating agents (penicillamine [Cuprimine] and trientine hydrochloride [Syprine]), zinc (to block enterocyte absorption of copper), and tetrathiomolybdate (TM), a copper chelator that forms complexes with albumin in the circulation, which require the affected individual to take medicines for their whole life. Furthermore, those treatments may cause side effects, such as drug induced lupus, myasthenia, paradoxical worsening, and do not restore normal copper metabolism. Liver transplantation is curative for Wilson's disease but transplant recipients are required to maintain a constant immune suppression regimen to prevent rejection.

3. SUMMARY

The embodiments described herein relate to an AAV gene therapy vector for delivering normal human copper-transporting ATPase 2 (ATP7B) to a subject in need thereof, following intravenous (IV) administration of the vector resulting in long-term, perhaps 10 years or more, of clinically meaningful correction of Wilson's Disease ("WD"). The vector dose is intended to deliver blood levels of ATP7B to reduce circulating copper levels by about 25% or more. In one embodiment, the level of circulating copper is assessed via the excretion of copper in the urine. In another embodiment, the level of circulating copper in the plasma is assessed.

In one aspect, this application provides the use of a replication deficient adeno-associated virus (AAV) to deliver a human copper-transporting ATPase 2 (ATP7B) gene to liver cells of patients (human subjects) diagnosed with WD. The recombinant AAV vector (rAAV) used for delivering the hATP7B gene ("rAAV.hATP7B") should have a tropism for the liver (e.g., a rAAV bearing an AAV8 capsid), and the hATP7B transgene should be controlled by liver-specific expression control elements. In one embodiment, the expression control elements include one or more of the following: an enhancer; a promoter; an intron; a WPRE; and a polyA signal. Such elements are further described herein. Due to the size of the hATP7B coding sequence, selection of control elements which allow for effective expression is important. If expression of the transgene is not sufficient, the vector dosage required for correction of the defect will be too high to be practical. Thus, as described herein, selection of the e.g., enhancer, promoter and polyA is important.

In one embodiment, the hATP7B coding sequence is shown in SEQ ID NO: 1. In one embodiment, the ATP7B protein sequence is shown in SEQ ID NO: 2. The coding sequence for hATP7B is, in one embodiment, codon optimized for expression in humans. Such sequence may share less than 80% identity to the native hATP7B coding sequence (SEQ ID NO: 3). In one embodiment, the hATP7B coding sequence is that shown in SEQ ID NO: 1.

In another aspect, provided herein is an aqueous suspension suitable for administration to a WD patient which includes the rAAV described herein. In some embodiments, the suspension includes an aqueous suspending liquid and about $1 \times 10^{12}$ to about $1 \times 10^{14}$ genome copies (GC) of the rAAV/mL. The suspension is, in one embodiment, suitable for intravenous injection. In other embodiment, the suspension further includes a surfactant, preservative, and/or buffer dissolved in the aqueous suspending liquid.

In another embodiment, provided herein is a method of treating a patient having WD with a rAAV as described herein. In one embodiment, about $1 \times 10^{11}$ to about $3 \times 10^{13}$ genome copies (GC) of the rAAV/kg patient body weight are delivered the patient in an aqueous suspension.

3. BRIEF DESCRIPTION OF THE DRAWINGS

FIG. 1 is a schematic representation of AAV8.En34.TBG-S1.hATP7Bco.PA75 vector.

Figure 2A:
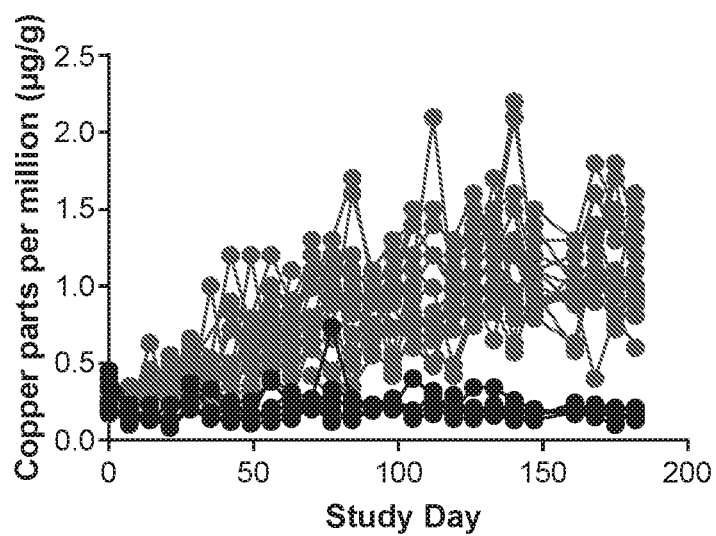
Figure 2B:
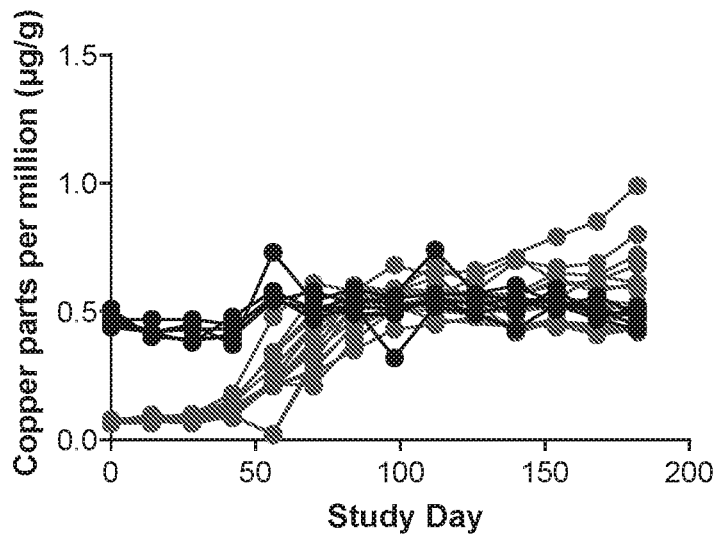

FIGS. 2A-2B demonstrate that urinary and serum copper levels increase over time in Atp7b KO mice. (A) Urine and (B) serum copper levels in Atp7b KO mice over time (black). Heterozygous littermates (Het) served as control (gray). Samples were collected weekly in the natural history study and inductively coupled plasma-mass spectrometry was performed to assess the copper level.

Figure 3A:
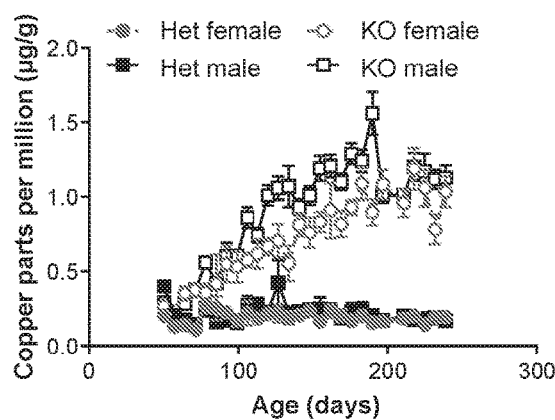
Figure 3B:
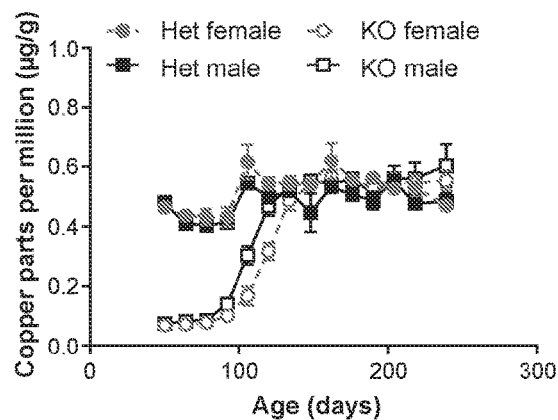
Figure 3C:
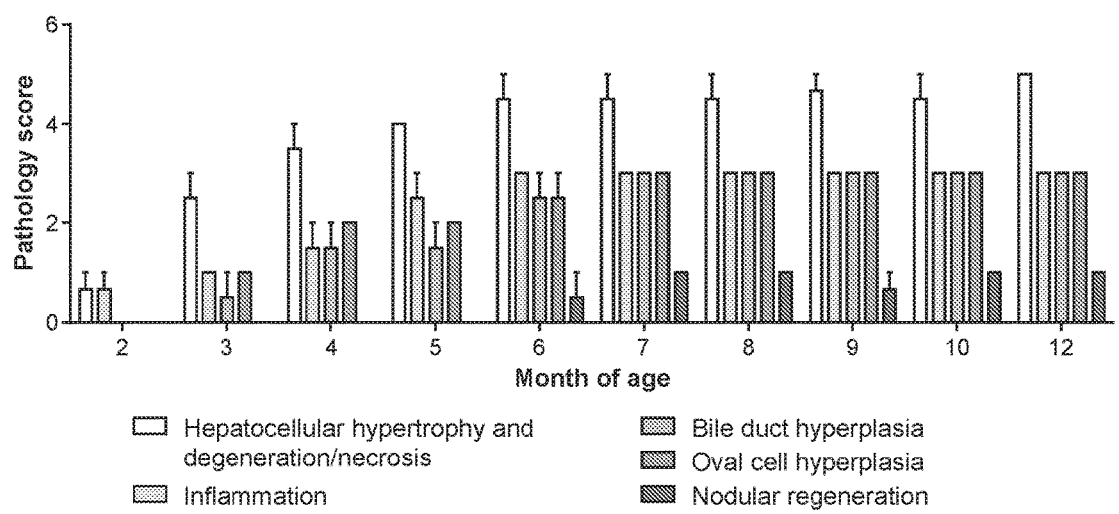

FIGS. 3A-3C demonstrate urine, copper levels, serum copper levels, and liver disease scoring in Atp7b KO mice. (A) Urine and (B) serum copper levels were evaluated by inductively coupled plasma-mass spectrometry in male and female heterozygous (Het) and Atp7b KO mice over time (KO). (C) Atp7b KO mice were necropsied at 2, 3, 4, 5, 9, 10, and 12 months of age. Liver was harvested, stained with H&E, and evaluated histologically according to the 1-5 scoring system. Values expressed as mean±SEM.

Figure 4:
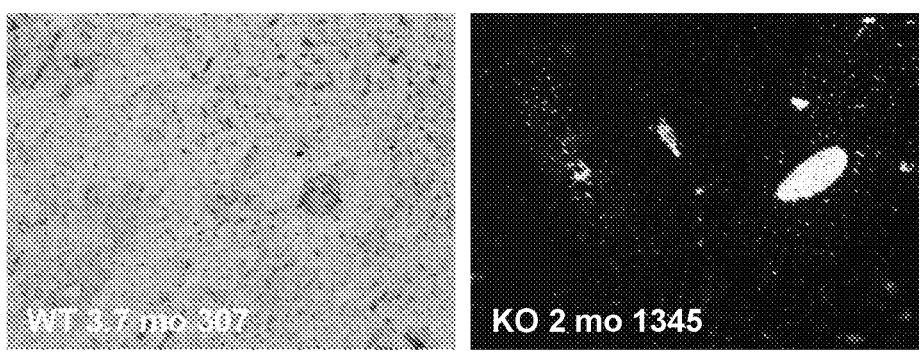

FIG. 4 demonstrates Timm's staining in Atp7b KO mice. Representative result of Timm's staining for copper in the liver of a 2 month-old Atp7b KO mouse with identification number 1345. Black deposits indicate positive staining for copper. A 3.7 month-old wild type mouse with identification number 307 served as a negative control.

Figure 5:
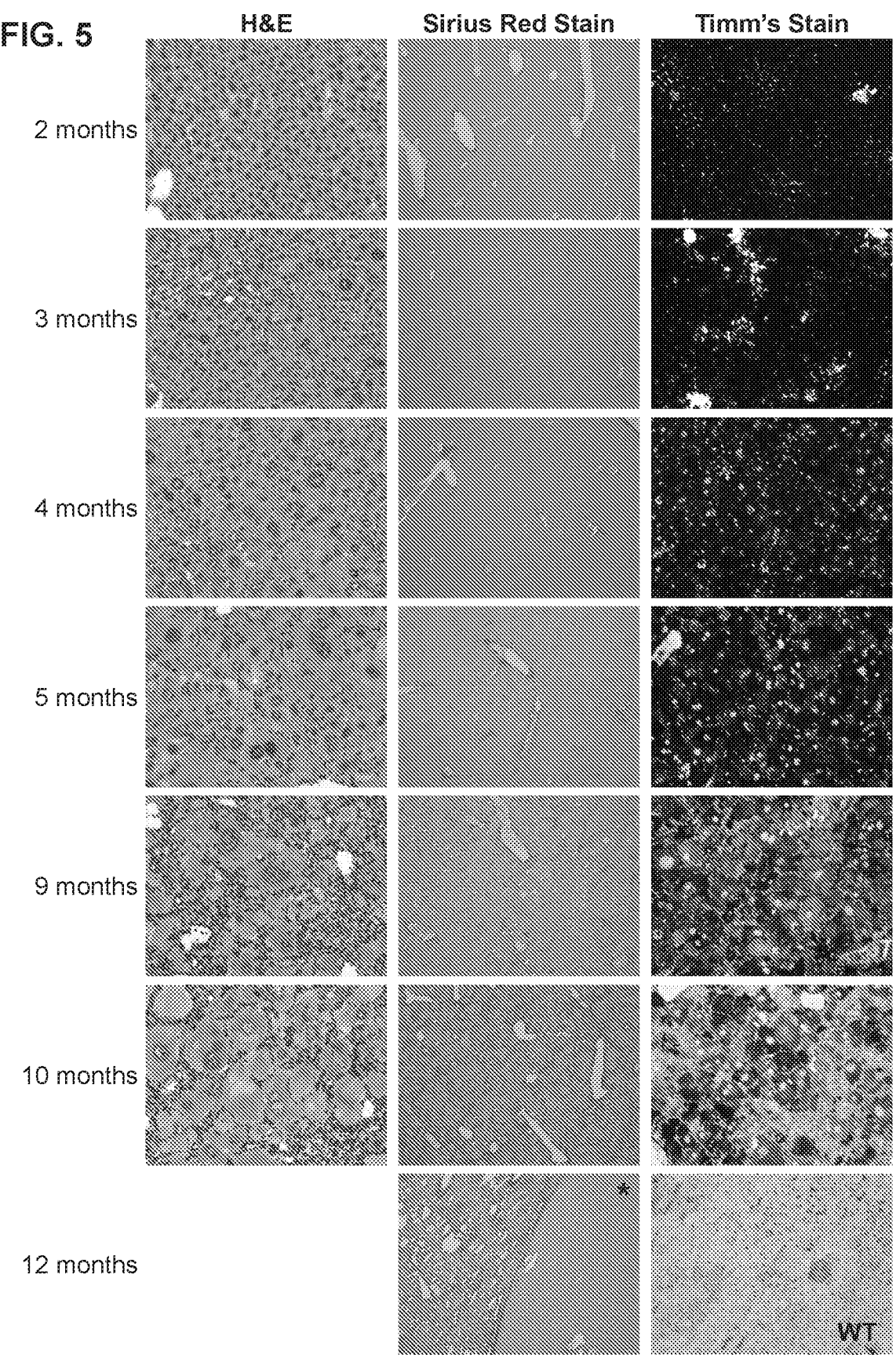

FIG. 5 demonstrates that liver disease develops over time in Atp7b KO mice. Atp7b KO mice were necropsied at 2, 3, 4, 5, 9, 10, and 12 months of age and liver was harvested to evaluate liver disease. H&E, Sirius Red, and Timm's stain were performed for histopathologic evaluation of liver lesions, including fibrosis, and copper accumulation. *, area of regeneration within the liver of a 12 month old Atp7b KO mouse. WT, section from a wild type mouse as a negative control for copper accumulation as seen by the Timm's stain.

Figure 6A:
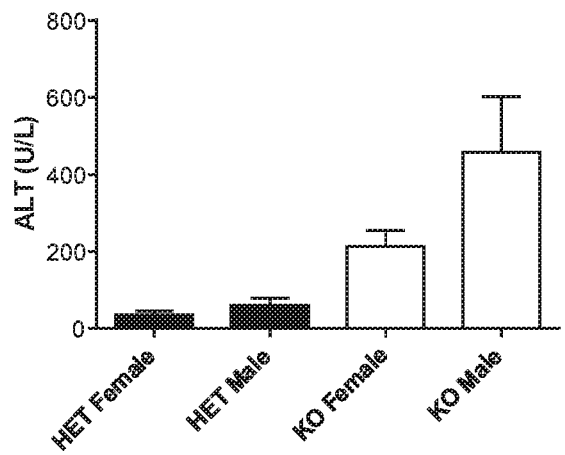
Figure 6B:
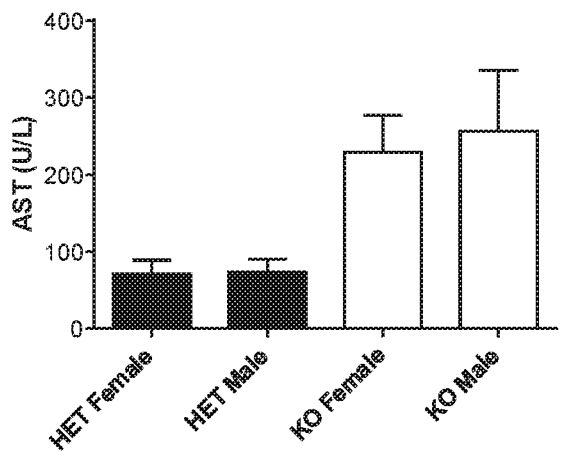
Figure 6C:
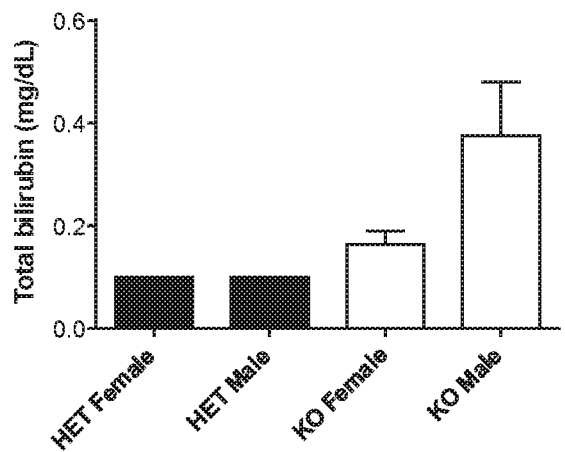

FIGS. 6A-6C demonstrate serum chemistry values in 8 month old Atp7b KO mice. (A) ALT, (B) AST, and (C) total bilirubin levels in 8 month old Atp7b KO mice (KO) and heterozygous mice (Het).

Figure 7:
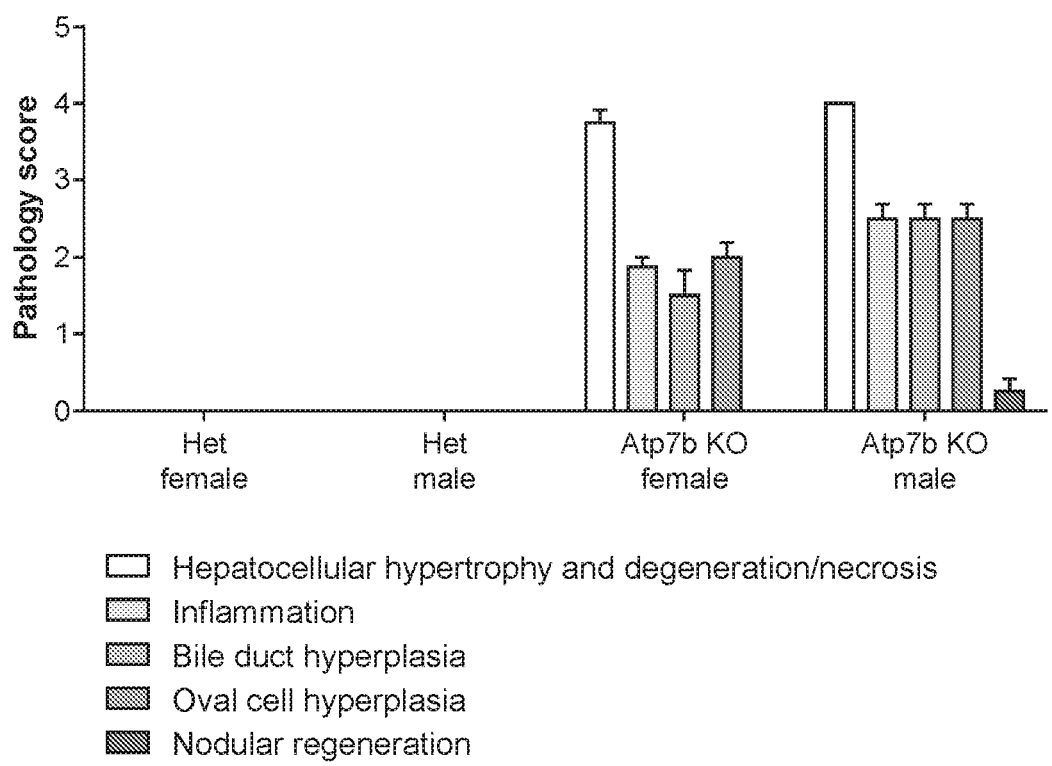

FIG. 7 demonstrates liver disease in 8 month old Atp7b KO mice. Atp7b KO and heterozygous (Het) mice were necropsied at 8 months of age. Liver was harvested, stained with H&E, and evaluated histologically according to the 1-5 scoring system. Values expressed as mean±SEM.

FIGS. 8A and 8B demonstrate liver fibrosis and copper accumulation in 8 month old Atp7b KO mice. Atp7b KO (KO) and heterozygous (Het) mice were necropsied at 8 months of age. Liver was harvested, stained with Sirius Red and Timm's stain for evaluation of fibrosis and copper accumulation, respectively. Histopathologic evaluation of liver lesions, including (A) fibrosis and (B) copper accumulation, was performed according to the 1-5 scoring system. Values expressed as mean±SEM.

Figure 9:
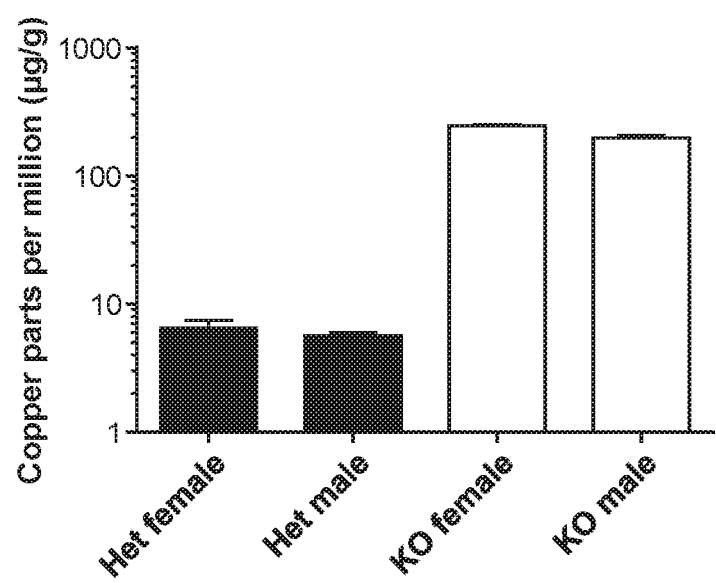

FIG. 9 demonstrates liver copper levels in 8 month old Atp7b KO mice Atp7b KO (KO) and heterozygous (Het) mice were necropsied at 8 months of age. Liver was harvested and liver copper levels were evaluated by inductively coupled plasma-mass spectrometry. Values expressed as mean±SEM.

Figure 10A:
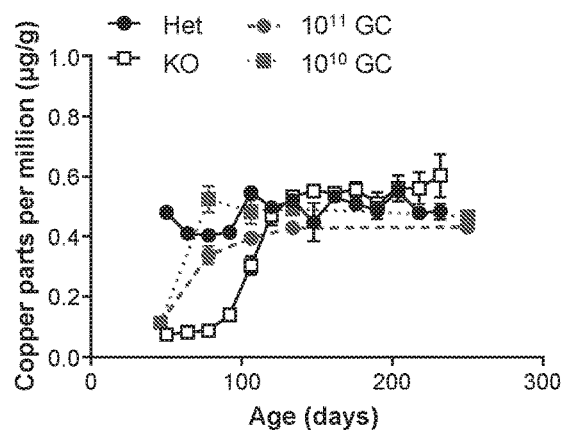
Figure 10B:
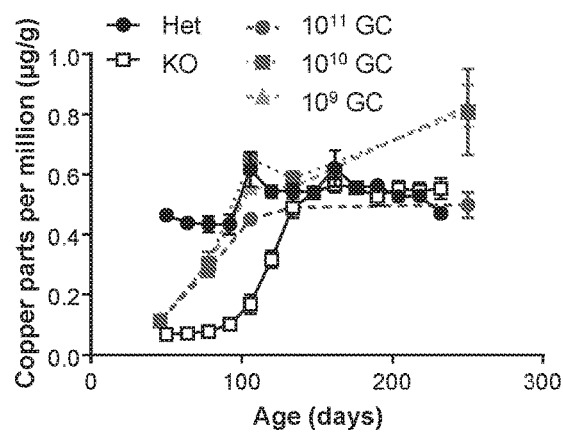
Figure 10C:
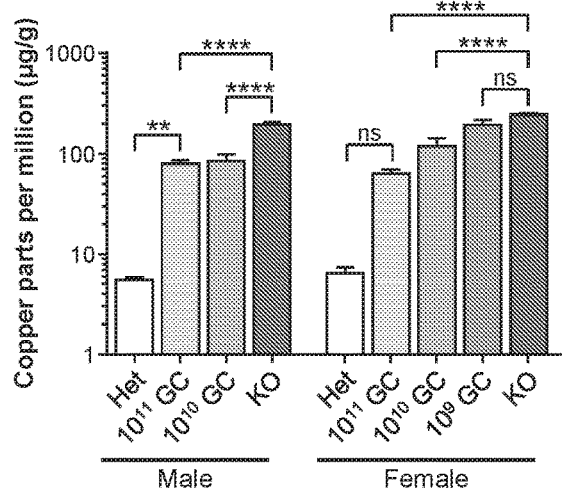

FIGS. 10A-10C demonstrates that AAV8 gene therapy can restore normal liver copper metabolism in Atp7b KO mice. Male Atp7b KO mice were injected i.v. with $10^{11}$ GC/mouse and $10^{10}$ GC/mouse of AAV8.TTR.hATP7Bco, and female Atp7b KO mice were injected i.v. with $10^{11}$, $10^{10}$; and $10^9$ GC/mouse of the same vector. Serum copper levels in (A) males and (B) females were evaluated by inductively coupled plasma-mass spectrometry and compared to serum copper levels from age-matched male and female heterozygous (het) and Atp7b KO mice. Mice were necropsied at 9 months of age and liver was harvested. (C) Liver copper levels were also evaluated by inductively coupled plasma-mass spectrometry and compared to age-matched uninjected heterozygous (het) and Atp7b KO mice. Values expressed as mean±SEM. ns, not significant; p<0.01, **p<0.0001.

Figure 11:
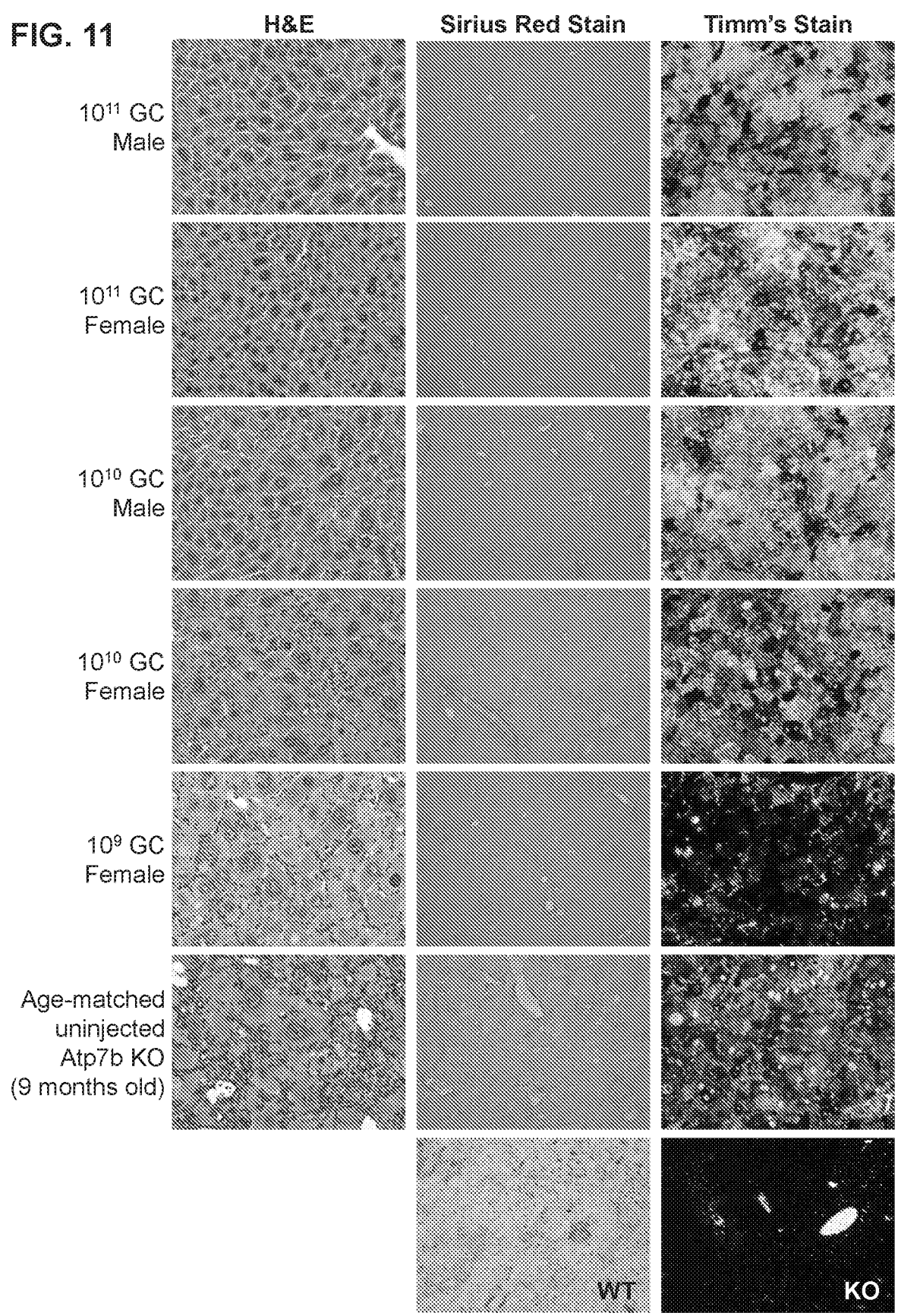

FIG. 11 demonstrates that high-dose AAV8 gene therapy prevents the development of liver disease in Atp7b KO mice. Male Atp7b KO mice were injected i.v. with $10^{11}$ GC/mouse and $10^{10}$ GC/mouse of AAV8.TTR.hATP7Bco, and female Atp7b KO mice were injected i.v. with $10^{11}$, $10^{10}$, and $10^9$ GC/mouse of the same vector. Mice were necropsied at 9 months of age and liver was harvested to evaluate liver disease. H&E; Sirius Red, and Timm's stain were performed to evaluate histopathological lesions of the liver, including, fibrosis and copper accumulation. Images from age-matched uninjected Atp7b KO mice are included for comparison (also presented in FIG. 2). WT, section from a wild type (WT) mouse as a negative control for copper accumulation as seen by the Timm's stain. KO, section from a two month old Atp7b KO mouse as a positive control for copper accumulation as seen by the Timm's stain.

Figure 12A:
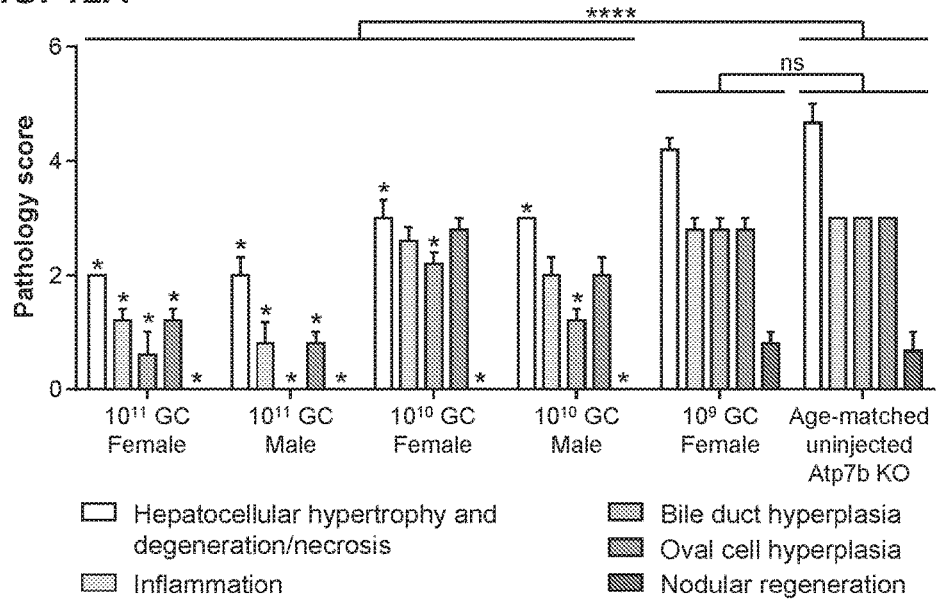
Figure 12B:
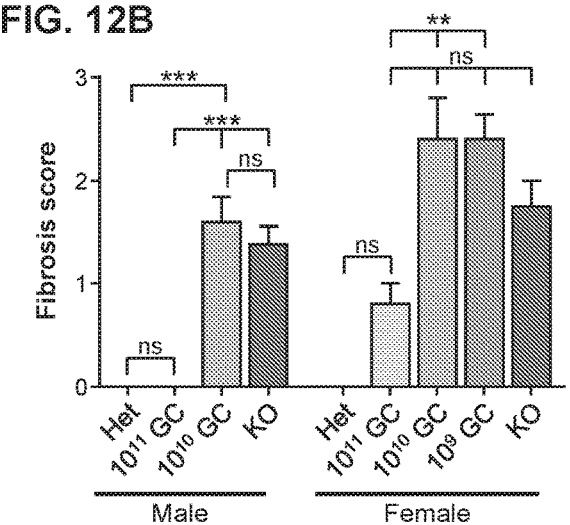
Figure 12C:
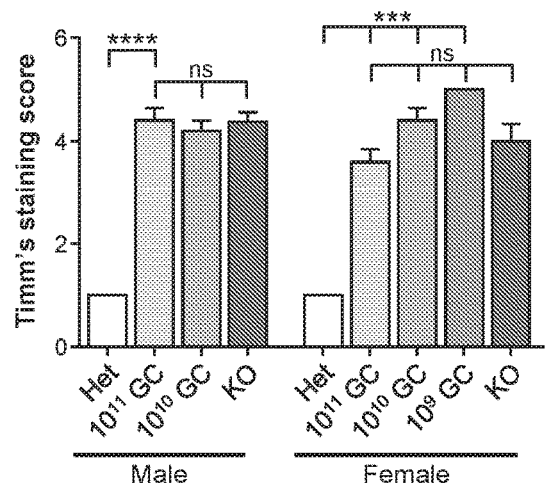

FIGS. 12A-12C demonstrates quantification of prevention of liver disease following high-dose AAV8 gene therapy in Atp7b KO mice. Male Atp7b KO mice were injected i.v. with $10^{11}$ GC/mouse and $10^{10}$ GC/mouse of AAV8.TTR.hATP7Bco and female Atp7b KO mice were injected i.v. with $10^{11}$, $10^{10}$, and $10^9$ GC/mouse of the same vector. Mice were necropsied at 9 months of age and liver was harvested for histologic to evaluation. (A) Liver sections were stained with H&E and evaluated histologically according to the 1-5 scoring system. (B) Liver sections were stained with Sirius Red and evaluated for fibrosis according to the 1-3 scoring system and (C) Timm's stain was performed on liver sections for evaluation of copper accumulation according to the 1-5 scoring system. Values expressed as mean±SEM were compared to age-matched uninjected heterozygous (Het) and Atp7b KO mice. ns, not significant; *p<0.05, p<0.01, *p<0.001, ****p<0.0001.

Figure 13A:
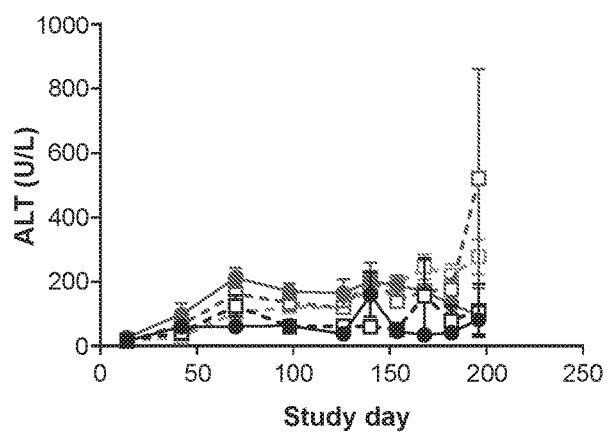
Figure 13B:
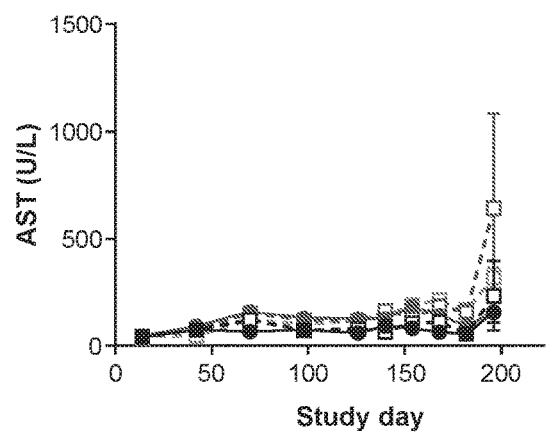
Figure 13C:
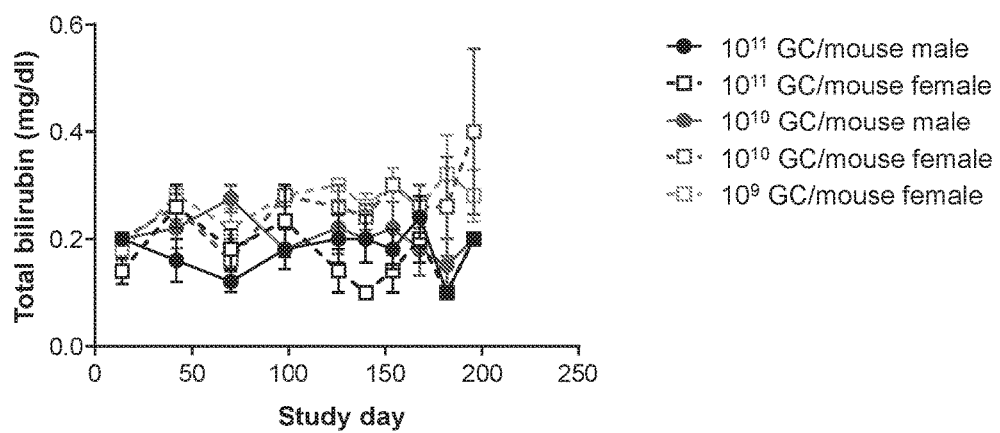

FIGS. 13A-13C demonstrate serum chemistry levels in Atp7b KO mice following AAV8 gene therapy. Male Atp7b KO mice were injected IV with $10^{11}$ GC/mouse and $10^{10}$ GC/mouse of AAV8.TTR.hATP7Bco and female Atp7b KO mice were injected i.v. with $10^{11}$, $10^{10}$, and $10^9$ GC/mouse of the same vector. (A) ALT, (B) AST, and (C) total bilirubin levels were evaluated in serum.

Figure 14:
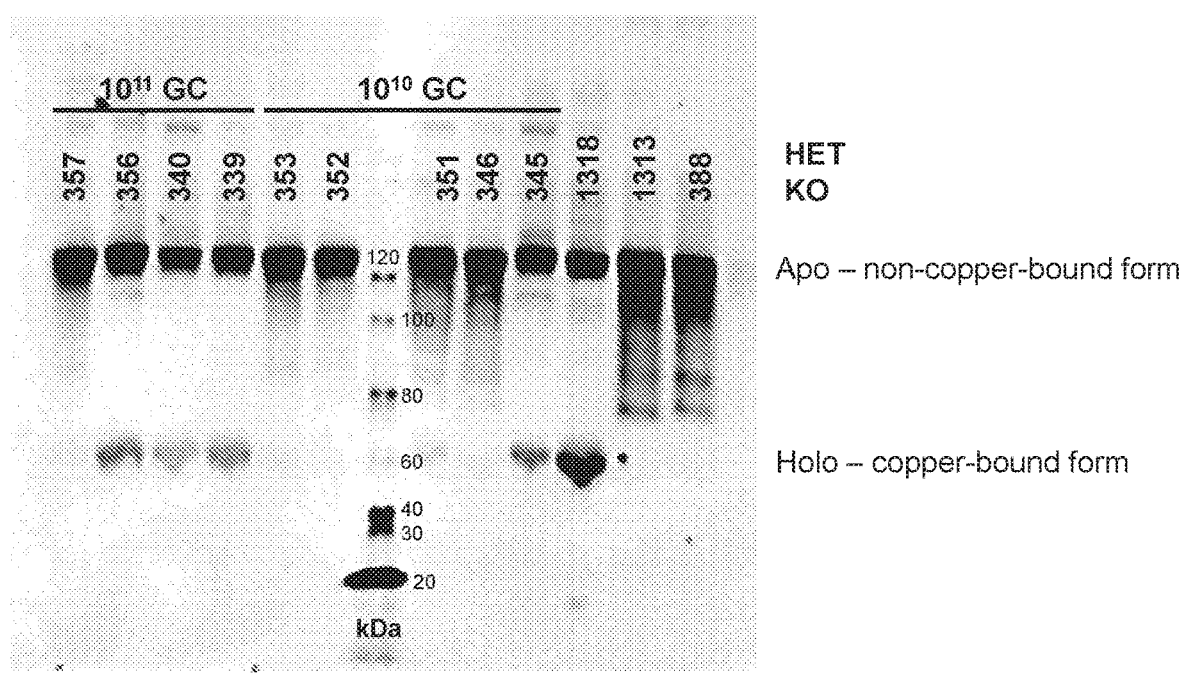

FIG. 14 demonstrates detection of ceruloplasmin by Western blot. Western blot detecting copper-bound (Holo, lower band) and non-copper-bound (Apo, upper band) forms of ceruloplasmin in Atp7b KO mice injected i.v. with $10^{10}$ or $10^{11}$ GC per mouse of AAV8.EnTTR.TTR.hATP7Bco.PA75. Blood samples were collected on Day 21 after the administration. Protein markers were provided in the center lane for comparison. Atp7b KO and heterozygous (het) littermates without vector injections served as controls (1318, 6 month old het; 1313, 6 month old Atp7b KO; 388, Atp7b KO).

Figure 15A:
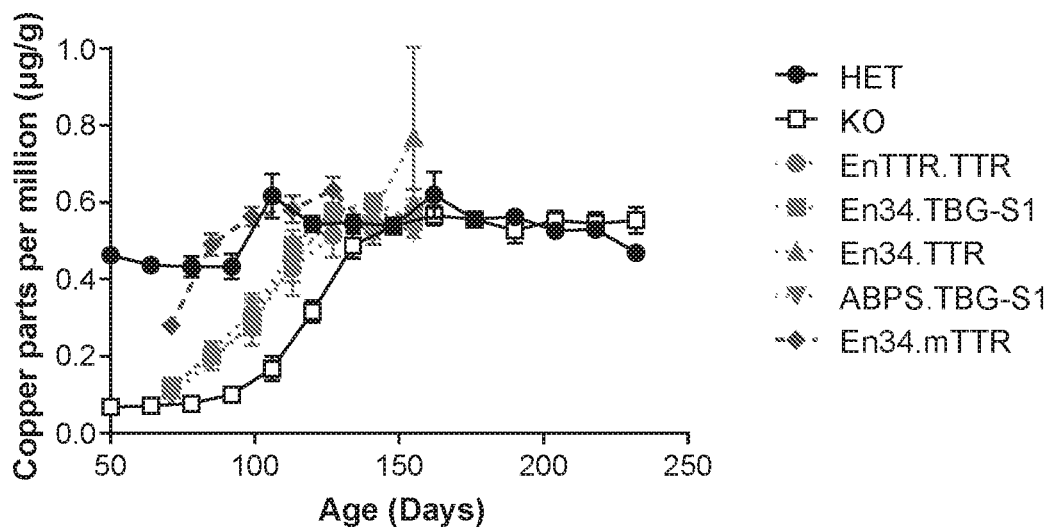
Figure 15B:
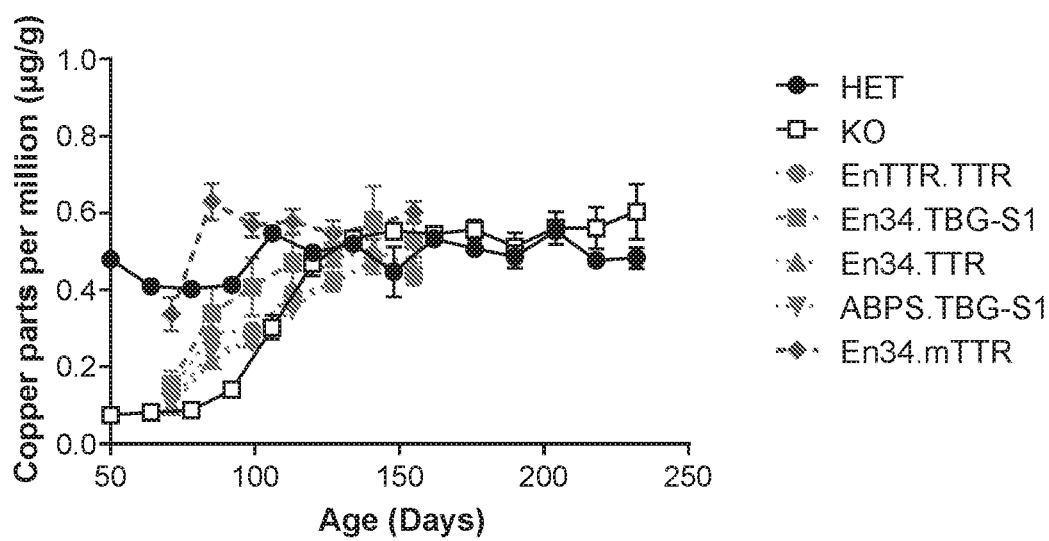

FIGS. 15A-15B demonstrates serum copper levels in female and male AAV8 vector administered Atp7b KO mice. Atp7b KO mice were administered i.v. with $3\times10^{12}$ GC/kg of AAV8 vectors for expression of hATP7Bco with different enhancer/promoter combinations (circles, EnTTR.TTR, AAV8.EnTTR.TTR.hATP7Bco.PA75; squares, En34.TBG-S1, AAV8.En34.TBG-S1.hATP7Bco.PA75; upright triangles, En34.TTR, AAV8.En34.TTR.hATP7Bco.PA75; inverted triangles, ABPS.TBG-S1, AAV8.ABPS.TBG-S1.hATP7Bco.PA75; diamonds, En34.mTTR, AAV8.En34.mTTR.hATP7Bco.PA75). Uninjected Atp7b KO and heterozygous (Het) mice served as controls. Serum copper levels were evaluated by inductively coupled plasma-mass spectrometry in (A) female and (B) male Atp7b KO mice. Values expressed as mean±SEM.

Figure 16A:
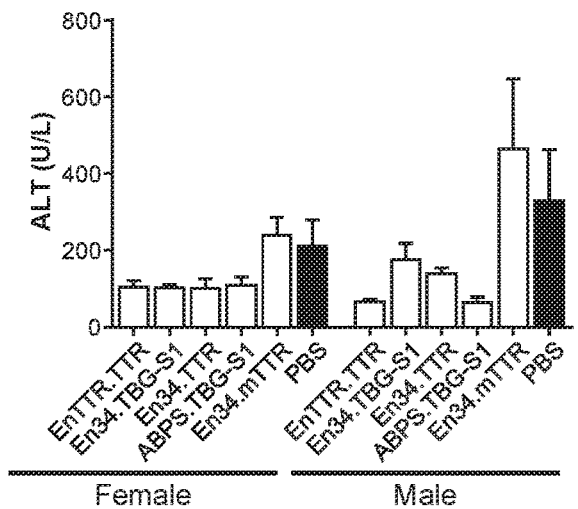
Figure 16B:
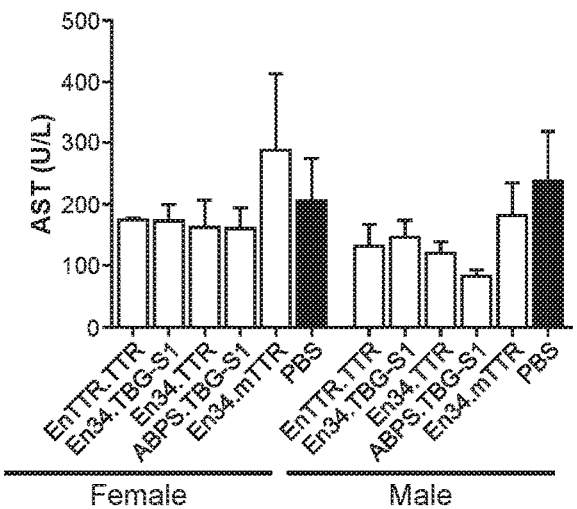
Figure 16C:
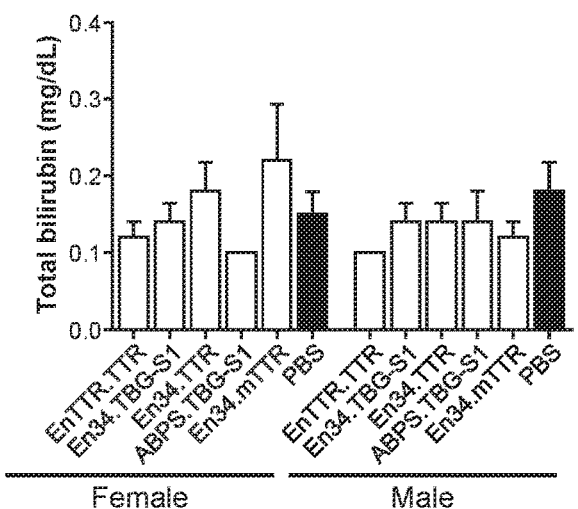

FIGS. 16A-16C demonstrates serum chemistries in female and male AAV8 vector administered Atp7b KO mice. Female and male Atp7b KO mice were administered i.v. with $3\times10^{12}$ GC/kg of AAV8 vectors for expression of hATP7Bco with different enhancer/promoter combinations (EnTTR.TTR, AAV8.EnTTR.TTR.hATP7Bco.PA75; En34.TBG-S1, AAV8.En34.TBG-S1.hATP7Bco.PA75; En34.TTR, AAV8.En34.TTR.hATP7Bco.PA75; ABPS.TBG-S1, AAV8.ABPS.TBG-S1.hATP7Bco.PA75; En34.mTTR, AAV8.En34.mTTR.hATP7Bco.PA75). Vehicle control administered Atp7b KO (PBS) mice served as controls. (A) ALT, (B) AST, and (C) total bilirubin levels were evaluated in serum. Values expressed as mean±SEM.

Figure 17:
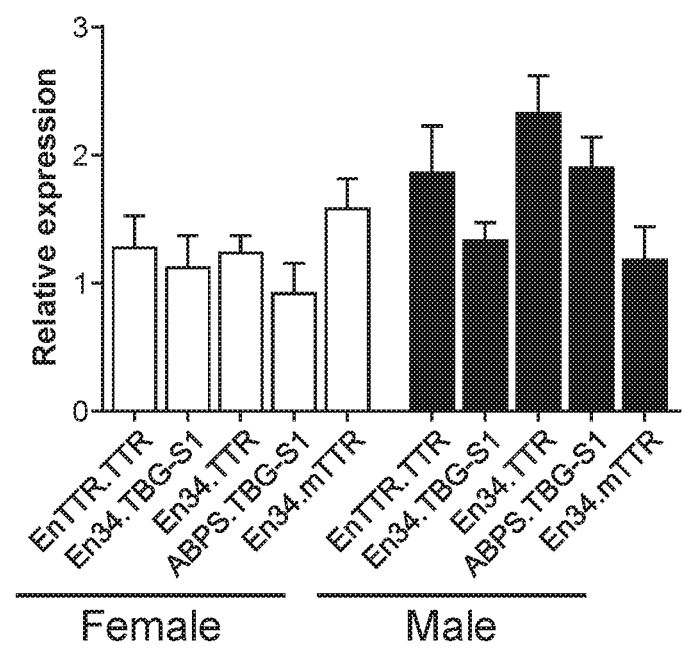

FIG. 17 demonstrates liver ATP7Bco expression determined by Western blot. Female and male Atp7b KO mice were administered i.v. with $3\times10^{12}$ GC/kg of AAV8 vectors for expression of hATP7Bco with different enhancer/promoter combinations (EnTTR.TTR, AAV8.EnTTR.TTR.hATP7Bco.PA75; En34.TBG-S1, AAV8.En34.TBG-S1.hATP7Bco.PA75; En34.TTR, AAV8.En34.TTR.hATP7Bco.PA75; ABPS.TBG-S1, AAV8.ABPS.TBG-S1.hATP7Bco.PA75; En34.mTTR, AAV8.En34.mTTR.hATP7Bco.PA75) and sacrificed at 6 months of age. Western blot detecting ATP7B in Atp7b KO mice was quantified by band densitometry. Values expressed as mean±SEM.

Figure 18:
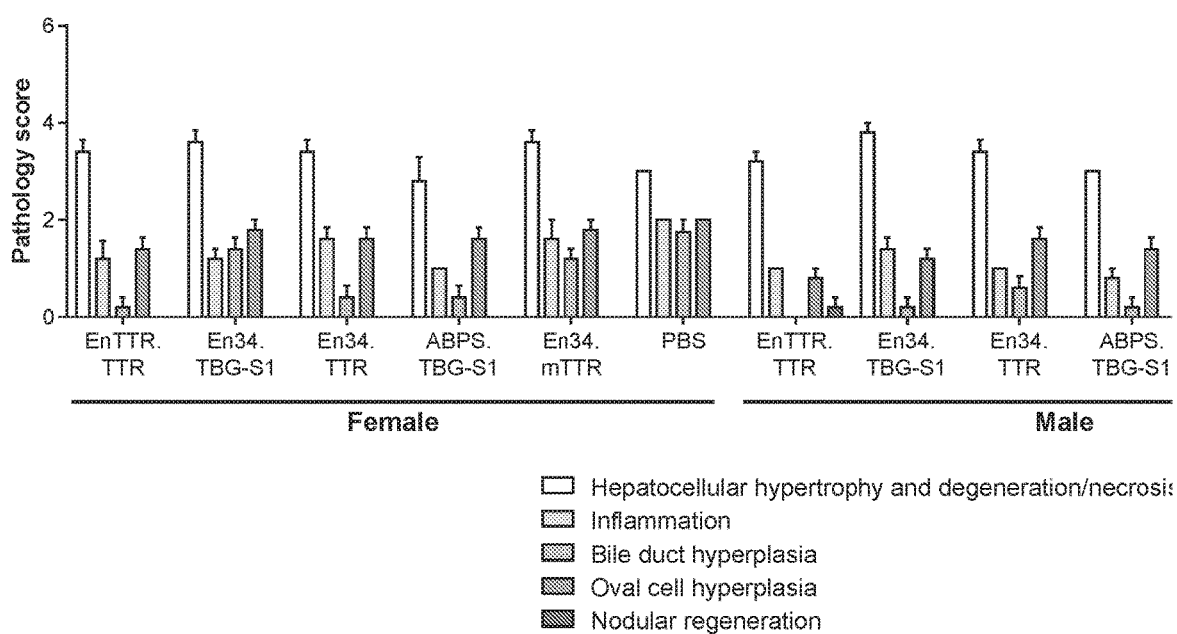

FIG. 18 demonstrates liver disease in female and male AAV8 vector administered Atp7b KO mice. Female and male Atp7b KO mice were administered i.v. with $3\times10^{12}$ GC/kg of AAV8 vectors for expression of hATP7Bco with different enhancer/promoter combinations (EnTTR.TTR, AAV8.EnTTR.TTR.hATP7Bco.PA75; En34.TBG-S1, AAV8.En34.TBG-S1.hATP7Bco.PA75; En34.TTR, AAV8.En34.TTR.hATP7Bco.PA75; ABPS.TBG-S1, AAV8.ABPS.TBG-S1.hATP7Bco.PA75; En34.mTTR, AAV8.En34.mTTR.hATP7Bco.PA75) and sacrificed at 6 months of age. Vehicle control administered Atp7b KO (PBS) mice served as controls. Liver sections were stained with H&E and evaluated histologically according to the 1-5 scoring system. Values expressed as mean±SEM.

Figure 19A:
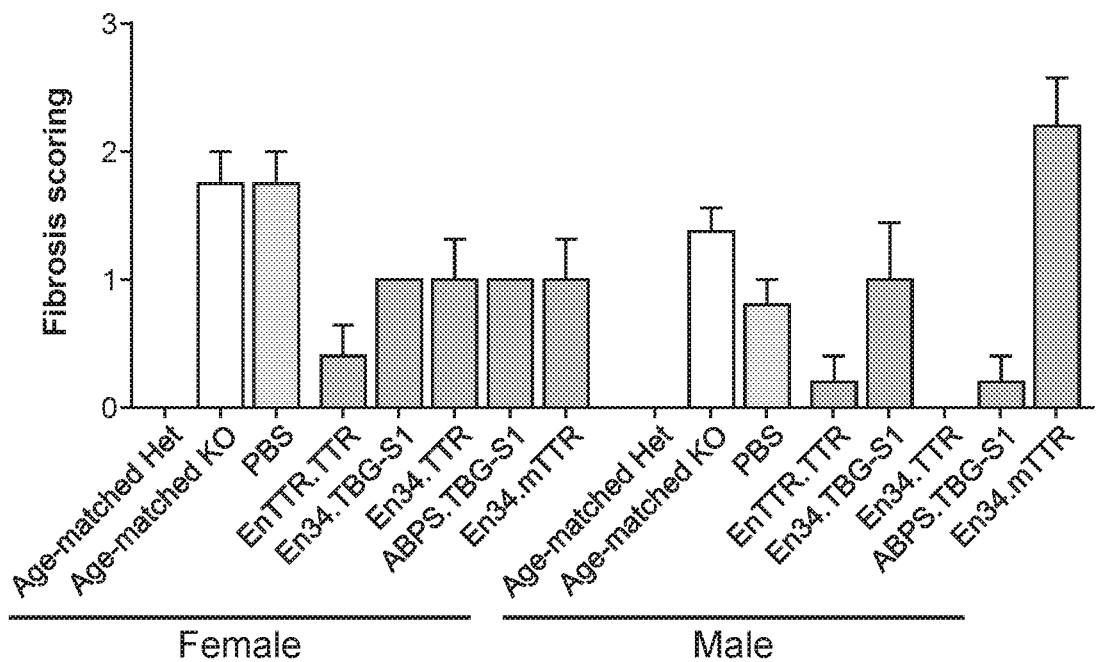
Figure 19B:
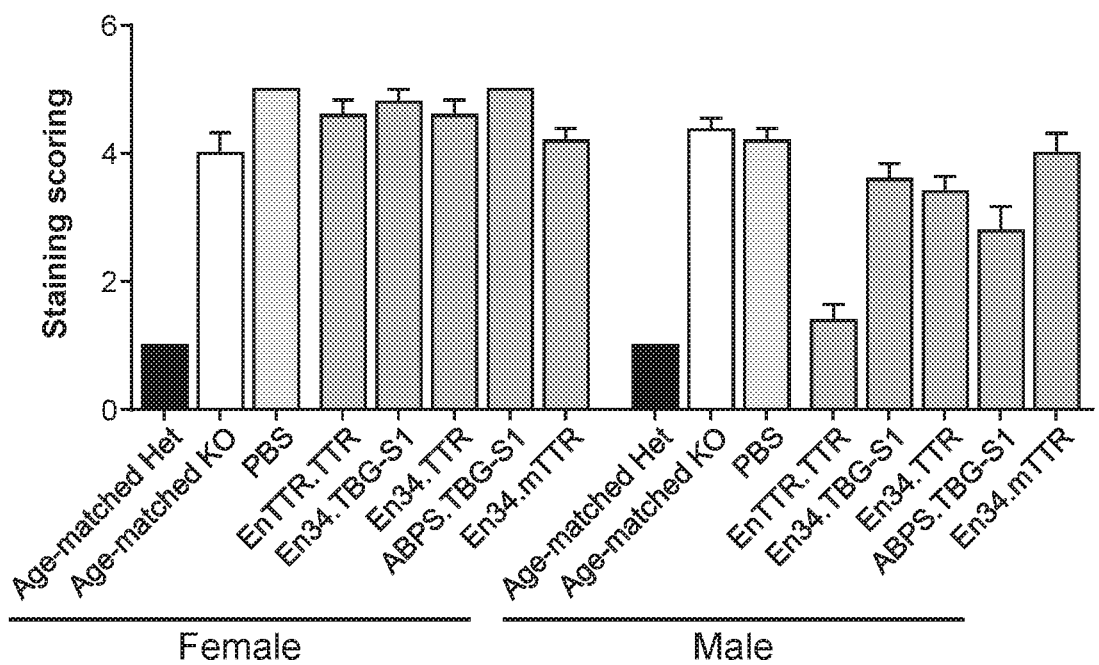

FIGS. 19A-19B demonstrate liver fibrosis and copper accumulation in female and male AAV8 vector administered Atp7b KO mice. Female and male Atp7b KO mice were administered i.v. with $3\times10^{12}$ GC/kg of AAV8 vectors for expression of hATP7Bco with different enhancer/promoter combinations (EnTTR.TTR, AAV8.EnTTR.TTR.hATP7Bco.PA75; En34.TBG-S1, AAV8.En34.TBG-S1.hATP7Bco.PA75; En34.TTR, AAV8.En34.TTR.hATP7Bco.PA75; ABPS.TBG-S1, AAV8.ABPS.TBG-S1.hATP7Bco.PA75; En34.mTTR, AAV8.En34.mTTR.hATP7Bco.PA75) and sacrificed at 6 months of age. Vehicle control administered Atp7b KO (PBS) mice served as controls. (A) Liver sections were stained with Sirius Red and evaluated for fibrosis according to the 1-3 scoring system and (B) Timm's stain was performed on liver sections for evaluation of copper accumulation according to the 1-5 scoring system. Values expressed as mean±SEM were compared to age-matched uninjected heterozygous (Het) and Atp7b KO (KO) mice.

Figure 20:
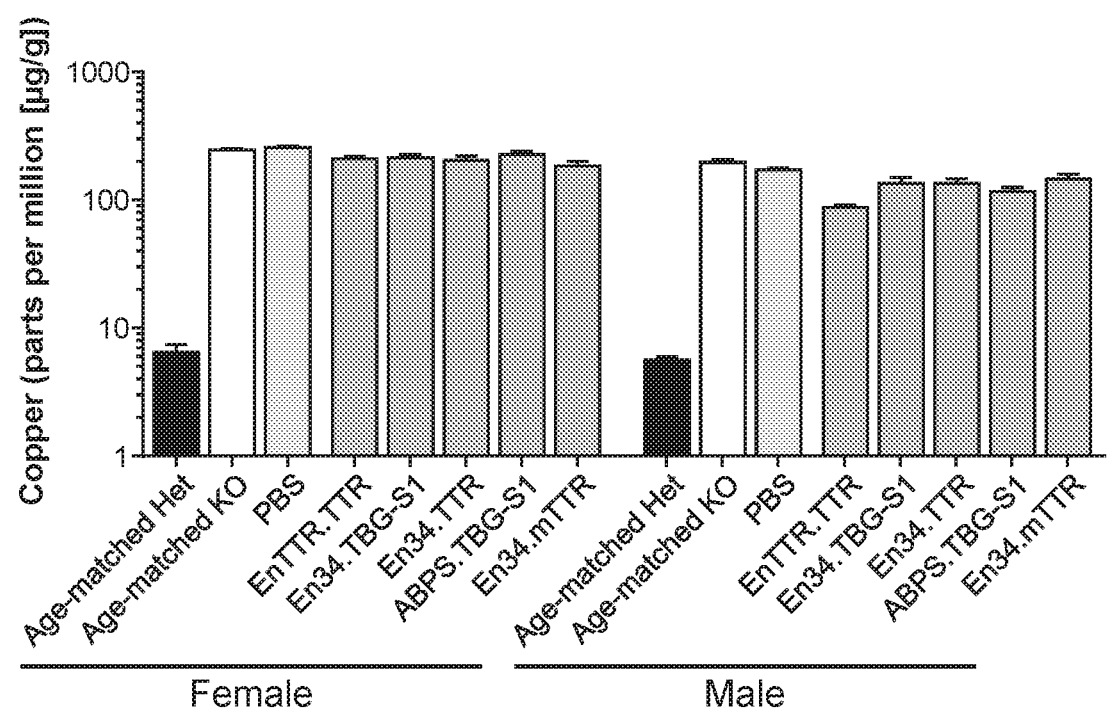

FIG. 20 demonstrates liver copper levels in female and male AAV8 vector administered Atp7b KO mice. Female and male Atp7b KO mice were administered i.v. with $3\times10^{12}$ GC/kg of AAV8 vectors for expression of hATP7Bco with different enhancer/promoter combinations (EnTTR.TTR, AAV8.EnTTR.TTR.hATP7Bco.PA75; En34.TBG-S1, AAV8.En34.TBG-S1.hATP7Bco.PA75; En34.TTR, AAV8.En34.TTR.hATP7Bco.PA75; ABPS.TBG-S1, AAV8.ABPS.TBG-S1.hATP7Bco.PA75; En34.mTTR, AAV8.En34.mTTR.hATP7Bco.PA75) and sacrificed at 6 months of age. Vehicle control administered Atp7b KO (PBS) mice served as controls. Liver copper levels were evaluated by inductively coupled plasma-mass spectrometry and compared to age-matched uninjected heterozygous (het) and Atp7b KO (KO) mice. Values expressed as mean±SEM.

Figure 21:
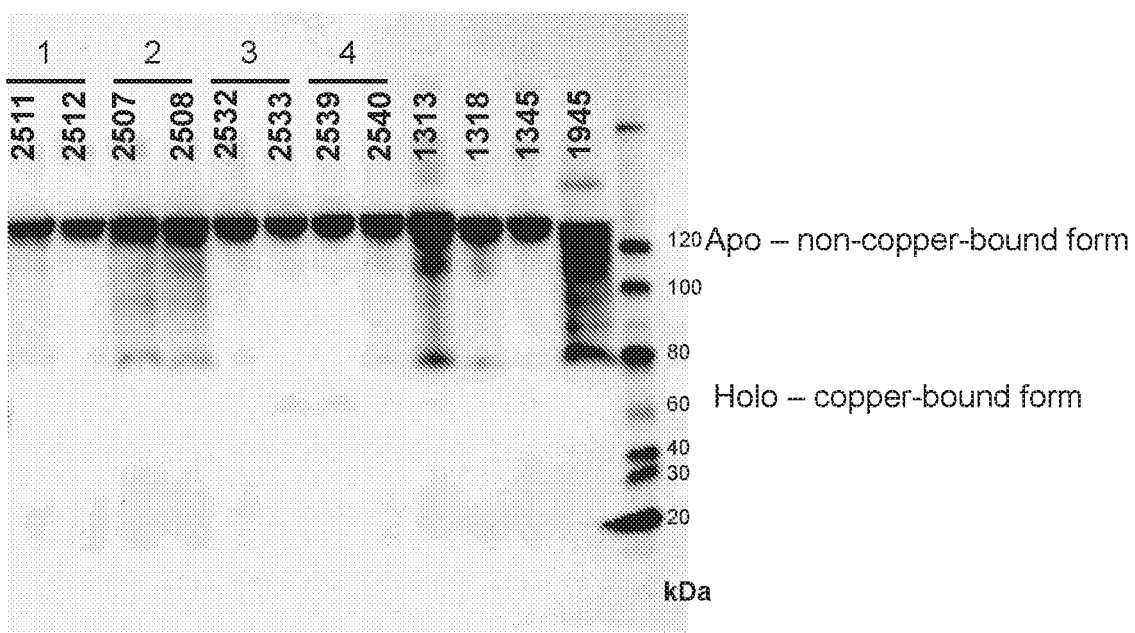

FIG. 21 demonstrates detection of ceruloplasmin by Western blot in male AAV8 vector administered Atp7b KO mice. Western blot detecting copper-bound (Holo, lower band) and non-copper-bound (Apo, upper band) forms of ceruloplasmin in male Atp7b KO mice were administered i.v. with $3\times10^{12}$ GC/kg of AAV8 vectors for expression of hATP7Bco with different enhancer/promoter combinations (1, AAV8.EnTTR.TTR.hATP7Bco.PA75; 2, AAV8.En34.TBG-S1.hATP7Bco.PA75; 3, AAV8.En34.TTR.hATP7Bco.PA75; 4, AAV8.ABPS.TBG-S1.hATP7Bco.PA75). Blood samples were collected on Day 21 after the administration. Protein markers were provided in the center lane for comparison. Atp7b KO, heterozygous (het), and wild type (WT) littermates without vector injections served as controls (1313, 6 month old Atp7b KO; 1318, 6 month old het; 1345, 2 month old Atp7b KO; 1945, WT).

Figure 22:
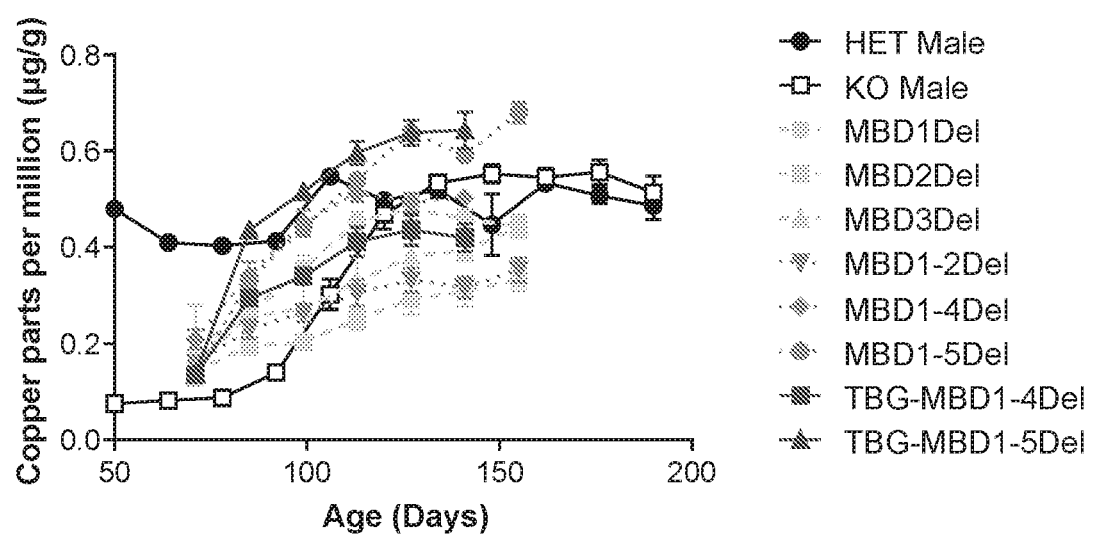

FIG. 22 demonstrates serum copper levels in male AAV8 truncated ATP7B vector administered Atp7b KO mice. Male Atp7b KO mice were administered i.v. with $3\times10^{12}$ GC/kg of AAV8 vectors for expression of different truncated versions of hATP7Bco (MBD1Del, AAV8.En34.TBG-S1.hATP7BcoMBD1Del.PA75; MBD2Del, AAV8.En34.TBG-S1.hATP7BcoMBD2Del.PA75; MBD3Del, AAV8.En34.TBG-S1.hATP7BcoMBD3Del.PA75; MBD1-2Del, AAV8.En34.TBG-S1.hATP7BcoMBD1-2Del.PA75; MBD1-4Del, AAV8.En34.TBG-S1.hATP7BcoMBD1-4Del.PA75; MBD1-5Del, AAV8.En34.TBG-S1.hATP7BcoMBD1-5Del.PA75; TBG-MBD1-4Del, AAV8.TBG.hATP7BcoMBD1-4Del.PA75; TBG-MBD1-5Del, AAV8.TBG.hATP7BcoMBD1-5Del.PA75). Serum copper levels were evaluated by inductively coupled plasma-mass spectrometry and compared to heterozygous (Het) and Atp7b KO mice (KO) over time. Values expressed as mean±SEM.

Figure 23A:
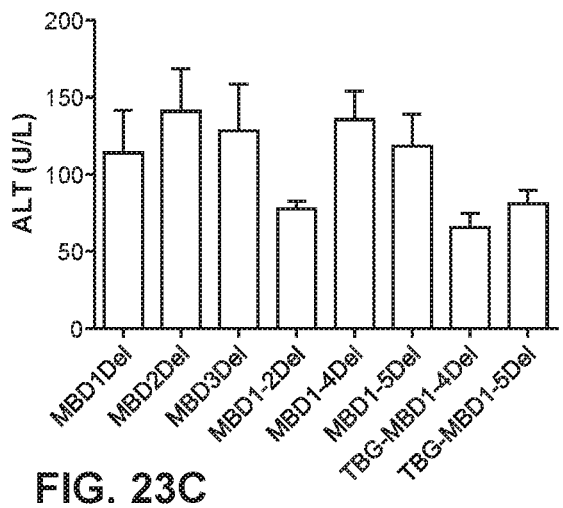
Figure 23B:
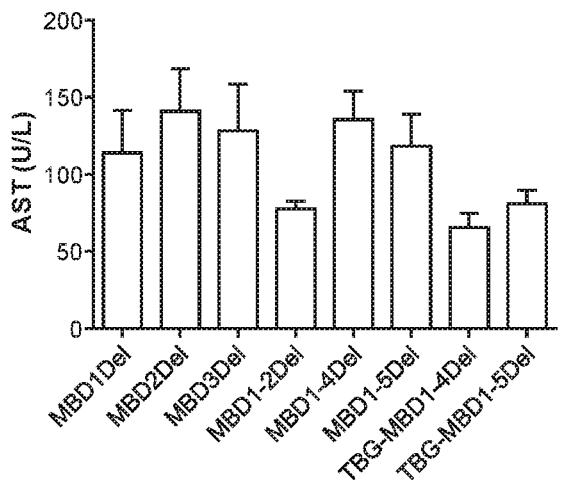
Figure 23C:
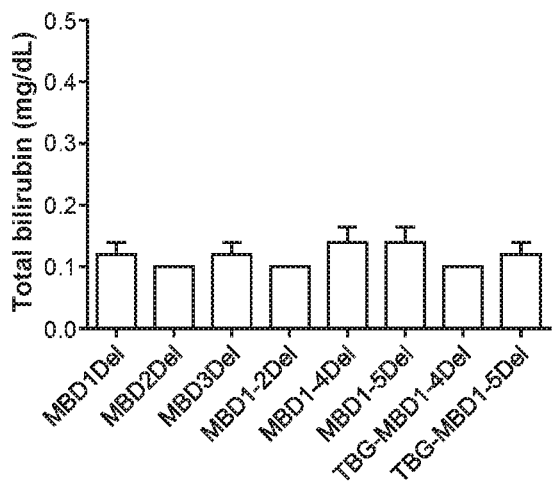

FIGS. 23A-23C demonstrates serum chemistries in male AAV8 truncated ATP7B vector administered Atp7b KO mice. Male Atp7b KO mice were administered i.v. with $3\times10^{12}$ GC/kg of AAV8 vectors for expression of different truncated versions of hATP7Bco (MBD1Del, AAV8.En34.TBG-S1.hATP7BcoMBD1Del.PA75; MBD2Del, AAV8.En34.TBG-S1.hATP7BcoMBD2Del.PA75; MBD3Del, AAV8.En34.TBG-S1.hATP7BcoMBD3Del.PA75; MBD1-2Del, AAV8.En34.TBG-S1.hATP7BcoMBD1-2Del.PA75; MBD1-4Del, AAV8.En34.TBG-S1.hATP7BcoMBD1-4Del.PA75; MBD1-5Del, AAV8.En34.TBG-S1.hATP7BcoMBD1-5Del.PA75; TBG-MBD1-4Del, AAV8.TBG.hATP7BcoMBD1-4Del.PA75; TBG-MBD1-5Del, AAV8.TBG.hATP7BcoMBD1-5Del.PA75). Mice were necropsied at 6 months of age and (A) ALT, (B) AST, and (C) total bilirubin levels were evaluated in serum. Values expressed as mean±SEM.

Figure 24:
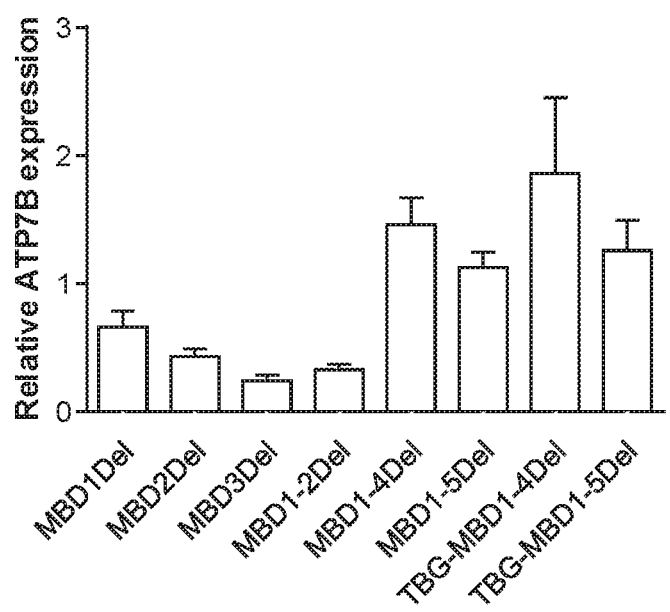

FIG. 24 demonstrates liver ATP7Bco expression determined by Western blot in male AAV8 truncated ATP7B vector administered Atp7b KO mice. Male Atp7b KO mice were administered i.v. with $3\times10^{12}$ GC/kg of AAV8 vectors for expression of different truncated versions of hATP7Bco (MBD1Del, AAV8.En34.TBG-S1.hATP7BcoMBD1Del.PA75; MBD2Del, AAV8.En34.TBG-S1.hATP7BcoMBD2Del.PA75; MBD3Del, AAV8.En34.TBG-S1.hATP7BcoMBD3Del.PA75; MBD1-2Del, AAV8.En34.TBG-S1.hATP7BcoMBD1-2Del.PA75; MBD1-4Del, AAV8.En34.TBG-S1.hATP7BcoMBD1-4Del.PA75; MBD1-5Del, AAV8.En34.TBG-S1.hATP7BcoMBD1-5Del.PA75; TBG-MBD1-4Del, AAV8.TBG.hATP7BcoMBD1-4Del.PA75; TBG-MBD1-5Del, AAV8.TBG.hATP7BcoMBD1-5Del.PA75). Mice were necropsied at 6 months of age. Western blot detecting ATP7B in Atp7b KO mice was quantified by band densitometry. Values expressed as mean±SEM.

Figure 25:
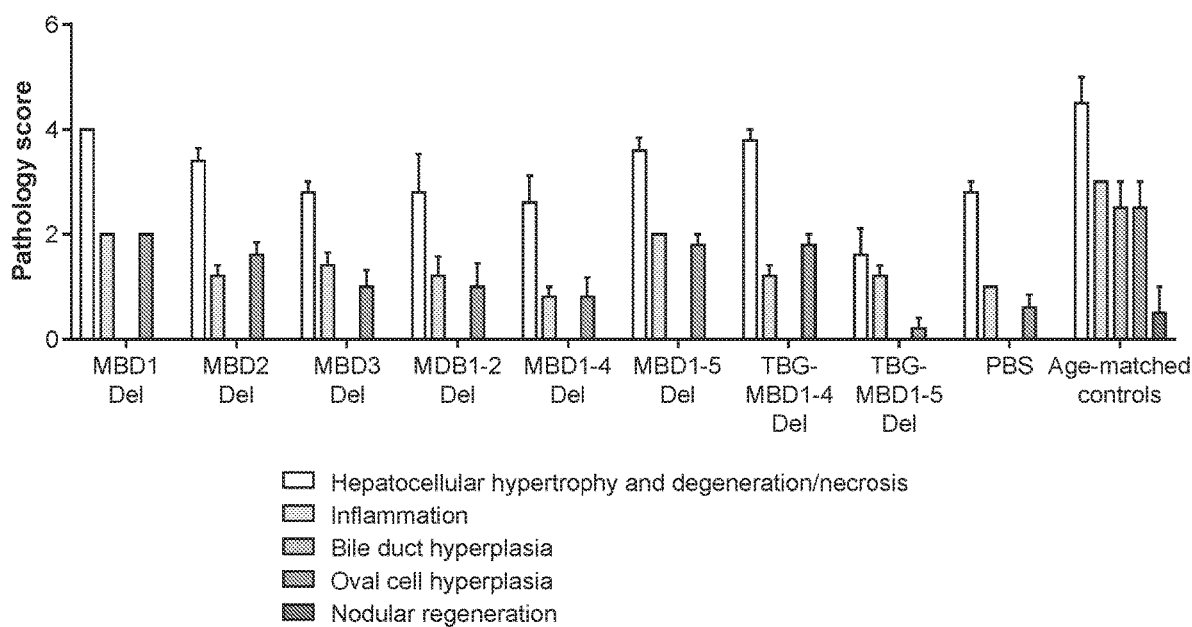

FIG. 25 demonstrates liver disease in male AAV8 truncated ATP7B vector administered Atp7b KO mice. Male Atp7b KO mice were administered i.v. with $3\times10^{12}$ GC/kg of AAV8 vectors for expression of different truncated versions of hATP7Bco (MBD1Del, AAV8.En34.TBG-S1.hATP7BcoMBD1Del.PA75; MBD2Del, AAV8.En34.TBG-S1.hATP7BcoMBD2Del.PA75;

MBD3Del, AAV8.En34.TBG-S1.hATP7BcoMBD3Del.PA75; MBD1-2Del, AAV8.En34.TBG-S1.hATP7BcoMBD1-2Del.PA75; MBD1-4Del, AAV8.En34.TBG-S1.hATP7BcoMBD1-4Del.PA75; MBD1-5Del, AAV8.En34.TBG-S1.hATP7BcoMBD1-5Del.PA75; TBG-MBD1-4Del, AAV8.TBG.hATP7BcoMBD1-4Del.PA75; TBG-MBD1-5Del, AAV8.TBG.hATP7BcoMBD1-5Del.PA75). Mice were necropsied at 6 months of age. Vehicle control administered Atp7b KO (PBS) mice served as controls. Liver sections were stained with H&E and evaluated histologically according to the 1-5 scoring system. Values expressed as mean±SEM.

Figure 26A:
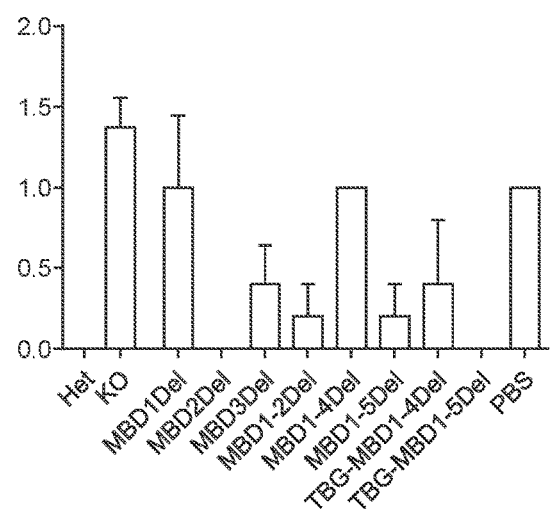
Figure 26B:
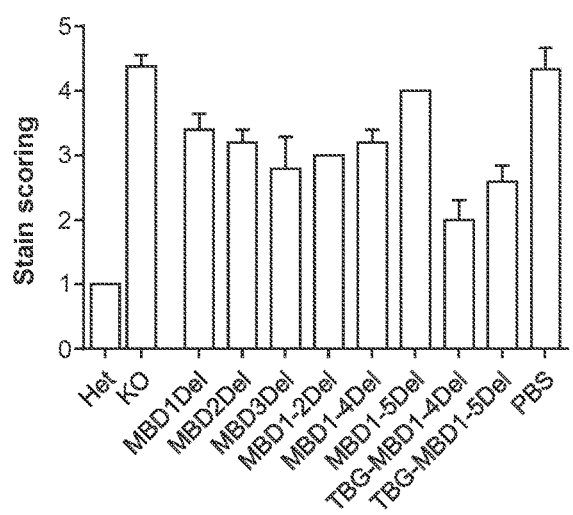

FIGS. 26A-26B demonstrate liver fibrosis and copper accumulation in male AAV8 truncated ATP7B vector administered Atp7b KO mice. Male Atp7b KO mice were administered i.v. with 3×10$^{12}$ GC/kg of AAV8 vectors for expression of different truncated versions of hATP7Bco (MBD1Del, AAV8.En34.TBG-S1.hATP7BcoMBD1Del.PA75; MBD2Del, AAV8.En34.TBG-S1.hATP7BcoMBD2Del.PA75; MBD3Del, AAV8.En34.TBG-S1.hATP7BcoMBD3Del.PA75; MBD1-2Del, AAV8.En34.TBG-S1.hATP7BcoMBD1-2Del.PA75; MBD1-4Del, AAV8.En34.TBG-S1.hATP7BcoMBD1-4Del.PA75; MBD1-5Del, AAV8.En34.TBG-S1.hATP7BcoMBD1-5Del.PA75; TBG-MBD1-4Del, AAV8.TBG.hATP7BcoMBD1-4Del.PA75; TBG-MBD1-5Del, AAV8.TBG.hATP7BcoMBD1-5Del.PA75). Mice were necropsied at 6 months of age. Vehicle control administered Atp7b KO (PBS) mice served as controls. (A) Liver sections were stained with Sirius Red and evaluated for fibrosis according to the 1-3 scoring system and (B) Timm's stain was performed on liver sections for evaluation of copper accumulation according to the 1-5 scoring system. Values expressed as mean±SEM were compared to age-matched uninjected heterozygous (Het) and Atp7b KO (KO) mice.

Figure 27:
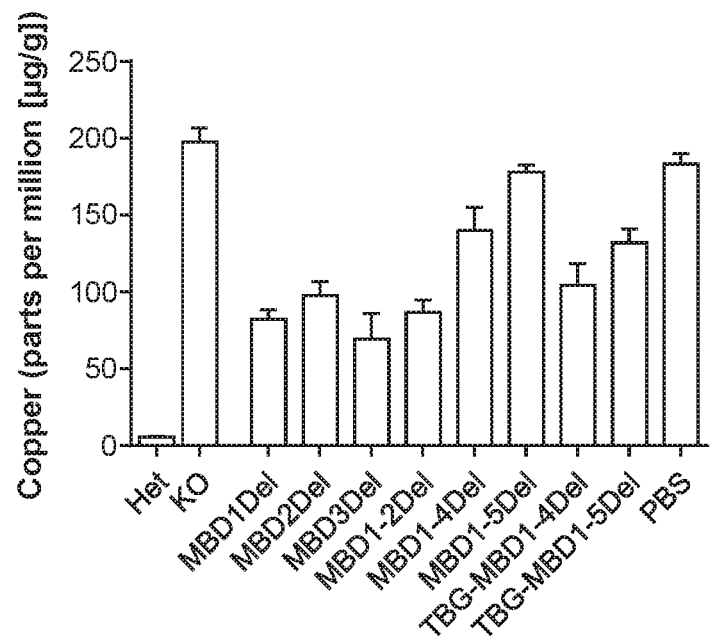

FIG. 27 demonstrates liver copper levels in male AAV8 truncated ATP7B vector administered Atp7b KO mice. Male Atp7b KO mice were administered i.v. with 3×10$^{12}$ GC/kg of AAV8 vectors for expression of different truncated versions of hATP7Bco (MBD1Del, AAV8.En34.TBG-S1.hATP7BcoMBD1Del.PA75; MBD2Del, AAV8.En34.TBG-S1.hATP7BcoMBD2Del.PA75; MBD3Del, AAV8.En34.TBG-S1.hATP7BcoMBD3Del.PA75; MBD1-2Del, AAV8.En34.TBG-S1.hATP7BcoMBD1-2Del.PA75; MBD1-4Del, AAV8.En34.TBG-S1.hATP7BcoMBD1-4Del.PA75; MBD1-5Del, AAV8.En34.TBG-S1.hATP7BcoMBD1-5Del.PA75; TBG-MBD1-4Del, AAV8.TBG.hATP7BcoMBD1-4Del.PA75; TBG-MBD1-5Del, AAV8.TBG.hATP7BcoMBD1-5Del.PA75). Mice were necropsied at 6 months of age. Vehicle control administered Atp7b KO (PBS) mice served as controls. Liver copper levels were evaluated by inductively coupled plasma-mass spectrometry and compared to age-matched uninjected heterozygous (het) and Atp7b KO (KO) mice. Values expressed as mean±SEM were compared to age-matched uninjected heterozygous (Het) and Atp7b KO (KO) mice.

4. DETAILED DESCRIPTION

The embodiments described in the application relate to the use of a replication deficient adeno-associated virus (AAV) to deliver a human copper-transporting ATPase 2 (ATP7B) gene to liver cells of patients (human subjects) diagnosed with Wilson's Disease (WD). The recombinant AAV vector (rAAV) used for delivering the hATP7B gene ("rAAV.hATP7B") should have a tropism for the liver (e.g., an rAAV bearing an AAV8 capsid), and the hATP7B transgene should be controlled by liver-specific expression control elements. In one embodiment, the expression control elements include one or more of the following: an enhancer; a promoter; an intron; a WPRE; and a polyA signal. Such elements are further described herein.

As used herein, "AAV8 capsid" refers to the AAV8 capsid having the amino acid sequence of GenBank, accession: YP_077180.1, SEQ ID NO: 16, which is incorporated by reference herein. Some variation from this encoded sequence is permitted, which may include sequences having about 99% identity to the referenced amino acid sequence in YP_077180.1 and WO 2003/052051 (which is incorporated herein by reference) (i.e., less than about 1% variation from the referenced sequence). Methods of generating the capsid, coding sequences therefore, and methods for production of rAAV viral vectors have been described. See, e.g., Gao, et al, Proc. Natl. Acad. Sci. U.S.A. 100 (10), 6081-6086 (2003) and US 2015/0315612.

As used herein, the term "NAb titer" a measurement of how much neutralizing antibody (e.g., anti-AAV Nab) is produced which neutralizes the physiologic effect of its targeted epitope (e.g., an AAV). Anti-AAV NAb titers may be measured as described in, e.g., Calcedo, R., et al., Worldwide Epidemiology of Neutralizing Antibodies to Adeno-Associated Viruses. Journal of Infectious Diseases, 2009. 199(3): p. 381-390, which is incorporated by reference herein.

The terms "percent (%) identity", "sequence identity", "percent sequence identity", or "percent identical" in the context of amino acid sequences refers to the residues in the two sequences which are the same when aligned for correspondence. Percent identity may be readily determined for amino acid sequences over the full-length of a protein, polypeptide, about 32 amino acids, about 330 amino acids, or a peptide fragment thereof or the corresponding nucleic acid sequence coding sequencers. A suitable amino acid fragment may be at least about 8 amino acids in length, and may be up to about 700 amino acids. Generally, when referring to "identity", "homology", or "similarity" between two different sequences, "identity", "homology" or "similarity" is determined in reference to "aligned" sequences. "Aligned" sequences or "alignments" refer to multiple nucleic acid sequences or protein (amino acids) sequences, often containing corrections for missing or additional bases or amino acids as compared to a reference sequence. Alignments are performed using any of a variety of publicly or commercially available Multiple Sequence Alignment Programs. Sequence alignment programs are available for amino acid sequences, e.g., the "Clustal Omega", "Clustal X", "MAP", "PIMA", "MSA", "BLOCKMAKER", "MEME", and "Match-Box" programs. Generally, any of these programs are used at default settings, although one of skill in the art can alter these settings as needed. Alternatively, one of skill in the art can utilize another algorithm or computer program which provides at least the level of identity or alignment as that provided by the referenced algorithms and programs. See, e.g., J. D. Thomson et al, Nucl. Acids. Res., "A comprehensive comparison of multiple sequence alignments", 27(13):2682-2690 (1999).

As used herein, the term "operably linked" refers to both expression control sequences that are contiguous with the gene of interest and expression control sequences that act in trans or at a distance to control the gene of interest.

A "replication-defective virus" or "viral vector" refers to a synthetic or artificial viral particle in which an expression cassette containing a gene of interest is packaged in a viral capsid or envelope, where any viral genomic sequences also packaged within the viral capsid or envelope are replication-deficient; i.e., they cannot generate progeny virions but retain the ability to infect target cells. In one embodiment, the genome of the viral vector does not include genes encoding the enzymes required to replicate (the genome can be engineered to be "gutless"—containing only the transgene of interest flanked by the signals required for amplification and packaging of the artificial genome), but these genes may be supplied during production. Therefore, it is deemed safe for use in gene therapy since replication and infection by progeny virions cannot occur except in the presence of the viral enzyme required for replication.

It is to be noted that the term "a" or "an" refers to one or more. As such, the terms "a" (or "an"), "one or more," and "at least one" are used interchangeably herein.

The words "comprise", "comprises", and "comprising" are to be interpreted inclusively rather than exclusively. The words "consist", "consisting", and its variants, are to be interpreted exclusively, rather than inclusively. While various embodiments in the specification are presented using "comprising" language, under other circumstances, a related embodiment is also intended to be interpreted and described using "consisting of" or "consisting essentially of" language.

As used herein, the term "about" means a variability of 10% from the reference given, unless otherwise specified.

Unless defined otherwise in this specification, technical and scientific terms used herein have the same meaning as commonly understood by one of ordinary skill in the art and by reference to published texts, which provide one skilled in the art with a general guide to many of the terms used in the present application.

5.1 Gene Therapy Vectors

In one aspect, a recombinant adeno-associated virus (rAAV) vector carrying the human ATP7B gene is provided for use in gene therapy. The rAAV.hATP7B vector should have a tropism for the liver (e.g., a rAAV bearing an AAV8 capsid) and the hATP7B transgene should be controlled by liver-specific expression control elements. The vector is formulated in a buffer/carrier suitable for infusion in human subjects. The buffer/carrier should include a component that prevents the rAAV from sticking to the infusion tubing but does not interfere with the rAAV binding activity in vivo.

5.1.1. The rAAV.hATP7B Vector
5.1.1.1. The hATP7B Sequence

Wilson's Disease is an inherited error of metabolism caused predominantly by mutations in the ATP7B gene, which encodes a copper-transporting P-type ATPase. ATP7B is responsible for transporting copper from intracellular chaperone proteins into the secretory pathway, both for excretion into bile and for incorporation into apo-ceruloplasmin for the synthesis of functional ceruloplasmin. The development of Wilson's disease is due to the accumulation of copper in affected tissues. See, EASL Clinical Practice Guidelines: Wilson's disease, EASL Journal of Hepatology, 2012, 56(671-85), which is incorporated herein by reference.

The clinical hallmark of Wilson's disease is the Kayser-Fleischer ring, which is present in 95% of patients with neurologic symptoms and somewhat over half of those without neurologic symptoms. Neurologic signs are variable, most often tremor, ataxia, and dystonia. Any type of liver disease may be encountered in patients with Wilson's disease. Clinically evident liver disease may precede neurologic manifestations by as much as 10 years and most patients with neurologic symptoms have some degree of liver disease at presentation. Presenting symptoms of liver disease can be highly variable, ranging from asymptomatic, with only biochemical abnormalities, to overt cirrhosis with all its complications. Wilson's disease may also present as acute hepatic failure sometimes associated with Coombs-negative hemolytic anemia and acute renal failure. The following table 1 provides a prognostic index in WD. (See, EASL Clinical Practice Guidelines: Wilson's disease, EASL Journal of Hepatology, 2012, 56(671-85), which is incorporated herein by reference.)

|  | 1* | 2* | 3* | 4* |
|---|---|---|---|---|
| Serum bilirubin (µmol/L) | 100-150 | 151-200 | 201-300 | >300 |
| AST (U/L) | 100-150 | 151-300 | 301-400 | >400 |
| INR | 1.3-1.6 | 1.7-1.9 | 2.0-2.4 | >2.4 |
| WBC [$10^9$/L] | 6.8-8.3 | 8.4-10.3 | 10.4-15.3 | >15.3 |
| Albumin [g/L] | 34-44 | 25-33 | 21-24 | <21 |

*= score points, upper limit of normal for AST = 20 IU/ml (at King's College). A score ≥11 is associated with high probability of death without liver transplantation.

ATP7B has eight transmembrane domains that form a path through cell membranes for copper translocation; and a large N-terminus with six metal-binding domains (MBDs), each comprising approximately 70 amino acids and the highly conserved metal-binding motif GMxCxxC (where x is any amino acid). Other domains include the intramembrane CPC motif that is required for copper translocation through the membrane, the N-domain containing the ATP-binding site, the P-domain containing the conserved aspartic acid residue and the A-domain comprising the phosphatase domain. Various mutations in the hATP7B gene and/or resulting protein are known which are present in some or all patients with Wilson's Disease. A complete listing of the known mutations contributing to WB can be found at http://www.uniprot.org/uniprot/P35670, which is incorporated herein by reference. Further, in addition to the canonical sequence (also called isoform a, which is the longest isoform; NCBI Reference Sequence: NP_000044.2), four additional isoforms are known: NCBI Reference Sequence NP_001005918.1, NP_001230111.1, NP_001317507.1, NP_001317508.1, each of which is incorporated herein by reference. The compositions and methods described herein may be used to treat subjects having any ATP7B variant protein which causes disease.

In one embodiment, the hATP7B gene encodes the hATP7B protein shown in SEQ ID NO: 2. Thus, in one embodiment, the hATP7B transgene can include, but is not limited to, the sequence provided by SEQ ID NO:1 or SEQ ID NO: 3 which are provided in the attached Sequence Listing, which is incorporated by reference herein. SEQ ID NO: 3 provides the cDNA for native human ATP7B. SEQ ID NO: 1 provides an engineered cDNA for human ATP7B, which has been codon optimized for expression in humans (sometimes referred to herein as hATP7Bco). It is to be understood that reference to hATP7B herein may, in some embodiments, refer to the hATP7B native or codon optimized sequence, or any of the variants described herein. Alternatively or additionally, web-based or commercially available computer programs, as well as service based companies may be used to back translate the amino acid sequences to nucleic acid coding sequences, including both RNA and/or cDNA. See, e.g., backtranseq by EMBOSS, www.ebi.ac.uk/Tools/st/; Gene Infinity (www.geneinfinity.org/sms-/sms_backtranslation.html); ExPasy (www.expasy.org/tools/). It is intended that all nucleic acids encoding the described hATP7B polypeptide sequences are encompassed, including nucleic acid sequences which have been optimized for expression in the desired target subject (e.g., by codon optimization).

The native coding sequence of ATP7B is over 4.3 kb (SEQ ID NO: 3; Genbank Accession number XM_005266430), resulting in a 1465 amino acid protein (SEQ ID NO: 2). Due to the large size of ATP7B, and the packaging capacity of viral vectors, including the AAV vector, in some embodiments, it is desirable that the ATP7B coding sequence is shortened. It has been shown that deletion of the first 5 MBD showed a level of catalytic phosphorylation of the resulting protein consistent with wild type. See, Huster and Lutsenko, J. Biological Chem, June 2003, which is incorporated herein by reference. Thus, in one embodiment, the ATP7B coding sequence is shortened by deleting one or more MDB. In one embodiment, the ATP7B coding sequence has MBD1-2 deleted (e.g., as shown in SEQ ID NO: 17 and nt 403 to nt 4368 of SEQ ID NO: 35). In another embodiment, the ATP7B coding sequence has MBD1-3 deleted. In another embodiment, the ATP7B coding sequence has MBD1-4 deleted (e.g., as shown in SEQ ID NO: 18, and nt 403 to nt 3762 of SEQ ID NO: 34 and nt 1059 to nt 4418 of SEQ ID NO: 29). In another embodiment, the ATP7B coding sequence has MBD1-5 deleted (e.g., as shown in SEQ ID NO: 19, nt 403 to nt 3369 of SEQ ID NO: 33 and nt 1059 to nt 4025 of SEQ ID NO: 28). In another embodiment, the ATP7B coding sequence has MBD1 deleted (e.g., as shown in SEQ ID NO: 20 and nt 403 to nt 4686 of SEQ ID NO: 32). In another embodiment the ATP7B coding sequence has MBD2 deleted (e.g., as shown in SEQ ID NO: 21 and nt 403 to nt 4617 of SEQ ID NO: 31). In another embodiment, the ATP7B coding sequence has MBD3 deleted (e.g., as shown in SEQ ID NO: 22 and nt 403 to nt 4719 of SEQ ID NO: 30). In another embodiment, the ATP7B coding sequence has MBD1-4 and 6 deleted (e.g., as described by Cater et al, Biochem J. 2004 Jun. 15; 380(Pt 3): 805-813, which is incorporated herein by reference). See also, Gourdon et al, Biol Chem. 2012 April; 393(4):205-16; Lutsenko, S., et al. (2007). "Function and regulation of human copper-transporting ATPases." Physiological reviews 87(3): 1011-1046; Safaei, R., et al. (2013). "The role of metal binding and phosphorylation domains in the regulation of cisplatin-induced trafficking of ATP7B." Metallomics 5(8): 964-972; and US Patent Publication No. 2015/0045284, each of which is incorporated herein by reference.

In one embodiment, the nucleic acid sequence encoding hATP7B shares at least 95% identity with the native hATP7B coding sequence of SEQ ID NO: 3 or SEQ ID NO: 1, or any of the variants shown in SEQ ID NO: 17, SEQ ID NO: 18, SEQ ID NO: 19, SEQ ID NO: 20, SEQ ID NO: 21, or SEQ ID NO: 22. In another embodiment, the nucleic acid sequence encoding hATP7B shares at least 90, 85, 80, 75, 70, or 65% identity with the native hATP7B coding sequence of SEQ ID NO: 3 or SEQ ID NO: 1, or any of the variants shown in SEQ ID NO: 17, SEQ ID NO: 18, SEQ ID NO: 19, SEQ ID NO: 20, SEQ ID NO: 21, or SEQ ID NO: 22. In one embodiment, the nucleic acid sequence encoding hATP7B shares about 79% identity with the native hATP7B coding sequence of SEQ ID NO: 3 or SEQ ID NO: 1, or any of the variants shown in SEQ ID NO: 17, SEQ ID NO: 18, SEQ ID NO: 19, SEQ ID NO: 20, SEQ ID NO: 21, or SEQ ID NO: 22. In one embodiment, the nucleic acid sequence encoding hATP7B is SEQ ID NO: 1. In another embodiment, the nucleic acid sequence encoding hATP7B is SEQ ID NO: 17, In another embodiment, the nucleic acid sequence encoding hATP7B is SEQ ID NO: 18. In another embodiment, the nucleic acid sequence encoding hATP7B is SEQ ID NO: 19. In another embodiment, the nucleic acid sequence encoding hATP7B is SEQ ID NO: 20. In another embodiment, the nucleic acid sequence encoding hATP7B is SEQ ID NO: 21. In another embodiment, the nucleic acid sequence encoding hATP7B is SEQ ID NO: 22.

Codon-optimized coding regions can be designed by various different methods. This optimization may be performed using methods which are available on-line (e.g., GeneArt), published methods, or a company which provides codon optimizing services, e.g., as DNA2.0 (Menlo Park, Calif.). One codon optimizing approach is described, e.g., in International Patent Publication No. WO 2015/012924, which is incorporated by reference herein. See also, e.g., US Patent Publication No. 2014/0032186 and US Patent Publication No. 2006/0136184. Suitably, the entire length of the open reading frame (ORF) for the product is modified. However, in some embodiments, only a fragment of the ORF may be altered. By using one of these methods, one can apply the frequencies to any given polypeptide sequence, and produce a nucleic acid fragment of a codon-optimized coding region which encodes the polypeptide.

A number of options are available for performing the actual changes to the codons or for synthesizing the codon-optimized coding regions designed as described herein. Such modifications or synthesis can be performed using standard and routine molecular biological manipulations well known to those of ordinary skill in the art. In one approach, a series of complementary oligonucleotide pairs of 80-90 nucleotides each in length and spanning the length of the desired sequence are synthesized by standard methods. These oligonucleotide pairs are synthesized such that upon annealing, they form double stranded fragments of 80-90 base pairs, containing cohesive ends, e.g., each oligonucleotide in the pair is synthesized to extend 3, 4, 5, 6, 7, 8, 9, 10, or more bases beyond the region that is complementary to the other oligonucleotide in the pair. The single-stranded ends of each pair of oligonucleotides are designed to anneal with the single-stranded end of another pair of oligonucleotides. The oligonucleotide pairs are allowed to anneal, and approximately five to six of these double-stranded fragments are then allowed to anneal together via the cohesive single stranded ends, and then they ligated together and cloned into a standard bacterial cloning vector, for example, a TOPO® vector available from Thermo Fisher Scientific Inc. The construct is then sequenced by standard methods. Several of these constructs consisting of 5 to 6 fragments of 80 to 90 base pair fragments ligated together, i.e., fragments of about 500 base pairs, are prepared, such that the entire desired sequence is represented in a series of plasmid constructs. The inserts of these plasmids are then cut with appropriate restriction enzymes and ligated together to form the final construct. The final construct is then cloned into a standard bacterial cloning vector, and sequenced. Additional methods would be immediately apparent to the skilled artisan. In addition, gene synthesis is readily available commercially.

The goal of therapies described herein would provide functional ATP7B enzyme resulting in a reduction of serum copper levels of 25% or more. In one embodiment, urinary copper excretion of 3-8 μmol or less per 24 hours is desirable.

Primary/secondary goals of the therapies described herein include, without limitation:
Normalization of serum non-ceruloplasmin bound copper (NCC) (<150 microg/L)
Normalization of serum aminotransferase (liver biochemistries, ALT/AST)
Normalization of urinary Cu (<40 microg/24 hours (0.6 micromol/24 hours) ULN)
Normalization of serum ceruloplasmin (>200 mg/L) [can be inconsistent]
Improvement of Clinician Global Impression (CGI) scale [1: severity & 2: global improvement)
Incidence of AEs
Exploratory:
$^{65}$Cu, a nonradioactive isotope for copper which can be detected by mass spec
Improvement in IQ, neurocognitive and psychiatric functions (Unified Wilson's Disease Rating Scale (UW-DRS) & Mini International Neuropsychiatric Interview (M.I.N.I.)); and
PROs (EQ5D, MMAS-8, TSQM)

In one embodiment, the "subject" or "patient" is a mammalian subject having WD as described above. It is intended that a patient having WD of any severity is the intended subject.

5.1.1.2. The rAAV Vector

Because ATP7B is natively expressed in the liver, it is desirable to use an AAV which shows tropism for liver. In one embodiment, the AAV supplying the capsid is AAV8. In another embodiment, the AAV supplying the capsid is AAVrh.10. In yet another embodiment, the AAV supplying the capsid is a Clade E AAV. Such AAV include rh.2; rh.10; rh.25; bb.1, bb.2, pi.1, pi.2, pi.3, rh.38, rh.40, rh.43, rh.49, rh.50, rh.51, rh.52, rh.53, rh.57, rh.58, rh.61, rh.64, hu.6, hu.17, hu.37, hu.39, hu.40, hu.41, hu.42, hu.66, and hu.67. This clade further includes modified rh.2; modified rh.58; and modified rh.64. See, WO 2005/033321, which is incorporated herein by reference. However, any of a number of rAAV vectors with liver tropism can be used.

In a specific embodiment described in the Examples, infra, the gene therapy vector is an AAV8 vector expressing an hATP7B transgene under control of a thyroxine binding globulin (TBG-S1) promoter referred to as AAV8.En34.TBG-S1.hATP7Bco.PA75. The external AAV vector component is a serotype 8, T=1 icosahedral capsid consisting of 60 copies of three AAV viral proteins, VP1, VP2, and VP3, at a ratio of 1:1:10. The capsid contains a single-stranded DNA rAAV vector genome.

In one embodiment, the rAAV.hATP7B genome contains an hATP7B transgene flanked by two AAV inverted terminal repeats (ITRs). In one embodiment, the hATP7B transgene includes one or more of an enhancer, promoter, an hATP7B coding sequence, and polyadenylation (polyA) signal. These control sequences are "operably linked" to the hATP7B gene sequences. The expression cassette containing these sequences may be engineered onto a plasmid which is used for production of a viral vector.

The ITRs are the genetic elements responsible for the replication and packaging of the genome during vector production and are the only viral cis elements required to generate rAAV. The minimal sequences required to package the expression cassette into an AAV viral particle are the AAV 5' and 3' ITRs, which may be of the same AAV origin as the capsid, or which of a different AAV origin (to produce an AAV pseudotype). In one embodiment, the ITR sequences from AAV2, or the deleted version thereof (ΔITR), are used. However, ITRs from other AAV sources may be selected. Where the source of the ITRs is from AAV2 and the AAV capsid is from another AAV source, the resulting vector may be termed pseudotyped. Typically, an expression cassette for an AAV vector comprises an AAV 5' ITR, the hATP7B coding sequences and any regulatory sequences, and an AAV 3' ITR. However, other configurations of these elements may be suitable. A shortened version of the 5' ITR, termed ΔITR, has been described in which the D-sequence and terminal resolution site (trs) are deleted. In other embodiments, the full-length AAV 5' and 3' ITRs are used. In one embodiment, the 5' ITR is that shown in SEQ ID NO: 14. In one embodiment, the 3' ITR is that shown in SEQ ID NO: 15.

In one embodiment, the expression control sequences include one or more enhancer. In one embodiment, the En34 enhancer is included (34 bp core enhancer from the human apolipoprotein hepatic control region), which is shown in SEQ ID NO: 4. In another embodiment, the EnTTR (100 bp enhancer sequence from transthyretin) is included. Such sequence is shown in SEQ ID NO: 5. See, Wu et al, Molecular Therapy, 16(2):280-289, February 2008, which is incorporated herein by reference. In yet another embodiment, the α1-microglogulin/bikunin precursor enhancer is included. In yet another embodiment, the ABPS (shortened version of the 100 bp distal enhancer from the al-microglogulin/bikunin precursor [ABP] to 42 bp) enhancer is included. Such sequence is shown in SEQ ID NO: 6. In yet another embodiment, the ApoE enhancer is included. Such sequence is shown in SEQ ID NO: 7. In another embodiment, more than one enhancer is present. Such combination may include more than one copy of any of the enhancers described herein, and/or more than one type of enhancer.

Expression of the hATP7B coding sequence is driven from a liver-specific promoter. Because of the size of the ATP7B transgene, the use of promoter of relatively small size is desirable. An illustrative plasmid and vector described herein uses the modified thyroxine binding globulin (TBG-S1) promoter (SEQ ID NO: 8). In another embodiment, the TBG promoter is used. The TBG promoter sequence is shown in SEQ ID NO: 9. Alternatively, other liver-specific promoters may be used such as the transthyretin promoter (TTR promoter), as shown in SEQ ID NO: 11, or a modified transthyretin promoter (mTTR promoter), as shown in nt 21 to nt 190 of SEQ ID NO: 11. Another suitable promoter is the alpha 1 anti-trypsin (A1AT), or a modified version thereof (which sequence is shown in SEQ ID NO: 10. Various promoter and enhancer combinations are discussed in the examples below.

Other suitable promoters include human albumin (Miyatake et al., J. Virol., 71:5124 32 (1997)), humAlb; the Liver Specific promoter (LSP), and hepatitis B virus core promoter, (Sandig et al., Gene Ther., 3:1002-9 (1996). See, e.g., The Liver Specific Gene Promoter Database, Cold Spring Harbor, http://rulai.schl.edu/LSPDrulai.schl.edu/LSPD, which is incorporated by reference. Although less desired, other promoters, such as viral promoters, constitutive promoters, regulatable promoters [see, e.g., WO 2011/126808 and WO 2013/04943], or a promoter responsive to physiologic cues may be used may be utilized in the vectors described herein.

In addition to a promoter, an expression cassette and/or a vector may contain other appropriate transcription initiation, termination, enhancer sequences, and efficient RNA processing signals. Such sequences include splicing and polyadenylation (polyA) signals; regulatory elements that enhance expression (e.g., WPRE); sequences that stabilize cytoplasmic mRNA; sequences that enhance translation efficiency (i.e., Kozak consensus sequence); sequences that enhance protein stability; and when desired, sequences that enhance secretion of the encoded product. In one embodiment, a KOZAK sequence is included. In one embodiment, a polyadenylation (polyA) signal is included to mediate termination of hATP7B mRNA transcripts. A polyA signal useful herein is an artificial polyA which is about 75 bp in size (PA75) shown in SEQ ID NO: 13. Examples of other suitable polyA sequences include, e.g., bovine growth hormone (SEQ ID NO: 12), SV40, rabbit beta globin, and TK polyA, amongst others.

In one embodiment, the regulatory sequences are selected such that the total rAAV vector genome is about 3.0 to about 5.5 kilobases in size. In one embodiment, it is desirable that the rAAV vector genome approximate the size of the native AAV genome. Thus, in one embodiment, the regulatory sequences are selected such that the total rAAV vector genome is about 4.7 kb in size. In another embodiment, the total rAAV vector genome is less about 5.2 kb in size. In a further embodiment, the total rAAV vector genome is about 5.1 kb or about 5.0 kb in size. The size of the vector genome may be manipulated based on the size of the regulatory sequences including the promoter, enhancer, intron, poly A, etc. See, Wu et al, Mol Ther, January 2010 18(1):80-6, which is incorporated herein by reference.

In one embodiment, the rAAV vector genome comprises nt 1 to nt 5134 of SEQ ID NO: 23, nt 1 to nt 5056 of SEQ ID NO: 24, nt 1 to nt 5064 of SEQ ID NO: 25, nt 1 to nt 5068 of SEQ ID NO: 26, nt 1 to nt 5048 of SEQ ID NO: 27, nt 1 to nt 4284 of SEQ ID NO: 28, nt 1 to nt 4677 of SEQ ID NO: 29, nt 1 to nt 4978 of SEQ ID NO: 30, nt 1 to nt 4876 of SEQ ID NO: 31, nt 1 to nt 4945 of SEQ ID NO: 32, nt 1 to nt 3628 of SEQ ID NO: 33, nt 1 to nt 4021 of SEQ ID NO: 34, or nt 1 to nt 4627 of SEQ ID NO: 35.

Exemplary production plasmids to generate rAAVs are shown in SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, and SEQ ID NO: 35.

5.1.2. Compositions

In one embodiment, the rAAV.hATP7B virus is provided in a pharmaceutical composition which comprises an aqueous carrier, excipient, diluent or buffer. In one embodiment, the buffer is PBS. In a specific embodiment, the rAAV.hATP7B formulation is a suspension containing an effective amount of rAAV.hATP7B vector suspended in an aqueous solution containing 0.001% Pluronic F-68 in TMN200 (200 mM sodium chloride, 1 mM magnesium chloride, 20 mM Tris, pH 8.0). However, various suitable solutions are known including those which include one or more of: buffering saline, a surfactant, and a physiologically compatible salt or mixture of salts adjusted to an ionic strength equivalent to about 100 mM sodium chloride (NaCl) to about 250 mM sodium chloride, or a physiologically compatible salt adjusted to an equivalent ionic concentration.

For example, a suspension as provided herein may contain both NaCl and KCl. The pH may be in the range of 6.5 to 8.5, or 7 to 8.5, or 7.5 to 8. A suitable surfactant, or combination of surfactants, may be selected from among Poloxamers, i.e., nonionic triblock copolymers composed of a central hydrophobic chain of polyoxypropylene (poly (propylene oxide)) flanked by two hydrophilic chains of polyoxyethylene (poly(ethylene oxide)), SOLUTOL HS 15 (Macrogol-15 Hydroxystearate), LABRASOL (Polyoxy capryllic glyceride), polyoxy 10 oleyl ether, TWEEN (polyoxyethylene sorbitan fatty acid esters), ethanol and polyethylene glycol. In one embodiment, the formulation contains a poloxamer. These copolymers are commonly named with the letter "P" (for poloxamer) followed by three digits: the first two digits×100 give the approximate molecular mass of the polyoxypropylene core, and the last digit×10 gives the percentage polyoxyethylene content. In one embodiment Poloxamer 188 is selected. The surfactant may be present in an amount up to about 0.0005% to about 0.001% of the suspension. In another embodiment, the vector is suspended in an aqueous solution containing 180 mM sodium chloride, 10 mM sodium phosphate, 0.001% Poloxamer 188, pH 7.3.

In one embodiment, the formulation is suitable for use in human subjects and is administered intravenously. In one embodiment, the formulation is delivered via a peripheral vein by bolus injection. In one embodiment, the formulation is delivered via a peripheral vein by infusion over about 10 minutes (±5 minutes). In one embodiment, the formulation is delivered via a peripheral vein by infusion over about 20 minutes (±5 minutes). In one embodiment, the formulation is delivered via a peripheral vein by infusion over about 30 minutes (±5 minutes). In one embodiment, the formulation is delivered via a peripheral vein by infusion over about 60 minutes (±5 minutes). In one embodiment, the formulation is delivered via a peripheral vein by infusion over about 90 minutes (±10 minutes). However, this time may be adjusted as needed or desired. Any suitable method or route can be used to administer an AAV-containing composition as described herein, and optionally, to co-administer other active drugs or therapies in conjunction with the AAV-mediated delivery of hATP7B described herein. Routes of administration include, for example, systemic, oral, inhalation, intranasal, intratracheal, intraarterial, intraocular, intravenous, intramuscular, subcutaneous, intradermal, and other parental routes of administration.

In one embodiment, the formulation may contain, e.g., about $1.0 \times 10^{11}$ genome copies per kilogram of patient body weight (GC/kg) to about $1 \times 10^{14}$ GC/kg, about $5 \times 10^{11}$ genome copies per kilogram of patient body weight (GC/kg) to about $3 \times 10^{13}$ GC/kg, or about $1 \times 10^{12}$ to about $1 \times 10^{14}$ GC/kg, as measured by oqPCR or digital droplet PCR (ddPCR) as described in, e.g., M. Lock et al, Hum Gene Ther Methods. 2014 April; 25(2):115-25. doi: 10.1089/hgtb.2013.131. Epub 2014 Feb. 14, which is incorporated herein by reference. In one embodiment, the rAAV.hATP7B formulation is a suspension containing at least $1 \times 10^{13}$ genome copies (GC)/mL, or greater, as measured by oqPCR or digital droplet PCR (ddPCR) as described in, e.g., M. Lock et al, supra.

In order to ensure that empty capsids are removed from the dose of AAV.hATP7B that is administered to patients, empty capsids are separated from vector particles during the vector purification process, e.g., using the method discussed herein. In one embodiment, the vector particles containing packaged genomes are purified from empty capsids using the process described in WO 2017/100676 and entitled "Scalable Purification Method for AAV8", which is incorporated by reference herein. Briefly, a two-step purification scheme is described which selectively captures and isolates the genome-containing rAAV vector particles from the clarified, concentrated supernatant of a rAAV production cell culture. The process utilizes an affinity capture method performed at a high salt concentration followed by an anion exchange resin method performed at high pH to provide rAAV vector particles which are substantially free of rAAV intermediates. Similar purification methods can be used for vectors having other capsids.

While any conventional manufacturing process can be utilized, the process described herein (and in WO 2017/100676) yields vector preparations wherein between 50 and 70% of the particles have a vector genome, i.e., 50 to 70% full particles. Thus for an exemplary dose of $1.6 \times 10^{12}$ GC/kg, and the total particle dose will be between $2.3 \times 10^{12}$ and $3 \times 10^{12}$ particles. In another embodiment, the proposed dose is one half log higher, or $5 \times 10^{12}$ GC/kg, and the total particle dose will be between $7.6 \times 10^{12}$ and $1.1 \times 10^{13}$ particles. In one embodiment, the formulation is be characterized by an rAAV stock having a ratio of "empty" to "full" of 1 or less, preferably less than 0.75, more preferably, 0.5, preferably less than 0.3.

A stock or preparation of rAAV8 particles (packaged genomes) is "substantially free" of AAV empty capsids (and other intermediates) when the rAAV8 particles in the stock are at least about 75% to about 100%, at least about 80%, at least about 85%, at least about 90%, at least about 95%, or at least 99% of the rAAV8 in the stock and "empty capsids" are less than about 1%, less than about 5%, less than about 10%, less than about 15% of the rAAV8 in the stock or preparation.

Generally, methods for assaying for empty capsids and AAV vector particles with packaged genomes have been known in the art. See, e.g., Grimm et al., Gene Therapy (1999) 6:1322-1330; Sommer et al., Molec. Ther. (2003) 7:122-128. To test for denatured capsid, the methods include subjecting the treated AAV stock to SDS-polyacrylamide gel electrophoresis, consisting of any gel capable of separating the three capsid proteins, for example, a gradient gel containing, 3-8% Tris-acetate in the buffer, then running the gel until sample material is separated, and blotting the gel onto nylon or nitrocellulose membranes, preferably nylon. Anti-AAV capsid antibodies are then used as the primary antibodies that bind to denatured capsid proteins, preferably an anti-AAV capsid monoclonal antibody, most preferably the B1 anti-AAV-2 monoclonal antibody (Wobus et al., J. Virol. (2000) 74:9281-9293). A secondary antibody is then used, one that binds to the primary antibody and contains a means for detecting binding with the primary antibody, more preferably an anti-IgG antibody containing a detection molecule covalently bound to it, most preferably a sheep anti-mouse IgG antibody covalently linked to horseradish peroxidase. A method for detecting binding is used to semi-quantitatively determine binding between the primary and secondary antibodies, preferably a detection method capable of detecting radioactive isotope emissions, electromagnetic radiation, or colorimetric changes, most preferably a chemiluminescence detection kit. For example, for SDS-PAGE, samples from column fractions can be taken and heated in SDS-PAGE loading buffer containing reducing agent (e.g., DTT), and capsid proteins were resolved on pre-cast gradient polyacrylamide gels (e.g., Novex). Silver staining may be performed using SilverXpress (Invitrogen, CA) according to the manufacturer's instructions. In one embodiment, the concentration of AAV vector genomes (vg) in column fractions can be measured by quantitative real time PCR (Q-PCR). Samples are diluted and digested with DNase I (or another suitable nuclease) to remove exogenous DNA. After inactivation of the nuclease, the samples are further diluted and amplified using primers and a TaqMan™ fluorogenic probe specific for the DNA sequence between the primers. The number of cycles required to reach a defined level of fluorescence (threshold cycle, Ct) is measured for each sample on an Applied Biosystems Prism 7700 Sequence Detection System. Plasmid DNA containing identical sequences to that contained in the AAV vector is employed to generate a standard curve in the Q-PCR reaction. The cycle threshold (Ct) values obtained from the samples are used to determine vector genome titer by normalizing it to the Ct value of the plasmid standard curve. End-point assays based on the digital PCR can also be used.

In one aspect, an optimized q-PCR method is provided herein which utilizes a broad spectrum scone protease, e.g., proteinase K (such as is commercially available from Qiagen). More particularly, the optimized qPCR genome titer assay is similar to a standard assay, except that after the DNase I digestion, samples are diluted with proteinase K buffer and treated with proteinase K followed by heat inactivation. Suitably samples are diluted with proteinase K buffer in an amount equal to the sample size. The proteinase K buffer may be concentrated to 2 fold or higher. Typically, proteinase K treatment is about 0.2 mg/mL, but may be varied from 0.1 mg/mL to about 1 mg/mL. The treatment step is generally conducted at about 55° C. for about 15 minutes, but may be performed at a lower temperature (e.g., about 37° C. to about 50° C.) over a longer time period (e.g., about 20 minutes to about 30 minutes), or a higher temperature (e.g., up to about 60° C.) for a shorter time period (e.g., about 5 to 10 minutes). Similarly, heat inactivation is generally at about 95° C. for about 15 minutes, but the temperature may be lowered (e.g., about 70 to about 90° C.) and the time extended (e.g., about 20 minutes to about 30 minutes). Samples are then diluted (e.g., 1000 fold) and subjected to TaqMan analysis as described in the standard assay.

Additionally, or alternatively, droplet digital PCR (ddPCR) may be used. For example, methods for determining single-stranded and self-complementary AAV vector gnome titers by ddPCR have been described. See, e.g., M. Lock et al. Hu Gene Therapy Methods, Hum Gene Ther Methods. 2014 April; 25(2):115-25. doi: 10.1089/hgtb.2013.131. Epub 2014 Feb. 14.

5.2 Patient Population

As discussed above, a subject having WD of any severity is the intended recipient of the compositions and methods described herein.

Subjects may be permitted to continue their standard of care treatment(s) (e.g., diet low in copper; treatment with chelating agents such as D-penicillamine and trientine. Other agents include sodium dimercaptosuccinate, dimercaptosuccinic acid, zinc, and tetrathiomolybdate) prior to and concurrently with the gene therapy treatment at the discretion of their caring physician. In the alternative, the physician may prefer to stop standard of care therapies prior to administering the gene therapy treatment and, optionally, resume standard of care treatments as a co-therapy after administration of the gene therapy.

Desirable endpoints of the gene therapy regimen would provide functional ATP7B enzyme resulting in a reduction of serum copper levels of 25% or more. In one embodiment, urinary copper excretion of 3-8 μmol or less per 24 hours is desirable.

Many tests can be used to investigate patients who may have Wilson disease, including non-ceruloplasmin-bound copper (NCC; also called the "free copper" or copper index), 24-h urine copper, hepatic copper, and genetic mutation testing. Methods for measurement of copper levels are known in the art e.g., as described by McMillin et al, Am J Clin Pathol. 2009; 131(2):160-165, which is incorporated herein by reference. In one embodiment, patients achieve desired circulating ATP7B levels after treatment with rAAV.hATP7B, alone and/or combined with the use of adjunctive treatments.

5.3. Dosing & Route of Administration

In one embodiment, the rAAV.hATP7B vector is delivered as a single dose per patient. In one embodiment, the subject is delivered the minimal effective dose (MED) (as determined by preclinical study described in the Examples herein). As used herein, MED refers to the rAAV.hATP7B dose required to provide functional ATP7B enzyme resulting in a reduction of serum copper levels of 25% or more.

As is conventional, the vector titer is determined on the basis of the DNA content of the vector preparation. In one embodiment, quantitative PCR or optimized quantitative PCR as described in the Examples is used to determine the DNA content of the rAAV.hATP7B vector preparations. In one embodiment, digital droplet PCR as described above is used to determine the DNA content of the rAAV.hATP7B vector preparations. In one embodiment, the dosage is about $1 \times 10^{11}$ genome copies (GC)/kg body weight to about $1 \times 10^{13}$ GC/kg, inclusive of endpoints. In one embodiment, the dosage is $5 \times 10^{11}$ GC/kg. In another embodiment, the dosage is $5 \times 10^{12}$ GC/kg. In specific embodiments, the dose of rAAV.hATP7B administered to a patient is at least $5 \times 10^{11}$ GC/kg, $1 \times 10^{12}$ GC/kg, $1.5 \times 10^{12}$ GC/kg, $2.0 \times 10^{12}$ GC/kg, $2.5 \times 10^{12}$ GC/kg, $3.0 \times 10^{12}$ GC/kg, $3.5 \times 10^{12}$ GC/kg, $4.0 \times 10^{12}$ GC/kg $4.5 \times 10^{12}$ GC/kg, $5.0 \times 10^{12}$ GC/kg, $5.5 \times 10^{12}$ GC/kg, $6.0 \times 10^{12}$ GC/kg, $6.5 \times 10^{12}$ GC/kg, $7.0 \times 10^{12}$ GC/kg, or $7.5 \times 10^{12}$ GC/kg. Also, the replication-defective virus compositions can be formulated in dosage units to contain an amount of replication-defective virus that is in the range of about $1.0 \times 10^9$ GC to about $1.0 \times 10^{15}$ GC. As used herein, the term "dosage" can refer to the total dosage delivered to the subject in the course of treatment, or the amount delivered in a single (of multiple) administration.

In some embodiments, rAAV.hATP7B is administered in combination with one or more therapies for the treatment of WD, such as a low copper diet or administration of D-penicillamine, trientine, sodium dimercaptosuccinate, dimercaptosuccinic acid, zinc, and/or tetrathiomolybdate.

5.4. Measuring Clinical Objectives

Measurements of efficacy of treatment can be measured by transgene expression and activity as determined by ATP7B activity and or non-ceruloplasmin-bound copper (NCC; also called the "free copper" or copper index), 24-h urine copper, or hepatic copper levels. Further assessment of efficacy can be determined by clinical assessment of dietary copper tolerance.

As used herein, the rAAV.hATP7B vector herein "functionally replaces" or "functionally supplements" the patients defective ATP7B with active ATP7B when the patient expresses a sufficient level of ATP7B to achieve ATP7B activity resulting a 25% or greater reduction in non-ceruloplasmin-bound copper, 24-h urine copper, and/or hepatic copper.

The following examples are illustrative only and are not intended to limit the present invention.

EXAMPLES

The following examples are illustrative only and are not intended to limit the present invention.

Example 1: AAV Vectors Containing hATP7B (AAV.hATP7Bco)

An exemplary gene therapy vector AAV8.En34.TBG-S1.hATP7Bco.PA75 was constructed by an AAV8 vector bearing a codon-optimized human hATP7B cDNA (hATP7Bco) under the control of a TBG-S1 promoter and an En34 enhancer (FIG. 1). The ATP7B expression cassette was flanked by AAV2 derived inverted terminal repeats (ITRs) and further included a Kozak consensus sequence and a PA75 poly (A) signal. The sequence of AAV8.En34.TBG-S1.hATP7Bco.PA75 genome is shown in nt 1 to nt 5056 of SEQ ID NO: 24.

The vector AAV8.En34.TTR.hATP7Bco.PA75 was constructed as described above with a hepatocyte specific TTR promoter instead of TBG-S1. The sequence of AAV8.En34.TTR.hATP7Bco.PA75 is shown in nt 1 to nt 5068 of SEQ ID NO: 26.

A modified TTR promoter with the sequence shown as nt 21 to nt 190 of SEQ ID NO: 11, instead of TBG-S1 was utilized to construct the vector AAV.En34.mTTR.hATP7Bco.PA75. The sequence of AAV.En34.mTTR.hATP7Bco.PA75 is shown in nt 1 to nt 5048 of SEQ ID NO: 27.

The ATP7B expression cassette of AAV8.EnTTR.TTR.hATP7Bco.PA75 vector was driven by an EnTTR enhancer and a TTR promoter with a Kozak consensus sequence and a PA75 poly (A) signal. The sequence of AAV8.EnTTR.TTR.hATP7Bco.PA75 is shown in nt 1 to nt 5134 of SEQ ID NO: 23.

The AAV8.EnABPS.TBG-S1.hATP7Bco.PA75 vector encodes a codon-optimized human ATP7B cDNA (hATP7Bco) under the control of an ABP-S2 (ABPS enhancer) enhancer and a TBG-S1 promoter, with a Kozak consensus sequence and a PA75 poly (A) signal. The sequence of AAV8.ABPS.TBG-S1.hATP7Bco.PA75 is shown in nt 1 to nt 5064 of SEQ ID NO: 25.

Additionally, truncated hATP7Bco vectors, including AAV8.En34.TBG-S1.hATP7Bco(MBD1Del).PA75 (as shown in nt 1 to nt 4945 of SEQ ID NO: 32), AAV8.En34.TBG-S1.hATP7Bco(MBD2Del).PA75 (as shown in nt 1 to nt 4876 of SEQ ID NO: 31), AAV8.En34.TBG-S1.hATP7Bco(MBD3Del).PA75 (nt 1 to nt 4978 of SEQ ID NO: 30), AAV8.En34.TBG-S1.hATP7Bco(MBD1-2Del).PA75 (nt 1 to nt 4627 of SEQ ID NO: 35), AAV8.En34.TBG-S1.hATP7Bco(MBD1-4Del).PA75 (nt 1 to nt 4021 of SEQ ID NO: 34), AAV8.En34.TBG-S1.hATP7Bco(MBD1-5Del).PA75 (nt 1 to nt 3628 of SEQ ID NO: 33), AAV8.TBG.hATP7Bco(MBD1-4Del).PA75 (nt 1 to nt 4677 of SEQ ID NO: 29), and AAV8.TBG.hATP7Bco(MBD1-5Del).PA75 (nt 1 to nt 4284 of SEQ ID NO: 28) were designed, constructed and produced as the indicated truncated hATP7Bco with a Kozak consensus sequence, a PA75 Ploy (A) signal and promoters and enhancers as shown in Table 2.

Briefly, plasmids expressing a codon-optimized version of hATP7B (hATP7Bco) from a reduced sized transthyretin enhancer and promoter were packaged with the AAV8 viral capsid.

The vector was prepared using conventional triple transfection techniques in 293 cells as described e.g., by Mizukami, Hiroaki, et al. *A Protocol for AAV vector production and purification*. Diss. Division of Genetic Therapeutics, Center for Molecular Medicine, 1998, which is incorporated herein by reference. All vectors were produced by the Vector Core at the University of Pennsylvania as previously described [Lock, M., et al, Hum Gene Ther, 21: 1259-1271 (2010)].

TABLE 2

| Key elements in the vector | | | Size ITR-ITR (bp) | Mouse sex (female or male) | Age of mice at study initiation (weeks) | Difference in serum copper levels from W0 to W2 | Percentage difference in serum copper from W0 to W2 | Difference in serum copper levels from W0 to W4 | Percentage difference in serum copper from W0 to W4 |
|---|---|---|---|---|---|---|---|---|---|
| Enhance | Promoter | Transgene | | | | | | | |
| EnTTR | TTR | hATP7Bco | 5134 | M | 12 | 0.150 | 31% | 0.158 | 33% |
| | TBG-S1 | hATP7Bco | 5056 | M | 11 | 0.182 | 38% | 0.252 | 52% |
| En34 | TTR | hATP7Bco | 5069 | M | 10 | 0.120 | 25% | 0.176 | 38% |
| ABPS | TBG-S1 | hATP7Bco | 5064 | M | 9 | 0 134 | 28% | 0.154 | 32% |
| En34 | mTTR | hATP7Bco | 5084 | M | 12 | 0.294 | 61% | 0.232 | 48% |
| En34 | TBG-S1 | hATP7Bco MBD1 Del | 4945 | M | 11 | 0.106 | 22% | 0.200 | 41% |
| En34 | TBG-S1 | hATP7Bco MBD2 Del | 4876 | M | 11 | 0.052 | 11% | 0.062 | 13% |
| En34 | TBG-S1 | hATP7Bco MBD3 Del | 4978 | M | 10 | 0.058 | 12% | 0.076 | 16% |
| | TBG-S1 | hATP7Bco MBD1-2 Del | 4627 | M | 11 | 0 072 | 15% | 0.106 | 22% |
| En34 | TBG-S1 | hATP7Bco MBD1-4 Del | 4021 | M | 11 | 0.132 | 27% | 0.240 | 50% |
| En34 | TBG-S1 | hATP7Bco MBD1-5 Del | 3628 | M | 10 | 0.190 | 39% | 0.302 | 63% |
| | Full TBG | hATP7Bco MBD1-4 Del | 4677 | M | 10 | 0.160 | 33% | 0.206 | 43% |
| | Full TBG | hATP7Bco MBD1-5 Del | 4284 | M | 10 | 0.300 | 52% | 0.380 | 79% |

Example 2: A Mouse Model of Wilson's Disease

Prior to the development of gene therapeutic approaches for the treatment of Wilson's disease, the animal model of the disease phenotype must be fully characterized. The studies described herein are the first detailed characterization of both the tx$^J$ mouse strain and the evaluation of copper metabolism and disease pathology following fostering of all Atp7b KO mice from birth. In the absence of the conflicting copper deficiency provided prior to weaning due to the Atp7b deficiency in the mammary glands of diseased mothers, the time line of disease progression was accurately determined. Atp7b KO mice accumulate copper in the liver from birth with severe copper accumulation evident by two months of age with concurrent liver disease.

Monogenic diseases affecting single organs are attractive targets for gene therapy approaches, especially if there is relatively little associated histologic lesions. However, for metabolic disorders affecting the liver, there can often be severe damage to the liver parenchyma as a result of the disease. One of the classical examples of this is Wilson's disease, an autosomal, recessive disease caused by mutations in the Wilson's disease protein (a copper-transporting P-type ATPase, Atp7b). Lack of functional Atp7b results in the accumulation of copper in the liver and other tissues, which manifests as liver disease with neurological or psychiatric symptoms. Wilson's disease can be treated by reducing copper absorption or removing excess copper from the body using chelation therapy, but, as for many other metabolic disorders, liver transplantation can both correct the genetic deficiency associated with disease and replace a dysfunctional organ.

Wilson's disease affects 1:30,000 people with different disease symptoms and progression. To enable the development of new therapeutic alternatives to chelation and liver transplantation, a reliable animal model of this disease must be fully characterized. There are several previously reported rat and mouse animal models of Wilson's disease, including the Long-Evans Cinnamon (LEC) rats and various transgenic mouse strains (1-6). For evaluation of the Wilson's disease phenotype in a mouse model, we selected the toxic milk mouse (tx$^J$) available from Jackson Labs (2). These mice have a Gly712Asp missense mutation in the Atp7b gene, which is located in the second putative membrane-spanning domain of the encoded protein and results in a dysfunctional Atp7b protein.

The original name for this strain, the toxic milk mouse, is a result of Atp7b also being expressed in mammary tissue in addition to liver. Therefore, the "spontaneous arising" of the toxic milk phenotype in this model is a direct result of Wilson's disease (7). Due to the deficiency in the Atp7b protein, copper cannot be transported from the mother into breastmilk (8). Diseased pups that suckle from diseased mothers will present with an inverse form of Wilson's disease (copper deficiency) as they are unable to receive any copper in their diet until they are weaned and consume normal mouse chow. This inverse form of Wilson's disease also accounts for the previously described white coat color and mental defects (9). Here, we prefer to describe this mouse model as an Atp7b knockout (KO), and not as the tx$^J$, due to the dysfunctional Atp7b protein and the fact that all mice used in these studies were fostered onto Balb/c foster mothers within 72 hours of birth to mitigate the toxic milk issue. Therefore, characterization of the Wilson's disease phenotype described here has been separated from any underlying issues related to copper deficiency prior to weaning.

All animal procedures were performed in accordance with protocols approved by the Institutional Animal Care and Use Committee (IACUC) of the University of Pennsylvania.

ATP7B KO mice do not express functional copper-transporting ATPase (Lutsenko et al, Function and Regulation of Human Copper-Transporting ATPases, Physiological Reviews, 87(3):1011-46 (July 2007), thus served as a mouse model for Wilson's disease. A natural history study was performed to evaluate the progression of Wilson's disease in ATP7B KO mice. The study was performed in two phases. In the first, the mice were necropsied at different ages for evaluation of liver disease. In the second phase, mice were followed to 9 months of age for evaluation of several biomarkers.

Atp7b heterozygous and KO mice were evaluated for urine and serum copper levels on a weekly and biweekly basis, respectively, from 2 months of age for 7 months (FIGS. 3A and 3B). Atp7b in the liver exports copper into the bile for excretion in feces (7). In the absence of Atp7b, excretion of copper will occur via the urinary tract. Urine copper levels were initially similar in both genotypes studied, but at 3 months of age the level of copper in the urine of the Atp7b KO mice started to increase compared to the heterozygous animals (FIG. 3A). At the completion of the study urine copper levels averaged 0.18 µg/g in heterozygous mice and 1.08 μg/g in Atp7b KO mice. Serum copper levels in the Atp7b KO mice at two months of age were significantly different from heterozygous animals at 0.07 μg/g compared to 0.47 μg/g (p<0.0001 by Student's t test, FIG. 3B). At 3-4 months of age, serum copper levels in the Atp7b KO mice began to rise, reaching levels equivalent to that of the heterozygous mice. There were little to no differences in either urine or serum copper levels in male or female mice. The results of the first phase show that accumulation of copper in the liver was observed from birth. When the Atp7b KO mice reached 2 month-old, Timm's copper stain revealed a severe copper accumulation in the liver (FIG. 4).

Monogenic diseases affecting liver metabolism can be divided into two subcategories, those with liver lesions and those without. Wilson's disease patients do exhibit moderate to severe liver disease, usually manifesting as cirrhosis (13, 14). Therefore, we wanted to evaluate the time course for development of liver pathology in this mouse model of Wilson's disease. Atp7b KO mice were necropsied at 2, 3, 4, 5, 9, 10, and 12 months of age for evaluation of liver lesions over time (FIG. 5). Sections of the liver were stained with H&E, and evaluated for histopathology according to the 1-5 scoring system (FIG. 3C). Minimal hepatocellular hypertrophy and degeneration along with single cell necrosis and inflammation were present in Atp7b KO mice from two months of age. The severity of hepatocellular hypertrophy, degeneration and necrosis was highest by 6 months of age and remained consistent thereafter. Other parameters evaluated, including inflammation, bile duct hyperplasia, and oval cell hyperplasia, increased over time from 2-3 months to 7 months of age. There was a concurrent rise in the liver transaminases, ALT and AST, from normal values at two months of age to 199 U/l and 381 U/l for ALT and AST, respectively, at 10 months (Table 3). The extent of liver damage at 10 months of age was also evident from the serum total bilirubin levels as these suddenly spiked at 2.5 mg/dl. In addition to the liver lesions, areas of hepatic nodular regeneration were evident in this mouse model from 6 months of age (an example is shown by the asterisk in FIG. 5). This is perhaps unsurprising due to the severity of the liver disease. Table 3

| | Age (months) | ALT (U/l) | AST (U/l) | Total bilirubin (mg/dl) | n |
|---|---|---|---|---|---|
| ATP7B KO | 2 | 16 | 30 | 0.2 | 1 |
| | 3 | 164 | 190 | 0.2 | 1 |
| | 4 | 174 | 224 | 0.3 | 2 |
| | 5 | 279 | 175 | 0.2 | 5 |
| | 9 | 152 | 266 | 0.6 | 18 |
| | 10 | 199 | 381 | 2.5 | 2 |
| WT | 2 | 28 | 50 | 0.2 | 13 |
| | 3 | 29 | 54 | 0.2 | 8 |
| | 4 | 49 | 39 | 0.2 | 4 |
| | 5 | 30 | 41 | 0.1 | 2 |

Liver sections were also evaluated for fibrosis and copper accumulation by Sirius Red and Timm stain, respectively (FIG. 5). Focal or multifocal periportal fibrosis was seen by 3 months of age in the Atp7b KO mice. This rapidly progressed to diffuse bridging fibrosis with architectural disruption by 7 months of age. The development of liver lesions was likely due to the massive accumulation of copper in the liver as seen by the Timm's stain (FIG. 5). From two months of age, the liver of Atp7b KO mice had become saturated with copper as shown by the black staining. Accumulation of copper in the liver occurs due to disrupted export of copper into the bile in the absence of functional Atp7b. The levels of copper in the liver decreased over time, likely due to hepatocyte damage and release of copper into the serum. This has been previously shown, where copper values are significantly reduced with submassive or massive necrosis, and reduced even further with regeneration and fibrosis (1, 15-17). The fibrous connective tissue and regenerating hepatocytes do not contain excess copper concentration (18).

The copper levels in the urine of ATP7B KO mice were also monitored. Samples were collected weekly in the natural history study and then inductively coupled plasma-mass spectrometry was performed to assess the copper concentration. The results demonstrate that while the heterozygous littermates maintained a low copper level, Atp7b KO mice exhibited an overflow of copper into urine starting at about the third week followed by a steady growth of the urinary concentration of copper over the observation period (FIG. 2A, 3A), representing the high urinary copper excretion rate observed in the Wilson's disease patients.

The serum of Atp7b KO mice was collected biweekly to assess the copper concentration via inductively coupled plasma-mass spectrometry. The result showed a very low serum copper level until 2 months of age compared to heterozygous littermates suggesting a compromised ability of extracting copper from the tissue to the blood in the Atp7b KO mice. When the Atp7b KO mice were 3 to 4 month old, the serum concentration of copper significantly increased and reached the level of the heterozygous littermates (FIG. 2B, 3B).

In this Atp7b KO mouse model, the progression of disease was as follows: Severe copper accumulation in the liver was seen by Timm's copper stain at two months of age, but did decrease over time similar to that previously described by others (1, 15-17). Due to fostering of the pups, copper is likely accumulating in the liver of Atp7b KO mice from birth and reaching saturation levels around 2-3 months of age. Following development of liver disease at two months of age, copper is likely released into the serum, resulting in an apparent decrease in accumulation in hepatocytes and rising serum copper levels by 3-4 months of age. This rise in serum copper levels from initially low levels to those similar to heterozygous mice is different to what has been reported previously for another mouse model of Wilson's disease (17), where serum copper levels in the Atp7b−/− strain are similar to that seen in wild type mice at 6 weeks of age and increase over time to 2 to 3-fold higher than wild type mice by 44 weeks of age.

We observed that the overflow of copper into urine starts at ~3 months of age, which similarly could be due to hepatocellular necrosis and subsequent release of accumulated copper. Alternative mechanisms for excretion of copper via the kidney have been suggested, including lack of Atp7b activity in the kidney resulting in increased excretion (23-25), or accumulation of copper in the liver leading to downregulation of the liver copper transporter, Ctr1, and urinary excretion by a small copper carrier (26). Again, the time course of urinary copper excretion differs in this mouse model to that reported previously. Here, urinary copper excretion is initially similar in heterozygous and Atp7b KO mice, but increases in the KO mice over the course of the study. In comparison, urinary copper levels are 3-fold greater than wild type mice at 6 weeks of age in the Atp7b−/− strain, increase up until 14-20 weeks old, and then decrease substantially at 20 weeks of age (26).

Hepatocellular hypertrophy, degeneration and necrosis peak at 6 months of age with likely concomitant observation of areas of hepatic nodular regeneration from this age onwards. This progression towards regeneration has been reported for other mouse models of Wilson's disease (17). However, unlike in the other mouse models, there was no evidence of cholangiocarcinoma in the Atp7b KO mouse described here. Regions of fibrosis were seen by 3 months of age, which rapidly increased in severity over time with architectural disruption by 7 months of age. While there are marked increases in serum transaminases by 3-4 months of age, increases in serum total bilirubin levels only start to occur at 9 months, indicating advanced liver disease.

In the second phase of the natural history study, Atp7b KO and heterozygous littermates were sacrificed at 8 months of age. ALT, AST and total bilirubin levels were obtained. FIG. 6A-6C. H&E stain and then histopathology evaluated by pathologist against a scoring scheme, which is shown in FIG. 7. Fibrosis score and copper staining score by Timm's Stain are shown in FIGS. 8A and 8B, respectively. Copper levels in the liver are shown in FIG. 9.

Example 3: AAV8.hATP7Bco Vectors in the Model of Wilson's Disease

Male Atp7b KO mice were injected IV with $10^{10}$ GC/mouse and $10^{11}$ GC/mouse of AAV8.TTR.hATP7Bco, and female Atp7b KO mice were injected IV with $10^9$, $10^{10}$, and $10^{11}$ GC/mouse of the same vector. Serum copper levels were monitored following vector injection (FIGS. 10A and 10B). Administration of $10^{10}$ or $10^{11}$ GC/mouse in male Atp7b KO mice increased serum copper levels from an average of 0.11 μg/g to 0.52 μg/g and 0.34 μg/g by two weeks post vector administration, respectively (FIG. 10A). However, there was a lesser effect in female mice (FIG. 10B). Mice were sacrificed at 7 months post vector administration at ~9 months of age, and liver was harvested for evaluation of liver copper levels. Liver copper levels in heterozygous and Atp7b KO mice averaged 6 μg/g and 222 μg/g, respectively (FIG. 10C). AAV8 vector administration at doses >$10^9$ GC/mouse resulted in significant decreases in liver copper levels compared to age-matched, uninjected Atp7b KO mice. However, there were no significant differences between liver copper levels in female mice administered with $10^9$ GC/mouse and control Atp7b KO mice. For this measurement, there was a stronger effect of the high vector dose in female mice as liver copper levels were not significantly different from heterozygous mice (FIG. 10C).

Mice administered with AAV8 vector were necropsied at 9 months of age, and liver was histologically evaluated for parameters of copper-associated liver disease, including fibrosis and copper levels by Timm's stain (FIG. 11). Sections of the liver were stained with H&E and histologically evaluated according to the 1-5 scoring system (FIG. 12A). Similar to that seen for liver copper levels, there was no significant difference in liver lesions between age-matched, uninjected Atp7b KO mice and female mice administered with $10^9$ GC/mouse of AAV8 vector. There was a dose-dependent decrease in liver lesions with male mice injected with $10^{11}$ GC/mouse, which were observed to have only mild karyocytomegaly (denoting hepatocellular hypertrophy and degeneration), mild inflammation, and focal or multifocal periportal oval cell hyperplasia. There was a significant reduction in hepatocellular hypertrophy, degeneration/necrosis and as well as bile duct hyperplasia compared to the age-matched, uninjected Atp7b KO mice in mice administered with $10^{10}$ and $10^{11}$ GC/mouse (p<0.05). For inflammation and oval cell hyperplasia, significant reduction compared to age-matched, uninjected Atp7b KO mice was only observed at a dose of $10^{11}$ GC/mouse (p<0.05). When the histopathologic parameters were combined and evaluated using Fisher's combined probability test, there was a significant difference compared to age-matched, uninjected Atp7b KO mice following administration of both $10^{10}$ and $10^{11}$ GC/mouse (p<0.0001).

Male mice that received the highest vector dose also did not have fibrosis, which was evaluated with Sirius Red staining (FIGS. 11 and 12B). For all other vector-administered mice, there was no significant difference in fibrosis compared to age-matched, uninjected Atp7b KO mice (FIG. 12B). However, the reduction in fibrosis seen in female mice administered with $10^{11}$ GC/mouse was sufficient that there was also no significant difference between liver fibrosis score in these mice and the female Atp7b heterozygous mice. Timm's staining for copper accumulation in the liver demonstrated similar results to that seen by the quantitative liver copper levels determined by inductively coupled plasma-mass spectrometry (FIG. 12C). There were no significant differences in Timm's staining score between age-matched, uninjected Atp7b KO mice and any of the vector-administered groups. To evaluate the efficacy of AAV8.hATP7Bco vectors, Atp7b KO mice received an i.v. administration of various gene therapy vectors at $3 \times 10^{12}$ GC/kg, including AAV8.EnTTR.TTR.hATP7Bco.PA75 (FIG. 21, group 1), AAV8.En34.TBG-S1.hATP7Bco.PA75 (FIG. 21, group 2), AAV8.En34.TTR.hATP7Bco.PA75 (FIG. 21, group 3) and AAV8.EnABPS.TBG-S1.hATP7Bco.PA75 (FIG. 21, group 4). Heterozygous and wild type littermates and Atp7b KO mice without treatment served as controls. Blood samples were collected weekly to evaluate the levels of both copper bound and non-copper-bound forms of ceruloplasmin via Western blot. On day 21 after the administration, appearance of copper-bound ceruloplasmin was observed in the Atp7b KO mice treated with AAV8.En34.TBG-S1.hATP7Bco.PA75, indicating a promoted copper extraction into blood (FIG. 21, group 2). However, under the experimental setting described above, the other three tested vectors did not display an increase in copper-bound ceruloplasmin (FIG. 21).

To assess the copper accumulation in the liver of the ATP7B KO mice injected with the AAV8.hATP7Bco vectors described herein, Timm's copper stain was performed on the liver sections thereof. Black deposits indicate copper accumulation. The results are shown in FIG. 19B. Injection with all five vectors to male Atp7b KO mice led to a decrease in the black deposits of the liver sections compared to the samples from non-treated or PBS-only mice while the AAV8.EnTTR.TTR.hATP7Bco.PA75 vector demonstrated the least black deposits and a pattern similar to wild type (FIG. 19B). Female Atp7b KO mice (FIG. 19B) demonstrated more copper deposits in liver compared to the male, indicating a gender difference. Still compared to non-treated mice, the female Atp7b KO mice demonstrated less copper deposits in liver. Generation of antibodies against human ATP7B protein in both male and female Atp7b KO mice injected with AAV.hATP7Bco vectors described herein is under investigation.

Meanwhile, the serum samples were collected and the copper concentrations were assessed as described in Example 2. The data was plotted in FIGS. 15A and 15B for female and male mice, respectively. The result demonstrates that the treatment of $3 \times 10^{12}$ GC/kg of the AAV8.hATP7Bco vectors described herein successfully increased the serum copper level in the Atp7b KO mice (FIGS. 15A and 15B).

Further tests were performed as follows:

| Cohort | Vector | Dose (GC/kg) | Sex | No. of mice | Age of mice at study initiation |
|---|---|---|---|---|---|
| 1 | EnTTR.TTR | $3.0 \times 10^{12}$ | F | 5 | 11 weeks |
| 2 | EnTTR.TTR | $3.0 \times 10^{12}$ | M | 5 | 12 weeks |
| 3 | En34.TBG-S1 | $3.0 \times 10^{12}$ | F | 5 | 11 weeks |
| 4 | En34.TBG-S1 | $3.0 \times 10^{12}$ | M | 5 | 11 weeks |
| 5 | En34.TTR | $3.0 \times 10^{12}$ | F | 5 | 10 weeks |
| 6 | En34.TTR | $3.0 \times 10^{12}$ | M | 5 | 10 weeks |
| 7 | APBS.TBG-S1 | $3.0 \times 10^{12}$ | F | 5 | 9 weeks |
| 8 | APBS.TBG-S1 | $3.0 \times 10^{12}$ | M | 5 | 9 weeks |
| 1 | En34.mTTR | $3.0 \times 10^{12}$ | F | 5 | 12 weeks |
| 2 | En34.mTTR | $3.0 \times 10^{12}$ | M | 5 | 12 weeks |

Serum copper levels over time are shown in FIGS. 15A and 15B. ALT, AST and total bilirubin levels were obtained. FIG. 16A-C. Relative ATP7B expression is shown in FIG. 17. H&E stain and then histopathology evaluated by pathologist against a scoring scheme, which is shown is FIG. 18. Fibrosis score and copper staining score by Timm Stain are shown in FIGS. 19A and 19B respectively.

Example 4: Oxidase Activity of Ceruloplasmin in the Model of Wilson's Disease Injected with AAV.hATP7Bco Vectors Copper is a potentially toxic metal but it is essential for a wide number of physiological functions acting as a co-factor of a variety of enzymes. After its intestinal absorption, copper is transported to hepatocytes where it binds to ATP7B located in the membrane of the trans-Golgi network (TGN). This large transmembrane protein is in charge of transferring the metal to copper-dependent enzymes. Loading of copper into ceruloplasmin is essential for the ferroxidase activity of this enzyme and constitutes an important secretory pathway for the metal, as 95% of copper present in the plasma of healthy individuals is bound to ceruloplasmin. Please see, e.g. Murillo, Oihana, et al. "Long-term metabolic correction of Wilson's disease in a murine model by gene therapy" Journal of Hepatology 64.2 (2016): 419-426, which is incorporated by reference herein.

To measure the oxidase activity, 20 µl of serum was processed using the Sigma Ceruloplasmin Activity Colorimetric Kit (MAK177) or the BioVision Ceruloplasmin Activity Colorimetric Kit following the protocols shown in the corresponding Product Information thereof, which is incorporated by reference herein. Oxidase activity assays were also performed according to the protocols shown in Schosinsky et al, "Measurement of ceruloplasmin from its oxidase activity in serum by use of o-dianisidine dihydrochloride" Clinical Chemistry 20.12 (1974): 1556-1563 and Murillo et al. "Long-term metabolic correction of Wilson's disease in a murine model by gene therapy" Journal of Hepatology 64.2 (2016): 419-426, which are incorporated by reference herein.

The oxidase activity of serum ceruloplasmin of the Atp7b KO mice was measured using the four assays described above. Samples from wildtype and heterozygous mice were served as control. No differences between wildtype and the Atp7b KO mice were detected.

Furthermore, Atp7b KO mice were treated with or without ammonium sulphate. Wildtype mice were provided as a control. No difference in the ceruloplasmin oxidase activity assay was detected between the wildtype or Atp7b KO mice using the protocol shown in Schosinsky et al, "Measurement of ceruloplasmin from its oxidase activity in serum by use of o-dianisidine dihydrochloride" Clinical Chemistry 20.12 (1974): 1556-1563.

In another experiment, Atp7b KO mice were treated with or without copper sulphate. Wildtype mice were provided as a control. The ceruloplasmin oxidase activity assay is performed to detect differences between the mice treated with or without copper sulphate using the four methods described above. Liver homogenates of the mice described herein are also collected and tested for oxidase activity of ceruloplasmin using the four methods described above. Copper sulphate was further added to liver homogenates and served as a positive control.

Example 5: Further Testing of AAV8.TTR.hATP7Bco Vector

To determine the dose-dependent effects and minimal effective dose (MED) of the AAV8.EnTTR.TTR.hATP7Bco.PA75 vectors, both male and female 2 month-old ATP7B KO mice were injected intravenously with $1 \times 10^9$, $1 \times 10^{10}$ or $1 \times 10^{11}$ GC/mouse of the vector. The western blot for ceruloplasmin demonstrated an appearance of copper-bound ceruloplasmin in the serum of three out of four tested mice which received $1 \times 10^{11}$ GC of AAV8.EnTTR.TTR.hATP7Bco.PA75, suggesting an increase of copper extraction (FIG. 14). While upon treatment with $1 \times 10^{10}$ GC of the same vector, one out of five tested mice showed copper-bound ceruloplasmin in the blood (FIG. 14). Those date validated that a single intravenous injection of AAV8.EnTTR.TTR.hATP7Bco.PA75 at the dose of $1 \times 10^{11}$ GC per mouse successfully promoted the copper extraction in a murine model of Wilson's disease.

Example 6: Truncated Vectors

Monogenic diseases are excellent candidates for gene replacement therapy approaches using AAV vectors. However, there is a limit to the size of the cDNA that can be packaged inside an AAV vector capsid. The wild type AAV genome is 4,700 bp, and requests to package larger genomes can reduce the integrity of the DNA sequence encapsulated within the AAV capsid (19). Previously, extensive research has been performed to investigate ways to reduce both the size of a given transgene and the transcriptional and polyA control sequences required for expression. One example of where this has been done successfully is development of a gene therapy vector for the treatment of hemophilia A, involving generation of B domain-deleted transgene sequence for human coagulation factor VIII that is 4,374 bp in length (19-21). For the treatment of Wilson's disease, the problem is increased as the ATP7B cDNA is 4,395 bp. Therefore, we chose to use a reduced size transthyretin enhancer and promoter (TTR) sequence for expression of a codon-optimized version of the human ATP7B transgene, in combination with a 75 bp synthetic polyA sequence (PA75) (19). The resulting AAV genome is 5.1 kb and was packaged within the AAV8 capsid.

Additionally, truncated hATP7Bco vectors, including AAV8.En34.TBG-S1.hATP7Bco(MBD1Del).PA75, AAV8.En34.TBG-S1.hATP7Bco(MBD2Del).PA75, AAV8.En34.TBG-S1.hATP7Bco(MBD3Del).PA75, AAV8.En34.TBG-S1.hATP7Bco(MBD1-2Del).PA75, AAV8.En34.TBG-S1.hATP7Bco(MBD1-4Del).PA75, AAV8.En34.TBG-S1.hATP7Bco(MBD1-5Del).PA75, AAV8.TBG.PI.hATP7Bco(MBD1-4Del).PA75, and AAV8.TBG.PI.hATP7Bco(MBD1-5Del).PA75, were designed, produced and injected into ATP7B KO mice intravenously at a dose of $3\times10^{12}$ GC/kg.

Atp7b KO mice treated with the various truncated vectors described above, and heterozygous littermates were studied and sacrificed at 6 months of age. Serum copper levels over time are shown in FIG. 22. ALT, AST and total bilirubin levels were obtained. FIG. 23. Relative ATP7B expression is shown in FIG. 24. H&E stain and then histopathology evaluated by pathologist against a scoring scheme, which is shown in FIG. 25. Fibrosis score and copper staining score by Timm's Stain are shown in FIG. 26. Liver copper levels at necropsy are shown in FIG. 27.

Example 7: Materials and Methods for Above Experiments

A. AAV Vector Production

All AAV vectors were produced by the Penn Vector Core at the University of Pennsylvania as described previously (10). Briefly, plasmids expressing a codon-optimized version of hATP7B (hATP7Bco) from a reduced sized transthyretin enhancer and promoter were packaged with the AAV8 viral capsid.

B. Mice

Breeding pairs of heterozygous $Atp7b^{+/-}$ mice were obtained from The Jackson Laboratory (Bar Harbor, Me., USA) and a colony was maintained at the University of Pennsylvania under specific pathogen-free conditions. All animal procedures and protocols were approved by the Institutional Animal Care and Use Committee (IACUC) of the University of Pennsylvania. Atp7b KO were generated and used for subsequent breeding. All pups generated from Atp7b KO mating pairs were fostered on Balb/c foster mothers within 72 hours of birth. Male and female Atp7b KO mice two months of age were injected IV with $10^9$-$10^{11}$ genome copies (GC)/mouse of AAV8.TTR.hATP7Bco via the tail vein (n=5/sex/group).

C. Serum Analyses

Blood was collected at the indicated time points in serum separator tubes, allowed to clot, and serum was isolated by centrifugation at 3,500×g for 5 minutes at room temperature. Serum was analyzed for alanine aminotransferase (ALT), aspartate aminotransferase (AST), and total bilirubin levels by Antech Diagnostics (Irvine, Calif., USA). Serum and urine was also analyzed for copper levels by Exova (Edinburgh, UK).

D. Liver Copper Analysis

Liver samples taken at necropsy were analyzed for copper levels by Exova (Edinburgh, UK).

E. Histopathology

Formalin-fixed paraffin-embedded tissue samples were sectioned and stained for hematoxylin and eosin (H&E) according to standard protocols. To detect liver fibrosis, Sirius Red staining was performed on paraffin sections. Sections were deparaffinized and stained for 90 minutes in a solution of 0.1% (w/v) Direct Red (Sigma), 4% (w/v) picric acid (Sigma), washed with 0.01 N HCl (2×1 min), dehydrated through an ethanol and xylene series, and cover slips applied.

F. Timm's Copper Stain

Sections from formalin-fixed paraffin-embedded livers were dewaxed and incubated sequentially in 0.5% ammonium sulfide (5 min), deionized water (1 min rinse), 0.1N HCl (2-3 min), deionized water (2-3 min rinse), and developer (1 part 5% silver nitrate, 5 parts 2% (w/v) hydroquinone/5% (w/v) citric acid, for approximately 10 min). Liver sections from control animals (wild type and ATP7B KO) were included in each run and monitored for consistent staining intensity. Sections were finally washed in water, counterstained with Nuclear Fast Red, dehydrated, and cover slips applied.

G. Histopathology Scoring

The histopathologic lesions were scored based on the following criteria. Hepatocellular hypertrophy and degeneration: 0, no significant lesions; 1, minimal karyocytomegaly (rare to occasional, 1-2 hepatocytes within a lobule), 2, mild karyocytomegaly (<10% of hepatocytes within a lobule); 3, moderate karyocytomegaly (10-50% of hepatocytes within a lobule) with hepatocyte dissociation and rare to few single cell necrosis; 4, severe karyocytomegaly (51-90% of hepatocytes within a lobule) with extensive hepatocyte dissociation and frequent single cell necrosis; relatively normal hepatic architecture is maintained; 5, marked karyocytomegaly (>90% of hepatocytes within a lobule) with lobular collapse and numerous single cell necrosis. Inflammation: 0, none; 1, mild—few aggregates within portal areas and rare foci within parenchyma; considered within normal limits; 2, moderate—extending into surrounding periportal hepatocytes or multifocally within parenchyma; 3, marked—bridging or dissecting hepatocytes or multifocal to coalescing within parenchyma. Bile duct hyperplasia: 0, none; 1, focal or multifocal within portal areas; 2, dissecting hepatocytes in periportal region; 3, bridging or dissecting hepatocytes with architectural distortion. Oval cell hyperplasia: 0, none; 1, focal or multifocal (periportal); 2, bridging or dissecting hepatocytes; 3, bridging or dissecting hepatoytes with architectural distortion. Nodular regeneration: 0, absent; 1, present.

The grading scheme for fibrosis based on Sirius red staining was derived from those reported in the literature (11): 0, none; 1, focal or multifocal; 2, bridging; 3, bridging with architectural disruption, with notation on whether the distribution was centrilobular, midzonal, periportal, or diffuse.

H. The grading scheme for copper accumulation based on Timm's staining was the same as has been previously described in the literature (12): 1, absence or few copper-containing granules in the cytoplasm of an occasional hepatocyte; considered within normal limits; 2, obvious copper-containing granules in some centrilobular hepatocytes; considered within normal limits; 3, mild—numerous granules in most centrilobular hepatocytes (one-third of each lobule); 4, moderate—presence of numerous granules in all centrilobular and midzonal hepatocytes (approximately two-thirds of the hepatocytes in all lobules); 5 marked—abundant granules in more than two-thirds of the liver cells in all lobules. Statistical analysis For all data, group average and standard error of the mean (SEM) was calculated and reported. Student's t test was performed to compare two groups and a one-way analysis of variance (AVOVA) with Tukey's multiple comparisons test was performed across groups and stratified by sex. The five pathology parameters were analyzed in vector administration and compared with those in age-matched uninjected Atp7b KO mice. Comparisons were carried out using the Wilcoxon rank sum test within the R program (version 3.3.1; https//cran.r-project.org). The difference in combined pathology parameters was also evaluated for each dose group compared to age-matched uninjected ATP7B KO mice using Fisher's combined probability test within the R program using function "sumlog" in the "metap" package. A p value of 0.05 was considered to be significant.

Example 8: Discussion

Before a mouse model of disease can be used to assess the translatability of a therapeutic approach to the clinic, the model must be extensively characterized. While characterization of other mouse models of Wilson's disease have been performed (1, 15, 17), this study is the first detailed characterization of both the tx$^J$ mouse strain and the evaluation of copper metabolism and liver disease following fostering of all Atp7b KO mice from birth. In the absence of the conflicting copper deficiency that occurs prior to weaning due to the Atp7b deficiency in the mammary glands of diseased mothers, the time line of disease progression in these mice can be more accurately determined by ensuring separation of the disease phenotype from any underlying issues related to copper deficiency prior to weaning. The development of liver disease and nodular regeneration in this mouse model was similar to what has been previously reported for the Atp7b$^{-/-}$ strain developed by others (1, 17). However, the time line was slightly increased in this mouse strain, likely due to the fostering of pups from birth resulting in a continuous supply of copper.

In this Atp7b KO mouse model, the progression of disease was as follows: Severe copper accumulation in the liver was seen by Timm's copper stain at two months of age, but did decrease over time similar to that previously described by others (1, 15-17). Due to fostering of the pups, copper is likely accumulating in the liver of Atp7b KO mice from birth and reaching saturation levels around 2-3 months of age. Following development of liver disease at two months of age, copper is likely released into the serum, resulting in an apparent decrease in accumulation in hepatocytes and rising serum copper levels by 3-4 months of age. This rise in serum copper levels from initially low levels to those similar to heterozygous mice is different to what has been reported previously for another mouse model of Wilson's disease (17), where serum copper levels in the Atp7b$^{-/-}$ strain are similar to that seen in wild type mice at 6 weeks of age and increase over time to 2 to 3-fold higher than wild type mice by 44 weeks of age.

We observed that the overflow of copper into urine starts at ~3 months of age, which similarly could be due to hepatocellular necrosis and subsequent release of accumulated copper. Alternative mechanisms for excretion of copper via the kidney have been suggested, including lack of Atp7b activity in the kidney resulting in increased excretion (23-25), or accumulation of copper in the liver leading to downregulation of the liver copper transporter, Ctr1, and urinary excretion by a small copper carrier (26). Again, the time course of urinary copper excretion differs in this mouse model to that reported previously. Here, urinary copper excretion is initially similar in heterozygous and Atp7b KO mice, but increases in the KO mice over the course of the study. In comparison, urinary copper levels are 3-fold greater than wild type mice at 6 weeks of age in the Atp7b$^{-/-}$ strain, increase up until 14-20 weeks old, and then decrease substantially at 20 weeks of age (26).

Hepatocellular hypertrophy, degeneration and necrosis peak at 6 months of age with likely concomitant observation of areas of hepatic nodular regeneration from this age onwards. This progression towards regeneration has been reported for other mouse models of Wilson's disease (17). However, unlike in the other mouse models, there was no evidence of cholangiocarcinoma in the Atp7b KO mouse described here. Regions of fibrosis were seen by 3 months of age, which rapidly increased in severity over time with architectural disruption by 7 months of age. While there are marked increases in serum transaminases by 3-4 months of age, increases in serum total bilirubin levels only start to occur at 9 months, indicating advanced liver disease.

Following characterization of this Atp7b KO mouse model, we developed a gene therapy approach for treatment of Wilson's disease. IV administration of an AAV8 vector expressing a codon-optimized version of the human ATP7B transgene into Atp7b KO mice at two months of age resulted in an increase in serum copper levels by two weeks post vector administration. The higher doses of vector evaluated here (>10$^9$ GC/mouse) resulted in significant decreases in liver copper levels compared to age-matched, uninjected Atp7b KO mice. There was a significant, dose-dependent decrease in liver lesions, with only mild histopathological findings present in male mice injected with 10$^{11}$ GC/mouse and a complete lack of liver fibrosis. Therefore, administration of a gene therapy approach during the early stages of disease onset prevented liver damage and corrected copper metabolism in a mouse model of Wilson's disease.

All publications cited in this specification, as well as U.S. Provisional Patent Application Nos. 62/440,659 and 62/473,656, are incorporated herein by reference. Similarly, the SEQ ID NOs which are referenced herein and which appear in the appended Sequence Listing are incorporated by reference. While the invention has been described with reference to particular embodiments, it will be appreciated that modifications can be made without departing from the spirit of the invention. Such modifications are intended to fall within the scope of the appended claims.

| Sequence Listing Free Text | |
|---|---|
| Seq ID NO | Free Text |
| 4-15 | <213> Artificial Sequence |
| | <223> constructed sequence |
| 17-35 | <213> Artificial Sequence |
| | <223> constructed sequence |

REFERENCES

1. Buiakova O I, Xu J, Lutsenko S, Zeitlin S, Das K, Das S, Ross B M, et al. Null mutation of the murine ATP7B (Wilson disease) gene results in intracellular copper accumulation and late-onset hepatic nodular transformation. Hum Mol Genet 1999; 8:1665-1671.
2. Coronado V, Nanji M, Cox D W. The Jackson toxic milk mouse as a model for copper loading. Mamm Genome 2001; 12:793-795.
3. Theophilos M B, Cox D W, Mercer J F. The toxic milk mouse is a murine model of Wilson disease. Hum Mol Genet 1996; 5:1619-1624.
4. Sasaki N, Hayashizaki Y, Muramatsu M, Matsuda Y, Ando Y, Kuramoto T, Serikawa T, et al. The gene responsible for LEC hepatitis, located on rat chromosome 16, is the homolog to the human Wilson disease gene. Biochem Biophys Res Commun 1994; 202:512-518.
5. Wu J, Forbes J R, Chen H S, Cox D W. The LEC rat has a deletion in the copper transporting ATPase gene homologous to the Wilson disease gene. Nat Genet 1994; 7:541-545.
6. Terada K, Sugiyama T. The Long-Evans Cinnamon rat: an animal model for Wilson's disease. Pediatr Int 1999; 41:414-418.
7. Lutsenko S, Barnes N L, Bartee M Y, Dmitriev O Y. Function and regulation of human copper-transporting ATPases. Physiol Rev 2007; 87:1011-1046.
8. Michalczyk A, Bastow E, Greenough M, Camakaris J, Freestone D, Taylor P, Linder M, et al. ATP7B expression in human breast epithelial cells is mediated by lactational hormones. J Histochem Cytochem 2008; 56:389-399.
9. Bronson R T, Sweet H O, Davisson M T. Acute cerebral neuronal necrosis in copper deficient offspring of female mice with the toxic milk mutation. Mouse Genome 1995; 93:152-154.
10. Gao G, Lu Y, Calcedo R, Grant R L, Bell P, Wang L, Figueredo J, et al. Biology of AAV serotype vectors in liver-directed gene transfer to nonhuman primates. Mol Ther 2006; 13:77-87.
11. Bernard J M, Newkirk K M, McRee A E, Whittemore J C, Ramsay E C. Hepatic lesions in 90 captive nondomestic felids presented for autopsy. Vet Pathol 2015; 52:369-376.
12. Thornburg L P, Shaw D, Dolan M, Raisbeck M, Crawford S, Dennis G L, Olwin D B. Hereditary copper toxicosis in West Highland white terriers. Vet Pathol 1986; 23:148-154.
13. Stromeyer F W, Ishak K G. Histology of the liver in Wilson's disease: a study of 34 cases. Am J Clin Pathol 1980; 73:12-24,
14. Roberts E A, Schilsky M L, American Association for Study of Liver D. Diagnosis and treatment of Wilson disease: an update. Hepatology 2008; 47:2089-2111.
15. Biempica L, Rauch H, Quintana N, Sternlieb I. Morphologic and chemical studies on a murine mutation (toxic milk mice) resulting in hepatic copper toxicosis. Lab Invest 1988; 59:500-508.
16. Haywood S, Loughran M, Batt R M. Copper toxicosis and tolerance in the rat. III. Intracellular localization of copper in the liver and kidney. Exp Mol Pathol 1985; 43:209-219.
17. Huster D, Finegold M J, Morgan C T, Burkhead J L, Nixon R, Vanderwerf S M, Gilliam C T, et al. Consequences of copper accumulation in the livers of the Atp7b-/- (Wilson disease gene) knockout mice. Am J Pathol 2006; 168:423-434.
18. Smedley R, Mullaney T, Rumbeiha W. Copper-associated hepatitis in Labrador Retrievers. Vet Pathol 2009; 46:484-490.
19. Greig J A, Wang Q, Reicherter A L, Chen S J, Hanlon A L, Tipper C H, Clark K R, et al. Characterization of Adeno-Associated Viral Vector-Mediated Human Factor VIII Gene Therapy in Hemophilia A Mice. Hum Gene Ther 2017; 28:392-402.
20. Toole J J, Pittman D D, Orr E C, Murtha P, Wasley L C, Kaufman R J. A large region (approximately equal to 95 kDa) of human factor VIII is dispensable for in vitro procoagulant activity. Proc Natl Acad Sci USA 1986; 83:5939-5942.
21. Ward N J, Buckley S M, Waddington S N, Vandendriessche T, Chuah M K, Nathwani A C, McIntosh J, et al. Codon optimization of human factor VIII cDNAs leads to high-level expression. Blood 2011; 117:798-807.
22. Davidoff A M, Ng C Y, Zhou J, Spence Y, Nathwani A C. Sex significantly influences transduction of murine liver by recombinant adeno-associated viral vectors through an androgen-dependent pathway. Blood 2003; 102:480-488.
23. Bull P C, Thomas G R, Rommens J M, Forbes J R, Cox D W. The Wilson disease gene is a putative copper transporting P-type ATPase similar to the Menkes gene. Nat Genet 1993; 5:327-337.
24. Petrukhin K, Fischer S G, Pirastu M, Tanzi R E, Chernov I, Devoto M, Brzustowicz L M; et al. Mapping, cloning and genetic characterization of the region containing the Wilson disease gene. Nat Genet 1993; 5:338-343.
25. Tanzi R E, Petrukhin K, Chernov I, Pellequer J L, Wasco W, Ross B. Romano D M, et al. The Wilson disease gene is a copper transporting ATPase with homology to the Menkes disease gene. Nat Genet 1993; 5:344-350.
26. Gray L W, Peng F, Molloy S A, Pendyala V S, Muchenditsi A, Muzik O, Lee J, et al. Urinary copper elevation in a mouse model of Wilson's disease is a regulated process to specifically decrease the hepatic copper load. PLoS One 2012; 7:e38327.

The invention claimed is:

1. A recombinant adeno-associated virus (rAAV) useful as a liver-directed therapeutic for Wilson's Disease (WD), said rAAV comprising an AAV capsid, and a vector genome packaged therein, said vector genome comprising:
   (a) an AAV 5' inverted terminal repeat (ITR) sequence;
   (b) a transthyretin (TTR) promoter sequence and a TTR enhancer sequence;
   (c) a coding sequence encoding a truncated human copper-transporting ATPase 2 (ATP7B) comprising metal-binding domains (MBD) 4-6 and comprising a deletion of MBD_1-3; and
   (d) an AAV 3' ITR sequence.

2. The rAAV according to claim 1, wherein the coding sequence of (c) is a native coding sequence.

3. The rAAV according to claim 1, wherein the AAV capsid is an AAV8 capsid or variant thereof.

4. The rAAV according to claim 1, wherein the TTR promoter sequence is a modified TTR promoter sequence.

5. The rAAV according to claim 1, wherein the AAV 5' ITR and/or AAV 3' ITR sequence is from AAV2.

6. The rAAV according to claim 1, wherein the vector genome further comprises a polyA signal sequence.

7. The rAAV according to claim 6, wherein the polyA is about 75 bp in length.

8. The rAAV according to claim 1, wherein the vector genome further comprises an intron sequence.

9. The rAAV according to claim 8, wherein the intron sequence is from human beta globin IVS2 or SV40.

10. The rAAV according to claim 1, wherein the vector genome is about 3 kilobases to about 5.5 kilobases in size.

11. A method of treating a patient having Wilson's Disease with the rAAV according to claim 1, wherein the rAAV is delivered at about $1\times10^{12}$ to about $1\times10^{14}$ genome copies (GC)/kg in an aqueous suspension, wherein the GC are calculated as determined based on oqPCR or ddPCR.

12. The rAAV according to claim 1, wherein the coding sequence of (c) is a codon-optimized sequence.

13. An aqueous suspension for administration to a Wilson's Disease patient, said suspension comprising an aqueous suspending liquid and about $1\times10^{12}$ GC/mL to about $1\times10^{14}$ GC/mL of a recombinant adeno-associated virus (rAAV) useful as a liver-directed therapeutic for Wilson's Disease, said rAAV having an AAV capsid, and having packaged therein a vector genome comprising:
   (a) an AAV 5' inverted terminal repeat (ITR) sequence;
   (b) a TTR promoter sequence and a TTR enhancer sequence;
   (c) a coding sequence encoding a truncated human copper-transporting ATPase 2 (ATP7B) comprising metal-binding domains (MBD) 4-6 and comprising a deletion of MBD_1-3; and
   (d) an AAV 3' ITR sequence.

14. The aqueous suspension according to claim 13, wherein the suspension is suitable for intravenous injection.

15. The aqueous suspension according to claim 13, wherein the suspension further comprises a surfactant, preservative, and/or buffer dissolved in the aqueous suspending liquid.

16. The aqueous suspension according to claim 13, wherein the AAV capsid is an AAV8 capsid.

* * * * *

UNITED STATES PATENT AND TRADEMARK OFFICE
CERTIFICATE OF CORRECTION

PATENT NO. : 11,473,106 B2
APPLICATION NO. : 16/474958
DATED : October 18, 2022
INVENTOR(S) : James M. Wilson, Jenny Agnes Sidrane and Lakshmanan Govindasamy It is certified that error appears in the above-identified patent and that said Letters Patent is hereby corrected as shown below:

In the Claims

Column 165, Line 33, Claim 1, amend as follows:
-- 1. A recombinant adeno-associated virus (rAAV) useful as a liver-directed therapeutic for Wilson's Disease (WD), said rAAV comprising an AAV capsid, and a vector genome packaged therein, said vector genome comprising:
    (a) an AAV 5' inverted terminal repeat (ITR) sequence;
    (b) a transthyretin (TTR) promoter sequence and a TTR enhancer sequence;
    (c) a coding sequence encoding a truncated human copper-transporting ATPase 2
        (ATP7B) comprising metal-binding domains (MBD) 4-6 and comprising a
        deletion of MBD 1-3; and
    (d) an AAV 3' ITR sequence. --

Column 166, Line 39, Claim 13, amend as follows:
-- 13. An aqueous suspension for administration to a Wilson's Disease patient, said suspension comprising an aqueous suspending liquid and about $1 \times 10^{12}$ GC/mL to about $1 \times 10^{14}$ GC/mL of a recombinant adeno-associated virus (rAAV) useful as a liver-directed therapeutic for Wilson's Disease, said rAAV having an AAV capsid, and having packaged therein a vector genome comprising:
    (a) an AAV 5' inverted terminal repeat (ITR) sequence;
    (b) a TTR promoter sequence and a TTR enhancer sequence;
    (c) a coding sequence encoding a truncated human copper-transporting ATPase 2
        (ATP7B) comprising metal-binding domains (MBD) 4-6 and
        comprising a deletion of MBD 1-3; and
    (d) an AAV 3' ITR sequence. --

Signed and Sealed this
Seventh Day of March, 2023

Katherine Kelly Vidal
*Director of the United States Patent and Trademark Office*